US010869800B2

(12) United States Patent
Augustine et al.

(10) Patent No.: US 10,869,800 B2
(45) Date of Patent: *Dec. 22, 2020

(54) RELOCATION MODULE AND METHODS FOR SURGICAL EQUIPMENT

(71) Applicant: Augustine Biomedical + Design, LLC, Eden Prairie, MN (US)

(72) Inventors: Scott D. Augustine, Deephaven, MN (US); Susan D. Augustine, Deephaven, MN (US); Garrett J. Augustine, Deephaven, MN (US); Brent M. Augustine, Savage, MN (US); Ryan S. Augustine, Minneapolis, MN (US); Randall C. Arnold, Minnetonka, MN (US)

(73) Assignee: Augustine Biomedical + Design, LLC, Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/879,406

(22) Filed: May 20, 2020

(65) Prior Publication Data

US 2020/0281790 A1 Sep. 10, 2020

Related U.S. Application Data

(63) Continuation-in-part of application No. 16/601,924, filed on Oct. 15, 2019, now Pat. No. 10,702,436, (Continued)

(51) Int. Cl.
*A61B 50/15* (2016.01)
*A61B 50/13* (2016.01)
(Continued)

(52) U.S. Cl.
CPC ............ *A61G 13/108* (2013.01); *A61B 50/13* (2016.02); *A61B 50/15* (2016.02); *A61M 16/06* (2013.01);
(Continued)

(58) Field of Classification Search
CPC ..... A61G 13/108; A61M 16/06; A61M 16/18; A61M 16/01; A61B 50/15; A61B 50/13;
(Continued)

(56) References Cited

U.S. PATENT DOCUMENTS

| 4,105,028 A | 8/1978 | Sadlier et al. |
| 4,531,956 A | 7/1985 | Howorth |

(Continued)

FOREIGN PATENT DOCUMENTS

WO  WO-2019191081 A1  10/2019

OTHER PUBLICATIONS

U.S. Appl. No. 15/935,524 10,512,191, Mar. 26, 2018, Relocation Module for Patient Monitors and Surgical Equipment.

(Continued)

*Primary Examiner* — Minh Chau T Pham
(74) *Attorney, Agent, or Firm* — Schwegman Lundberg & Woessner, P.A.

(57) ABSTRACT

An anesthetic equipment storage and waste air management module configured to housing electronic and electromechanical surgical equipment including a system to measure and record administration of one or more IV medications or fluids for IV administration. The module can include a housing having a lower section and a tower-like upper section, wherein the lower section is configured to house unrelated waste heat-producing electronic and electromechanical surgical equipment. The module can also include a cowling that substantially confines waste heat generated by the unrelated waste heat-producing electronic and electromechanical surgical equipment, and can include a system for measuring and recording the administration of the one or more IV medications and fluids.

26 Claims, 57 Drawing Sheets

Related U.S. Application Data which is a continuation of application No. 16/593,033, filed on Oct. 4, 2019, now Pat. No. 10,653,577, which is a continuation of application No. 16/364,884, filed on Mar. 26, 2019, now Pat. No. 10,507,153, which is a continuation-in-part of application No. 15/935,524, filed on Mar. 26, 2018, now Pat. No. 10,512,191.

(60) Provisional application No. 62/782,901, filed on Dec. 20, 2018.

(51) Int. Cl.
| | |
|---|---|
| *A61M 16/06* | (2006.01) |
| *A61M 16/18* | (2006.01) |
| *A61B 90/50* | (2016.01) |
| *A61B 46/10* | (2016.01) |
| *A61M 16/01* | (2006.01) |
| *A61G 13/10* | (2006.01) |
| *B01D 46/00* | (2006.01) |

(52) U.S. Cl.
CPC .............. *A61M 16/18* (2013.01); *A61B 46/10* (2016.02); *A61B 90/50* (2016.02); *A61B 2050/155* (2016.02); *A61M 16/01* (2013.01); *B01D 46/0093* (2013.01)

(58) Field of Classification Search
CPC ... A61B 46/10; A61B 90/50; A61B 2050/155; B01D 46/0093
USPC ........ 55/385.1, 385.2, 385.4, 467, 473, 485, 55/410, 356, DIG. 34; 96/134, 146; 604/319, 322, 902
See application file for complete search history.

(56) References Cited

U.S. PATENT DOCUMENTS

| | | | |
|---|---|---|---|
| 5,399,007 | A | 3/1995 | Marconet |
| 5,409,511 | A | 4/1995 | Paul |
| 5,516,313 | A | 5/1996 | Lumpkin |
| 5,695,536 | A | 12/1997 | Fabrizi |
| 7,597,731 | B2 | 10/2009 | Palmerton et al. |
| 7,674,436 | B1 | 3/2010 | Feldman et al. |
| 7,753,977 | B2 | 7/2010 | Lyons et al. |
| 9,603,956 | B2 | 3/2017 | Newham |
| 10,507,153 | B2 | 12/2019 | Augustine et al. |
| 10,512,191 | B2 | 12/2019 | Augustine et al. |
| 10,638,638 | B2 | 4/2020 | Augustine et al. |
| 10,653,577 | B2 | 5/2020 | Augustine et al. |
| 2001/0035702 | A1 | 11/2001 | Murphy et al. |
| 2003/0033790 | A1 | 2/2003 | Hague |
| 2003/0150328 | A1 | 8/2003 | Hansson et al. |
| 2004/0103789 | A1 | 6/2004 | Lan et al. |
| 2004/0247016 | A1* | 12/2004 | Faries, Jr. .............. A61B 50/13 374/162 |
| 2004/0249673 | A1 | 12/2004 | Smith |
| 2005/0060974 | A1 | 3/2005 | Palmerton et al. |
| 2005/0097870 | A1 | 5/2005 | Moshenrose |
| 2006/0042205 | A1 | 3/2006 | Kalous et al. |
| 2007/0199287 | A1 | 8/2007 | Wiser |
| 2007/0225690 | A1* | 9/2007 | Sekiguchi .............. A61B 90/50 606/1 |
| 2008/0097315 | A1 | 4/2008 | Miner et al. |
| 2008/0173178 | A1 | 7/2008 | Metteer |
| 2010/0094262 | A1 | 4/2010 | Tripathi et al. |
| 2010/0324380 | A1 | 12/2010 | Perkins et al. |
| 2011/0030560 | A1 | 2/2011 | Bohlen et al. |
| 2011/0196304 | A1 | 8/2011 | Kramer et al. |
| 2011/0317004 | A1 | 12/2011 | Tao |
| 2012/0024154 | A1 | 2/2012 | Augustine et al. |
| 2012/0305787 | A1 | 12/2012 | Henson |
| 2013/0243647 | A1 | 9/2013 | Garner et al. |
| 2014/0262553 | A1 | 9/2014 | Pollock et al. |
| 2015/0168207 | A1 | 6/2015 | Pollock et al. |
| 2015/0224237 | A1 | 8/2015 | Reasoner et al. |
| 2017/0112954 | A1 | 4/2017 | Dayton |
| 2017/0209658 | A1 | 7/2017 | Tobia et al. |
| 2018/0132966 | A1* | 5/2018 | Desaulniers ............. G05D 1/12 |
| 2019/0105120 | A1 | 4/2019 | Norman et al. |
| 2019/0290524 | A1 | 9/2019 | Augustine et al. |
| 2019/0297745 | A1 | 9/2019 | Augustine et al. |
| 2019/0357382 | A1 | 11/2019 | Augustine et al. |
| 2020/0038274 | A1 | 2/2020 | Augustine et al. |
| 2020/0046590 | A1 | 2/2020 | Augustine et al. |

OTHER PUBLICATIONS

U.S. Appl. No. 16/529,283 10,638,638, Aug. 1, 2019, Relocation Module for Patient Monitors and Surgical Equipment.
U.S. Appl. No. 16/364,884 10,507,153, Mar. 26, 2019, Relocation Modules and Methods for Surgical Field.
U.S. Appl. No. 16/593,033 10,653,577, Oct. 4, 2019, Relocation Modules and Methods for Surgical Field.
U.S. Appl. No, filed Oct. 15, 2019, Relocation Modules and Methods for Surgical Field.
"U.S. Appl. No. 15/935,524, Corrected Notice of Allowability dated Jul. 18, 2019", 2 pgs.
"U.S. Appl. No. 15/935,524, Corrected Notice of Allowability dated Aug. 21, 2019", 2 pgs.
"U.S. Appl. No. 15/935,524, Non Final Office Action dated Mar. 8, 2019", 8 pgs.
"U.S. Appl. No. 15/935,524, Non Final Office Action dated Sep. 19, 2018", 8 pgs.
"U.S. Appl. No. 15/935,524, Notice of Allowance dated Jun. 12, 2019", 9 pgs.
"U.S. Appl. No. 15/935,524, Response filed May 15, 2019 to Non Final Office Action dated Mar. 8, 2019", 10 pgs.
"U.S. Appl. No. 15/935,524, Response filed Dec. 12, 2018 to Non Final Office Action dated Sep. 19, 2018", 18 pgs.
"U.S. Appl. No. 16/364,884, Corrected Notice of Allowability dated Aug. 29, 2019", 3 pgs.
"U.S. Appl. No. 16/364,884, Corrected Notice of Allowability dated Nov. 8, 2019", 3 pgs.
"U.S. Appl. No. 16/364,884, Non Final Office Action dated Jul. 3, 2019", 9 pgs.
"U.S. Appl. No. 16/364,884, Notice of Allowance dated Aug. 20, 2019", 10 pgs.
"U.S. Appl. No. 16/364,884, Response filed Jun. 18, 2019 to Restriction Requirement dated May 1, 2019", 9 pgs.
"U.S. Appl. No. 16/364,884, Response filed Jul. 24, 2019 to Non Final Office Action dated Jul. 3, 2019", 9 pgs.
"U.S. Appl. No. 16/364,884, Restriction Requirement dated May 1, 2019", 5 pgs.
"U.S. Appl. No. 16/519,677, Non Final Office Action dated Nov. 13, 2019", 6 pgs.
"U.S. Appl. No. 16/519,677, Response filed Dec. 17, 2019 to Non Final Office Action dated Nov. 13, 2019", 9 pgs.
"U.S. Appl. No. 16/529,283, Corrected Notice of Allowability dated Mar. 6, 2020", 2 pgs.
"U.S. Appl. No. 16/529,283, Non Final Office Action dated Sep. 18, 2019", 8 pgs.
"U.S. Appl. No. 16/529,283, Notice of Allowance dated Jan. 10, 2020", 10 pgs.
"U.S. Appl. No. 16/529,283, Response filed Dec. 13, 2019 to Non Final Office Action dated Sep. 18, 2019", 8 pgs.
"U.S. Appl. No. 16/593,033, Notice of Allowance dated Jan. 14, 2020", 10 pgs.
"U.S. Appl. No. 16/601,924, Non Final Office Action dated Dec. 5, 2019", 6 pgs.
"U.S. Appl. No. 16/601,924, Notice of Allowance dated Mar. 11, 2020", 8 pgs.
"U.S. Appl. No. 16/601,924, Response filed Feb. 26, 2020 to Non Final Office Action dated Dec. 5, 2019", 9 pgs.
"International Application Serial No. PCT/US2019/024054, International Search Report dated Jul. 25, 2019", 5 pgs.

(56) References Cited

OTHER PUBLICATIONS

"International Application Serial No. PCT/US2019/024054, Invitation to Pay Additional Fees dated May 29, 2019", 3 pgs.
"International Application Serial No. PCT/US2019/024054, Written Opinion dated Jul. 25, 2019", 7 pgs.
"International Application Serial No. PCT US2020 033804, International Search Report dated Aug. 28, 2020", 3 pgs.
"International Application Serial No. PCT US2020 033804, Written Opinion dated Aug. 28, 2020", 10 pgs.
"U.S. Appl. No. 16/885,715, Response filed Sep. 2, 2020 to Non Final Office Action dated Jun. 23, 2020", 12 pgs.

\* cited by examiner

RELOCATION MODULE AND METHODS FOR SURGICAL EQUIPMENT

PRIORITY

This application is a continuation-in-part of U.S. application Ser. No. 16/601,924, filed Oct. 15, 2019, which is a continuation of U.S. application Ser. No. 16/593,033, filed Oct. 4, 2019, now issued as U.S. Pat. No. 10,653,577, which is a continuation of U.S. application Ser. No. 16/364,884, filed Mar. 26, 2019, now issued as U.S. Pat. No. 10,507,153, which claims the benefit of priority to U.S. Provisional Patent Application 62/782,901, filed Dec. 20, 2018. U.S. application Ser. No. 16/364,884, filed Mar. 26, 2019, now issued as U.S. Pat. No. 10,507,153 is also a continuation-in-part of U.S. application Ser. No. 15/935,524, filed Mar. 26, 2018, now issued as U.S. Pat. No. 10,512,191. The disclosure of all of these applications are incorporated herein by reference in their entirety.

TECHNICAL FIELD

This document pertains generally, but not by way of limitation, to systems and methods for improving safety in operating rooms. In particular, the systems and methods described herein may include but are not limited to, anesthetic equipment storage, waste air management, cable and hose management and automated anesthetic and patient monitoring data capture and electronic record input.

BACKGROUND

Anesthesia monitors and equipment as well as surgical equipment have been invented, developed and sporadically introduced into surgical practice over more than a century. This equipment is made by a wide variety of companies who have no incentive to coordinate with one another to create the most efficient operating room. Equipment throughout the operating room has been placed in one location or another, generally without a plan and then decades later, is still sitting in that unplanned location. For example, the first of the electronic monitors used during anesthesia was the electrocardiogram (ECG or EKG), which was introduced into the operating room in the 1960's. When EKGs became small enough to be placed on a shelf, getting it off of the floor, the most available shelf space somewhat near the patient, was above the anesthesia gas machine. As more anesthesia related electronic monitors were developed and introduced into practice over the next 40 years, they were simply stacked on top of one another on the same shelf above the anesthesia machine. Soon it was simply tradition that dictated that vital sign patient monitors are located over the anesthesia machine. Eventually the independent anesthesia related monitors were consolidated into single units for convenience. These consolidated multifunction anesthesia monitors were still placed on the same shelf above the anesthesia machine or on a mounting bracket attached to the anesthesia machine.

Just because a shelf happens to be available does not mean that the anesthesia related monitors are ideally located. The anesthesia machine is generally located to the side of and slightly behind the anesthetist, when standing at the head end of the surgical table facing the patient. In many cases, the anesthesia machine is located behind the anesthetist. Therefore, it is axiomatic that looking at or adjusting the anesthesia related monitors means that the anesthetist is not looking at the patient but rather looking away from the patient. Therefore, when the patient is experiencing a problem and the anesthesia related monitors are reporting confusing or adverse information, the anesthetist is focused away from the patient.

When the anesthesia related monitors are located in their present location over the anesthetic gas machine, the numerous wires, cables and hoses connecting the monitors to the patient are generally 10-12 feet long. There is a minimum of 5 wires and 2 hoses and frequently as many as 10 wires, cables and 2 hoses connecting the monitors to the patient. Electric patient warming blankets, mattresses and fluid warmers are also rapidly gaining acceptance. The controller for the electric warming products is generally located adjacent the anesthesia machine and the 3-6 cables connecting the controller to the warming blankets and mattresses on the patient are 12-15 feet long. Cables and hoses tangled and laying on the floor are clearly a problem in the operating room, causing not only inconvenience but getting contaminated and causing a tripping hazard for operating room personnel.

Cable and hose management on the surgical side of the anesthetic screen (e.g., sheet perpendicular to the table across the neck region of a patient) is also a problem that has developed haphazardly over the past century. Numerous pieces of surgical equipment have been parked somewhat randomly in the middle of the operating room, each causing an obstruction to traffic flow. Each of these pieces of equipment has a power cord or hose that lays on the floor extending to the wall outlet. Each of these pieces of equipment has one or more cables and/or hoses that lays on the floor extending to the sterile field of the surgical table. Every cable and hose on the floor is a hazard for tripping operating room personnel. Every cable and hose on the floor is an obstruction for other rolling equipment and carts and is at risk of damage from these carts, needing replacement.

A typical operating room (OR) has numerous alarms that monitor the patient's vital signs during a procedure, like heart rate and blood pressure, but the complication of multiple alarms ringing simultaneously, and frequent false positives creates a very distracting OR environment.

The various equipment such as electrosurgical units, smoke evacuation pumps, sequential compression sleeve pumps, blood/fluid suction units, and air mattress pumps are scattered about the operating room creating their own obstacles. Wherever the surgical equipment is located in the operating room on the surgical side of the anesthesia screen, the cables and hoses traverse to the sterile field on the surgical table by way of laying on the floor and becoming obstacles.

Waste heat and air discharged from heater-cooler units (HCU) near the floor can form into convection currents of rising warm air and mobilize bacteria up and into the sterile surgical field.

Flow-boundary layers of still air form next to the surgeons and anesthesia screen, preventing the downward airflow from even the best operating room ceiling ventilation systems from reaching the sterile field. When the ventilation airflow slows, the airborne contaminants and bacteria have the opportunity to settle into the open wound.

In some situations, oxygen and alcohol vapors trapped under the surgical drape pose a burn hazard to the patient in the presence of an electro-cautery spark.

Over the past 20 years, there has been a gradual movement to replacing paper anesthetic records with electronic anesthetic records (EAR). The electronic data outputs of the patient monitors have been relatively easy to input into the EAR. However, the identity, dosing and timing of IV and inhaled drug administration, IV fluid administration and oxygen and ventilation gas administration, has required manual input to the EAR by way of a computer keyboard and mouse. Blood, fluid and urine outputs as well as anesthetic events have also required manual input to the EAR by way of a computer keyboard and mouse.

SUMMARY

The modules, systems and methods described herein overcome various problems in the operating room. For example, like the cockpit of the fighter plane, the electronic monitors used during anesthesia and surgery should be located near the patient so that the anesthetist's field of vision simultaneously includes: the patient, the monitors and the surgical procedure. However, this is not the case in conventional operating rooms. The modules, systems and method described herein, overcome this and other problems in the operating room, creating a safer environment for the patient and the operating room personnel.

It would also be advantageous if the surgical support equipment and their cables, cords and hoses could be removed from the floor of the operating room.

A reduction of noises and interruptions associated with alarms meant to signal anesthesiologists, that frequently result in distractions to other OR personnel, would be beneficial.

A way of eliminating flow-boundary dead zones from obstructing the ventilation airflow and thus keeping the airborne contaminants and bacteria airborne and out of the wound, would be useful to protect the open wound from airborne contamination.

Waste heat and air discharged from heater-cooler units (HCU) near the floor can form into convection currents of rising warm air and mobilize bacteria up and into the sterile surgical field. Similar contamination of the sterile field with bacteria and contaminates from the floor has been shown in many studies of the waste heat and air from forced-air warming devices. The US Centers for Disease Control has warned that due to the positive link to implant infections, "Nothing that blows air should be in an operating theater, if possible." and " . . . it is important not to blow air in the operating theater." Therefore, there is a need to safely manage waste heat and air from surgical equipment and monitors in order prevent contamination of the sterile surgical field.

With regard to flammable alcohol and oxygen vapors concentrating in particular areas of the OR, eliminating the alcohol vapors and oxygen trapped under the surgical drape would add to the fire safety of the surgical experience.

Illustrative examples of a relocation module systematizes surgical safety for patients and OR personnel. In some examples, this module designed to house nearly all of the operating room patient monitors and support equipment. Even dissimilar types of equipment that are normally kept separate from one another. In some examples, this unique module is specially designed to fit next to and under the arm-board of the surgical table—a location traditionally occupied by an IV pole. For the past 100 years, this location has been a wasted "no-man's land" between the anesthesia and surgical sides of the operating room. In reality, the unique space next to and under the arm-board, is truly the "prime real estate" of the entire operating room: it is immediately adjacent the patient for optimal monitoring while simultaneously maintaining observation of the patient and surgical procedure; equipment controls can be conveniently accessed by both the anesthesia and surgical staff; short cables and hoses are adequate to reach the patient; and it is uniquely accessible from both the anesthesia and surgical sides of the anesthesia screen. The unique space next to and under the arm-board is the only location in the entire operating room where cables, cords and hoses from both the anesthesia side and the sterile surgical field side, do not need to traverse the floor or even touch the floor in order to connect to their respective monitor or patient support equipment—truly a remarkable location that has been wasted by conventional systems.

In some examples, an illustrative relocation module can house both anesthesia related and non-anesthesia related equipment. In some examples, the illustrative relocation module can house a variety of non-proprietary OR equipment such as patient vital sign monitors and electro-surgical generators. In some examples, the module is designed to also house newer proprietary safety equipment such as: air-free electric patient warming, surgical smoke evacuation, waste alcohol and oxygen evacuation, evacuation of the flow-boundary dead-zones that cause disruption of the OR ventilation and the evacuation and processing of waste heat and air discharged from OR equipment. In some examples, this module may also house dissimilar equipment (e.g., unrelated to anesthesia monitoring) such as: air mattress controls and air pumps; sequential compression legging controls and air pumps; capacitive coupling electrosurgical grounding; RFID counting and detection of surgical sponges; the waste blood and fluid disposal systems; and "hover" mattress inflators. Any of these devices may be stored in the relocation module together with (or without) anesthesia equipment.

In some examples, the relocation module is a specialized and optimally shaped rack for holding and protecting the patient monitors and other electronic and electromechanical surgical equipment, in a unique location. A location that is very different from just setting anesthesia monitors on top of the anesthesia machine and scattering other equipment across the floor of the operating room.

In some examples the preferred new location is adjacent the anesthesia side of one or the other of the out-stretched arm-boards of the surgical table, a location currently occupied by an IV pole on a rolling stand. In this location, the relocated monitor screens are 1-2 feet lateral to the patient's head, allowing the anesthesia related monitors, the patient and the surgical field to be observed by the anesthetist in a single field of vision. In some examples, with the monitors, the patient and the surgical field to be observed by the anesthetist in a single field of vision, it is highly likely that the anesthetist will be looking in that direction most of the time. Because the anesthetist is naturally looking toward the patient and monitors, a relatively bright warning light mounted on the tower or on one of the monitors that are mounted on the tower in this field of vision and aimed at the anesthetist, may be substituted for an audible alarm. The unique location of the tower on the module allows this warning light to be aimed away from the surgical field and it is therefore not distracting or even visible to the surgeon. Only if the warning light is ignored by the anesthetist, would a backup audible alarm which is distracting to the surgeon and OR staff be necessary.

Locating the module adjacent the arm-board has several advantages. First, that space is currently occupied by an IV pole, so it is not currently being used for personnel traffic. Second, the arm-board and the anesthesia screen above the arm-board, traditionally are the separation boundary between the anesthesia side of the operating room and the surgical side of the operating room—essentially an empty "no-man's land" between the two sides. The raised head end of the surgical drape that is tethered between two IV poles, creates a physical barrier between the anesthetist and the surgical field, is commonly known as the "anesthesia screen" or "ether screen." As a "no-man's land," the space under the arm-board is currently unoccupied. The space under the arm-board is unique in that it can be accessed from both the surgical and the anesthesia sides of the anesthesia screen. Access to the module from the surgical side can be from below the lower edge of the surgical drape hanging down over the arm board, or more conveniently from the side of the module facing away from the patient, at the distal end of the arm-board. There is no other location in the operating room that can be simultaneously accessed from both the surgical and anesthesia staff, while maintaining the traditional boundary or "no-man's land" between the two. Therefore, this location is uniquely suited for a module that can contain both surgical and anesthesia equipment.

In some examples, locating the module adjacent the arm-board means that one of the side faces of the module is facing the patient and is within 24 inches of the patients' head and chest. This location close to the patient allows for a cable and hose management system with relatively short cables and hoses, which are much easier to manage than long cables and hoses. The traditional long cables and hoses that need to reach from the patient to the electronic monitors located on top of the anesthesia machine by way of draping to the floor, are easily tangled, end up laying on the floor getting contaminated and damaged. The probability of cables becoming tangled are not linearly correlated to cable length but rather exponentially correlated with cable length. In other words, longer cables are far more likely to get tangled. Because they are a nuisance to wind for storage, they are frequently left lying on the floor or draped over a gas machine. Long cables and hoses are also difficult to clean.

In some examples, the side of the module facing the patient includes a cable management system. In some examples the cable management system comprises an array of straps with snaps or Velcro fasteners to retain the individual cables and hoses. In some examples the cable management system comprises an array of hooks to retain the cables and hoses. Other cable and hose retention mechanisms are anticipated.

In some examples, the cable management system includes cables that are naturally coiled during the process of forming (e.g., molding) the outer insulation, somewhat like the traditional telephone cord. In some examples, the coils of cable or hoses may be much larger diameter than the traditional telephone cord. Coils that are 2-5 inches in diameter, much like a "slinky" may be preferable. Coils of larger diameter may have superior "memory" to retain the coiled shape. Electrical insulation materials such as urethane and nylon also provide superior "memory" characteristics compared to the PVC coating historically used on telephone cords.

These larger coils are easily stretched because the elongation is accomplished primarily by the lateral movement of adjacent coils, basically elongating the tubular shape, a movement that is minimally opposed by the "memory" of the molding process. This contrasts with an attempt to unwind each of the individual coils, a movement that is maximally opposed by the "memory" of the molding process. This is identical to the principals the make a "slinky" work; very easy to stretch in the direction of the coiled tube but nearly impossible to unwind an individual coil. The larger coils easily stretch laterally between the planes of each adjacent coil and stretch minimally in the plane of each coil.

In some examples, the coils of the cable management system are created by extrusion molding an electrically insulating plastic sheath over the wires of the cable. In some examples, the coils of the cable management system are created by extrusion molding a coil of plastic tubing and then inserting the wires of the cable into the tubing as a second operation.

Each piece of equipment on the surgical side of the anesthesia screen has traditionally been mounted on castor wheels and parked freestanding, somewhere on the floor surrounding the surgical table. In these locations, each of these pieces of equipment require a power cord or vacuum hose that lays on the floor and extends from the individual equipment to the wall plug or outlet. Additionally, each piece of equipment also has one or more cables and/or hoses that extend from the sterile surgical field, down to the floor, across the floor and are then plugged into the equipment. The freestanding equipment in the middle of the operating room floor is an obstruction to the movement of personnel, carts and gurneys. The cords, cables and hoses laying on the floor create a tripping hazard for operating room personnel, and also create an obstruction to rolling carts.

In some examples, the module can solve these problems, and other problems as well. In some examples, the module includes a lower section that can fit under the arm-board of the surgical table, utilizing the currently wasted space under the arm-board. In some examples, this lower section may have a larger footprint than the tower-like upper section that may be located against the anesthesia side of the arm-board. In some examples, a bulbous-shaped lower section creates much more space and volume for accommodating more pieces of electronic and electromechanical equipment—the added volume filling the unused volume under the arm-board.

In some examples, the bulbous lower section allows heavier equipment to be mounted down low in the module for added stability. In some examples, the larger footprint of the bulbous lower section allows a broader base for added stability. In some examples, it may be advantageous to mount heavier equipment near the rear of the module to balance the weight of the tower-like upper section that may be mounted over the front of the bulbous lower section. This prevents the tendency for the forward mounted tower to cause forward tipping. In some examples, the module may be suspended from the ceiling of the operating room on a "boom." Equipment suspended from ceiling mounted booms are well-known in the operating room.

In some examples, the rear side of the bulbous lower section may be positioned approximately in the same plane as the surgical drape hanging down from the surgical side of the arm-board. The surgical drape generally terminates 18-24 inches above the floor, allowing the rear of the bulbous lower section to be uniquely accessed from the surgical side of the anesthesia screen, below the lower edge of the surgical drape. In some examples, electrical plug-ins and hose connections for the various pieces of surgical equipment housed in the module may be located on the rear side of the bulbous lower section.

Alternately or in addition, in some examples, if the staff prefers to access cable and hose plug-ins at a higher, more convenient level, the cable and hose plug-ins may be positioned on the side of the module facing away from the patient or on the top surface of the lower section, near the side of the module facing away from the patient, since there is no surgical drape hanging down in this area.

In some examples, cables and hoses exiting the sterile surgical field may uniquely be dropped off of the sterile field adjacent the anesthesia screen. From this location, the cables and hoses drop nearly straight down to be attached to the cable and hose plug-ins on the rear the bulbous lower section or the side of the bulbous lower section facing away from the patient. In this unique location, there is no need for the cables and hoses to lay on the floor while traversing the distance to the equipment. In this unique location, there is no need for the cables and hoses to even touch the floor while traversing the distance to the equipment. This unique location next to the surgical drape and below the arm-board is the only place in the entire operating room where cables and hoses from supporting equipment can access the sterile surgical field without traversing or even touching the floor of the operating room and creating a tripping hazard for operating room personnel.

In some examples, consolidating the surgical equipment into the module also eliminates the obstructions caused by that equipment when it is free-standing in the middle of the operating room floor. It also eliminates the need for power cords and vacuum hoses traversing the floor to connect the equipment to the wall outlets.

Locating electrical and electromechanical equipment under the arm-board, can subject that equipment to a potential hazard from spilled water, spilled saltwater (saline) and blood. In some examples, in order to protect this equipment from spilled fluids, the module is substantially covered in a water-resistant housing or "cowling."

For many decades, it has been an accepted axiom in the operating room; the air below the level of the surgical table is contaminated with skin cells (squames) and bacteria shed from the skin of the surgical personnel. These squames are shed from the skin of the operating room personnel into the air of the operating room. Once airborne, the squames are pushed toward the floor and vents near the floor, by the downward operating room ventilation airflow.

Waste heat from surgical equipment released near the floor, for example, heater-cooler units and forced-air warming units, has been proven to form into convection currents of rising warm air. When this waste heat is released near the floor, the rising convection currents can mobilize contaminates and bacteria that normally resident near or on the floor, up and into the sterile surgical field. If waste heat could be prevented from being within 4 feet of the floor where most of the airborne contaminates are concentrated, basically the height of the surgical table, it is believed that infections can be reduced.

The various pieces of electronic and electromechanical equipment housed within the module disclosed herein can produce relatively large amounts of waste heat. The bulbous lower section of the module is placed on the floor next to the surgical table and is below table height since it is under the arm-board. Releasing waste heat in this location on the floor next to the surgical table may cause a risk of sterile field contamination from the rising waste heat that may include squames and other contaminants. In some examples, the module may include a waste heat management system to safely dispose of the waste heat created by the electronic and electromechanical equipment housed within the module.

It would be difficult or even impossible to manage the uncontained waste heat produced by electronic and electromechanical equipment mounted on a simple open rack because it can escape in any direction. In some examples, the module can include a "cowling" covering substantially the entire outer surface. The cowling not only protects the equipment from accidental fluid damage but also confines the waste heat from the electronic and electromechanical equipment mounted within the module, to the inside of the module and cowling. In some examples, the confined waste heat can then be safely managed.

In some examples, the cowling cover of the module can form or support a waste heat management system. In some examples, the cowling can be provided on an inner surface of the housing, In some examples, the cowling can be described as an insulation. In some examples, the housing can include other types of insulation from heat and/or water. Any suitable type of insulated housing suitable for use in a surgical field can be provided.

In some examples, the module includes a tower-like upper section attached to the topside of the lower section. In some examples, the tower-like upper section extends substantially vertically from the top side, near the front of the lower section. In some examples, the tower-like upper section is used for mounting monitor screens and cable management retentions at an easily accessible and convenient height. In some examples, the top of the tower-like upper section, is 5 feet or more above the operating room floor. At this height, waste heat can be exhausted from vents near the top of the tower-like upper section is vented into the operating room, well above the height of most airborne contaminates. In contrast, if the waste heat vented low (<4 feet above the floor), it may mobilize airborne contaminants up and into the sterile field causing a significant infection risk.

In some examples, the cowling of the tower-like upper section serves as a chimney, containing the rising waste heat until it can be safely discharged from outlet vents located near the top of the tower. In this case, air may be allowed to enter the module through inlet vents in the lower section, the air gets heated by the electronic and electromechanical equipment in the module and then by natural convection, the heated air rises within the tower-like upper section and is discharged through outlet vents near the top. In some examples, a filter and fan may be added to the waste heat management system in order to filter the waste heated air before discharging it into the operating room, or to filter inlet air.

In some examples, the inlet vents for the cooling air may be located in the tower-like upper section, above the level of the airborne contamination. At this level, the inlet air is relatively pure and therefore there is no risk of contaminating the equipment housed within the module with contaminated air. In some examples, a duct may connect the inlet vent in the tower-like upper section to the equipment space in the lower section. The clean inlet air may be drawn into inlet vents mounted high on the upper section and then ducted down to the equipment that needs cooling and then ducted back up to the tower to be discharged at a safe height above the airborne contaminates. In some examples, ionized air filter plates may be included in the ducting to provide added filtration of the air without added resistance to the airflow.

In some examples, a waste air management system may be included in the module. In this case, the waste air management system may be designed to safely process and discharge waste air that may or may not contain waste heat. The waste air may be the by-product of equipment contained within the module or may be a waste product of other OR equipment, besides the monitors. An example of waste air producing equipment may include the smoke evacuation suction; used for evacuating electrosurgical smoke and filtering the smoke which has been shown to periodically contain virus particles.

Waste air producing equipment can also include operating room ventilation dead zone evacuation equipment; by vacuuming the air from the flow-boundary dead zones that naturally forms in front of the surgeons and anesthesia screen, the interference of the flow-boundary layers with the operating room ventilation can be reduced. This allows the ventilation airflow from the ceiling to reach the wound unimpeded by a flow-boundary dead zone. When ventilation airflow is kept moving, airborne contaminates in that air are kept airborne. As long as the airborne contaminates remain airborne, they do not land in the wound where they can cause an infection. When the ventilation airflow slows or even stops due to dead zone interference, gravity takes over and the airborne contaminates settle into the wound where they may cause infections. These dead zones of non-moving air that interfere with the operating room ventilation can be evacuated by placing vacuum hoses into the dead zone. The evacuated air can then be processed in order to safely discharge the air, back into the operating room. In some examples, the ventilation dead zone evacuation system may simultaneously serve as the surgical smoke evacuation suction. In this case the vacuum hose does not need to be attached to the electrosurgical pencil electrode, which many surgeons find to be cumbersome.

Waste air producing equipment can also include heater-cooler units (HCU) that produce contaminated waste heated air that needs to be processed and safely discharged. In this case, the waste heated air is a byproduct of cooling the refrigeration compressor of the HCU. Forced-air warming units (FAW) also produce contaminated waste heated air that needs to be processed and safely discharged. The FAW systems exhaust waste air from under the surgical drape where it escapes from under the surgical table near the floor. In some examples, this waste heated air can be contained and vacuumed up for safe disposal. Electrosurgical units and other surgical equipment also produce waste heated air that needs to be processed and safely discharged.

In some examples, the waste air management system may be used to evacuate and/or dilute the air under the surgical drape, especially near the patient's head, neck and chest. Alcohol from the surgical prep solution may pool under the drapes and then evaporate providing fuel for a fire. Waste oxygen from an unrestricted oxygen supplementation system such as nasal prongs may also pool under the drapes providing an oxidant for a fire. Then, add a spark from either the electro-cautery or a laser and highly dangerous operating room fires can occur. These fires occur far too frequently. Even the surgical drape can burn in the presence of an oxygen-enriched environment.

In some examples, it may be advantageous to remove the air and oxygen and alcohol vapors trapped under the surgical drape. In some examples, a vacuum hose may be placed near the shoulders, chest and neck of the patient. In some examples, the proximal end of the vacuum hose may plug into the inlet side of the waste air management system, for a convenient source of low velocity, low pressure vacuum.

In all of the instances, the waste heated air can be vacuumed, filtered and discharged at a height that does not allow any waste heat to mobilize contaminates normally resident near the floor, up and into the sterile field. In a possibly preferred example, the air discharge can be at a height that is greater than 4 feet off of the floor.

In some examples, the waste air management system includes an air plenum containing an air filter. One or more air inlets allow waste air to enter the plenum from either the equipment housed in the module or from external equipment sources. A fan propels the waste air through the filter and exhausts the air from the plenum into a substantially vertical vent tube. In some examples, the substantially vertical vent tube extends upward to a height of more than 5 feet above the floor, before discharging the processed waste air from outlet vents near the top of the substantially vertical vent tube. In some examples, ultraviolet lights (UV) may be included in the plenum on one or both sides of the filter. In this location, the UV radiation can kill any living organisms that may have been captured by the filter. In some examples, a fabric sock-like filter may be attached to an outlet vent. The sock-like filter diffuses the air being discharged into the operating room to avoid jets and turbulent air currents. A sock-like filter can muffle the sound of the fan reducing OR noise created by various equipment cooling and smoke evacuation fans.

In some examples, the substantially vertical vent tube may be a rigid tube. In some examples the substantially vertical vent tube may traverse mostly in a vertical direction but can include non-vertical portions. In some examples, the substantially vertical vent tube may be the tower-like upper section of the module. In some examples, the substantially vertical vent tube is an inflatable, collapsible tube made of fabric, plastic film or fabric laminated to or coated with a plastic film. In some examples, the inflatable, collapsible tube may be disposable.

In some examples, the inflatable tube includes a substantially sealed distal end with one or more holes in the walls of the tube to allow the air to escape but create a flow obstruction causing the pressure within the inflatable tube to increase. The increased pressure in the inflatable tube causes the inflatable tube to assume an erect shape. In some examples, the erect inflatable tube extends substantially vertically, in order to terminate at a height of more than 5 feet above the floor. In some examples, the erect inflatable tube extends diagonally at an upward angle.

In some examples, it may be advantageous to dilute the air and oxygen and alcohol vapors trapped under the surgical drape with air. In some examples, an air hose may be placed near the shoulders, chest and neck of the patient. In some examples, a proximal end of the air hose may plug into a diversion from the discharge side of the waste air management system, for a convenient source of low velocity, positive pressure air.

In some examples, the output of the waste air management system may be diverted into a hose that may be hooked to an inflatable "hover" mattress for moving the patient off of the surgical table at the end of surgery. These "hover" mattresses are known in the arts and are inflated with pressurized air, which is released through holes on the bottom side of the mattress. The released air is effectively trapped under the mattress forming an air cushion on which the mattress and the patient effectively float, allowing the patient to be easily slid from the table to the gurney.

In some examples, the fan in the waste air management system also conveniently provides the pressurized air for a "hover" mattress. Air may be diverted from the outlet side of the waste air management system, into a hose that is attached to a "hover" mattress.

In some examples, the module of the instant invention may also contain the components of the anesthesia gas machine. So-called "gas machines" are relatively simple assortments of piping, valves, flow meters, vaporizers and a ventilator. These could be located within the module or attached to the module for further consolidation of equipment and for improved access to the patient. The close proximity to the patient not only shortens the ventilation tubing but also shortens the sampling tubing for the carbon dioxide monitor. The close proximity of the anesthesia gas machine to the patient also allows continuous observation of the patient while adjusting the gas and anesthetic flows.

In some examples, the module (e.g., 10) may include an air/oxygen blender to supply oxygen-enriched air to the patient for facemask and nasal prong delivery. This may be especially advantageous because of the very short distance between the module and the patient's head. Adding an air/oxygen blender may also be advantageous because many of the anesthesia machines do not include these devices. In some examples, the emergency oxygen, air and nitrous oxide tanks for the anesthesia machine may be mounted on the lower portion of the module in order to keep the center of gravity as low as possible. In some examples, it may be advantageous to mount these tanks horizontally on the sides or rear of the lower portion of the module rather than their traditional vertical mounting orientation, in order to avoid interfering with the arm board of the surgical table. In some examples, it may be advantageous to mount these tanks diagonally on the sides of the lower portion of the module rather than their traditional vertical mounting orientation, in order to avoid interfering with the arm board of the surgical table. In this case, a tank that is longer than the depth of the module can still be accommodated by locating the valve of the tank at the upper end of the diagonal near the front of the module. The closed end of the tank can thus be located at the lower end of the diagonal near the rear of the module where it fits nicely under the arm-board. In some examples, the oxygen, air and nitrous oxide hoses supplying the anesthesia machine may advantageously hang from the ceiling and connect to gas inlets in the top of the upper section of the module. In this location, the gas hoses are uniquely unobtrusive to the operating room staff.

In some examples, locating the anesthesia machine in or on the module allows direct access for and sensors and monitors related to the anesthesia machine, to input data to the electronic anesthetic record being recorded by equipment in the module.

In some examples, the shared fan, plenum, filter and discharge system of the waste air management system improves the efficiency, space requirements and cost in the operating room by consolidating multiple pieces of equipment into one. Currently, individual pieces of surgical equipment that produce waste air and waste heat are generally located on the floor, somewhere around the surgical table. This is exactly the worst place for this equipment to be located because the waste air and heat from this equipment is vented near the floor. The waste heat and air can then heat the contaminated air normally resident near the floor, and then carry contaminating particles and bacteria from the floor, up and into the sterile surgical field. Consolidating all the surgical support equipment in the bulbous lower section of the module with a single waste air management system eliminates waste air and heat from being vented near the floor, reducing the risk of airborne contamination.

Locating that single waste air management system in the bulbous lower section of the module and placing it under the arm-board of the surgical table totally removes it from all operating room traffic while providing the shortest possible hose distance to the patient, either on the surgical or anesthesia side of the anesthesia screen. Locating the waste air management system under the arm-board and surgical drape also minimizes and muffles the annoying fan noise.

Poor teamwork between anesthesia and surgery may be due to poor communication. For example, the anesthesia personnel may be experiencing problems maintaining normal vital signs and this may not be communicated quickly and clearly to the surgeon. "Yeah, the anesthesiologist mentioned his blood pressure was decreasing but I didn't realize it was to a critical level, so I went ahead and finished the procedure." A failure of the surgeon to understand the situation, can result in a wide variety of complications ranging in severity from mild to fatal. In some examples, a solution to this problem may be to mount a vital signs display screen on the rear of the tower-like upper section of the module, facing the surgeon. In this unique location viewable over the top of the anesthesia screen, the surgeon can be constantly aware of the patient's vital signs.

In some examples, the collection canisters for waste fluid and blood may be conveniently mounted on the module. Mounting the canisters on the module eliminates the need for vacuum tubing to lay on the floor while traversing from the wall outlet to the canister and from the surgical field to the canister. Optical or infrared fluid level sensors 153 may be conveniently mounted in the module, adjacent the canister(s). In some examples, the fluid level monitors may automatically activate or deactivate the vacuum to a given canister, thereby automatically shifting the blood and fluid flow to a new canister as the previous one is filled.

In some examples, the controls and display screens for the surgical equipment housed in the module may be wirelessly connected to a portable display screen such as an iPad or "smart tablet," for convenient access by the nurse anywhere in the room. This allows the surgical nurse to monitor and control the equipment without walking across the room. This is convenient for the nurse and increases awareness of equipment conditions. Staff moving around the OR kick up contaminates from the floor into the air where they can be carried to the sterile surgical field by waste heat. A portable display screen minimizes surgical staff movement in the OR which has been shown to reduce airborne contamination and surgical site infections.

Doctors and nurses dislike record keeping and the switch to the electronic record has made the act of record keeping more difficult and time consuming. Entering the electronic record into the computer sometime after the event occurred and the case has settled down, is not only distracting from patient care but leads to inaccurate records. Hand entered records also bypass the opportunity for the computer to add to patient safety by checking drug identities, dosages, side effects, allergies and alerting the clinician to potential problems or even physically stopping the drug administration. Manually entered records are not useful for managing drug inventories because a given medication administration is not tied to a specific drug bottle or syringe. Finally, the computer mouse and keyboards have been shown to be contaminated by a wide variety of infective organisms and are virtually impossible to clean. Automatic anesthetic data entry to the EAR would improve patient safety, improve clinician job satisfaction and improve OR inventory management.

In general, doctors and nurses are not interested in replacing themselves and their jobs with automated drug delivery or automated anesthesia systems. However, they may be more open to automated record keeping. The challenge with automated record keeping is automating the data input that documents the numerous activities, anesthesia related events, fluid, gas and medication administration that constitute an anesthetic experience or another medical situation The second challenge in implementing an automated electronic anesthetic record (EAR) or electronic medical record (EMR) is to force as little change in routine as possible onto the anesthesiologist and other clinicians using this system. Anesthesiologists and surgeons are notoriously tradition-bound and resistant to any changes in their "tried and true" way of doing things. Therefore, a successful automated EAR must interact seamlessly with current anesthesia practices and operating room workflow without causing any disruptions.

In some examples, the automated EAR of this disclosure includes a system for automatically measuring and recording the administration of IV medications and fluids. The system for automatically measuring and recording the administration of IV medications and fluids can include one or more sensors, such as one or more of a barcode reader and an RFID interrogator for accurately identifying a medication or fluid for IV administration.

The system for automatically measuring and recording the administration of IV medications and fluids can also include one or more digital cameras with machine vision software ("machine vision") for accurately measuring the volume of medication administered from a syringe or fluid administered from an IV bag through a drip chamber into an IV tubing. The digital cameras with machine vision software essentially duplicate the clinician's vision of an activity, injection of a drug from a syringe for example, without interfering in the normal activity and yet allows automatic recording of the activity in the EAR. The machine vision software can include one or more machine-readable mediums that when implemented on hardware processing circuitry of the system or in electrical communication with the system, can perform the functions described herein.

In some examples, the automated EAR of this disclosure uses machine vision to unobtrusively "observe" the flow rate of the ventilation gas flow meters and inhaled anesthetic vaporizers.

In some examples, the automated EAR of this disclosure captures input data from the blood and fluid collection and urine output collection systems of this disclosure.

In some examples, the automated EAR of this disclosure captures anesthetic event data by capitalizing on the fact that anesthesiologists, surgeons and nurses compulsively tend to meticulously follow their routines. For example, a particular anesthesiologist may routinely intubate all adult male patients with an 8.0 endotracheal tube unless there is an abnormality. Therefore, if the EAR knows who is providing the anesthesia, knows their preferences and knows that the patient is an adult male, the automated EAR can "automatically" enter the intubation event into the record and will be correct more than 95% of the time. In the unusual event of a patient abnormality requiring an alteration of the routine, the anesthesia provider can manually enter the variant information to provide an accurate record. In some examples, the relative rarity of data being manually entered into the EAR allows for the elimination of the computer keyboard and mouse, to be replaced by an easy-to-clean touch screen display.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document. Any combination of the features shown and described in this disclosure, including combinations of fewer or more features is within the content of this disclosure. Modules, systems and methods including individual features described herein, without combinations of features as shown in the examples (for the sake of brevity), are also within the scope of this disclosure

DETAILED DESCRIPTION

The following detailed description is exemplary in nature and is not intended to limit the scope, applicability, or configuration of the invention in any way. Rather, the following description provides practical illustrations for implementing exemplary examples of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

As described herein, operably coupled can include, but is not limited to, any suitable coupling, such as a fluid (e.g., liquid, gas) coupling, an electrical coupling or a mechanical coupling that enables elements described herein to be coupled to each other and/or to operate together with one another (e.g., function together).

In some examples, a module includes an equipment rack in a protective housing or "cowling." The module can be designed to advantageously fit into the unique location adjacent and/or under the arm-board of the surgical table—a location currently occupied by an IV pole on a rolling stand.

Figure 1:
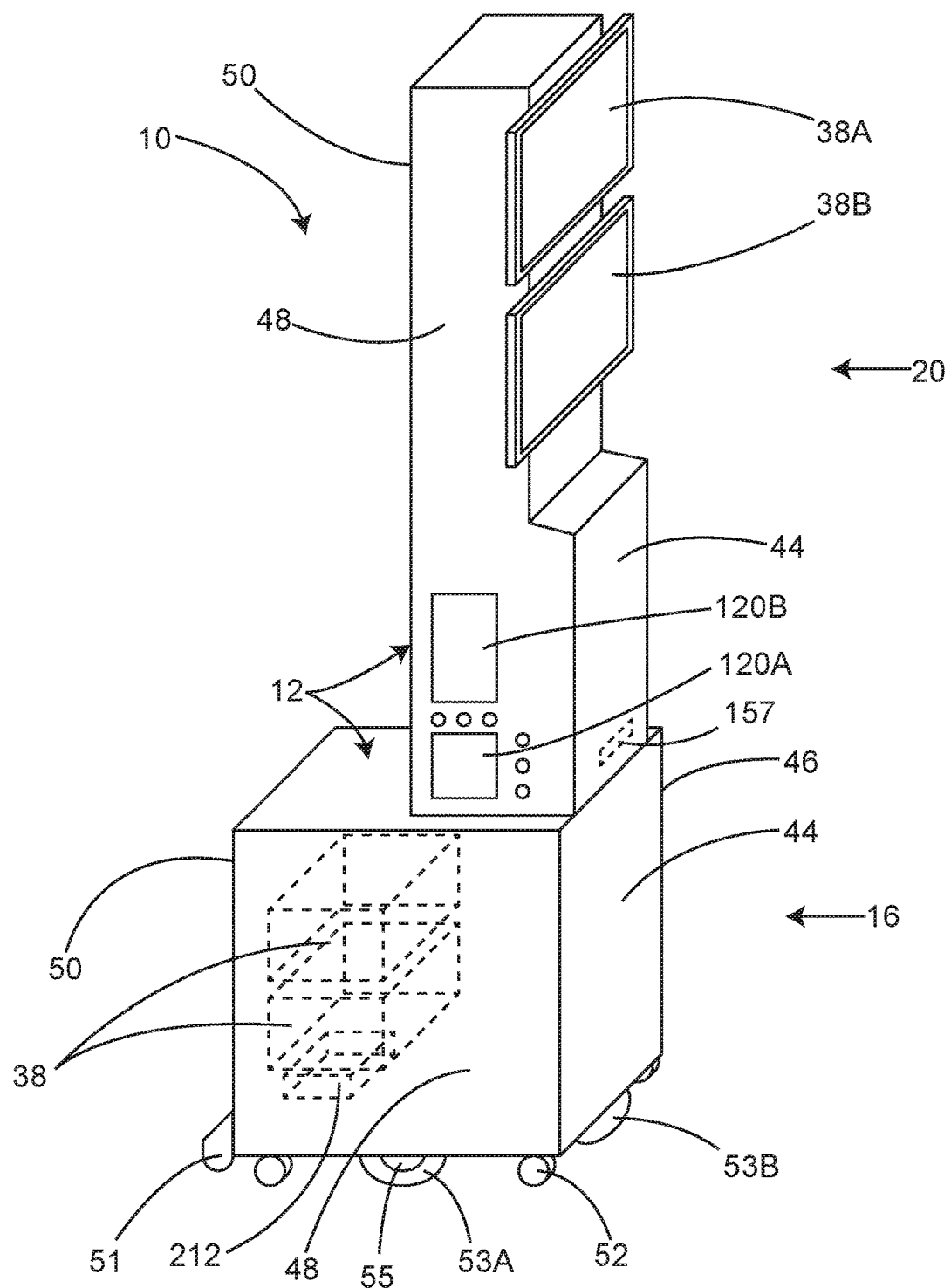
FIG. 1 shows a perspective view of an illustrative module that can include storage, airflow and cord management systems, among other systems, in accordance with at least one example.

An example of such a module is shown in FIG. 1, the module 10 (and variations of module 10) can include a system to provide any combination of features described herein. In some examples, the module 10 can include features such as storage of unrelated surgical equipment, control and/or filtering airflow and waste heat, a cord management system, sanitizing system, waste fluid system, air vacuum system, fluid dispensing system, display system, and a user input system and any other system described herein. These systems can also be provided individually and still provide benefits; the combinations are not required.

Figure 2:
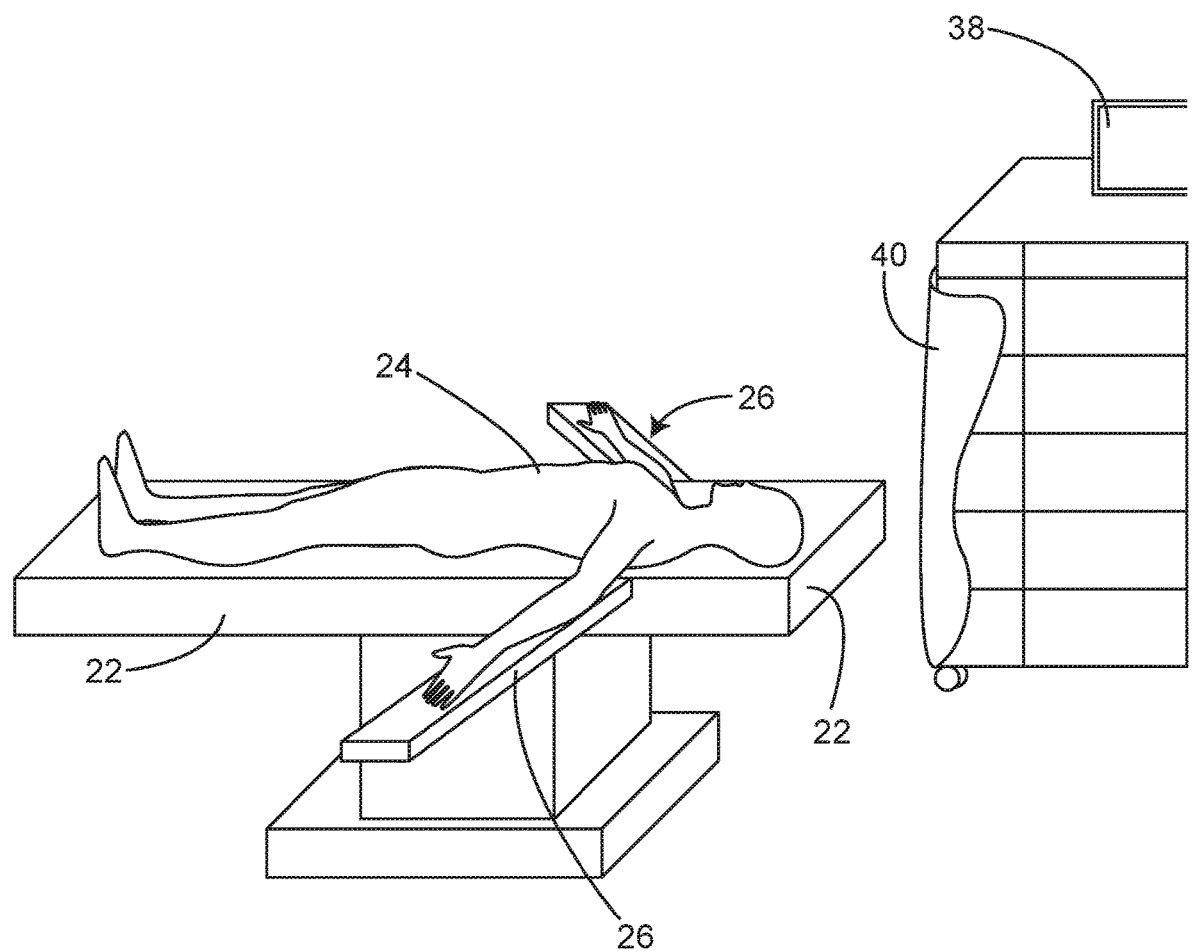
FIG. 2 shows a perspective view of an example standard operating room including a surgical table, and a patient laying on the table, in accordance with at least one example.

As shown in FIG. 2, the standard operating room includes a surgical table 22 on which the patient 24 is laying. Typically, the surgical table 22 includes arm-boards 26 that are attached to side rails of the table 22 and extend laterally from the table 22 at a slightly less than perpendicular angle. The patient's arms are rested on the arm-boards 26, which help to protect the arms from nerve damage and allow convenient access to the IV tubing. This general configuration for surgery has evolved over the past century and is now a firmly embedded tradition.

Figure 3:
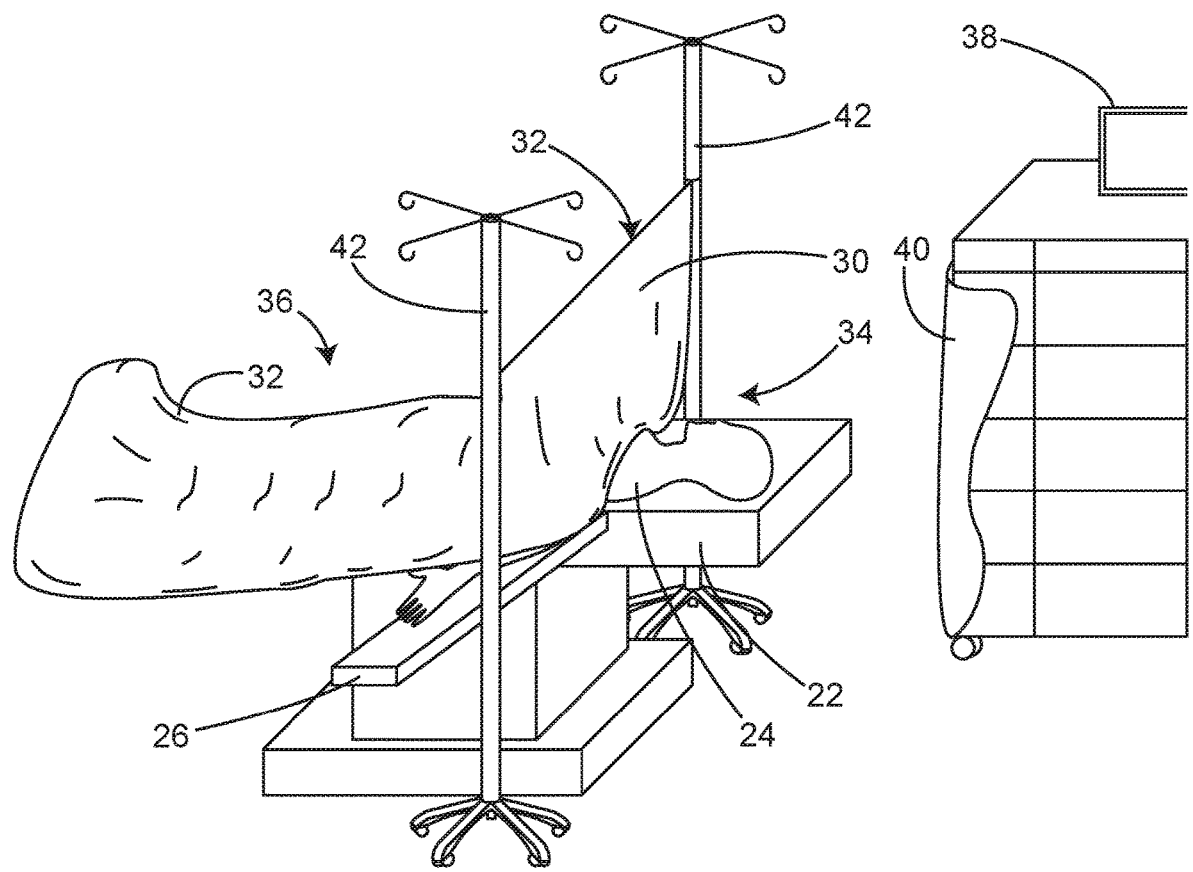
FIG. 3 shows a perspective view of the example standard operating room of FIG. 2, including two IV poles and a surgical drape, in accordance with at least one example.

As shown in FIG. 3, there are typically two IV poles 42 that are positioned adjacent the anesthesia side of the arm-boards 26, one on each side of the surgical table 22. Typically, the head end of the surgical drape 32 is elevated and attached between the two IV poles 42, creating a barrier between the surgical field and the anesthesia personnel who are located at the head end of the surgical table 22. This anesthesia screen 30 is a tradition that is meant to prevent skin contaminates shed from the anesthesia providers who are not wearing sterile gowns, from contaminating the sterile field.

The standard surgical draping shown in FIG. 3 naturally leads to surgery-related personnel and equipment being relegated to the surgical side 36 of the anesthesia screen 30. Further, the anesthesia-related personnel and equipment are naturally relegated to the anesthesia side 34 of the anesthesia screen 30.

Effectively, the anesthesia screen 30 and arm-boards 26 and the space under the arm-boards 26 have evolved into a "no-man's land" separating the surgical side 36 from the anesthesia side 34. Except for the IV pole 42 holding up the anesthesia screen 30, this "no-man's land" is totally wasted space in the modern operating room.

In some examples, as depicted throughout this disclosure, a module 10 (e.g., FIG. 4) of this invention not only advantageously utilizes the currently wasted space under and adjacent the arm-board 26, but also capitalizes on the uniqueness of that wasted "no-man's land" floor space and the volume under the arm-board 26.

In some examples, the uniqueness of the space under and adjacent to the arm-board 26 includes but is not limited to the fact that it is less than 2 feet from the patient's head and less than 1 foot from the patient's arm. This is the only location in the operating room from which cables, wires, hoses and IV tubing do not need to traverse a walkway or lay on the floor, in order to reach the patient 24.

As shown in FIGS. 2 and 3, typically, an anesthesia gas machine 40 is located to the side of and slightly behind the anesthetist, who should be standing at the head end of the surgical table. Wires, cables and hoses originating from patient monitors 38 must necessarily traverse across the distance between the anesthesia gas machine 40 and the patient 24. The wires, cables and hoses connecting the patient monitors 38 to the patient 24 are generally 10-12 feet long. The wires, cables and hoses hang to the floor, then traverse the floor and then ascend to the patient 24 laying on the surgical table 22. It is axiomatic that 5-8 monitoring cables and hoses along with 2-6 electric patient warming cables (e.g., that are 12-15 feet long), can create a tangled mess laying on the floor.

The tangled mess of cables and hoses on the floor create not only considerable additional work for the OR staff requiring coiling and cleaning between cases, but also create a tripping hazard for the staff. Finally, cables and hoses laying on the floor of the OR are easily damaged by rolling carts and gurneys.

However, in the example systems described herein, the close proximity of the space adjacent the arm-board 26 is taken advantage of to provide for shorter monitoring, warming system and equipment cables and hoses. In some examples, this short distance to the patient eliminates the cables and hoses from even touching the floor, much less traversing the floor. In some examples, this is accomplished by relocating the patient monitors 38 into the module 10. However, in some examples, the monitor electronics 38 may remain located at a distance from the surgical table 22, perhaps on the anesthesia gas machine 40, with only the terminations of the patient monitor 38 cables and hoses attached to module 10. In some examples, the cables may be connected to the monitors located a distance away from the surgical table 22, by wireless communications or by a trunk cable.

Figure 4:
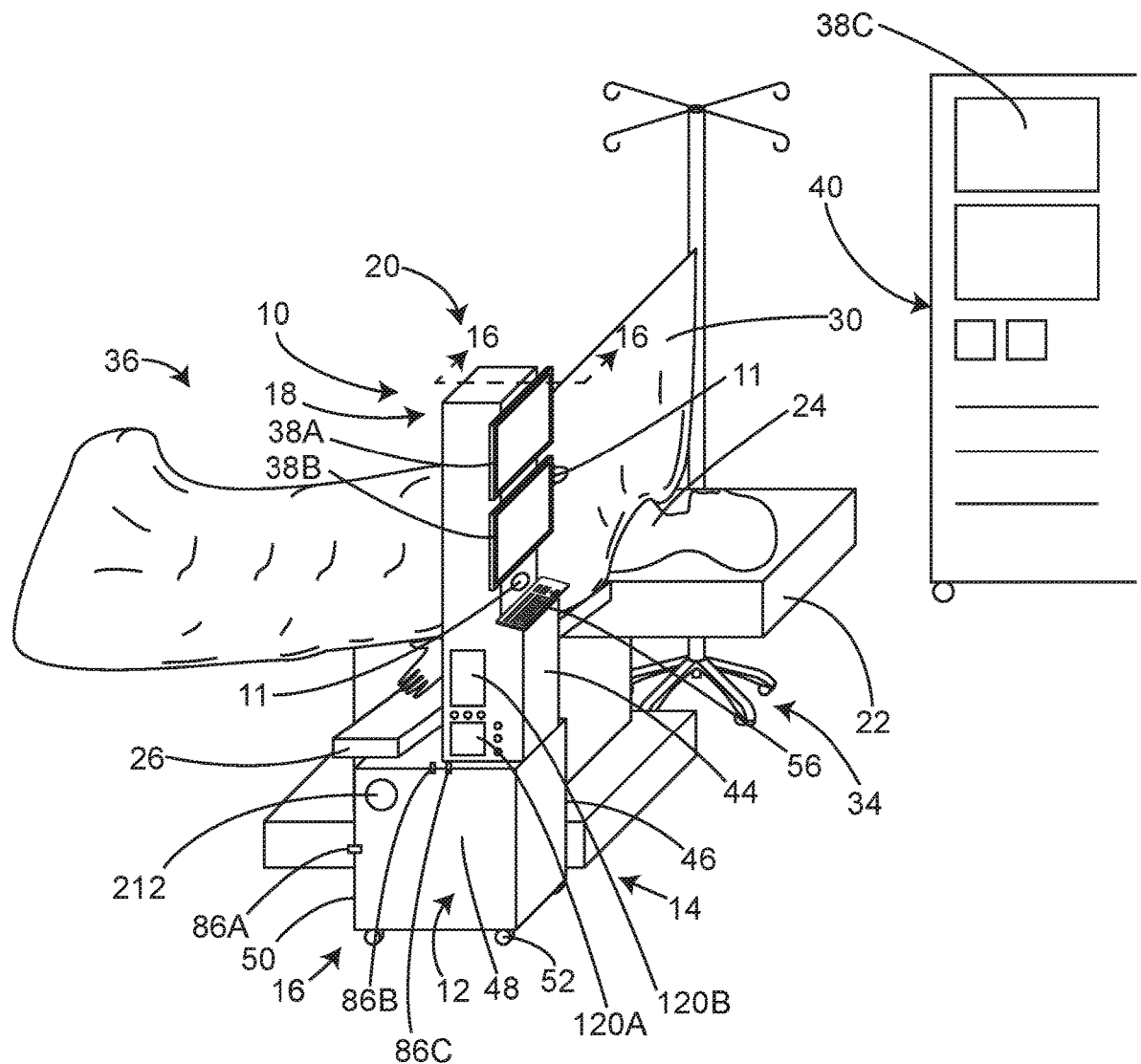
FIG. 4 shows a perspective view of the illustrative module of FIG. 1 in an operating room, in accordance with at least one example.

As shown in FIG. 4, in some examples, the module 10 can occupy a unique space under and adjacent to the arm-board 26. Benefits of this location include but are not limited to the fact that it is less than 2 feet from the patient's head and less than 1 foot from the patient's arm. Additionally, a benefit of the module 10 fitting into this unique location is that it is the only location in the operating room from which the patient monitoring displays 38A, 38B can be viewed by the anesthetist in the same field of vision as the patient's head and the surgical field, while standing at the head end of the surgical table 22.

This location is in sharp contrast to the current location of patient monitor 38 mounted on the anesthesia gas machine 40 beside and behind the anesthetist. If the anesthetist is looking sideways at the patient monitors 38 located on the anesthesia machine 40, he or she is clearly not simultaneously observing the patient (e.g., observing signs of distress or alertness on the face of the patient). Looking sideways at the monitors 38 located on the anesthesia machine 40, as is traditionally done, is a whole different field of vision—away from the patient, a distraction from the primary monitor: observation of the patient.

Currently, when the patient monitors 38 audibly alarm, the anesthetist's attention is drawn away from the patient to the monitors 38, accentuating the distraction caused by the current location of the patient monitors 38 on the anesthesia machine 40. In some examples, the module 10 makes it possible for the anesthetist to observe not only patient monitor displays 38A, 38B, the patient 24 and the surgical field in a single field of vision, but also an alert or alarm light 11 shining from that field of vision back toward the anesthetist. In some examples, the light 11 may substitute for an audible alarm. Audible vital sign alarms from the patient monitors 38 are not only distractions for the surgical staff but significantly add to the noise in the OR. In some examples, one or more relatively bright warning lights 11 mounted on a tower 20 or on one of the patient monitors 38A, 38B that are mounted on the tower 20 in this field of vision and advantageously aimed at the anesthetist, may be substituted for audible alarms.

In some examples, the warning or alarm light 11 may advantageously be a directional LED that focuses its light in specific direction—toward the anesthesia provider. Mounting the one or more alarm lights 11 on the patient monitor display 38A or 38B that is adjustably mounted on the tower 20 to provide the best viewing angle to the anesthetist, will automatically preferentially aim the alarm light(s) 11 at the anesthetist. Lights mounted anywhere else may not aim at the anesthetist most of the time. Even lights mounted on a display of the patient monitor 38 would not usually be aimed at the anesthetist when the display of the patient monitor 38 is located in its traditional location on the anesthesia gas machine 40 located to the side of the anesthetist. In contrast, the location of the tower 20 (e.g., of module 10) next to the patient with the patient monitor display 38A, 38B mounted on the tower at eye level and adjustably "aimed" at the anesthetist, uniquely allows lights 11 mounted on the patient monitor display 38B or tower of the module 10 to be substituted for audible alarms. In some examples, if the alarm condition is severe, the light 11 may flash to increase noticeability. The warning or alarm lights 11 may advantageously be red but other colors including white are anticipated. In some examples, the lights 11 may be color coded, for example: patient monitor alarms may be red; IV infusion pump alarms may be orange; oxygen and ventilator alarms may be yellow; and miscellaneous non-critical equipment alarms such as warming blankets, may be blue.

In some examples, when the anesthetist acknowledges the alarm light 11 by pressing a button (or functionally equivalent response), the light 11 may decrease in intensity. In some examples, the light 11 automatically turns off only when the alarm condition is resolved. In some examples, if the anesthetist fails to acknowledge the alarm light 11 by pressing a button within a given amount of time, for example 20-30 seconds, a backup or secondary audible alarm may sound. In some examples, if the anesthetist acknowledges the alarm light 11 by pressing a button (or functionally equivalent response) within a given amount of time, for example 20-30 seconds, the backup audible alarm may be muted so as not to distract the surgical staff and add to OR noise. In some examples, if the overhead lights in the OR have been dimmed, the alarm light 11 may automatically decrease in intensity so as not to be an unnecessary distraction to the surgical staff.

The unique location of the tower 20 on the module 10 allows these one or more warning lights 11 to be aimed away from the surgical field, which is therefore not distracting to the surgeon. Only if the warning light 11 is not noticed or ignored by the anesthetist, would a backup audible alarm which is distracting to the surgeon and OR staff be necessary.

In some examples, the patient monitors and monitor display screens 38A, 38B may be located on the module 10 next to the patient. In some examples, the patient monitor display screens 38A, 38B may be located on the module 10 next to the patient, while the monitor electronics 38C may remain mounted to the anesthetic gas machine 40 or elsewhere (e.g., FIG. 4). In this instance, the output of the patient monitors 300A, 300B may be wirelessly transmitted to at least one patient monitor display screens 38A, 38B mounted on module 10, for convenient viewing. In some examples, the patient monitor display 38A, 38B can include a small digital LCD projector or equivalent electronic projector may be mounted on the module 10 or on an articulating mount connected to module 10, next to the patient. From this location, the projector may be used to project vital signs and other monitor information on to the anesthesia screen 30, or another screen substantially above the patient's head. Alternately in some examples, a small projection screen may fold down from the module 10 and unfurl the projection screen adjacent and parallel to the anesthesia screen 30 substantially above the patient's head. Vital sign information projected on to the anesthesia screen 30 or small projection screen optimizes the simultaneous visualization of the patient and the monitors, in a single field of vision—much like a pilot's "heads-up" display.

As shown in FIG. 4, in some examples the rear side 50 of the module 10 is roughly in the same vertical plane (or a plane parallel to or substantially parallel to) as the surgical drape 32 hanging down from the arm-board 26, when the module 10 is located under the arm-board 26. In this unique location, wires, cables and hoses can exit the sterile surgical field adjacent the surgical side 36 of the anesthesia screen 30 and drop substantially downward to be plugged into electrical plug-ins and air inlet vents 86 located on the rear side 50 of the module 10. The wires, cables and hoses do not even have to touch the floor at that location. However, even if they do touch the floor, they do not cross any location where a surgeon would be standing, nor do they cross any walking pathway. In this unique location adjacent the surgical side 36 of the arm-board 26, even wires, cables and hoses that are on the floor do not create a tripping hazard or an obstacle for small wheels. In some examples, a half pipe-shaped cable and hose cradle may be attached near the lower edge of the rear side 50 of the module 10. Cables and hoses draping from the surgical field to the rear side 50 of module 10 may safely elevated off of the floor by laying in this half pipe-shaped cradle 51. Locating module 10 adjacent to and under the arm-board 26, allows this unique and safe access for wires, cables and hoses from the sterile surgical field.

In some examples, it may be preferable to locate the wire and cable plug-ins and the hose inlet vents 86 on the side 48 of the module 10 facing away from the patient. On this side, the electrical plug-ins and hose inlet vents 86 can be located higher on the module 10 for more convenient access by staff. When the plug-ins and connectors are located on the side 48 of the module 10 facing away from the patient, it is possible that the wires, cable and hoses may lay on the floor at the rear 50 of the module 10 and then rise to connect with the plug-ins and connectors. However, wires, cables and hoses laying on the floor directly adjacent to the rear side 50 of the module 10, which is located under the arm-board 26 and surgical drape 32, will not create an obstacle for standing or walking.

The inlet vents 86 can be located on any suitable surface of the module 10, including under the bottom of the module 10 in order to collect air from near the floor. The inlet vents can include a flapper door or other suitable movable sealing device so that the vent stays closed unless a hose is plugged into the inlet vent 86.

The equipment location illustrated in FIG. 4 is unique in the entire operating room from the perspective of safe wire, cable and hose management, exiting the surgical field. All other locations for surgical support equipment require that wires, cables and hoses exit the surgical field and traverse the floor between the surgical table 22 and the equipment. As a result, this creates a tripping hazard for personnel and obstacle for small wheels.

As shown in FIG. 4, in some examples the rear side 50 of tower-like upper section 18 is directly adjacent the anesthesia screen 30. The anesthesia screen 30 can include a sheet that separates the sterile surgical field from the non-sterile anesthesia work area. This exact location is uniquely the closest non-sterile location to the sterile surgical field. Nowhere else around the surgical table is any piece of non-sterile equipment this close to the sterile surgical field. In some examples the rear side 50 of the upper section 18 may be taller than the upper edge of the anesthesia screen 30, therefore it is visible from or accessible from the surgical side, over the top of the anesthesia screen 30. Since the rear side 50 of the upper section 18 may be directly adjacent the anesthesia screen 30, it does not create any new flow-boundary layer obstructions to the ventilation airflow.

Figure 23:
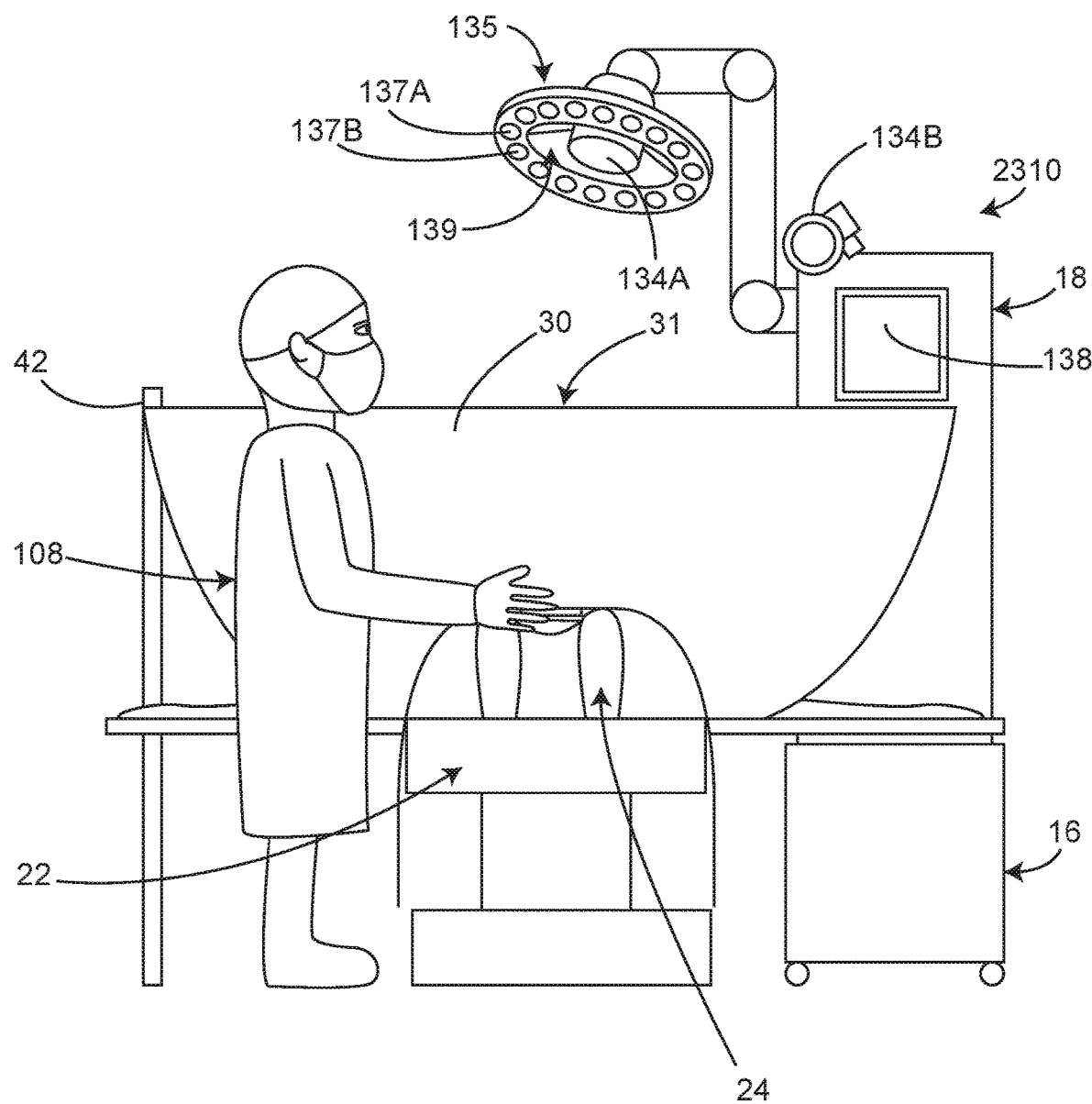
FIG. 23 shows a surgical field viewed facing towards an anesthesia screen from a surgical side of the screen with a surgeon positioned in a surgery performing position, and an illustrative system (e.g., any of the systems described herein) positioned adjacent a surgical table, in accordance with at least one example.

In some examples the rear side 50 of the upper section 18 is taller than the upper edge 31 of the anesthesia screen 30. Therefore, the rear side 50 of the upper section 18 can be uniquely situated to mount various pieces of equipment that may be useful for the surgeon. For example, as shown in FIG. 23, one or more surgical monitor screens 138 such as: patient vital sign monitor screens, surgical scope monitor screens, surgical check list monitor screens, safety check list monitor screens, communications and message monitor screens, clocks and timing device screens. In some examples the rear side of the upper section 18 may be uniquely useful for mounting a fan or surgical lights aiming at the surgical field.

As shown in the illustrative module 2310 of FIG. 23, in some examples, a fan 134A or 134B is positioned to blow air from the head end of the sterile surgical field to the foot end. It is well known that moving air keeps suspended particles suspended. In contrast, suspended particles settle out of suspension in still, non-moving air. The ventilation airflow in the region between the surgeons standing on each side of the surgical table is frequently obstructed due to flow-boundary layers adjacent the surgeon's bodies (e.g., FIG. 21A). Therefore, the ventilation airflow is prevented from flowing which allows airborne contaminating particles to settle into a surgical wound 114. An airflow created by the fan 134A or 134B at the head end of the sterile field can prevent or reduce the air between the surgeons from becoming still and thus allowing settling.

A traditional surgical light is shaped like a disc and is generally about 24-36 inches in diameter. As shown in FIG. 23, in some embodiments, a surgical light 135 of this disclosure may be shaped like a ring with a hole 139 passing through its middle and individual lights 137 located around the ring. The hole 139 in the middle of the light 135 may allow the ventilation airflow from the ceiling to pass through the surgical light 135. Air passing through the middle of the ring-shaped light 134 eliminates the dead zone of no airflow that typically forms under flow obstructing disc-shaped surgical lights.

Figure 21A:
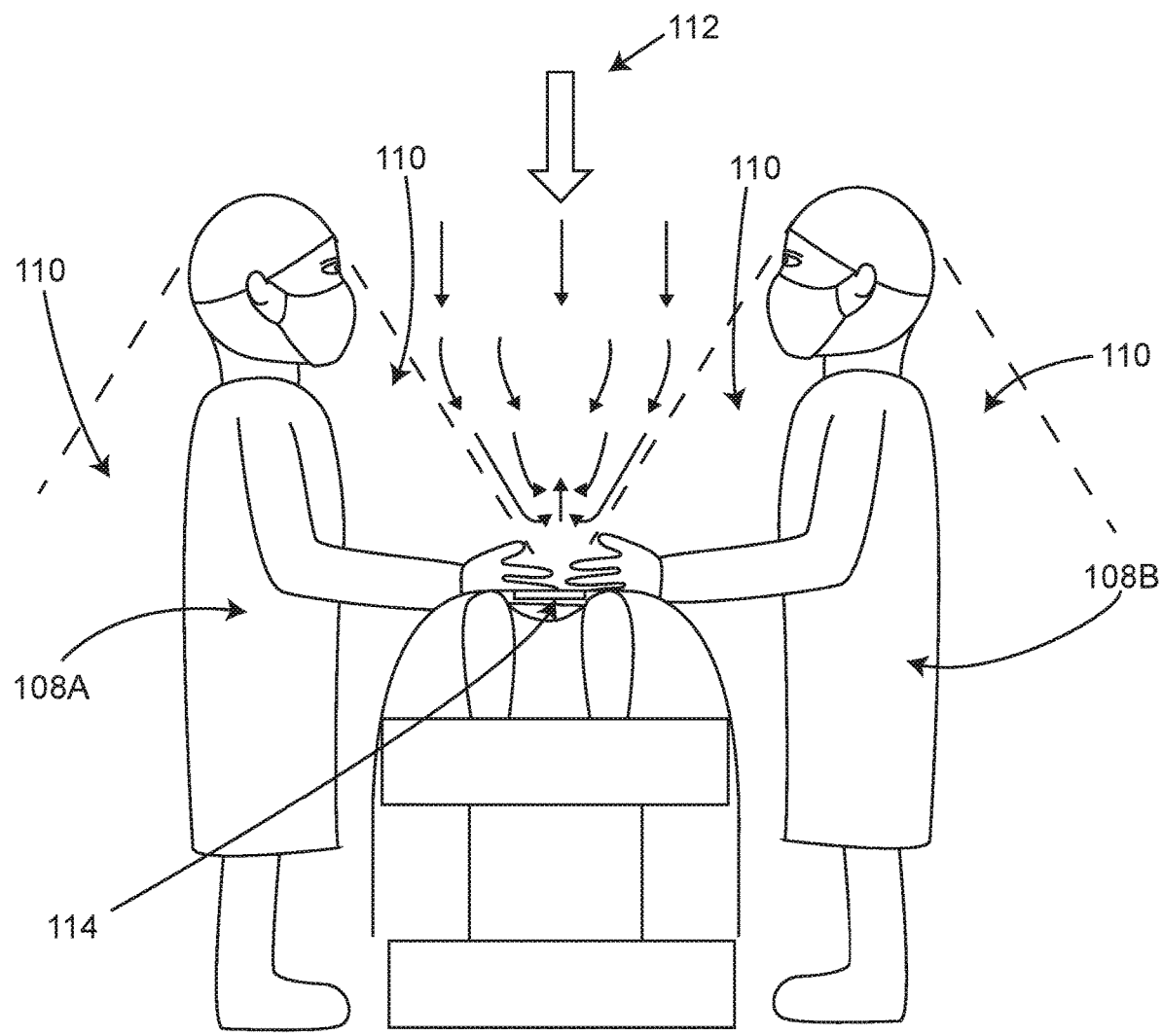
FIG. 21A shows an illustrative surgical field depicting flow-boundary dead zones, in accordance with at least one example.

In some examples, the fan 134A or 134B can be located at the head end of the sterile field. The fan 134A may be mounted in the hole passing through the ring-shaped light. From this location, the airflow from the fan 134A may advantageously be aimed at the surgical wound when the light is aimed at the surgical wound 114 (FIGS. 21A, 21C).

Figure 24:
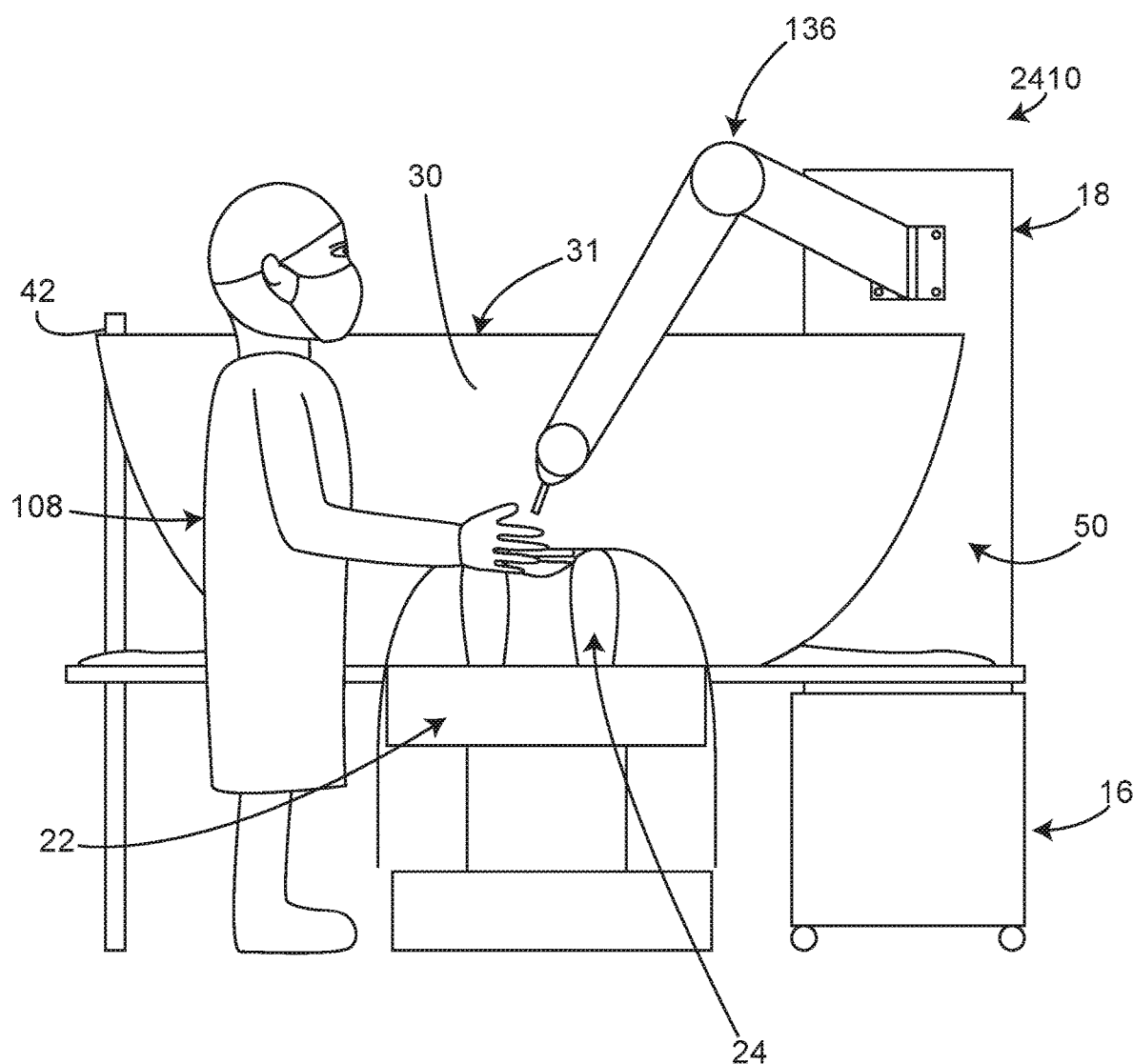
FIG. 24 shows a surgical field viewed facing towards an anesthesia screen from a surgical side of the screen with a surgeon positioned in a surgery performing position, and an illustrative system positioned adjacent a surgical table, in accordance with at least one example.

As shown in the illustrative module 2410 of FIG. 24, in some examples, the rear side 50 of the upper section 18 may be uniquely useful for mounting articulating arms that can "reach" across the upper edge of the anesthesia screen 30, into the sterile surgical field and hold surgical lights, surgical instruments, surgical scopes or surgical retractors. Locating module 10 directly adjacent the anesthesia screen 30 uniquely allows access to the surgical field from the head end of the surgical table. Mounting surgical lights, surgical instruments, surgical scopes or surgical retractors to articulating arms that are attached to the rear side 50 of the upper section 18 obviates the need for attachment of this equipment to the side rails of the surgical table. This is especially useful because mounting the articulating arms to the side rail of the surgical table is difficult or even impossible when the patient and the side rail is fully covered by a surgical drape. In some examples, the articulating arms that can "reach" across the upper edge of the anesthesia screen 30 may be covered by custom sterile plastic drapes to prevent contamination of the sterile field. "Reaching" over the top (e.g., upper edge 31) of the anesthesia screen both avoids the need for the side rail mounting and uniquely provides access to the surgery from the head end.

In some examples the rear side 50 of the upper section 18 is taller than the upper edge 31 of the anesthesia screen 30 and may be used as a mount one or more video cameras for recording the surgical procedure for: training and education purposes, inter operating room communication, communication with the family in the waiting room or video documentation for liability avoidance (much like police body cameras). In some examples a video camera mounted on the rear side 50 of the upper section 18 can show its image on one of the patient monitor display screens 38A, 38B, so that the anesthetist can view the surgical procedure without standing next to the anesthesia screen 30 and thus avoiding the disruption of the ventilation airflow caused by standing next to the anesthesia screen 30. A view of the surgical procedure on the patient monitor display screens 38A, 38B would both improve the anesthetists' situational awareness and reduce airborne contamination of the sterile surgical field.

Figure 25:
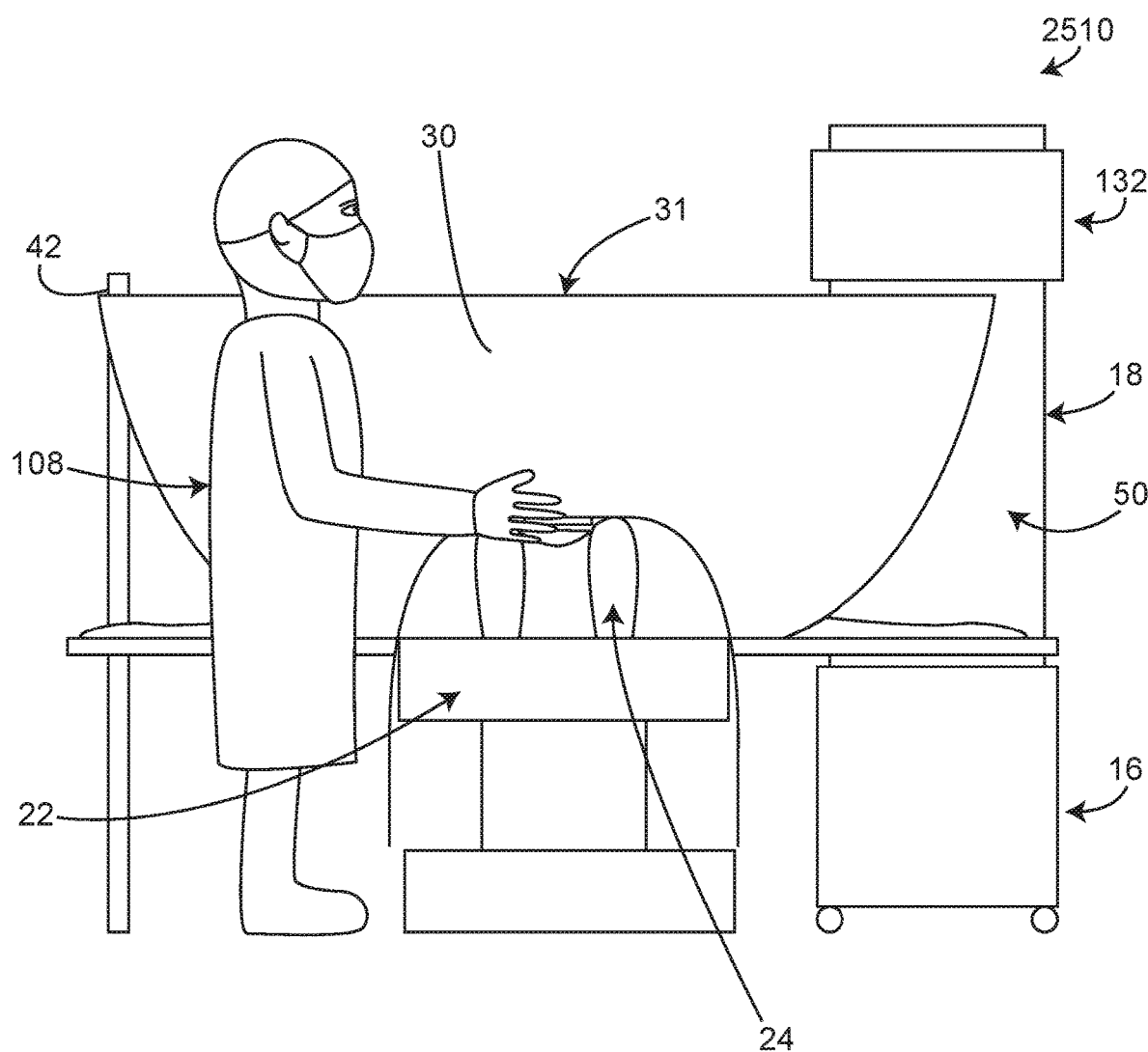
FIG. 25 shows a surgical field viewed facing towards an anesthesia screen from a surgical side of the screen and with a surgeon positioned in a surgery performing position, and an illustrative module positioned adjacent a surgical table, in accordance with at least one example.

In some examples as shown in FIG. 25, the rear side 50 of the upper section 18 may be taller than the upper edge 31 of the anesthesia screen 30 and may include a mount for a sterile storage container 132 for surgical supplies. The sterile storage container 132 may be accessed directly from the sterile field, reducing the time that the surgical team must wait for various sterile supplies. Negating the need for the circulating nurse to approach the sterile surgical field to deliver that given sterile supply also avoids the nurse kicking up contaminates off of the floor or disrupting the ventilation airflow during the supply delivery.

In some examples, as shown in FIG. 4, the module 10 can include 4 or more sides (e.g., regions, side portions, faces). When positioned in the unique "no-man's land" under and adjacent the arm-board 26, two of the sides 48 and 50 of module 10 are naturally available for surgical staff access and surgical equipment connections. In this position, two of the sides 44 and 46 of module 10 are naturally available for anesthesia staff access and anesthesia equipment connections. There is no other location in the operating room that can be advantageously "shared" by both anesthesia and surgery (two teams that do not historically share very well).

In some examples, the front face 44 of module 10 is substantially facing the anesthesia provider. Therefore, the front face 44 may naturally include controls and displays 38A, 38B for the anesthesia monitors and equipment. The front face 44 may also include plug-ins for certain equipment such as a heated clinician warming vest or specialty monitors. In some examples, the front face 44 includes a keyboard 56 and mouse pad for data entry. Other equipment such as IV bag pressurizers, IV pumps and drug infusion pumps may also be mounted on the front face 44 for convenient access by the anesthetist.

In some examples, the patient monitor display 38A, 38B and/or keyboard 56 (or other user input) may be mounted on swiveling brackets that allow side-to-side and/or up and down adjustment for improved viewing angles. In some examples, the patient monitor display 38A, 38B may be mounted on brackets that swing into a position even closer to the patient (lateral to the centered midpoint of the module 10). From this unique location, the anesthetist has a very clear view of the monitor displays 38A, 38B in the same field of vision as the patient's head and the surgical field. No other monitor display 38A, 38B mounting location in the operating room can provide this simultaneous visual access to both the monitors 38A, 38B and the patient 24. With the monitor display (e.g., screen) "aiming" at the anesthetist, an alarm light attached to the monitor display will also aim directly at the anesthetist, assuring that it will be noticed.

In some examples, the side 46 of the module 10 facing the patient 24 (e.g., as viewed in FIGS. 8-11, 14 and 26), can advantageously be used for its close proximity to the patient 24. In some examples, wire, cable and hose management may be located on the side 46 facing the patient 24 (e.g. patient side of the module, patient face of the module). Most of these cables and hoses are for anesthesia purposes, including but not limited to electronic patient monitors, end-tidal carbon dioxide sampling, automated blood pressure monitors, electrically heated blankets and mattresses and waste oxygen scavenging and dilution.

In some examples, cables and hoses for surgical equipment may be advantageously managed from the side 46 of the module 10 facing the patient 24. Examples include but are not limited to air mattresses, pressure sensing mats, sequential compression leggings, capacitive coupling electrosurgical grounding electrodes and RFID antennae for detecting retained surgical items.

Figure 26:
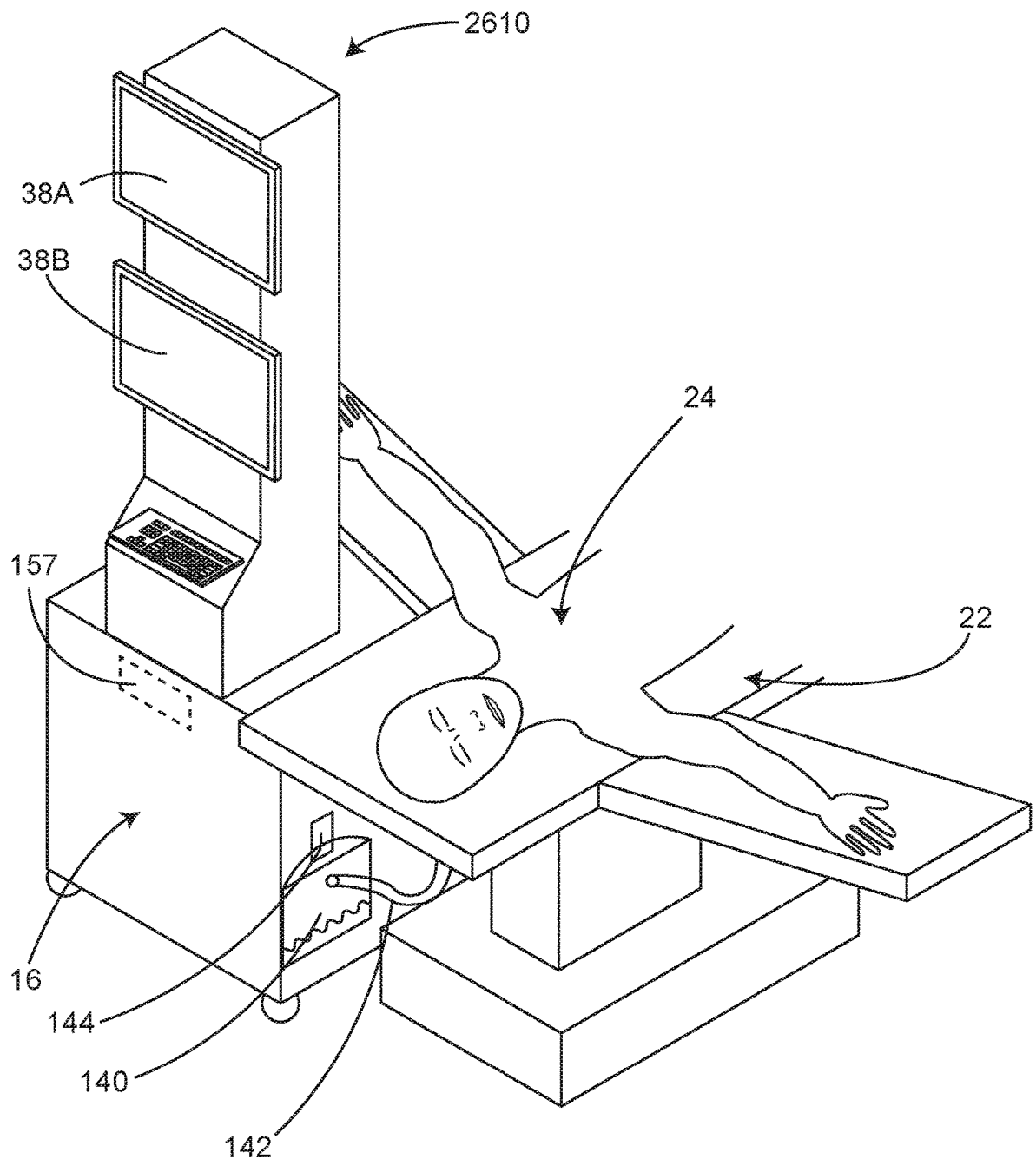
FIG. 26 shows a perspective view from the anesthesia side of a surgical field of a patient on a surgical table, and an illustrative system at least partially disposed under an armboard of the table, in accordance with at least one example.

In some examples, the module 10 also includes a hanger 144 for holding and securing a urine bag 140 off of the floor. In some examples, and as shown in FIG. 26, the urine bag hanger 144 may be advantageously mounted on side 46 of the bulbous lower section 16 facing the patient 24. From this position, the urine bag tubing 142 can easily reach the module 10 from the sterile field or from under the surgical table, without traversing or touching the floor. From this position, the urine bag 140 can conveniently be accessed by the anesthetist from the front face 44 of the module. In some examples, the urine bag hanger 144 can include a hook-like element. In some examples, other urine bag hanger 144 elements including but not limited to, clips, straps, snaps or Velcro, or any other suitable attachment mechanism may be provided In some examples, the urine bag hanger 144 is attached to a scale 145 for measuring the weight of the urine bag 140 plus the weight of the urine in the bag. Measuring the weight of the urine is far more accurate than the traditional method of visually measuring the volume of urine in a collapsible plastic urine bag 140. Since urine has virtually the same specific gravity as water, each 1 gram of urine weight equates to 1 ml of urine volume.

In some examples, the urine bag hanger 144 is attached to an electronic scale 145 for measuring the weight of the urine bag 140 plus the urine in the bag. In some examples, the digital output of the electronic scale 145 that is attached to urine bag hanger 144 is directly reported on a patient monitor display 38A or 38B. In some examples, the electronic output of the electronic scale 145 that is attached to urine bag hanger 144 (e.g., generated sensor data) is digitalized and received by the processor that is programmed to record the beginning weight of the urine bag (the weight of the urine bag plus any urine already in the bag) and automatically subtract that beginning weight from subsequent recorded urine bag weights, calculate the urine output during surgery. In some examples, the electronic output of the electronic scale 145 is digitized and reported (e.g., generated and a signal sent) to a processor (e.g., processing circuitry 157) In some examples, the total urine output and in some cases urine output per hour determined by the processor, are then displayed on a patient monitor display 38A or 38B. In some examples, the total urine output and in some cases urine output per hour determined by the processor, may be automatically recorded in the electronic anesthetic record, a non-transitory computer readable medium. Including an electronic scale attached to urine bag hanger 144 conveniently obviates the need to empty the urine bag 140 at the beginning of the operation in order to "zero" the system, as is traditional with a visual urine measuring system. The electronic scale 145 allows the beginning weight of the urine bag plus any urine already in the bag to be easily subtracted from the running weight (e.g., The processor can calculate a zero point). Time measurements do not need to be limited to per hour measurements, any unit of time, such as per minute, or per second, may be used. In some examples, a urine measurement per surgery can be displayed or saved.

To perform determinations and calculations and take action, the processor can receive and processor signals (including sensor data and other input data) and can generate signals that are communicated to a controller that is operably coupled to the processor. The controller can include one or more control modules, for example electronic control modules (ECMs), electronic control units (ECUs) and the like. The one or more control modules may include processing units, memory, sensor interfaces, and/or control signal interfaces for receiving and transmitting signals. The processor may represent one or more logic and/or processing components used by the control module to perform certain communications, control, and/or diagnostic functions. For example, the processing components may be adapted to execute routing information among devices within and/or external to the control module.

In some examples, the urine bag 140 may include an inlet near its top for attaching a vacuum or suction hose from the module 10. In some examples, a hydrophobic, air-permeable membrane may be added to the proximal end of the urine bag tubing 142, near the patient's catheter. Introducing a mild vacuum in the urine bag 140 pulls air through the hydrophobic, air-permeable membrane into the urine bag tubing 142. The resulting air bubble in the urine bag tubing 142 near the patient end of the tubing, is pulled to the urine bag 140 by the vacuum. The moving air bubble breaks any air "vapor locks" that may have formed in the urine bag tubing 142 and that may be obstructing the flow of urine through the urine bag tubing 142, allowing free flow of the urine into the urine bag 140.

In some examples, and as shown in FIG. 4, the rear side 50 of the module 10 is open to the surgical side 36 of the anesthesia screen 30, below the surgical drape 32 hanging down from the arm-board 26. From this location, the rear side 50 can be accessed directly for plugging in wires, cables and hoses exiting the sterile surgical field. However, the low height of the access, below the lower edge of the surgical drape, may be considered to be inconvenient.

In some examples, the side 48 of module 10 facing away from the patient 24 may be advantageously accessed by the surgical nurse without encroaching on the anesthetist, the anesthetist's space or the anesthesia side 34 of the anesthesia screen 30. In some examples, the side 48 facing away from the patient 24 may include the controls and display screens 120 for surgical equipment (e.g., surgical support equipment) contained within the module 10. This surgical equipment includes but is not limited to: an electrosurgical unit, an air mattress, a pressure sensing mat, a smoke evacuation unit, a dead-zone evacuation system, blood and fluid suction and disposal, sequential compression leggings and an RFID surgical sponge and instrument counting and detection system.

In some examples, most of the surgical support equipment may be incorporated into module 10, which allows the surgical nurse or technician to monitor and control all of this equipment from a single location—the side 48 of the module 10 facing away from the patient 24. The consolidated surgical equipment controls and displays 120 become very efficient for the nurse to monitor compared to having the equipment scattered all over the operating room. This is also far more likely that problems will be noticed early than if the individual pieces of equipment are scattered all over the operating room as is the current practice. Efficient monitoring also means that patient safety is improved. In some examples, the displays and controls 120 for the surgical equipment may be located on the front face 44 of the module 10, or another face of the module.

In some examples, the controls and display screens for the surgical equipment housed in the module 10 may be wirelessly connected to a portable display screen such as an iPad or "smart tablet," for convenient access by the nurse anywhere in the room. This allows the surgical nurse to monitor and control the equipment without walking across the room. Minimizing surgical staff movement in the OR has been shown to reduce airborne contamination and surgical site infections because less contaminates are "kicked up" by walking around the OR.

In this unique location adjacent the arm-board 26, the various sides 44, 46, 48, 50 of module 10 are naturally and advantageously adapted for different functions. The rear side 50 and the side 48 facing away from the patient can be adapted for surgical purposes. The front side 44 and the side 46 facing the patient can be adapted for anesthesia purposes. The only place that this unique combination could be achieved is in the currently unoccupied "no-man's land" between the anesthesia 34 and surgical sides 36 of the operating room—the anesthesia screen 30 and arm-board 26. The module 10 is uniquely adapted to advantageously fit this location.

As described herein, sides (e.g., faces) 44, 46, 48, 50 can be distinct sides as in the planar sides of a rectangular cuboid shape, or another cuboid shape. In some examples, the faces can include any shape including non-cuboid shapes having more than 4 outward facing sides accessible to medical personnel.

However, in other examples the sides can refer to side portions of a curved or irregular shaped volume. In some examples, the sides can refer to an approximately 90 degree or quarter span of the volume that forms the module 10.

In some examples, as shown in FIGS. 4-7, the module 10 includes a lower section 14 and an upper section 18. In general, the lower section 14 may contain the heavier equipment such as one or more power supplies 212, the electro-surgical unit and monitor electronics. In general, the upper section 18 may contain lighter equipment and components such as ducting, fans, filters, cable management systems, wiring harnesses and monitoring screens 38A, 38B. Keeping the heavy equipment in the lower section 14 improves the stability and reduces the risk of tipping.

Figure 5:
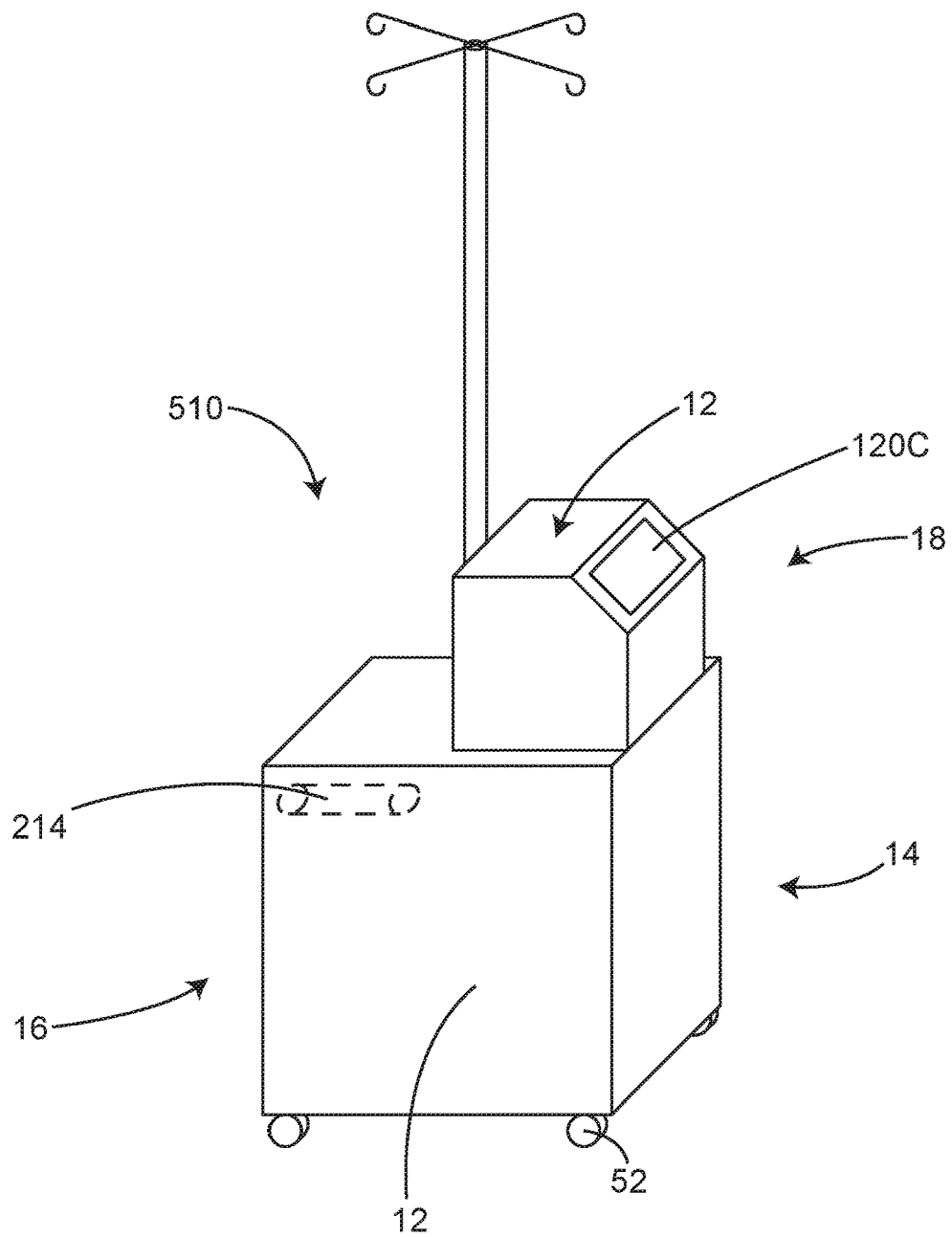
FIG. 5 shows a perspective view of another example of an illustrative module, in accordance with at least one example.
Figure 6:
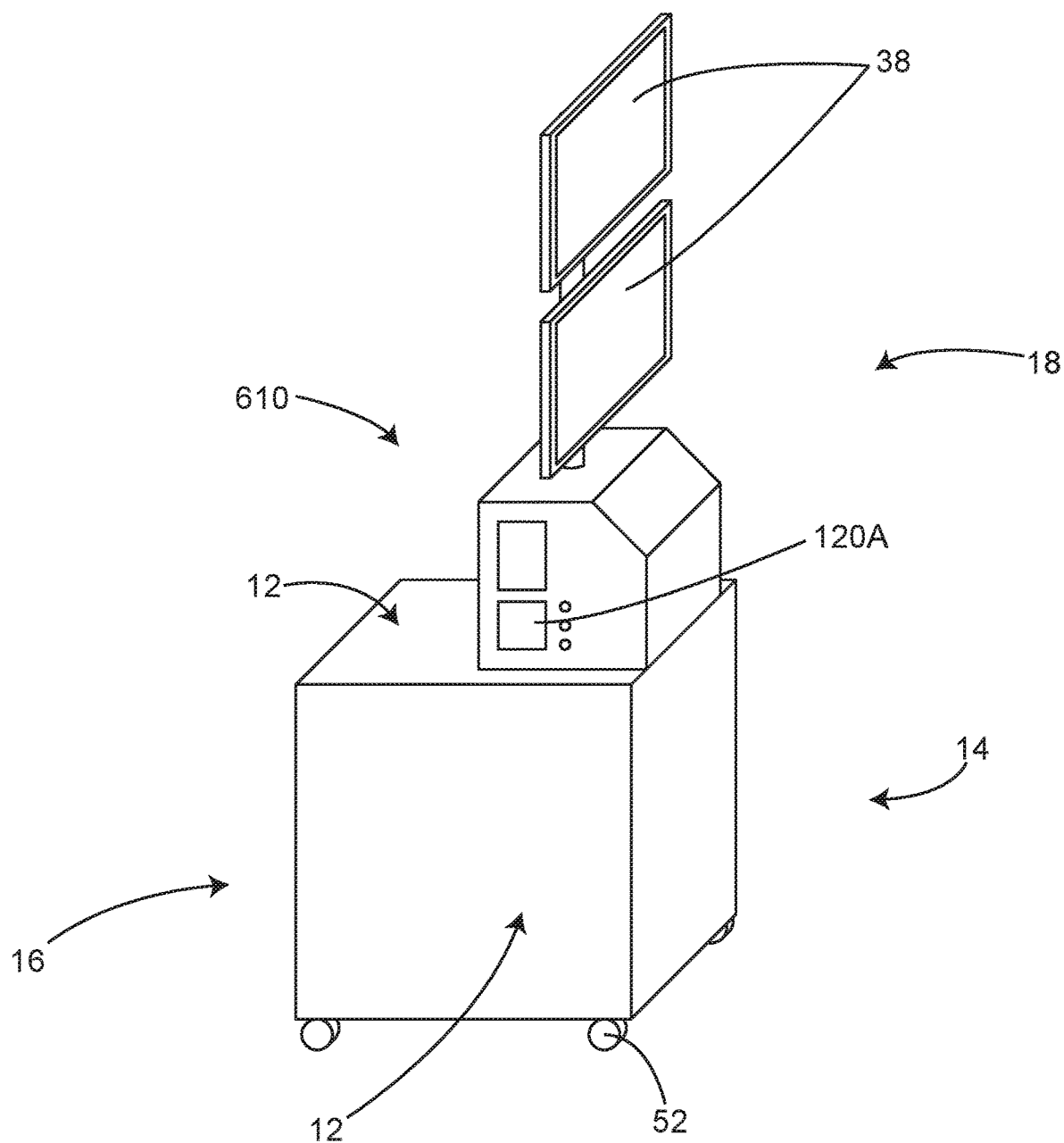
FIG. 6 shows a perspective view of another example of an illustrative module, in accordance with at least one example.

In some examples, and as shown in FIGS. 4-6, the lower section 14 could be called a bulbous lower section 16. "Bulbous" is compared to the upper section 18. There are several advantages for the lower section 16 being "bulbous." The bulbous lower section 16 has an increased internal volume that can house much more equipment. The bulbous lower section 16 efficiently utilizes the otherwise wasted space under the arm-board 26. The bulbous lower section 16 substantially increases the footprint of the base of module 10, allowing the rear wheels to be much further to the rear of the module, substantially increasing the stability of the module 10. Heavier equipment may be located toward the rear of the bulbous lower section 16, which further increases the stability and lessens the likelihood of module 10 tipping forward.

In some examples, the bulbous lower section 16 may be of any size. In some examples, a cube roughly 24 inches on each side can fit under the arm-board 26. Other sizes and shapes are anticipated. A 24 inch cube may appear to be rather large and cumbersome, but it is worth noting that the standard 5-wheeled base for an IV pole 42 is an area roughly 24 inches in diameter. Therefore, the floor occupied by and the traffic patterns affected by the 24 inch square of the bulbous lower section 16, is virtually identical to the 24 inch diameter circle of the current IV pole 42 that can sometimes be located in that same position. However, the volume above an IV pole base is wasted in contrast to the bulbous lower section 16 which may include 8 cubic feet or more, of volume that can house various surgical and anesthetic equipment. The bulbous lower section 16 very efficiently utilizes otherwise wasted volume under and adjacent to the arm-board 26. In some examples the bulbous lower section may include between 4 and 12 cubic feet of volume. In a possibly more preferred example, the bulbous lower section 16 may include between 6 and 10 cubic feet of volume.

In some examples, the bulbous lower section 16 may include standardized 19" electronic component racks. In this case, the modular electronic and electromechanical components stored in the bulbous lower section 16 can be easily added or removed. For the standardized 19" electronic component rack systems to work, the various pieces of electronic and electromechanical anesthesia and surgical equipment to be relocated into the module 10, will need to be reconfigured to fit the standardized 19" electronic component rack.

In some examples, the module 10 may be additionally stabilized and prevented from tipping by suctioning the module to the floor of the OR. The floors of most ORs are very smooth and polished, with no crevasses that can collect contaminates. This creates an ideal surface for creating a vacuum in a suction cup. In some examples, instead of or in conjunction with wheels 52, one or more suction cups 53, much like the suction cups for handling large glass panes, may be extended downward from the bottom of module 10 to engage with the floor. In some examples, when the module 10 has been positioned properly, one or more actuator pneumatic cylinders or electromechanical mechanisms may be triggered to lower the one or more suction cups 53 until they contact the floor. In some examples, the actuator can be a hand-powered or manually actuated actuator. In some examples the actuator can be electronically controlled by processing circuitry receiving instructions from an indictor such as a switch or touch screen element. A vacuum is then applied to the one or more suction cups 53. The vacuum can be applied, for example, by the hospital vacuum system or from a vacuum pump located within the module 10. When the module 10 is suctioned to the floor, it will exhibit significantly more stability and be less likely to tip or move than a similar module left freestanding. In other words, the suction cups can create a suction coupling with the floor.

The vacuum can be applied to the suction cups at a discrete point in time, intermittently or continuously. In the suction cups that are for handling large glass panes, the vacuum is generally created with a single discrete lever action. In contrast, in some examples, the vacuum in the present disclosure may be continuously applied by connecting the suction cup to the hospital vacuum system or the vacuum system in module 10. A continuous vacuum supply may be advantageous over a single vacuum application when there is dust, lint or dirt on the floor that may foul the seal of the suction cup, making it leak air and slowly lose its vacuum. A continuous vacuum supply can overcome a slow air leak. To decouple the module 10 from the floor, the vacuum can be released and the suction cups elevated off of the floor by the one or more actuator pneumatic cylinders, electromechanical mechanisms or hand-powered actuators, before the module 10 can be moved.

Figure 7:
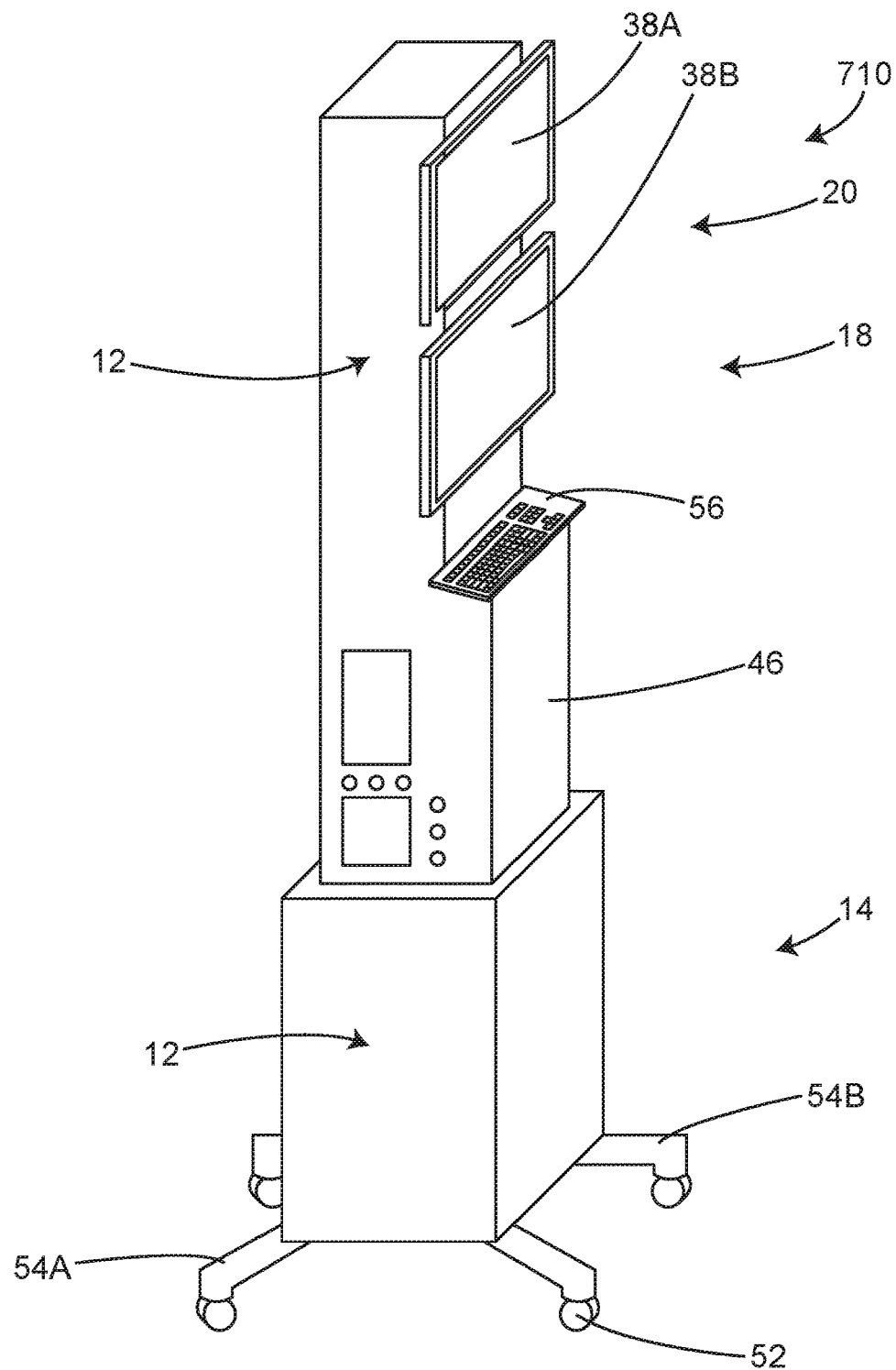
FIG. 7 shows a perspective view of another example of an illustrative module, in accordance with at least one example.

In some examples, as shown in FIG. 7, the lower section 14 may not be bulbous. In some examples, the lower section 14 may be designed to fit adjacent the arm-board 26 but may not go under the arm-board 26. In some examples, the lower section 14 may fit minimally under the arm-board 26. In this instance, the space under the arm-board 26 may be utilized for stability by adding short legs 54 extending rearward to mount castor wheels further rearward. Even if the volume under the arm-board 26 is not utilized for equipment storage, the volume adjacent the arm-board 26 may be efficiently utilized for storing equipment in the lower section 14 of the module 10.

In some examples, the module 10 of can include a shell or "cowling" 12 covering substantially the entire outer surface. Open equipment racks with various pieces of equipment stacked on their shelves that remain open and exposed must be kept at a safe distance from the surgical table 22. In contrast, creating an enclosed module 10 for storing various unrelated pieces of equipment is unique in the operating room. Creating an enclosed module 10 for storing various unrelated pieces of equipment makes it possible to place the module 10 near the surgical table 22 during a surgery. The cowling 12 can protect the equipment in the module 10 from accidental fluid damage by IV fluids, irrigation fluids and blood. Any equipment on an open rack adjacent and under the arm-board 26, may be at high risk for damage from water, saltwater and blood in this hazardous environment.

In some examples, the cowling 12 of module 10 is made of molded plastic, 3-D printed plastic, molded fiberglass, aluminum, steel or other suitable materials. In some examples, the cowling 12 may preferably be fluid resistant if not fluid proof. In some examples, the cowling 12 can be shaped so that water naturally runs off of it and that it has smooth surfaces for easy cleaning. In some examples, any air inlet vents can include overhangs that protect them from fluid ingress from spilled fluids and the access ports of the cowling 12 may preferably be sealed when closed, to prevent fluid ingress.

In some examples, the cowling 12 of module 10 confines the waste heat from the electronic and electromechanical equipment mounted within the module 10, to the inside of the module 10 and cowling 12. In some examples, the confined waste heat can then be safely managed. Confining waste heat from unrelated equipment can be the first step in safely managing the waste heat. Waste heat can only be confined and captured for processing if there is a relatively air-impermeable cowling 12 surrounding the equipment. It is difficult or even impossible to manage the unconfined waste heat produced by electronic and electromechanical equipment mounted on a simple open rack or free-standing in the middle of the operating room floor.

In some examples, the cowling cover of the module 10 described herein contributes to a waste heat management system. The cowling 12 can substantially seal in the waste heat and control the discharge of the waste heat to exit at a predetermined location, such as an outlet vent. In some examples as shown at least in FIGS. 1, 4 and 7-12, the module 10 can include a tower-like upper section 20 attached to or integrally formed with the topside of the lower section 14. In some examples, the tower-like upper section 20 extends substantially vertically from the topside, near the front of the lower section 14. In some examples, the cowling 12 of the tower-like upper section 20 serves as a chimney, containing the rising waste heat until it can be safely discharged from outlet vents located near the top of the tower.

In some examples, the top of the tower-like upper section 20 is 5 feet or more above the operating room floor. At this height, waste heat exhausted from vents near the top of the tower-like upper section 20 is vented into the operating room well above the height of most airborne contaminates. In some examples, air is allowed to enter the module 10 through inlet vents 86 (FIGS. 4, 16, 17) in the lower section 14, the air gets heated by the electronic and electromechanical equipment in the module 10 and then by natural convection, the heated air may rise within the tower-like upper section 20 and be discharged through outlet vents near the top of module 10.

In some examples, the air discharge can occur at a height between 3 and 12 feet above the floor that the module 10 is configured to rest on. In a preferred example, the air discharge can occur at a height of at least 4 feet off the floor. In a more preferred example, the air discharge can occur at a height of at least 5 feet off the floor. In some examples, the air discharge can be connected to an OR venting system which removes the discharged air from the OR.

In some examples, a filter and fan may be added to the waste heat management system in order to filter the waste heated air before discharging it into the operating room, or to filter inlet air. The resistance to airflow caused by adding a filter to the airflow path may necessitate adding a fan to the waste heat management system. In some examples, a sock-like filter may be added to the outlet vent in order to diffuse the outlet air and muffle any fan noise.

In some examples, the inlet vents for the cooling air may be located in the tower-like upper section 20, four or more feet above the floor, above the level of the airborne contamination. At this level, the inlet air is relatively pure and therefore there is no risk of contaminated air causing contamination of the equipment housed within the module 10. In some examples, a duct may connect the inlet vent in the tower-like upper section 20 to the equipment space in the lower section 14. The clean inlet air can be drawn into inlet vents mounted high on the upper section 18 and then ducted down to the equipment that needs cooling and then ducted back up to the tower 20 to be discharged at a safe height above the airborne contaminates. In some examples, ionized air filter plates may be included in the ducting to provide added filtration of the air without added resistance to the airflow.

In some examples, the lower section 14 includes castor wheels 52. The castor wheels 52 may be located substantially in the four corners of the lower section 14. In some examples, the lower section may include more than 4 castor wheels. In some examples, and as shown in FIG. 7, the lower section 14 may include short "legs" 54 that stick 2-10 inches out from the perimeter of the base of the lower section 14. Castor wheels 52 may be attached near the distal ends of these short legs 54 to improve the stability of the module 10.

In some examples, the module 10 does not have wheels but is rather mounted to a movable boom hanging from the ceiling of the operating room. The boom can include two or more arms that articulate and are attached to a pivot point on the ceiling. This configuration allows the module 10 which is attached to the end of the boom, to be moved into a position adjacent the arm-board 26 and then moved away from that position, if for example a gurney needs to be placed against the side of the surgical table. In some examples, even the boom-mounted modules 10 advantageously include bulbous lower sections 16 to maximally capitalize on the wasted volume under the arm-board 26. In some examples, booms from the ceiling may advantageously include power cords, communication cables, air, oxygen and vacuum hoses that conveniently connect outlets in the ceiling to the module 10.

In some examples, the module 10 includes an upper section 18 as shown in FIGS. 4-7. In general, the upper section 18 is for housing or mounting lighter equipment and locating controls 120 and monitor displays 38A, 38B at a height where they can be conveniently accessed. In some examples, the upper section 18 may be a tower-like upper section 20 as shown in FIGS. 4 and 7. In this instance the top of the tower-like upper section 20 may be more than 4 feet above the floor. In some examples, the top of the tower-like upper section 20 may advantageously be 6 feet or more above the floor.

Using the example modules 10 described herein, heat and air can be more safely discharged at higher heights in the operating room because the heat discharged at that height cannot mobilize contaminates that normally reside near the floor. Therefore, a taller tower-like upper section 20 may advantageous.

In some examples, a patient monitor display 38A, 38B may be mounted on the rear of the tower-like upper section 20 of the module 10, facing the surgeon. In this unique location, viewable over the top of the anesthesia screen 30, the surgeon 108 can be constantly aware of the patient's vital signs.

In some examples, the upper section 18 of module 610 may be a medium height, for example 3-4 feet above the floor as shown in FIG. 6. In some examples, the upper section 20 may be a relatively low height of 2-3 feet above the floor as shown in FIG. 5. In each case, the upper section 18 places the controls 120 and monitor displays 38A, 38B for the equipment can be enclosed in the module 510 or 610, at a more convenient height for the operator. FIG. 5 also illustrates a tank 214 disposed in (or on) the module 610. Illustrative tank 214 can supply any of the anesthesia gasses, pressurized air or vacuum etc., as described herein.

In some examples, patient monitor display screens 38A, 38B may be mounted on one or more sides (e.g., faces, side portions) of the upper section 18 of module 10 as shown in FIGS. 4 and 7. In some examples, the patient monitor display screens 38A, 38B may be mounted on arms that attach to the top of the upper section 18 as shown in FIG. 6. In some examples, a keyboard 56 and/or mouse pad may also be mounted to the upper section 18 of module 10 (FIG. 4).

In some examples, upper section 18 includes a side 46 facing the patient. In some examples, if the upper section 18 is tower-like, the side 46 facing the patient is a relatively large surface area. For example, the side 46 facing the patient may be 12 inches wide (or more) and 48 inches tall (or more) which results in 4 square feet of surface area on the side 46 of the upper section 18. This large surface near the patient and facing the patient is uniquely located and sized for a cable and hose management system 58.

Figure 8:
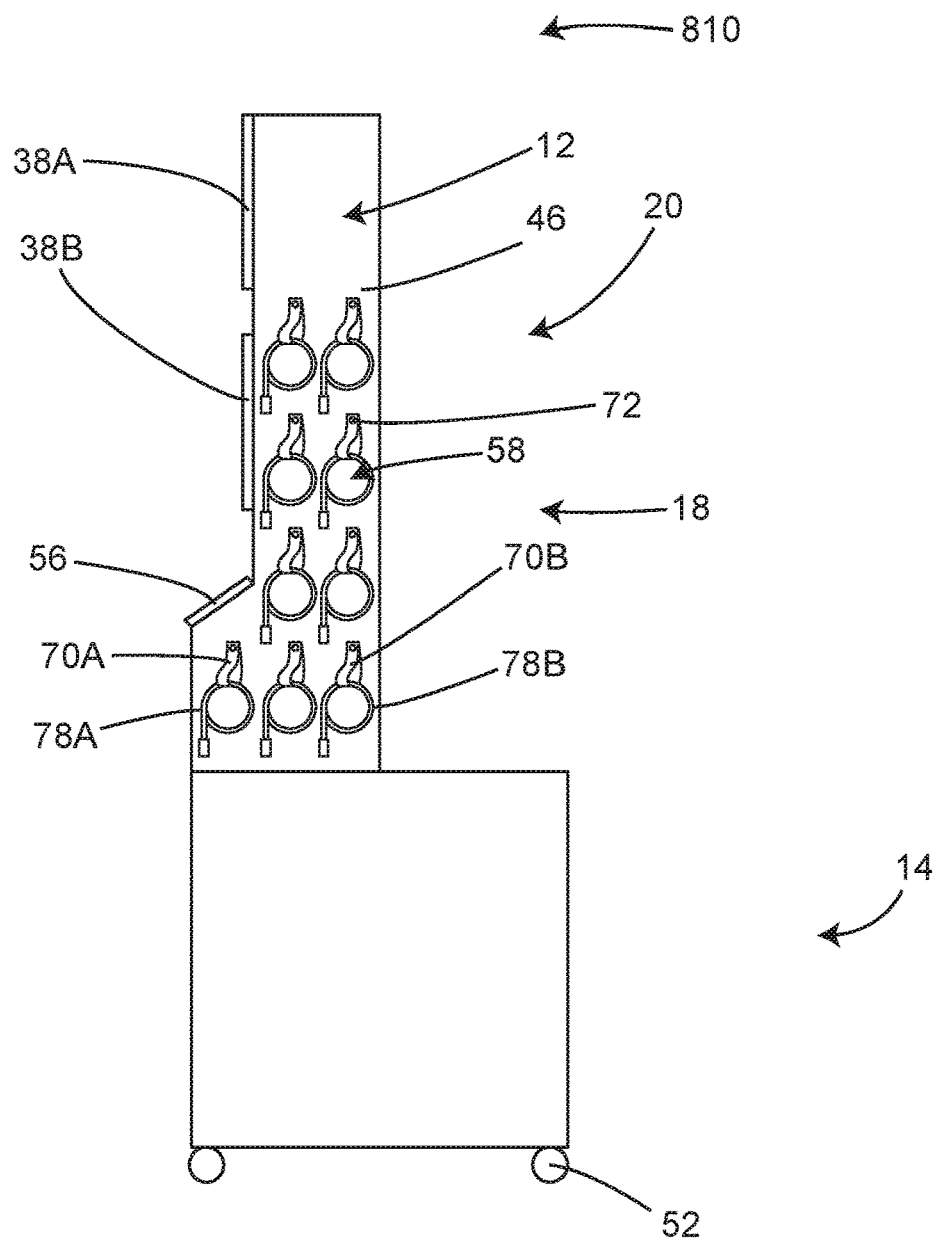
FIG. 8 shows a side view of an illustrative example of a cable and hose management system of the illustrative system of FIG. 4, in accordance with at least one example.

In some examples, and as shown in illustrative module 810 of FIG. 8, the cable and hose management system 58 may comprise one or more straps 70 mounted on the side 46 facing the patient (e.g., configured to face the patient, configured to face the surgical table). In some examples, there may be an array of 3-15 straps 70. Each strap 70 may retain an individual cable or hose. These straps 70 may include a snap, Velcro or other closures means 72 in order to create an openable loop that can retain a coiled cable or hose.

Figure 9:
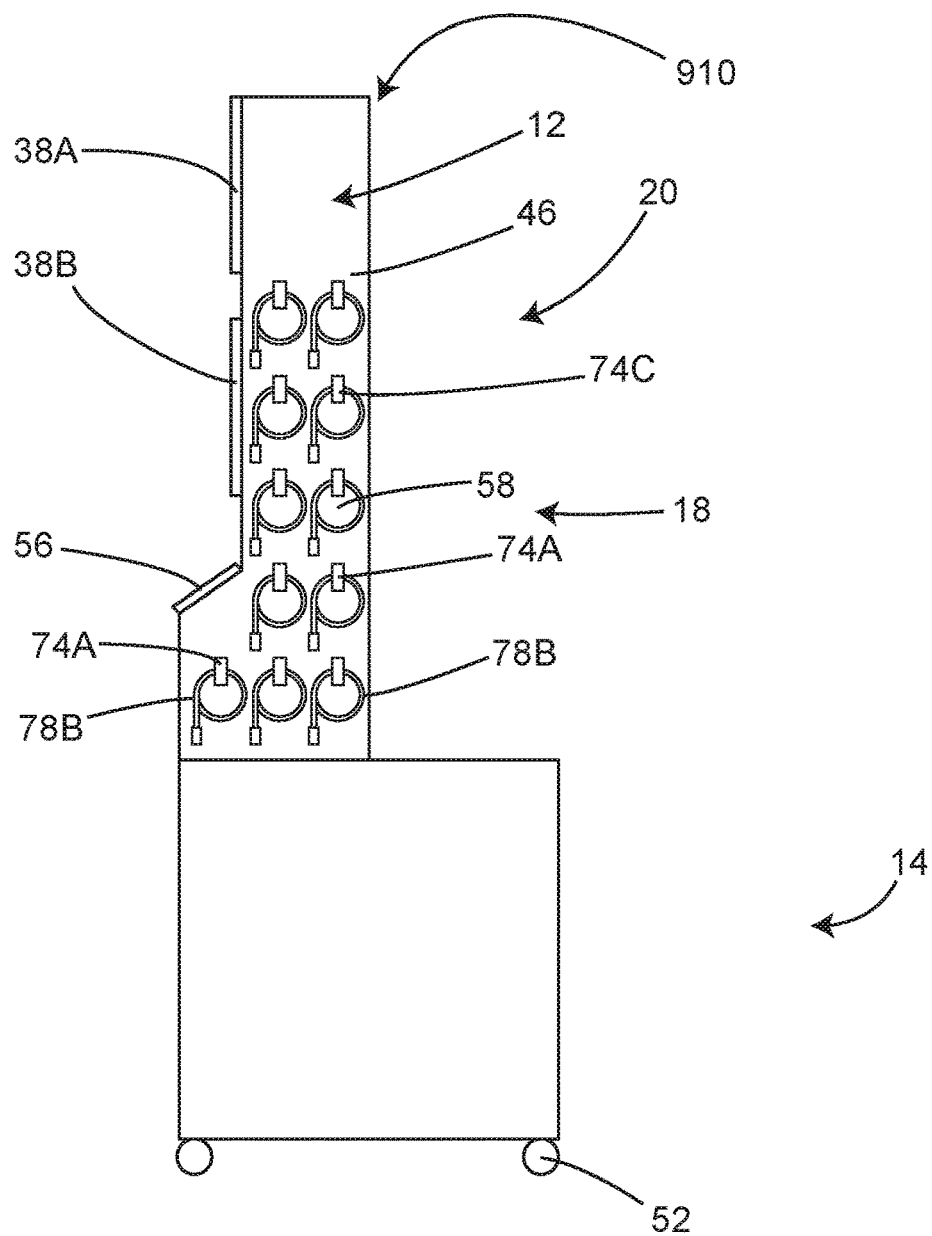
FIG. 9 shows a side view of another illustrative example of a cable and hose management system of the illustrative system of FIG. 4, in accordance with at least one example.

In some examples, as shown in illustrative module 910 of FIG. 9, the cable and hose management system 58 may comprise one or more hooks 74 mounted on the side 46 facing the patient. In some examples, there may be an array of 3-15 hooks 74. Each hook 74 may retain an individual cable or hose.

Figure 10:
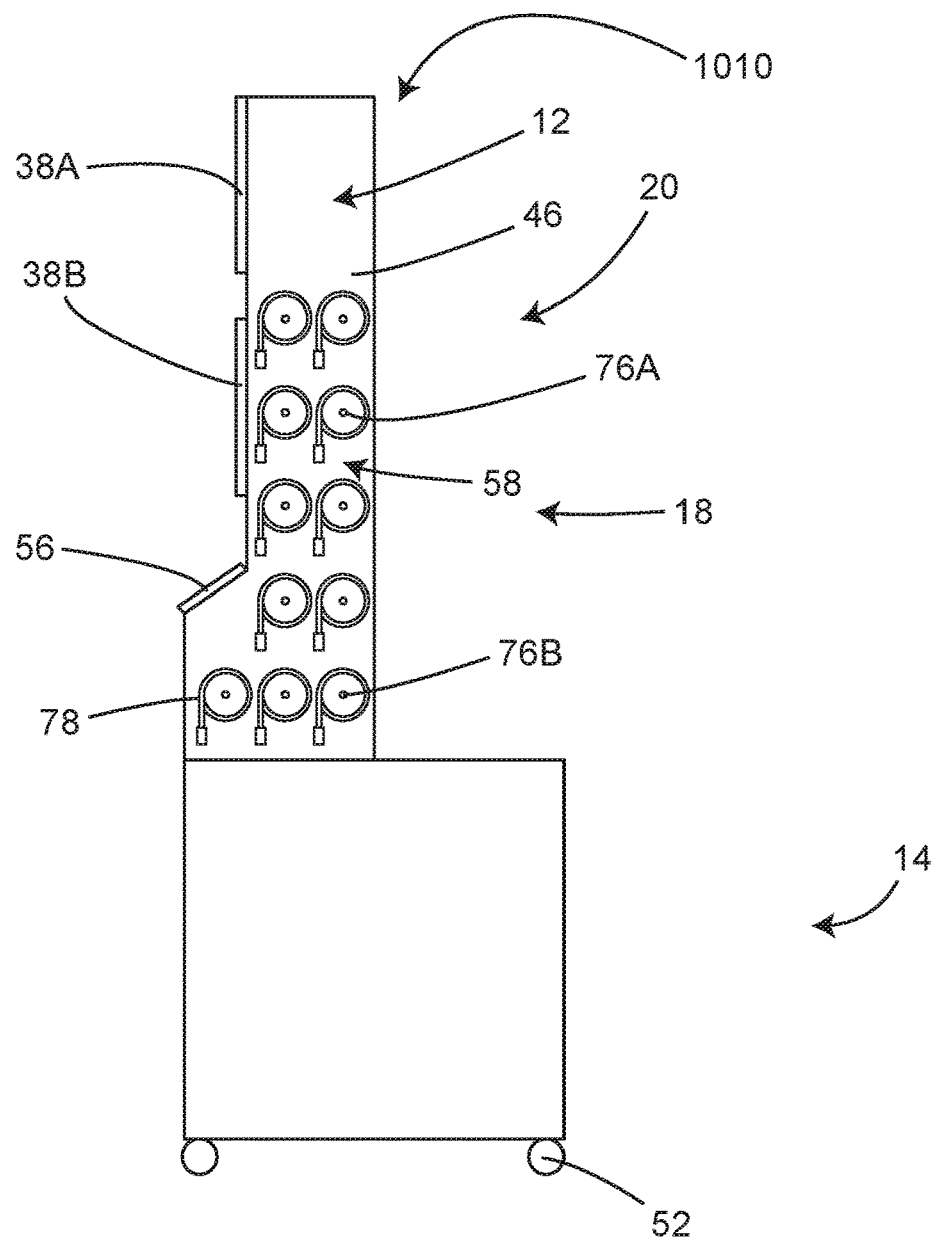
FIG. 10 shows a side view of another illustrative example of a cable and hose management system of the illustrative system of FIG. 4, in accordance with at least one example.

In some examples, as shown in illustrative module 1010 of FIG. 10, the cable and hose management system 58 may comprise one or more reels 76 mounted on the side 46 facing the patient. In some examples, there may be an array of 3-15 reels 76. Each reel 76 may retain an individual cable or hose. These reels 76 may be used to wind the cables and hoses on to a spool for secure storage. The reels 76 may be manually operated, spring powered or powered by electric motors.

Figure 11:
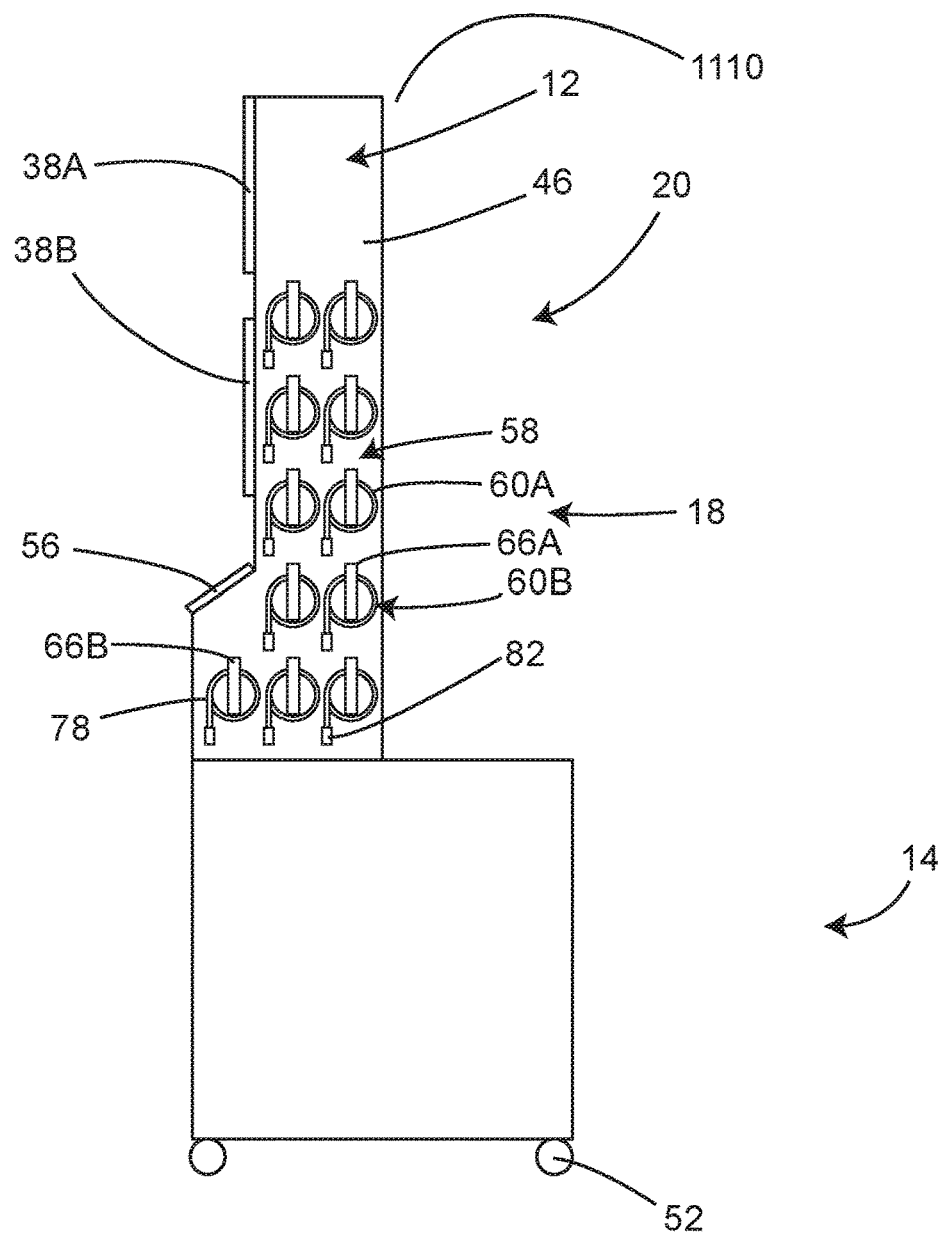
FIG. 11 shows a side view of another illustrative example of a cable and hose management system of the illustrative system of FIG. 4, in accordance with at least one example.
Figure 12:
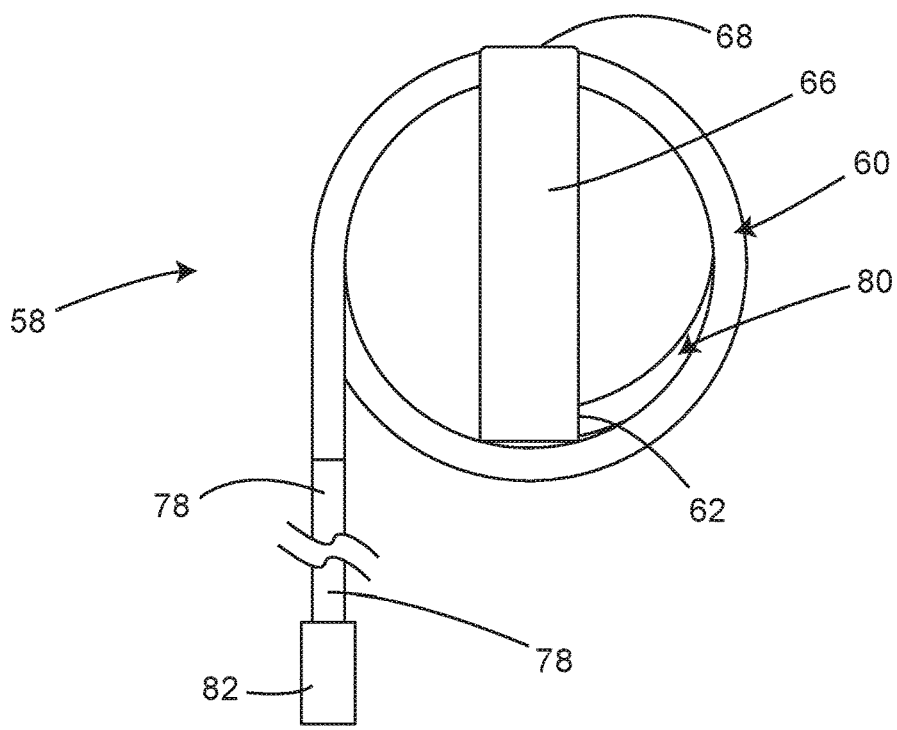
FIG. 12 shows a side view of an illustrative individual cable and hose management system of FIG. 11, in accordance with at least one example.
Figure 13:
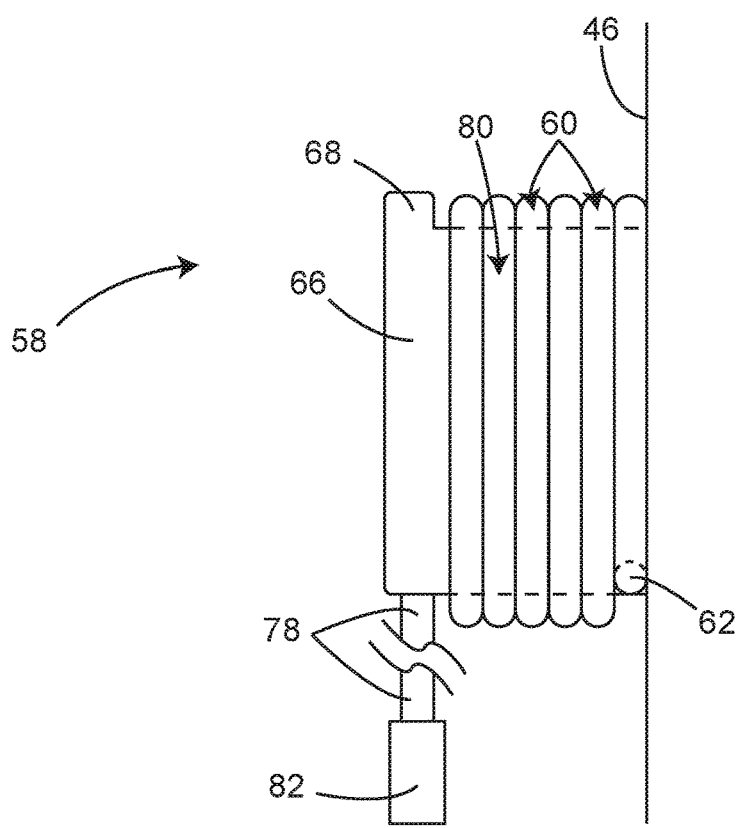
FIG. 13 shows a rear view of an illustrative cord of the cable and hose management system of FIG. 11, in accordance with at least one example.

In some examples, and as shown in illustrative module 1110 in FIG. 11, the cable management system can include cables that are naturally coiled during the molding process of the outer insulation, somewhat like the traditional telephone cord. In some examples, the coils 60 of cable or hose may be much larger than the traditional telephone cord. As shown in FIGS. 12 and 13, coils 60 that are 2-5 inches in diameter, much like a "slinky" may be preferable. Coils 60 of larger diameter may have superior "memory" to retain the coiled shape. Electrical insulation materials such as urethane and nylon also provide superior "memory" characteristics compared to the PVC coating historically used for telephone cords.

Figure 14:
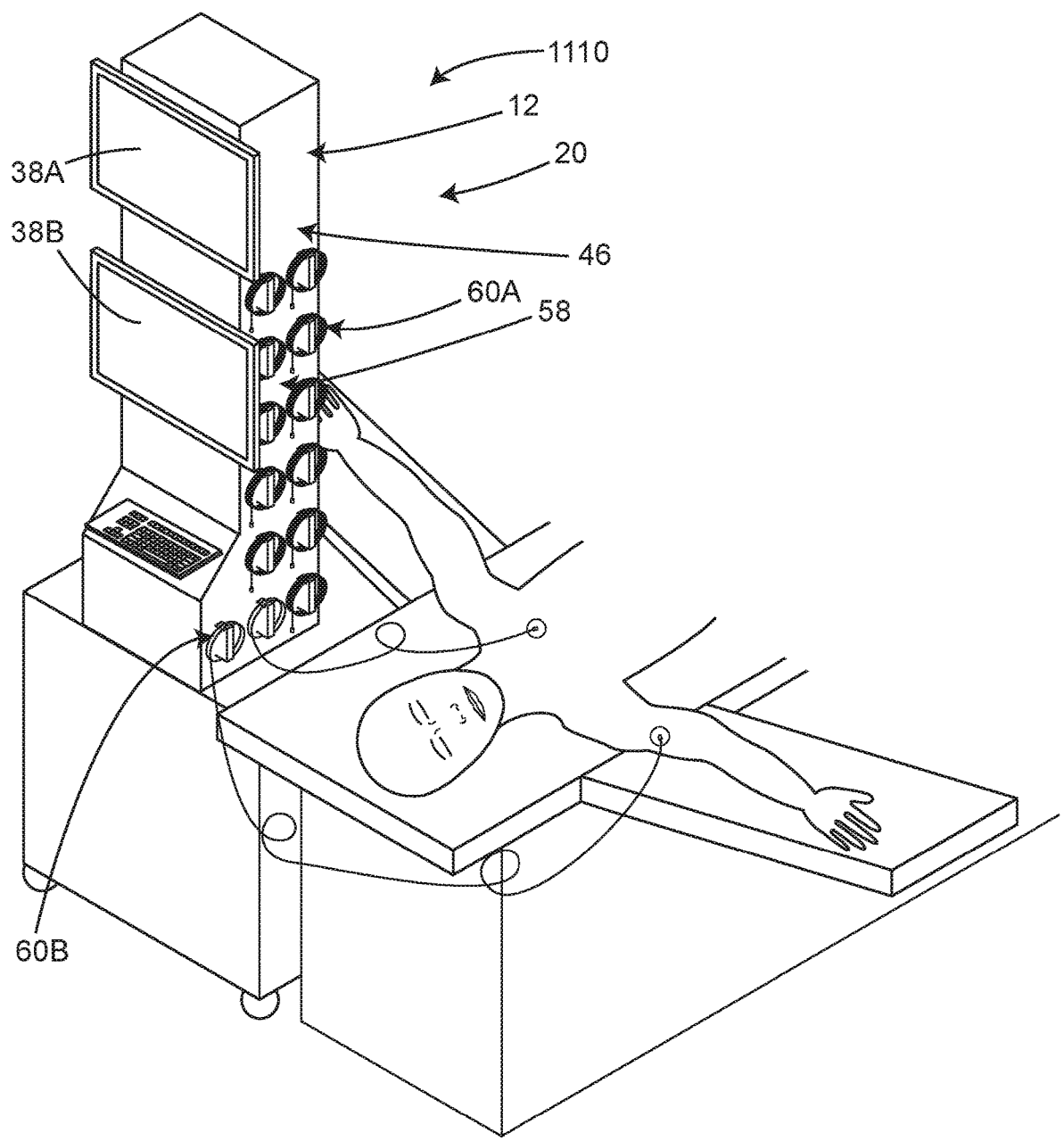
FIG. 14 shows a perspective view of the illustrative system of FIG. 10 with two of the cables unwound and attached to the patient, in accordance with at least one example.

As shown in FIG. 14, these larger coils 60 are easily stretched because the elongation is accomplished primarily by the lateral movement of adjacent coils, perpendicular to the plane of the individual coils, basically elongating the tubular shape, a movement that is minimally opposed by the "memory" of the molding process. This is in contrast to an attempt to unwind each of the individual coils 60, a movement that is maximally opposed by the "memory" of the molding process. The larger coils 60 easily stretch laterally between each adjacent coil 60 and stretch minimally in the plane of each coil 60. This is identical to the principals the make a "slinky" work, very easy to stretch in the direction of the coiled tube but nearly impossible to unwind an individual coil. The larger coils 60 easily stretch laterally between each adjacent coil 60 which makes them far less prone to twisting and tangling than if an individual coil 60 is "unwound."

In some examples the coils 60 of the cable management system 58 are created by extrusion molding an electrically insulating plastic sheath over the wires of the cable. In some examples the coils 60 of the cable management system 58 are created by extrusion molding a coil of plastic tubing 80 and then inserting the wires of the cable 78 into the tubing 80 as a second operation. In some examples, when tubing 80 is used to create the coils 60, the tubing 80 may be 0.25-0.6 inches in outside diameter. Larger tubing 80 diameters may work better with larger coil 60 diameters. In some examples the preferred tubing material is urethane. Any other suitable tubing materials may be used, including but not limited to nylon and PVC.

There are several advantages to adding a cable 78 to a molded coil 60 of plastic tubing 80 as a second process rather than molding the insulation layer of the cable into a coiled shape. The extruded tubing 80 has a thicker outer layer of very uniform extrusion thickness, which results in a more durable outer layer with superior memory for the coiled shape 60. The diameter of the tubing 80 may be significantly greater than an equivalent diameter of extruded cable insulation. The greater diameter of the tubing 80 accentuates the principle that makes a "slinky" work, very easy to stretch in the direction of the coiled tube but difficult to unwind an individual coil 60.

In some examples, one construction is to add 0.5-4 feet of standard cable 78 to the distal end of the coiled tubing 80 and pull the individual wires through the coiled tubing 80 to the proximal end of the tubing 80. In this case, the distal 0.5-4 feet may be a much more flexible cable 78 than the coiled tubing 80 because the cable 78 is not intended to retain a memory for a coiled shape. The tubing 80 and the cable 78 may be made of different materials, or different durometers of the same material, or different stiffness's of the same material for their outer insulation layers, each of which optimize the intended function (coil memory vs. flexibility). The wall thickness of the tubing 80 can also be adjusted to optimize coil memory vs. flexibility.

The 0.5-4 feet of standard cable 78 attached to the distal end of the coiled tubing 80 also presents a lower profile as it encounters the patient. For example, if the cable 78 is an EKG lead laying on top of the patient's chest, a flexible non-coiled wire or cable 78 can be more comfortable than coiled tubing 80.

In some examples, this design optimizes the recoil function at the proximal coiled tubing 80 portion of the cable. This design also optimizes the patient interface for flexibility, low profile and comfort by transitioning from the coiled tubing 80 to a standard cable 78 for the distal 0.5-4 feet.

In some examples as shown in FIGS. 12 and 13, the proximal end 62 of the proximal coil 60 is firmly attached to the side 46 of the module (e.g., 1110, FIG. 11) facing the patient, in order to prevent the tubing 80 from twisting when removed from the storage bracket 66. In some examples, the firm non-twisting attachment may preferably orient the plane of the first coil 60 and thus the planes of all of the coils 60, essentially parallel to the plane of side 46. Orientation of the first coil 60 to be parallel to the plane of side 46 makes the entire stack of coils 60 naturally form into a tubular or stack shape for easy storage. In some examples, a storage bracket 66 protrudes from the side 46 to provide a storage location for the naturally coiled tubing 80 cables and hoses. The natural coiled shape makes loading the tubular stack of coils 60 onto the storage bracket 66 so easy that it almost occurs spontaneously.

Figure 15:
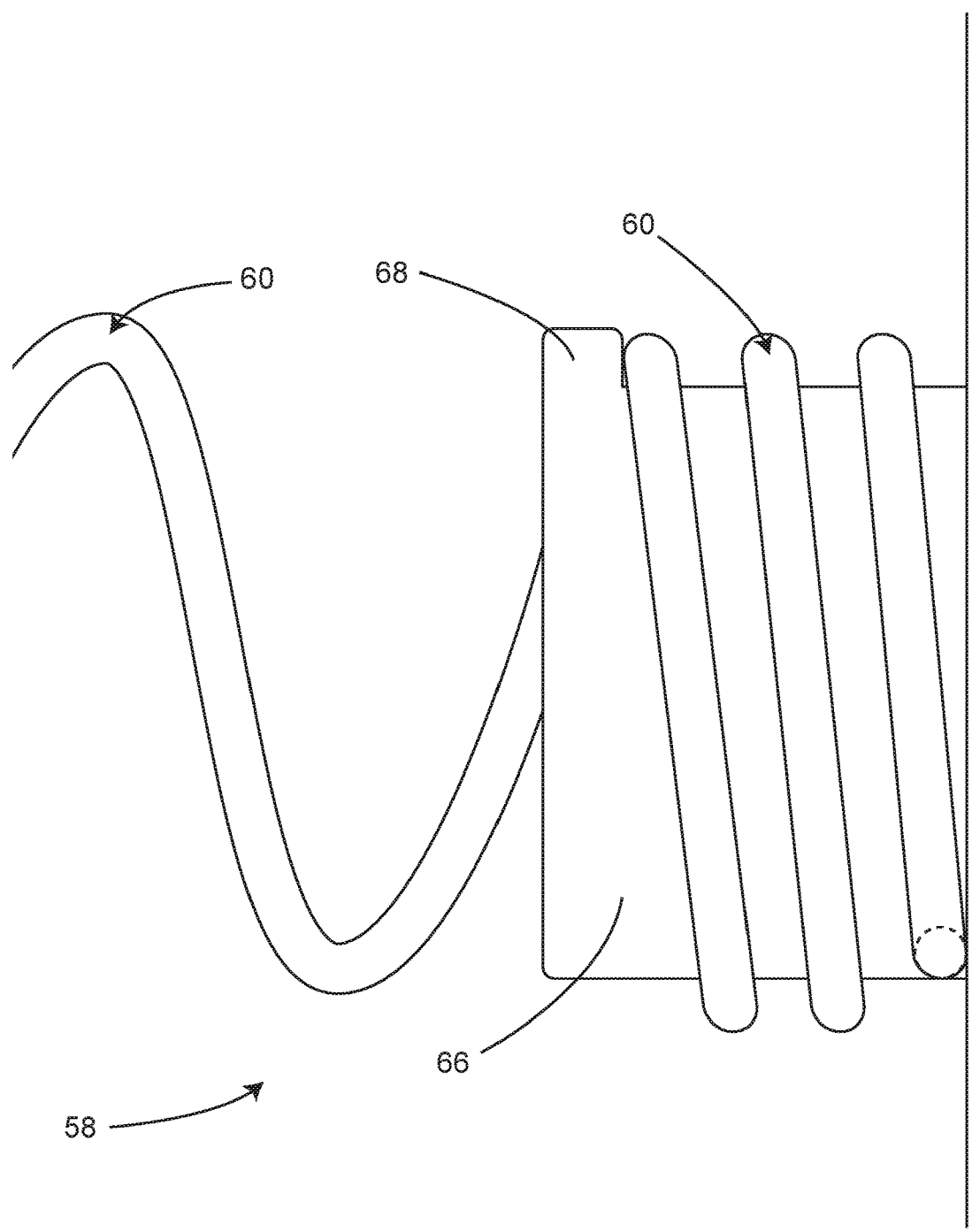
FIG. 15 shows a rear view of a storage bracket and cable of the illustrative system of FIG. 11, in accordance with at least one example.

In some examples as shown in FIGS. 12, 13 and 15, the storage bracket 66 may include a retaining lip 68 that helps to prevent the coils 60 from inadvertently slipping off of the storage bracket 66. In some examples as shown in FIG. 15, the retaining lip 68 may also advantageously allow one or more individual coils 60 to be removed from the storage bracket 66 while retaining the remaining coils 60. This conveniently allows variable lengths of tubing, cables and hoses to be extended from the cable and hose management system 58. Cables and hoses that need to reach further, for example to the foot of the surgical table or to the arm-board on the opposite side of the surgical table, may require all of the coils 60 to be removed from the storage bracket 66 and stretched to their limits. Alternately, if a given cable or hose is only traveling a short distance, for example to the patient's chest or the head end of the mattress, perhaps only one or two individual coils 60 may be removed from storage bracket 66 and the remaining coils 60 are retained on the bracket 66. This minimizes the excess cable and hose from cluttering and tangling.

In some examples, with minimal force six, 3-inch diameter coils 60 of this invention can be stretched perpendicularly to the plane of the individual coils 60, a distance of more than 4 feet. In the stretched configuration, the coils 60 may preferably still exhibit recoil forces but the recoil forces are not so great as to pull the plug or sensor 82 loose from the patient connection.

The recoil of the molded coils 60 naturally cause the adjacent individual coils 60 to form into an orderly stack or tubular shape which can easily be loaded onto the storage bracket 66. Storing the stack of individual coils 60 on a storage bracket 66 helps the individual coils 60 and the stack of coils 60 "rest" and thus may retain their molded "memory" for a coiled shape over years of use.

In some examples, the natural recoil of the coils 60 can advantageously prevent the electrical plug 82 or hose connector from touching the floor when not loaded on the storage bracket 66 and not in use. The natural recoil of the coils 60 may advantageously prevent the plug 82 or hose connector from touching the floor even if the coiled tubing 80, cable 78 or hose is not properly stored on the storage bracket 66. Keeping cables 78 and hoses off of the floor vastly reduces their contamination and need for cleaning. This is in contrast to the current cable and hose situation in the OR, where they typically lay on the floor when not in use.

In some examples the cable and hose management system 58 using coiled tubing 80 may be adapted to a location that is remote to the module 10. In some examples the cable and hose management system 58 using coiled tubing 80 may be adapted to the outer shell or case of another piece of equipment such as a patient warming system or a patient monitor.

Figure 27:
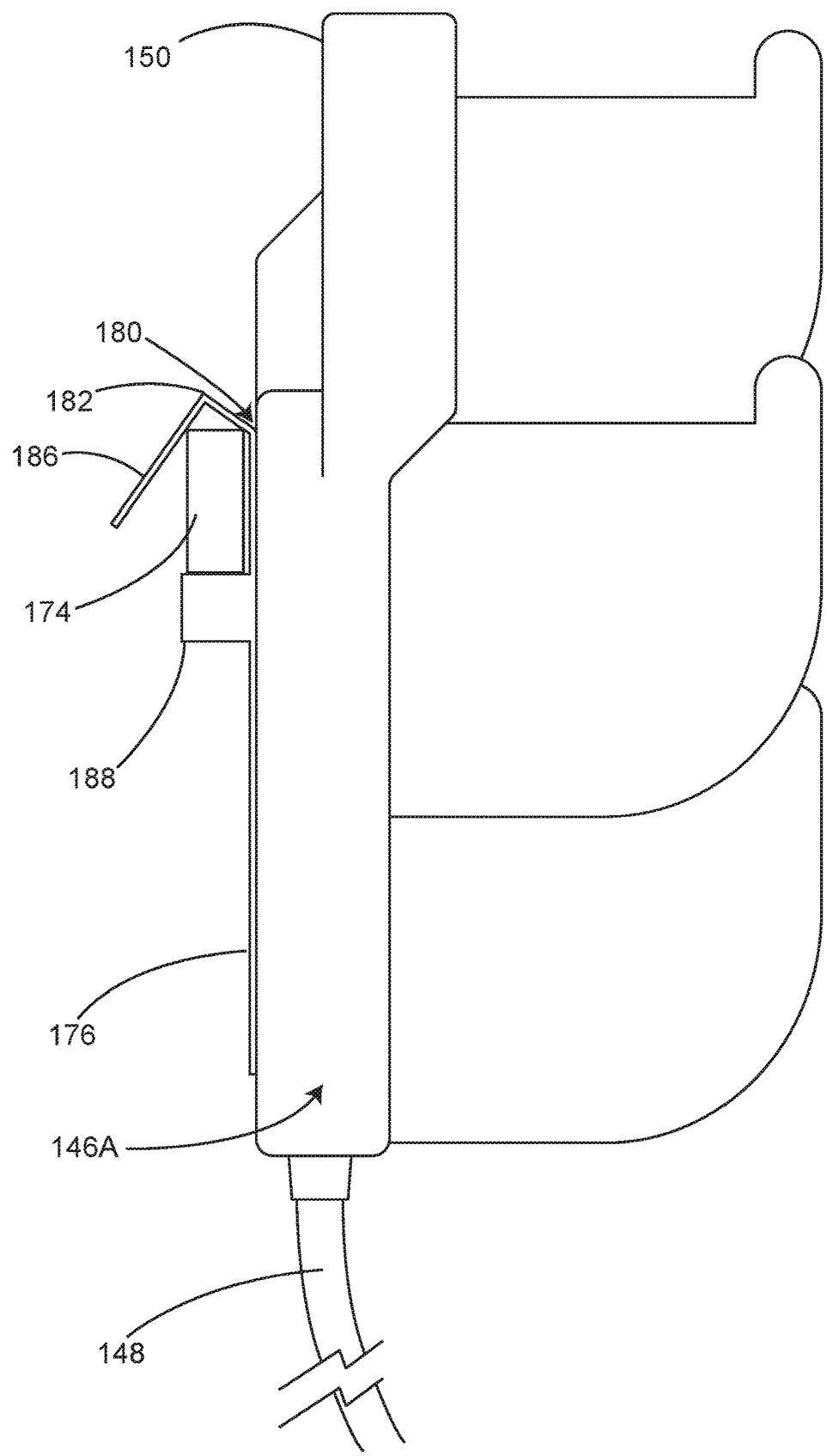
FIG. 27 shows a side view of an illustrative distribution pod hanging from a side rail of a surgical table, in accordance with at least one example.

In some examples, and as shown in FIG. 27, the cable and hose management system 58 (e.g., FIGS. 8-15), rather than being included in module (e.g., 10 and example variants of 10), may be adapted to be a free-standing distribution pod 146A that may be attached to the side of the surgical table 22 and may be used to distribute and connect the distal end of the wires contained in a trunk cable 148, to the patient 24 and surgical table 22. In some examples the cable and hose management system 58 adapted to a free-standing distribution pod 146A includes coiled cables 60, coiled tubing 80, cables 78, mounting and storage brackets 66 previously described that may be advantageously used to store the cables and hoses for various surgical and anesthetic equipment and monitors in a convenient location immediately adjacent the patient (e.g., FIGS. 8-15). Attaching the free-standing distribution pod 146A to the side rail of the surgical table 22, locates the pod 146A as close to the patient as possible keeping cable and hose lengths reaching to the patient as short as physically possible. Short hoses and cables result in less tangling, less chance of laying on the floor and are easier to clean and store.

In some examples the cable and hose management system 58 adapted to a free-standing distribution pod 146A, is attached to one end of a trunk cable 148 and the other end of the trunk cable may be attached to any electronic or electrical equipment including but not limited to: the module 10, a patient warming controller, a patient monitor, air mattress controls, an electrosurgical generator, an automated blood pressure monitor or sequential compression legging controls. The trunk cable combines all of the wires from the individual cables into a single multi-wire cable in order to reduce the number of wires that can tangle and require cleaning.

In some examples, the free-standing distribution pod 146A includes a substantially waterproof shell 150. In some examples the distribution pod 146A, like the module 10, can include a fluid-resistant or heat confining cowling. In addition to the trunk cable 148, the inputs and outputs to the shell 150 of distribution pod 146A include but are not limited to: coiled cables 60, coiled tubing 80, cables 78, electrical plug-ins 152, air hose and vacuum hose connectors. In some examples, the free-standing distribution pod 146A may include air pumps, vacuum pumps and monitor electronics housed in the shell 150.

In some examples, the free-standing distribution pod 146A may be attached to the proximal end of a second trunk cable, the distal end of which may be attached to a second free-standing distribution pod (e.g., a second one of 146A). In effect, the two distribution pods 146A may be "daisy chained" together via the second trunk cable and in this case the first trunk cable 148 includes the combined wires for both distribution pods 146A, connecting back to the originating electronic and electrical equipment. In some examples for example, the second free-standing distribution pod 146A may distribute the cables and hoses that connect the patient to the patient monitors. In this case the first free-standing distribution pod 146A may distribute the cables connecting the patient warming blankets and mattresses to the patient warming controller. The second trunk cable may also include electrical power to the second free-standing distribution pod 146A for powering various electronics and pumps that may be housed within its shell 150.

Figure 32A:
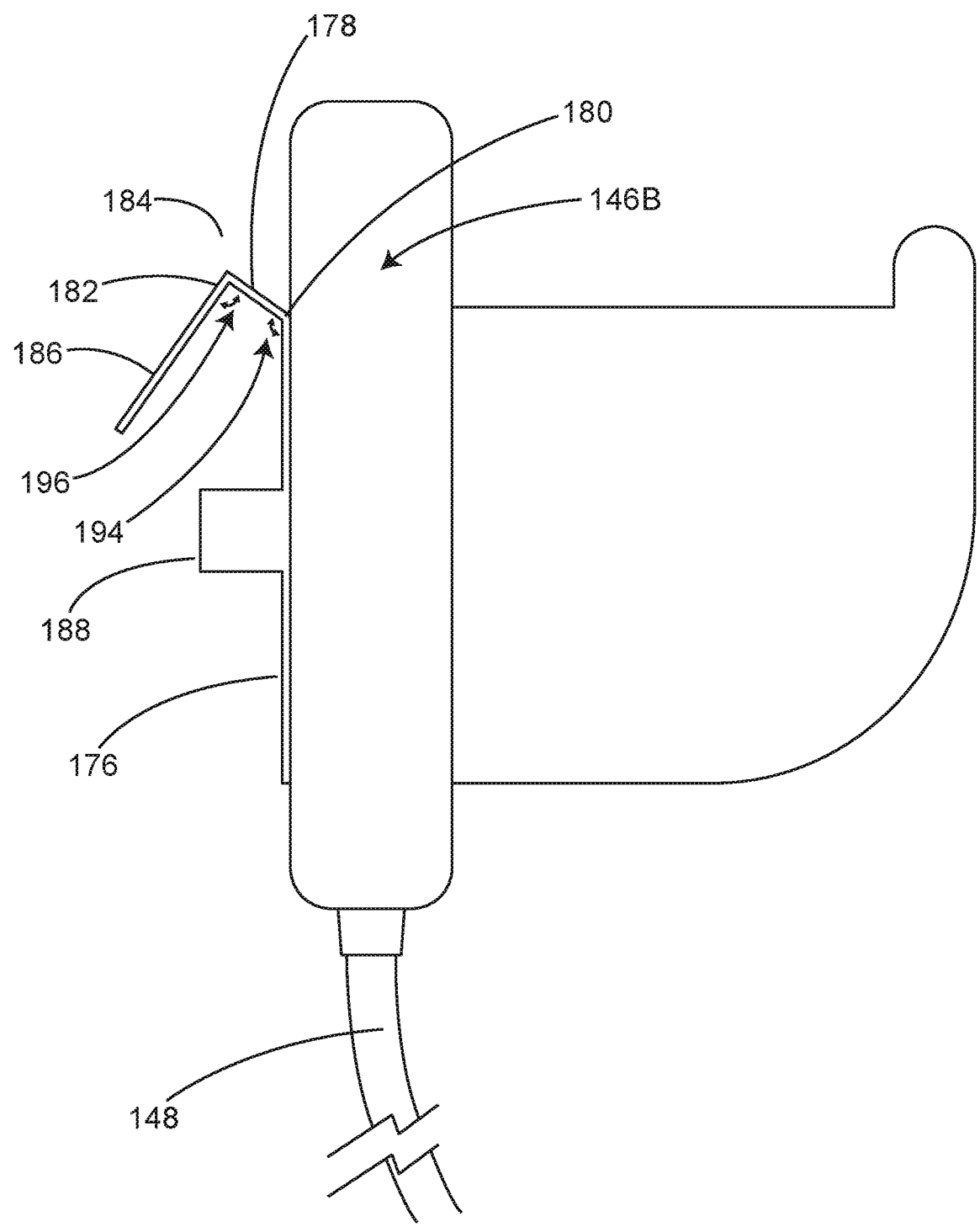
FIG. 32A shows a side view of an illustrative distribution pod not attached to a side rail, in accordance with at least one example.

In some examples, the free-standing distribution pod 146A or other pieces of surgical equipment, may be removably attached to one of the rails 174 that run along the sides of the surgical table 22. FIG. 32A shows another example of a distribution pod 146B that can include all the features of distribution pod 146A and vice-versa. As shown in FIG. 32A, the attachment mechanism for removably attaching the distribution pod 146B to one of the rails 174 may comprise a metal plate 176, mounted on the back side of the distribution pod 146B. The upper edge 178 of the metal plate 176 may be bent into a generally "hooked" shape for hanging on the side rail 174. In some examples, the upper edge 178 may be attached to a "side rail" element that is included in the module 10.

In some examples, and as shown in FIG. 32A, the generally "hooked" shape of the upper edge 178 of the metal plate 176 may be formed by bending the metal plate 176 twice. In some examples, the first bend 180 in metal plate 176, nearest the mounting to the back side of the distribution pod 146B or other pieces of surgical equipment, may create a first angle 194 of greater than 90° between the metal plate 176 and the top of the "hook" 184. In some examples, the first bend 180 in metal plate 176, nearest the mounting to the back side of the distribution pod 146B or other pieces of surgical equipment, may create an angle of 95° to 135° between the metal plate 176 and the top of the "hook" 184. In some examples, the second bend 182 in metal plate 176 creates the retaining lip portion 186 of the generally "hooked" shape 184, may create a second angle 196 of approximately 90° between the top of the "hook" 184 and the retaining lip portion 186. In some examples, the distance between first bend 180 in metal plate 176 and the second bend 182 as measured on the inside of the "hook" 184, may be equal or slightly more than the width of the rail 174. The standard width of rail 174 is ⅜".

In some examples, one or more retainer tabs 188 are located slightly more than one rail height below the first bend 180 in metal plate 176. The standard height of rail 174 is 1⅛". The retainer tabs 188 may be formed by bending the metal plate 176 along a vertical axis. In some examples, the retainer tabs 188 may be located near the lateral edges of metal plate 176. In some examples, the retainer tab 188 may be formed by welding or attaching an added piece of metal to protrude from the back side of metal plate 176.

Figure 32B:
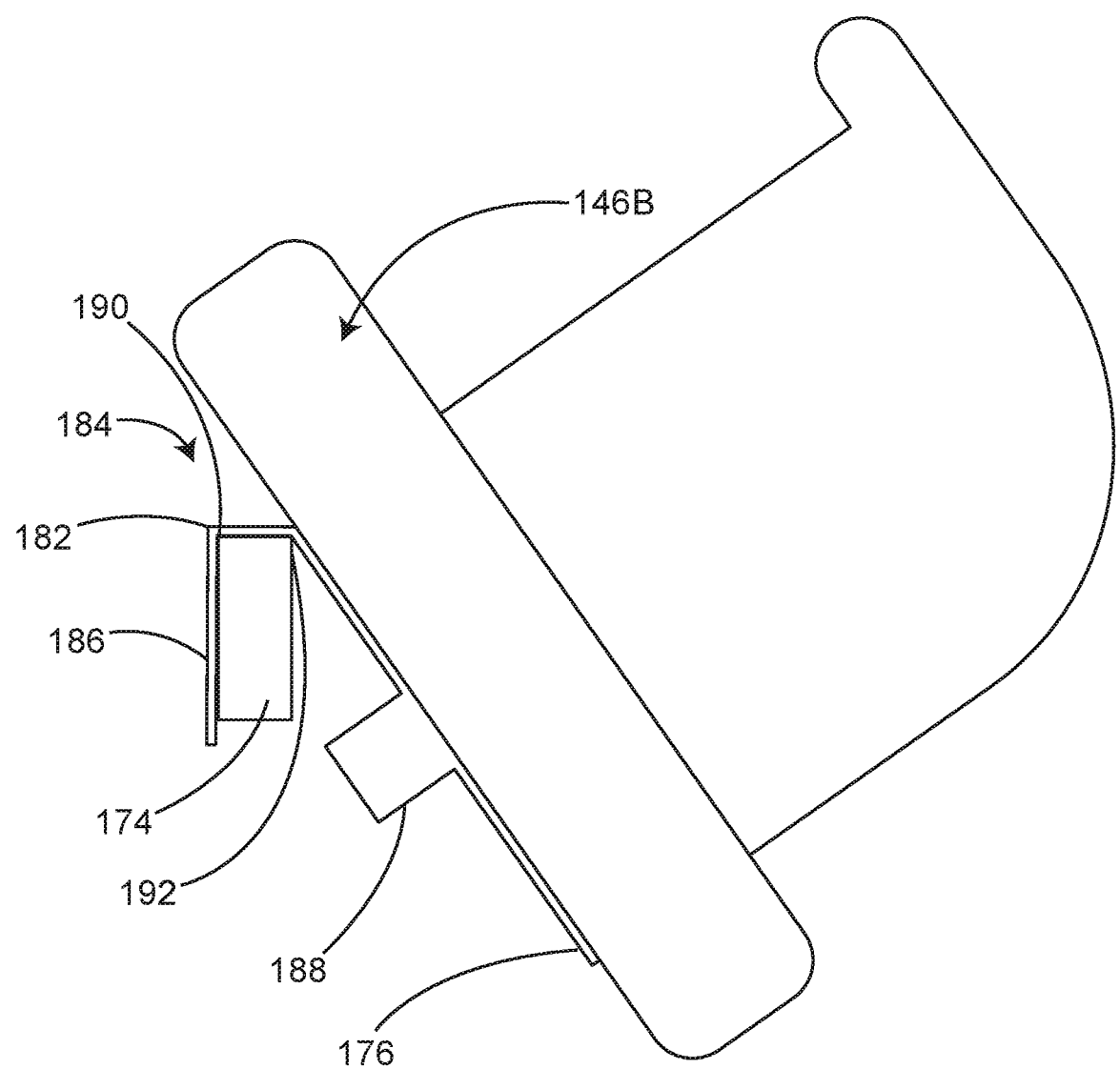
FIG. 32B shows a side view of a distribution pod angled and being placed on to a side rail, in accordance with at least one example.
Figure 32C:
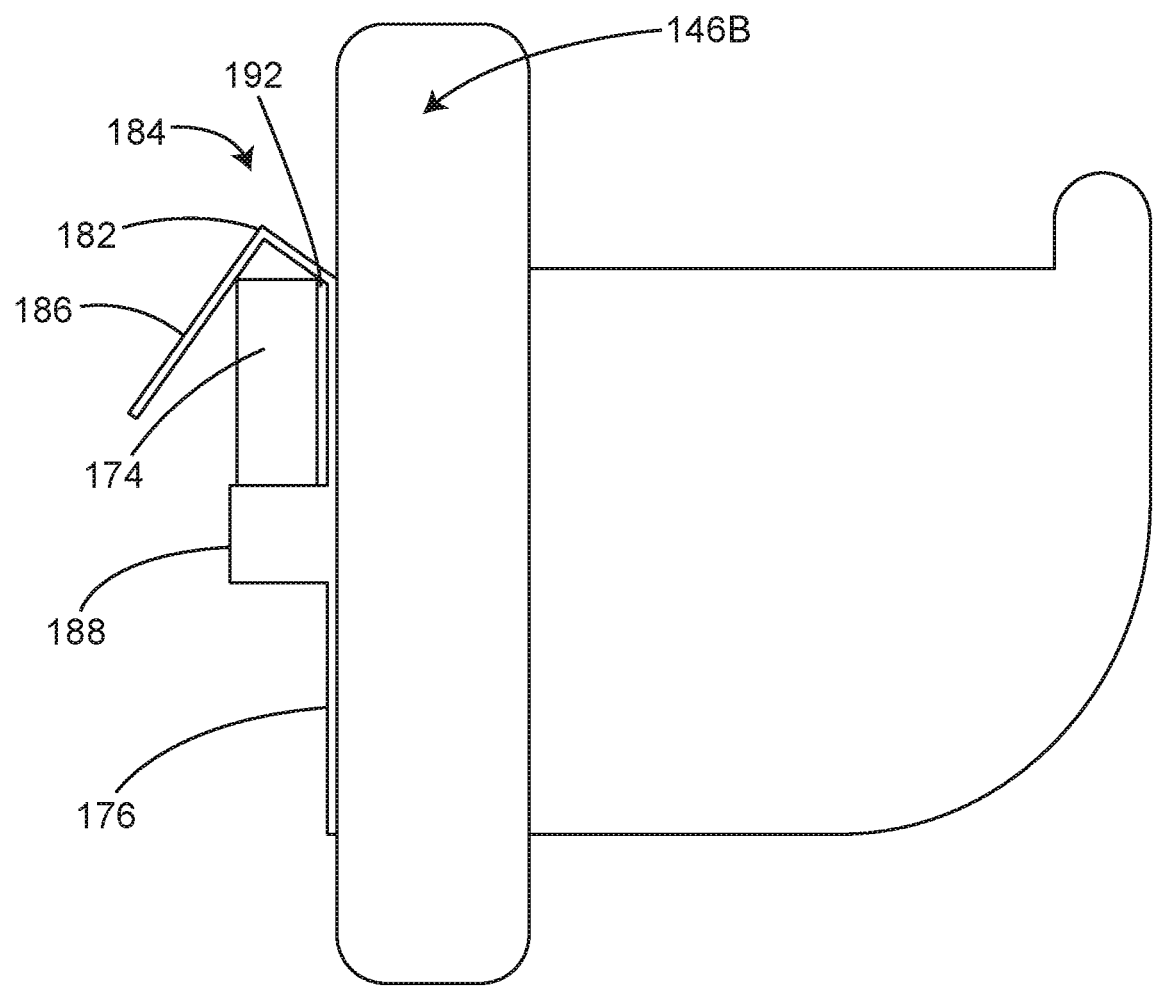
FIG. 32C shows a side view of a distribution pod attached to and hanging from a side rail, in accordance with at least one example.

In some examples, the first bend 180 creating an angle of greater than 90° between the metal plate 176 and the top of the "hook" 184 and the second bend 182 creating an angle of approximately 90° between the top of the "hook" 184 and the retaining lip portion 186, allows the retaining lip portion 186 to be angled outward relative to the plane of metal plate 176. As shown in FIG. 32B, the outward angle of the retaining lip portion 186 allows the bottom portion of the distribution pod 146B or other pieces of surgical equipment to be pivoted away from the side of the surgical table 22 while the retaining lip portion 186 initially engages rail 174. In this orientation one or more retainer tabs 188 clear the outer side of rail 174 while the rail 174 is engaging the "hook" 184. As shown in FIG. 32C, the bottom portion of the distribution pod 146B or other pieces of surgical equipment are then rotated toward the side of the surgical table 22, engaging retainer tabs 188 under the rail 174. The snug fit of retainer tabs 188 under the rail 174 secures the distribution pod 146B or other pieces of surgical equipment to the rail 174. The snug fit of retainer tabs 188 under the rail 174 is allowed because the first bend 180 creates an angle of greater than 90° between the metal plate 176 and the top of the "hook" 184, and becomes the axis of rotation against the upper, outer angle 190 of rail 174, when the distribution pod 146B or other pieces of surgical equipment are rotated toward the side of the surgical table, engaging retainer tabs 188 under the rail 174. Therefore, the distance between the first bend 180 and the top of the retainer tabs 188 can be exactly the height of the rail 174, in order to create a snug fit between retainer tabs 188 underside of rail 174.

In contrast, when both the first bend 180 and the second bend 182 create angles of approximately 90°, the distance between the bends have to be much greater than the width of the rail 174 in order to allow distribution pod 146B or other pieces of surgical equipment to be angled away from the side of the surgical table, allowing retainer tabs 188 to clear the outer side of rail 174, while the rail 174 is engaging the "hook" 184 during mounting. Additionally, when both the first bend 180 and the second bend 182 created angles of approximately 90°, the axis of rotation during the rotation of the distribution pod 146B or other pieces of surgical equipment toward the side of the surgical table 22, would be somewhere between first bend 180 and the second bend 182 and the axis of rotation would against the upper, inner angle 192 of rail 174. In this arrangement, the first bend 180 has to be elevated off the upper surface of rail 174 when the distribution pod 146B or other pieces of surgical equipment are rotated away from the side of the surgical table 22. With this unfavorable axis of rotation, the distance between the first bend 180 and the top of the retainer tabs 188 may have to be significantly greater than the height of the rail 174, in order for retainer tabs 188 to rotate under the rail 174. When the distance between the first bend 180 and the top of the retainer tabs 188 is significantly greater than the height of the rail 174, the retainer tabs 188 can fail to snuggly and securely attach the distribution pod 146B or other pieces of surgical equipment to the rail 174.

In some examples, the simple but secure attachment of the distribution pod 146B or other pieces of surgical equipment to rail 174, can prevent accidental detachment, falling and damage to the equipment. Detachment of the distribution pod 146B or other pieces of surgical equipment from rail 174 is accomplished by rotating the bottom portion of the distribution pod 146B or other pieces of surgical equipment outward, away from the side of the surgical table 22, which disengages the retainer tabs 188 from under the rail 174. Then lifting the distribution pod 146B to disengage the "hook" 184 from the rail 174.

Traditionally, electric power cords, air hoses, oxygen hoses, vacuum hoses and communications wires hanging from the ceiling of the OR, disrupt workflow and create hazards to personnel movement when not hooked to their intended equipment. Traditionally, electric power cords, air hoses, oxygen hoses, vacuum hoses and communications wires hanging from the ceiling of the OR are limited in length so as to not touch the floor when hanging free. This limited length severely limits the movement and flexibility of location for the anesthesia gas machine or any other any other equipment to which they may be hooked. The gas machine must be located directly below the ceiling outlets. In some examples, power cords, communication cables, air, oxygen and vacuum hoses from the ceiling can be more safely and unobtrusively connected to the top of a taller tower-like upper section 20.

In some examples, power cords, air hoses, oxygen hoses, vacuum hoses and communications wires are coiled similarly to coils of the cable management system 58 disclosed herein. In some examples, the coils are created by extrusion molding a coil of plastic tubing and then inserting the wires of the cable or cord into the tubing as a second operation. In some examples, the coils are created by extrusion molding a coil of plastic tubing for air hoses, oxygen hoses and vacuum hoses. In some examples, the coiled plastic tubing portion comprises the proximal end of the cable or hose, the end attached to the ceiling. The coiled tubing may be any length but may preferably be 6-16 feet when stretched in some examples.

In some examples, nylon may be the preferred material for the coiled tubing because of its superior springiness and memory, however, any suitable material may be used. The coiled portion allows the cables and hoses to be stretched and elongated, which greatly increases the floor area where the given OR equipment may be located, increasing the flexibility of the OR layout. The stretchable tubing also decreases the number of ceiling connection locations that are necessary to provide connection options for the whole OR.

In some examples, a "tail" portion (e.g., like 78 in FIG. 12) of relatively straight, relatively flexible cord, cable, tubing or hose is attached to the distal end of the coiled tubing hanging near the ceiling. In some examples, the transition between the coiled portion and the tail portion does not require the connection of two dissimilar materials. In some examples, the coiled tubing may be simply be straightened in a heating process that relaxes the memory of the coil. In this case the coiled portion and the tail portion are the proximal and distal ends of the same piece of tubing. In some examples, the tail portion hangs down to a level that can be reasonably reached by a person standing on the floor, and yet not hang down far enough to hit OR personnel in the head when not attached to equipment. In some examples, the distal end of the tail portion terminates approximately 7 feet above the floor. The coiled portion allows the stretched cables and hoses to recoil when not hooked to equipment, thus naturally lifting the distal connectors up to a level that can protect OR personnel from being hit in the head. The relatively straight tail portion reduces visual clutter hanging from the ceiling and reduces the chances of adjacent cables and hoses tangling when connected to a given piece of equipment.

In some examples, the coiled cords, cables, tubing or hoses may be attached near the distal end of a light-weight arm that can rotate around an axis near its proximal end. The proximal end of the arm can be attached to the ceiling at the axis. The supply lines for the cords, cables, tubing or hoses emerge from the ceiling near the axis and then run toward the distal end of the arm where they hook to the coiled cords, cables, tubing or hoses that can be pulled down and attached to the module 10. The rotation of the arm around its axis creates an arc that covers a large area of the ceiling and allows significant flexibility in where the coiled cords, cables, tubing or hoses may conveniently hang down to be attached to the module 10 or other surgical equipment.

Waste air is currently discharged from every piece of electrical and electromechanical surgical and anesthesia equipment in the operating room. The discharged air is simply blown into the operating room, usually near the floor where the given piece of equipment is located. Waste heat and air discharged near the floor has been shown to form into rising convection currents of heated air that can carry infectious contaminates from the floor up and into the sterile surgical field. Waste heat vented near the floor is a dangerous surgical infection risk. Contaminated waste air blowing from heater-cooler units has been genetically linked to heart valve infections.

The problem is that all electronic and electromechanical equipment produce waste heat that must be dissipated, or the equipment can be damaged. Typically, this is accomplished with a cooling fan that simply discharges the waste heat and waste air into the operating room. Additionally, some pieces of surgical and anesthesia equipment such as forced-air warming, produce heated air on purpose and then it becomes heated waste air. The waste air and heat from forced-air warming can cause contamination of the sterile surgical field and cause implant infections. Discharging waste heated air into the operating room, especially close to the surgical table and sterile field, is dangerous because it causes contamination of the sterile filed which has been linked to implant infections, especially joint implant infections. Therefore, this waste air and heat should be vacuumed, processed and safely discharged in order to prevent sterile surgical field contamination and catastrophic implant infections.

In other examples, the vacuumed air from the surgical field such as surgical smoke evacuation or ventilation deadzone evacuation or waste oxygen and alcohol evacuation, must also be processed and safely discharged.

Figure 16:
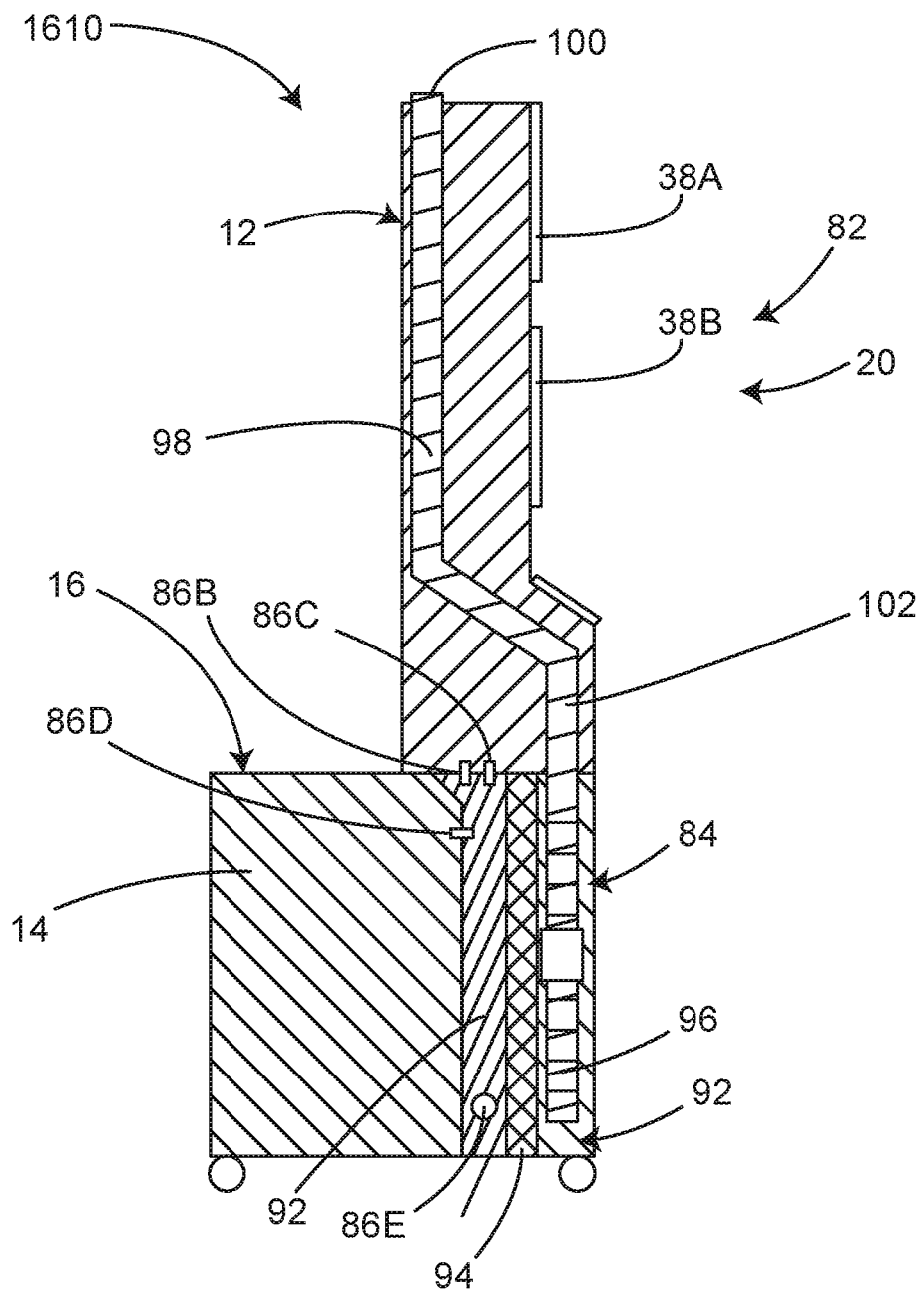
FIG. 16 shows a side view depicting internal components of an illustrative waste air management system that can be used with the system of FIG. 11, in accordance with at least one example.
Figure 17:
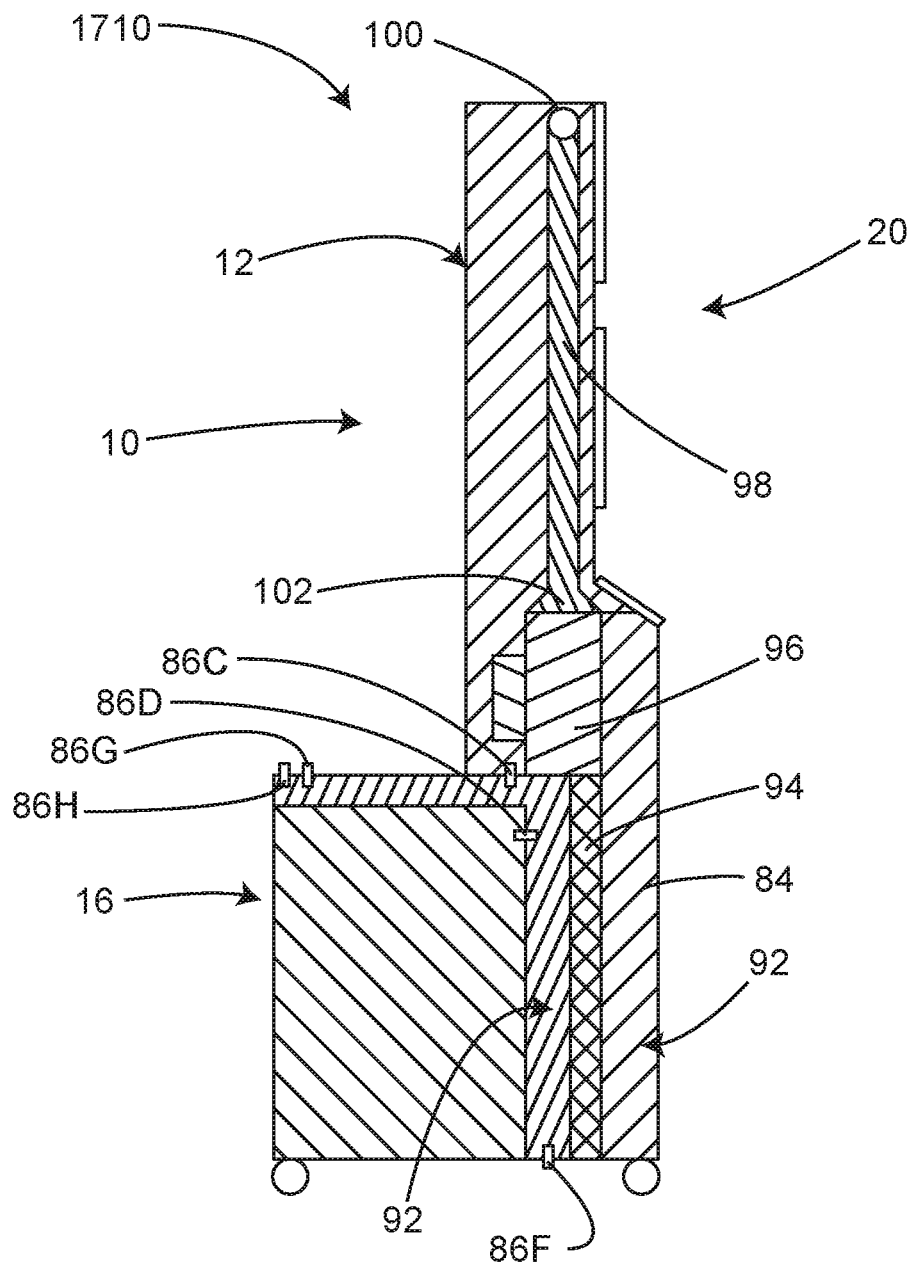
FIG. 17 shows a side view depicting internal components of another illustrative waste air management system that can be used with the system of FIG. 11, in accordance with at least one example.

In some examples, and as shown in illustrative module 1610 of FIGS. 16 and 17, the modules 1610 and 1710 can include a waste air management system 84. The waste air management system 84 may include an inlet vent 86 with a connector 88 that can connect to one or more vacuum hoses 90 (FIG. 20, 22) designed to vacuum waste air from a specific location. In some examples, where more than one inlet vent 86 is provided (e.g., 86, 86B-86H, it may be advantageous to have the various air and vacuum hoses 90 connected (e.g., operably couplable) to the waste air management system 84 by way of "keyed" connections 88 (FIG. 20, 22) so they are not mistakenly attached to the wrong inlet 86, 86B-86H. For example, the hose connection 88 may be any other shape than the traditional round shape, for example: triangular, square, five or six sided, oval, diamond shaped or any other shape. In some examples, the inlet vents 86, 86B-86H on the waste air management system 84 and the connectors 88 on the specific vacuum hose 90 may be color coded for easy identification.

In some examples, the waste air management system 84 includes an air plenum 92 containing an air filter 94. The filter 94 may advantageously be a HEPA (99.97% efficient) or "near HEPA" filter. The one or more air inlet vents 86, 86B-86H can allow waste air to enter the plenum 92 from either the equipment housed in the module 1610 or from external equipment sources. As previously described, a flapper door could be provided at the inlet vents 86 into the housing or into the plenum in order to keep the inlet vents 86 closed unless being used. In some examples, a low filtration efficiency pre-filter may be placed near the inlet vents 86 in order to prevent organic contaminates such as airborne body fluids, bone or tissue fragments, from entering and contaminating the interior of the waste air management system 84.

In some examples, plenum 92 may contain a particle ionizer that may be located in the airflow path before the filter 94. The particle ionizer adds electrical charges to the suspended particles in the airflow path, causing them to stick together and become larger. Larger particles are easier to capture in the filter 94 and thus the filtration efficiency of the entire waste air management system 84 is improved. In many cases, adding electrical charges to bacteria also results in killing the bacteria.

In some examples, inlet vents 86 may be purposefully located near the floor or even facing the floor and located under the module 10. When the waste air management system 84 has excess capacity compared to the amount of air being vacuumed from the surgical field and needed for equipment cooling, inlet vents 86 located near the floor may be opened to allow the intake of contaminated air from near the floor. For example, when the vacuum created by the fan 96 is greater than a specified amount, inlet vents near the floor automatically open up (either electronically or mechanically) to evacuate contaminated air from under the table so that when the surgeon is standing next to the table and moves around, the surgeon doesn't stir up particles.

The contaminated air from near the floor can then be filtered by the waste air management system 84 and discharged as clean air back into the operating room. In so doing, the waste air management system 84 uses its excess air cleaning capacity to decrease the total number of airborne contaminating particles in the OR and thus reducing the risk of surgical implant infections. This is particularly advantageous because it is uniquely vacuuming and filtering the contaminated air from near the floor adjacent the surgical table that has the highest probability of reaching the sterile surgical field.

In some examples, a fan 96 (e.g., any suitable blower) can propel waste air received via inlet vents 86 through the filter 94 and exhaust the waste air from the plenum 92 into a substantially vertical vent tube 98. In some examples, the substantially vertical vent tube 98 extends upward to a height of more than 5 feet above the floor, before discharging the processed waste air from outlet vents 100 near the top of the substantially vertical vent tube 98. In some examples, a sock-like filter may be added to the outlet vent 100 in order to diffuse the outlet air and muffle any fan noise. In some examples, the vertical vent tube can be any shaped channel configured to guide the flow of air. In some examples the vertical vent tube includes directing air more vertically than horizontally with respect to a ground the module is configured to be paced on. In some examples, the vertical vent tube can be linear, angled, bent or curved portions or can be solely linear, angled, bent or curved, such that discharging the waste air upward is achieved.

In some examples, the inlet vent 86 is attached to an air plenum 92 located in the module 1610. The air plenum 92 can be designed to direct inlet air through a filter 94 and fan 96 before safely discharging it into the operating room. In some examples, the filter 94 is located in the airflow path before the fan 96 so that the air contacting the fan 96 has already been cleaned by the filter 94. Contaminated air has been shown to contaminate fans, which are very difficult to clean and may aerosolize contaminates into the discharged air. In some examples, the fan 96 may be located between the air inlet vent 86 and the filter 94. In some examples, all of the ducting and plenums of the waste air management system 84, are accessible on their internal surfaces for cleaning and decontamination.

In some examples, the filtered waste air is then directed through ducting 102 which functions as a substantially vertical vent tube 98, up the tower-like upper section 20, to be vented 100 out near the top of the tower-like upper section 20. In some examples, the filtered waste air is then directed through the cowling 12 of the tower-like upper section 20 which functions as a substantially vertical vent tube 98, to be vented out 100 near the top of the tower-like upper section 20. In some examples, a sock-like filter may be added to the outlet vent 100 in order to diffuse the outlet air and muffle any fan noise.

In some examples, the substantially vertical vent tube 98 may be a rigid tube. In some examples, the substantially vertical vent tube 98 may be the tower-like upper section 20 of the module (e.g., 1610 and 1710).

Figure 18:
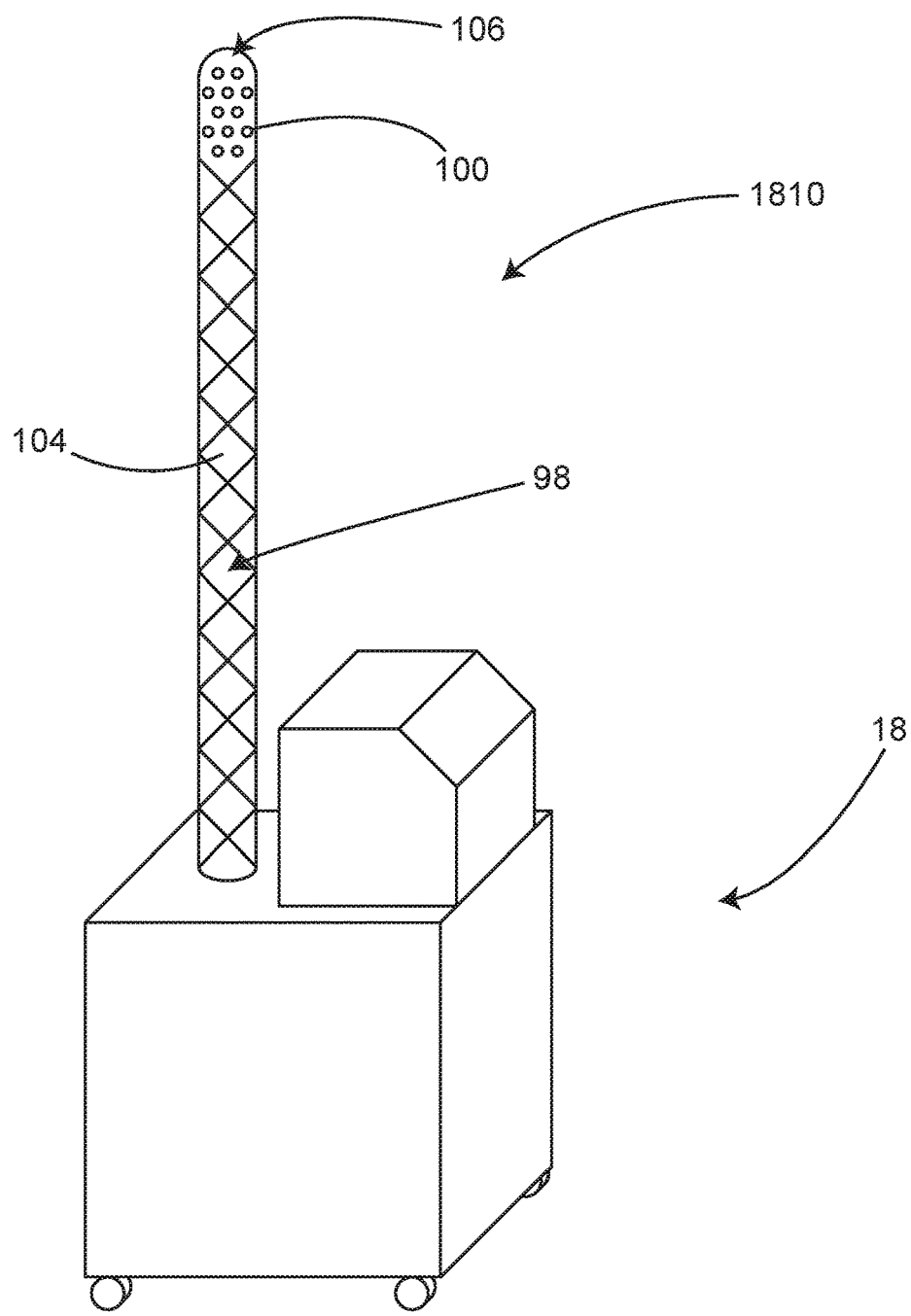
FIG. 18 shows a side perspective view of an illustrative module including an example vent tube, in accordance with at least one example.
Figure 19:
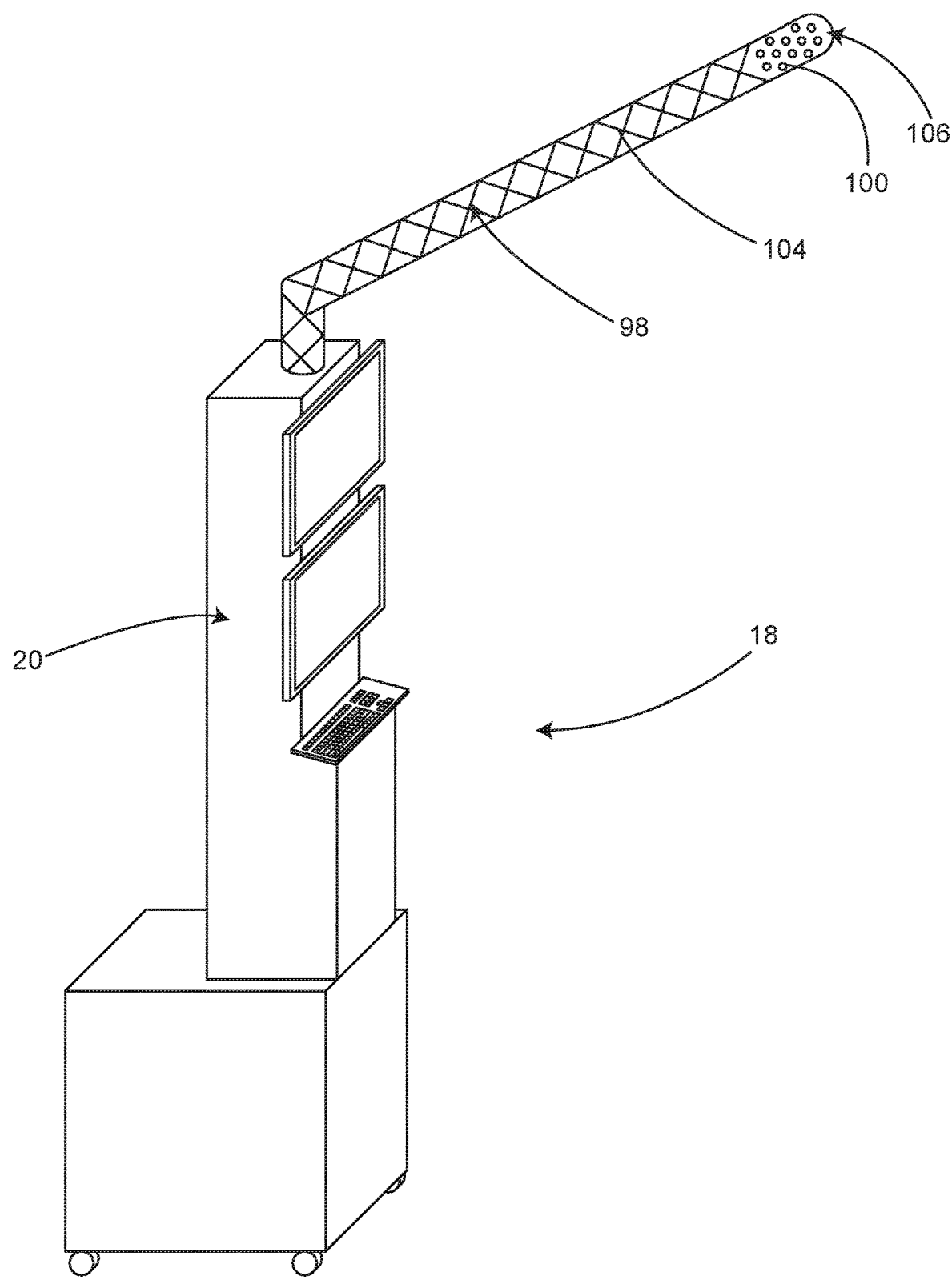
FIG. 19 shows a side perspective view of another module including another illustrative vent tube, in accordance with at least one example.

In some examples, and as shown in illustrative modules 1810 and 1910 of FIGS. 18 and 19, the substantially vertical vent tube 98 can be an inflatable, collapsible tube 104 made of fabric, plastic film or fabric laminated to or coated with a plastic film. In some examples, the inflatable, collapsible tube 104 may be disposable. In some examples, the distal end 106 of the inflatable, collapsible tube 104 is made of woven or non-woven fabric that serves both as a flow obstruction to increase the pressure in the tube and also as a final filter before the waste air is discharged.

In some examples, and as shown in FIGS. 18 and 19, the inflatable, collapsible tube 104 includes a substantially sealed distal end 106 with one or more holes in the walls of the tube to allow the air to escape but create a flow obstruction causing the pressure within the inflatable, collapsible tube 104 to increase. The increased pressure in the inflatable tube 104 causes the inflatable tube 104 to assume an erect shape. In some examples as shown in FIG. 18, the erect inflatable, collapsible tube 104 extends substantially vertically in order to terminate at a height of more than 5 feet above the floor. In some examples as shown in FIG. 19, the erect inflatable tube 104 extends diagonally at an upward angle. Depending on the direction of the angled portion, the distal top end 106 of the inflatable tube 104 may be positioned outside of the operating room ventilation flow field for added safety.

In some examples, the waste air management system 84 produces a relatively high-volume airflow (10-100 CFM) at relatively low positive and negative (vacuum) pressures (less than 2 inches of water). This allows the fan 96 in the lower section 14 to operate at relatively slow speeds under normal conditions in order to minimize the fan noise. The large volume of the bulbous lower section 16 of the module 10 advantageously allows the fan 96 of the waste air management system 84 to be relatively large in diameter. Large diameter fans may produce high volume airflows with relatively slow fans speeds. In some examples, the waste air management system 84 includes noise cancellation or active noise control electronics (e.g., noise canceling device 210. Noise cancellation technologies work by generating a sound waves that are in an inverted phase or antiphase to the sound waves of the noise to be cancelled. When the antiphase waves are superimposed on each other, they cancel each other out through destructive interference. Noise cancellation is particularly effective in cancelling repetitious sounds such as fan noise. The noise-canceling device 210 may be located in the module 10 or within the air-flow pathway or both (FIG. 4).

In some examples, the waste air management system 84 may safely process the waste air that is the by-product of equipment contained within the module 10. In some examples, inlet vents 86 into the plenum 92 are in fluid connection with the interior space of module 10. Waste heated air that has cooled the equipment in the module 10, may be vacuumed from the equipment space into the plenum 92 for safe processing and discharge.

In some examples, the waste air management system 84 may safely process the waste air that is the by-product of other surgical and anesthesia equipment. Waste air producing surgical equipment includes Heater-cooler units (HCU) that produce contaminated waste heated air that needs to be processed and safely discharged. In this case, the waste heated air is a by-product of cooling the refrigeration compressor of the HCU that has been contaminated by water leaking from the water chiller. Forced-air warming units (FAW) also produce contaminated waste heated air that needs to be processed and safely discharged. The FAW systems exhaust waste air from under the surgical drape where it may escape from under the surgical table near the floor. In some examples, this waste heated air from FAW can be contained and vacuumed up for safe disposal. Electrosurgical units and other surgical equipment also produce waste heated air that needs to be processed and safely discharged. Conventionally, these various pieces of equipment in the operating room are not stored proximate one another in a module 10 (e.g., module including a cowl or seal) with a common waste air management system 84. Anesthesia monitoring is generally located in the non-sterile anesthesia field, while the surgical focused equipment is located distal from the anesthesia monitors.

In some examples, a vacuum hose 90 may terminate near or in the waste heat and waste air producing equipment. In some examples, it may be advantageous to attach a collection "funnel" to the end of the vacuum hose in order to direct the waste air into the hose end. In some examples as shown in illustrative module 2010 of FIG. 20, the funnel 122 may be a rigid construction if it is gathering air from the outlet vent of a specific piece of equipment such as a heater-cooler unit. In some examples, the funnel 122 may be a flexible construction, for example a sheet of plastic film, if it is gathering air from the discharge area of a forced-air warming blanket. In some examples, the perimeter of the sheet of plastic film may be adhesively bonded to the open end of the underside of a FAW blanket.

In some examples, the vacuum hose 90 for the evacuation of waste air from surgical and anesthesia equipment may be lightweight, thin walled, inexpensive hose, ½-2 inches in diameter. The vacuum hose 90 may advantageously be made of polyethylene, polypropylene, PVC or other plastic materials. The vacuum hose 90 may advantageously be corrugated. In some examples, the proximal end of the vacuum hose 90 for the evacuation of waste air from surgical and anesthesia equipment is a uniquely shaped connector 88 such as square or triangular for example.

In some examples, the waste air management system 84 may safely process the waste air and smoke that is the by-product of the electro-cautery used for tissue cutting and coagulation. This smoke has been shown to be a hazard to the surgical staff because it may contain carcinogens and may contain viruses.

As shown in FIG. 21A, in some examples, a smoke evacuation suction system used for evacuating electrosurgical smoke may include a hose 90 hooked to a vacuum source. The distal end of the hose 90 may be located near the surgical wound that is being cauterized or tissue being cut with electro-cautery. The distal end of the hose 90 may be attached to the active electrode of the electro-cautery or it may be located near the surgical wound. If it is located near the surgical wound, the distal end 116 of the hose 90 may be secured to the sterile surgical drape with an adhesive element 130A, 130B. Any other suitable securing method, such as, but not limited to clips and ties may also be provided.

Figure 22:
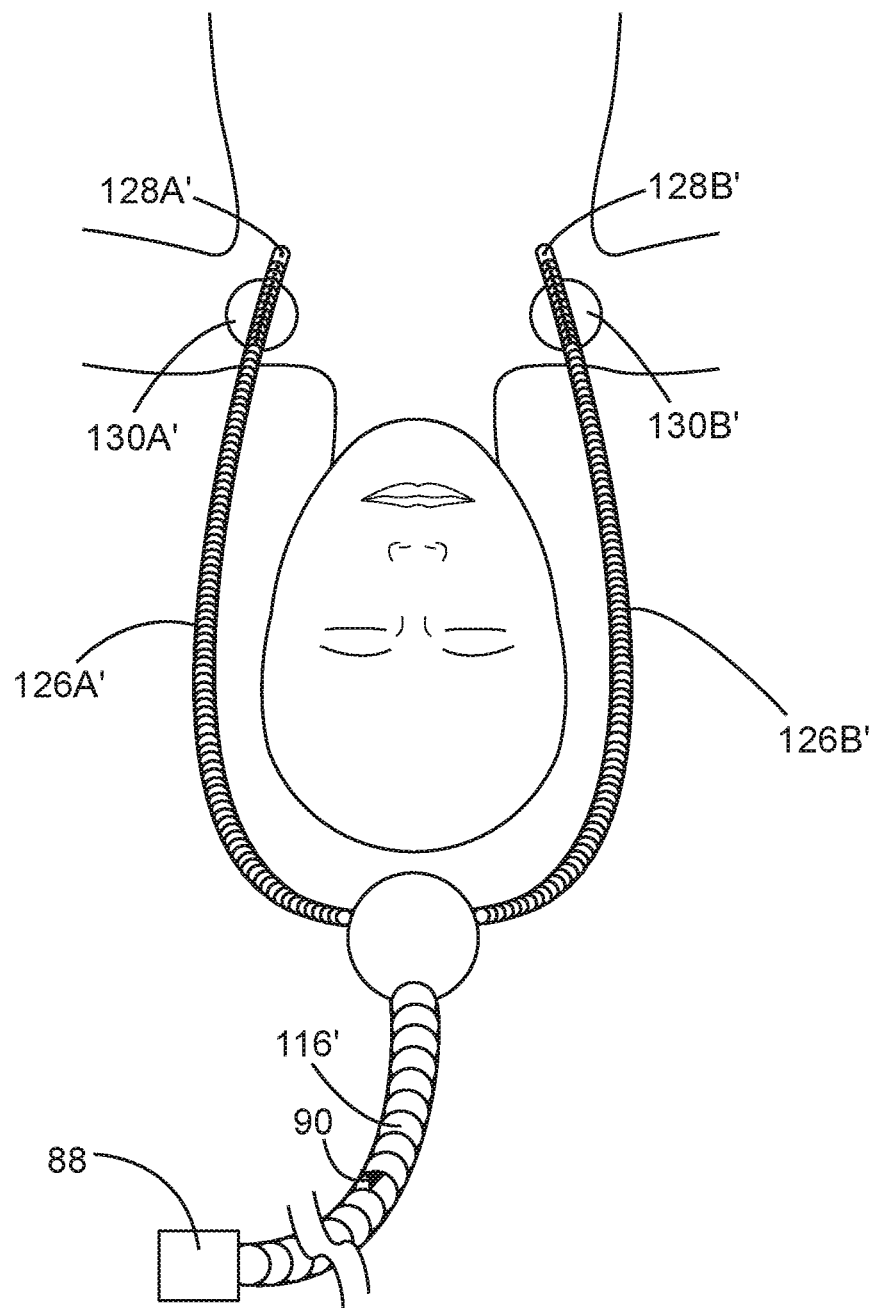
FIG. 22 shows an example of an air dilution system that can be used with the systems described herein, in accordance with at least one example.

In some examples, the proximal end connector 88 (e.g., FIG. 22 of the smoke evacuation hose 90 for smoke evacuation from the surgical field, may be attached to the inlet vent 86 of the waste air management system 84. The smoke from the electro-cautery may be safely vacuumed from the surgical field and then filtered in the waste air management system 84. In some examples, the hose 90 for smoke evacuation may be lightweight, thin walled, inexpensive hose, ⅜-¾ inches in diameter. The tubing may advantageously be made of polyethylene, polypropylene, PVC or other plastic materials. The hose 90 may advantageously be corrugated. In some examples, the proximal end connector 88 of the smoke evacuation hose 90 is a uniquely shaped connector 88 such as square or triangular for example.

In some examples, the waste air management system 84 may safely process the waste air that is the by-product of the operating room ventilation optimization system. It has been shown that flow-boundary dead zones naturally form around the surgeons and in front of anesthesia screen. This is a natural phenomenon that occurs anytime a fluid (or gas)

flows next to a non-moving object—a boundary layer of non-moving fluid (or gas) is formed as shown in FIG. 21A. These flow-boundary "dead zones" 110 that form around the surgeons 108 and staff, effectively prevent the downward ventilation airflow 112 from the ceiling of the operating room from reaching the open surgical wound 114. When the ventilation airflow 112 stops, contaminating particles and bacteria that had been kept airborne by the moving air, are allowed to settle into the wound 114. When the ventilation airflow 112 slows or even stops due to dead zone 110 interference, gravity takes over and the airborne contaminates settle into the wound 114 where they may cause infections.

Figure 21B:
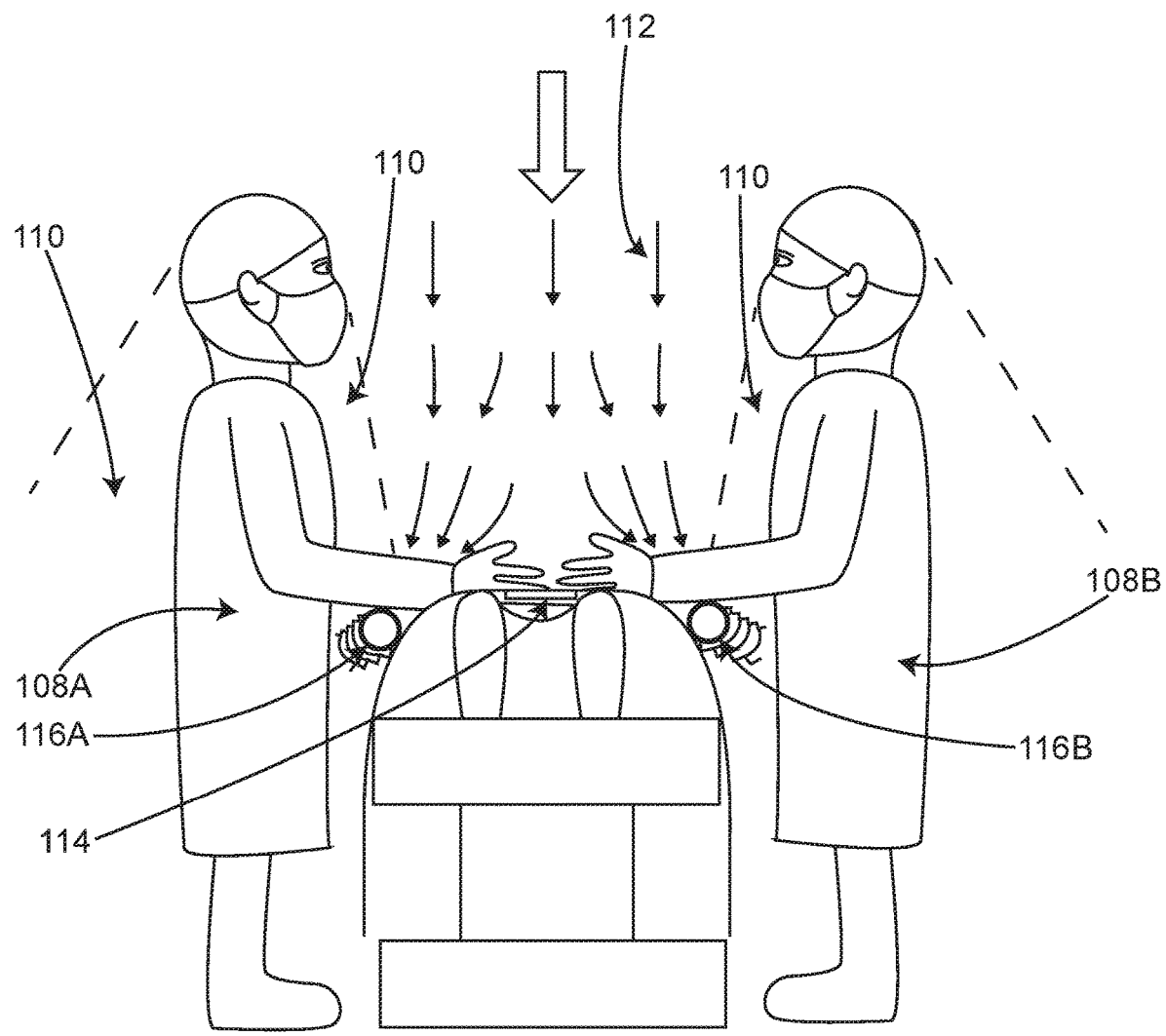
FIG. 21B shows the surgical field of FIG. 21A including an illustrative ventilation optimization system for improving the flow-boundary dead zones of FIG. 21A, in accordance with at least one example.
Figure 21C:
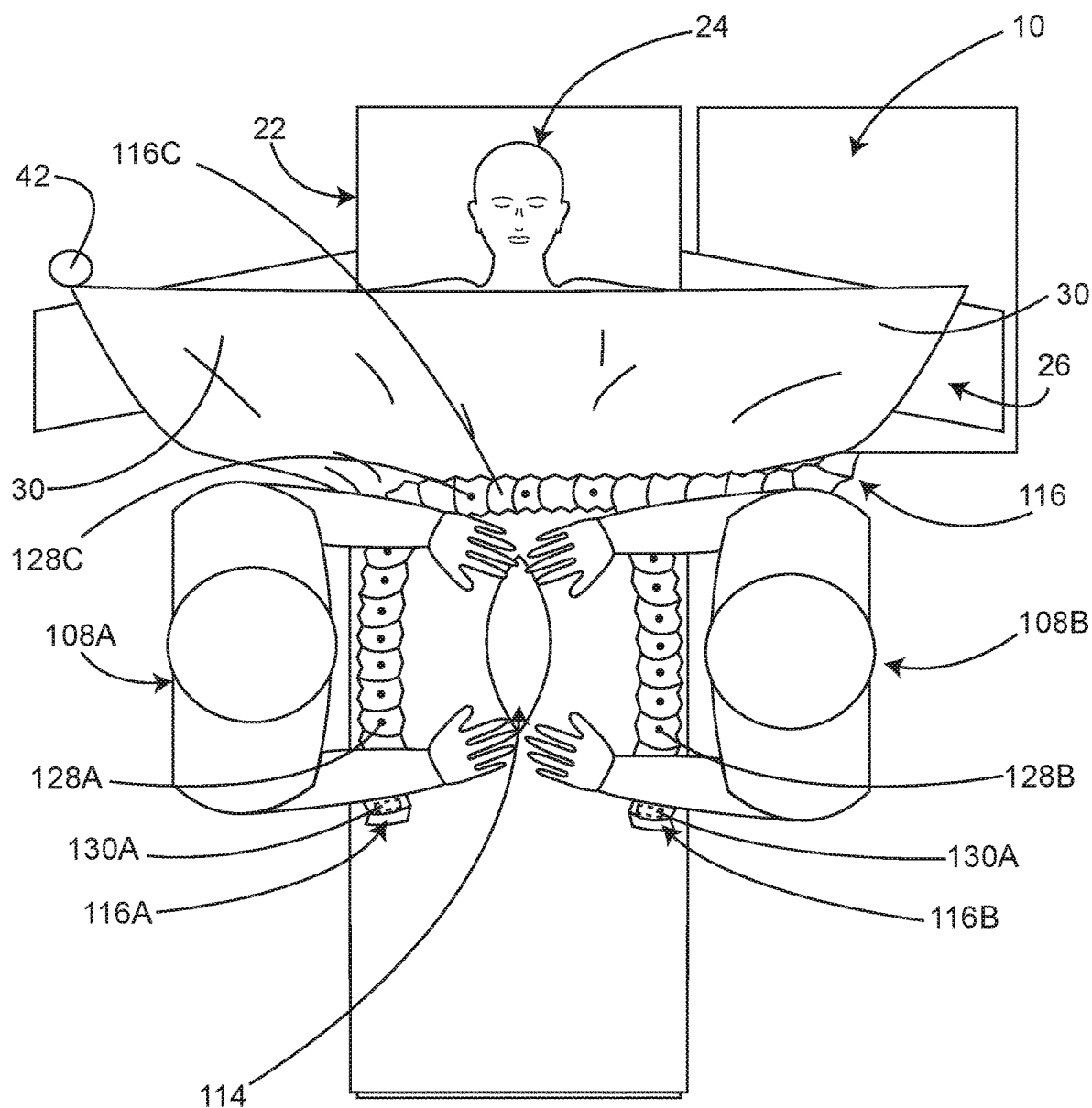
FIG. 21C is a top view of the surgical field and the ventilation optimization system of FIG. 21B, in accordance with at least one example.

In some examples, and as shown in FIG. 21B, we have shown that the negative effects of these dead zones 110 can be minimized by vacuuming out the dead zone air, which allows the ventilation air 112 to flow past the wound 114, keeping airborne contaminating particles and bacteria, airborne in the moving air where they do no harm.

In some examples, and as shown in FIG. 21B, a ventilation optimization system includes ventilation dead zone 110 evacuation; by vacuuming the air from the flow-boundary dead zones 110 that naturally form in front of the surgeons 108 and anesthesia screen 30, the interference of the flow-boundary layers with the operating room ventilation 112 is reduced. This allows the ventilation airflow 112 from the ceiling to reach the wound 114 unimpeded by a flow-boundary dead zone 110. These interfering dead zones 110 of non-moving air can be evacuated by placing a distal end 116, 116A-C (e.g., distal end portion) of vacuum hose(s) 90 into the dead zone 110 to suck out or literally deflate the deadzone. The evacuated air can then be processed in order to safely discharge the air, back into the operating room. In some examples, the distal end 116 of the vacuum hose 90 (e.g., dead zone evacuation hose) may be secured to the sterile surgical drape, such as near or in front of the surgeon 108 (e.g., surgeon position), with an adhesive element. Any other suitable securing method, such as, but not limited to clips and ties may also be provided.

In some examples, the distal end 116 of the vacuum hose 90 may include a single large hole between the inside and the outside of the vacuum hose 90. The single large hole may be substantially the same diameter as the vacuum hose 90. The large hole allows unimpeded airflow while producing minimal airflow noise. In some examples, there are multiple relatively large holes (>0.25 in. diameter) near the distal end 116 of the vacuum hose 90. In some examples, there are multiple smaller holes (<0.25 in. diameter) near the distal end 116 of the dead zone evacuation hose 90, essentially creating a screen-like air inlet to vacuum hose 90. The number of holes and the size of the holes is determined so as to allow an air flow of between 5 and 50 CFM.

In some examples, the distal end 116 of the vacuum hose 90 may be used to evacuate surgical smoke. Traditionally, surgical smoke is evacuated by an air hose attached directly to the end of the electrosurgical active electrode or "pencil." Surgeons find this added hose to be cumbersome. The distal end 116 of the vacuum hose 90 may be located adjacent the surgical wound 114 and can evacuate the surgical smoke from above the surgical wound 114 being carried in the ventilation airflow 112, as it flows past the distal end 116. In this case, a cumbersome hose attached directly to the end of the electrosurgical "pencil" may be unnecessary. By evacuating the dead zone 110 with the vacuum hose 90, the ventilation airflow 112 containing the surgical smoke is naturally directed from over the wound 114, laterally toward the distal end 116 of the vacuum hose 90 adjacent the surgeon 108.

In some examples, the distal end 116 of the vacuum hose may be placed in other flow boundary layer or ventilation dead zone areas such as those that form next to the anesthesia screen 30, under the surgical lights or under a Mayo stand. Similar to the ventilation flow dead zones that form in front of the surgeons, these other dead zones can be evacuated in order to allow the ventilation airflow 112 to flow unimpeded and thus keep the contaminating airborne particles airborne.

Features of the vacuum hose 90 and distal end 116, 116A-C can also be used to collect air from areas of the surgical field that are not considered dead zones, but that may benefit from air collection and filtering. Some of these areas can include areas of turbulent or non-laminar airflow. Air collection using vacuum hose 90 may also be performed in areas of generally laminar airflow.

Figure 20:
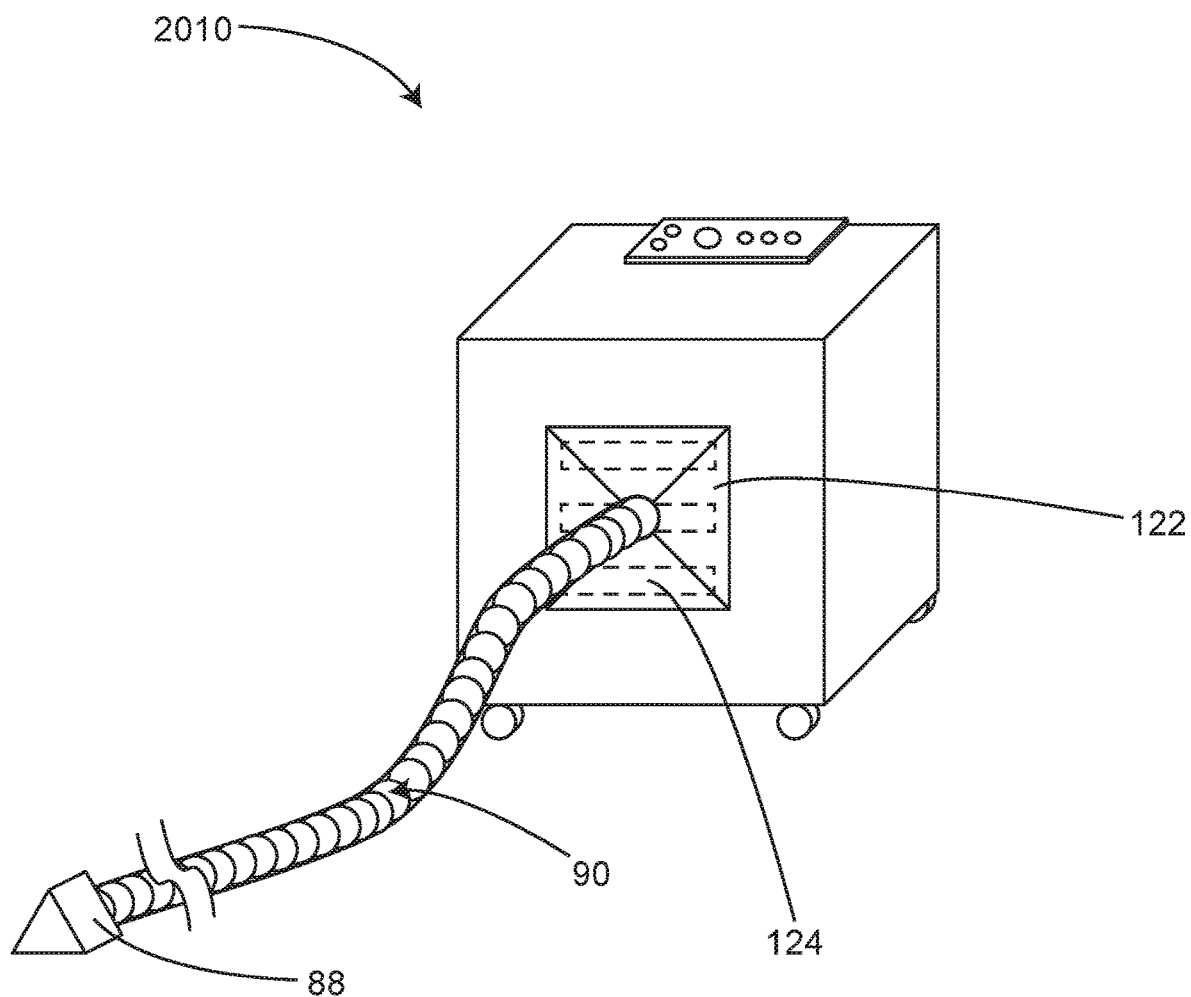
FIG. 20 shows an illustrative waste air management system including an illustrative vacuum hose, in accordance with at least one example.

In some examples, the proximal end of the dead zone evacuation hose 90 exiting from the surgical field may be attached to the inlet vent 86 of the waste air management system 84 (FIGS. 16, 17). The waste air from the dead zone evacuation may be safely filtered in the waste air management system 84. In some examples, the hose 90 for dead zone evacuation may be lightweight, thin walled, inexpensive hose, ½-2 inches in diameter. The hose 90 may advantageously be made of polyethylene, polypropylene, PVC or other plastic materials. The hose 90 may advantageously be corrugated. In some examples, the proximal end of the dead zone evacuation hose 90 is a uniquely shaped connector 88 such as square or triangular for example (FIGS. 20, 22).

In some examples, the waste air management system 84 may be used to evacuate or dilute the air under the surgical drape (e.g., 32 in FIG. 4), especially near the patient's head, neck and chest (e.g., near 24 in FIG. 4). Alcohol from the surgical prep solution may pool under the surgical drapes 32 and then evaporate. Waste oxygen from an unrestricted oxygen supplementation system such as nasal prongs or facemask may allow waste oxygen to pool under the surgical drape, especially near the patient's head, neck and chest. When a spark from either the electro-cautery or a laser is added, highly dangerous operating room fires can occur. Even the surgical drape can burn in the presence of an oxygen-enriched environment. It may be advantageous to remove the air and oxygen and alcohol vapors trapped under the surgical drape.

In some examples, and as shown in FIG. 22, a vacuum hose 90 may be placed near the shoulders, chest and neck of the patient. Vacuum hose 90 may include any of the features described with reference to vacuum hose 90 described with respect to FIGS. 20, 21A and 21B. The distal end 116' of the oxygen/alcohol vacuum hose 90 may terminate in a single hole, multiple holes or even multiple smaller hose "tentacles" 126A', 126B', each with one or more holes 128A' and/or 128B' and each located near the patient. In some examples, longer "tentacle" oxygen/alcohol vacuum hoses 126A', 126B' may extend over the patient's chest or along their sides to terminate with the holes 128A', 128B' near the abdomen. In some examples, the distal end of the "tentacle" hoses 126A', 126B' may be secured to the patient with one or more adhesive patches 130A' and/or 130B'. The adhesive patches can include any suitable coupling element, and can alternately be couplable to the anesthesia screen, surgical drape, etc.

In some examples, the proximal end of the vacuum hose 90 for evacuating oxygen/alcohol exiting from the surgical field may be attached to the inlet vent 86 of the waste air management system 84. The waste air from the oxygen/alcohol evacuation vacuum hose 90 may be safely filtered in the waste air management system 84. In some examples, the vacuum hose 90 for oxygen/alcohol evacuation may be lightweight, thin walled, inexpensive hose, ⅜-1 inch in diameter. The vacuum hose 90 may advantageously be made of polyethylene, polypropylene, PVC or other plastic materials. The vacuum hose 90 may advantageously be corrugated. In some examples, the proximal end of the oxygen/alcohol evacuation vacuum hose 90 is a uniquely shaped connector 88 such as square or triangular for example.

In some examples, the waste heated air can be vacuumed by the waste air management system 84, filtered and discharged at a height that does not allow any waste heat to mobilize contaminates normally resident near the floor, up and into the sterile field. In other words, the air discharged from the waste air management system 84 may advantageously be at a height that is greater than 4 feet off of the floor. However, in some examples, at least a portion of the air discharged from the waste air management system 84 may be diverted and used as a source of positive pressure air.

For example, the waste air management system 84 may be used to dilute the air under the surgical drape (e.g., 30, FIG. 4), especially near the patient's head, neck and chest. Alcohol from the surgical prep solution may pool under the drapes and then evaporate. Waste oxygen from an unrestricted oxygen supplementation system such as nasal prongs or facemask may allow waste oxygen to pool under the surgical drape, especially near the patient's head, neck and chest. When a spark from either the electro-cautery or a laser is added, highly dangerous operating room fires can occur. Therefore, in contrast to vacuuming waste air and oxygen, it may be advantageous to dilute the air and oxygen and alcohol vapors trapped under the surgical drape by blowing fresh air into the space under the drapes. In some examples, this air can be provided by the air discharged from the waste air management system 84.

In some examples, and again with reference to FIG. 22, the air hose 116' may be configured to be placed near the shoulders, chest and neck of the patient. The distal end of the oxygen/alcohol evacuation/dilution air hose 116' may terminate in a single hole, multiple holes or even multiple smaller hose "tentacles" 126A', 126B', each with one or more holes 128A', 128B' and each located near the patient. In some examples, longer "tentacle" oxygen/alcohol dilution air hoses 126A', 126B' may extend over the patient's chest or along their sides to terminate with the holes near the abdomen. In some examples, the distal end of the "tentacle" air hoses 126A' may be secured to the patient, a table or a surgical drape with an adhesive patch 130A' and/or 130B'.

In some examples, the proximal end of the oxygen/alcohol dilution air hose exiting from the surgical table may be attached to the outlet connector 118 of the waste air management system 84. The outlet connector 118 may attach to the discharge side of the waste air management system 84 in order to utilize the positive pressure air being discharged from the system 84. In some examples, the air hose 116' for oxygen/alcohol dilution air may be lightweight, thin walled, inexpensive hose, ⅜-¾ inch in diameter. The air hose 116 may advantageously be made of polyethylene, polypropylene, PVC or other plastic materials. The air hose 116 may advantageously be corrugated. In some examples, the proximal end of the oxygen/alcohol dilution air hose 116 is a uniquely shaped connector 88 such as square or triangular for example.

In some examples, the output of the waste air management system 84 may be diverted into an air hose (e.g., 116) that may be hooked to an inflatable "hover" mattress for moving the patient off of the surgical table at the end of surgery. The fan 96 in the waste air management system 84 conveniently provides the pressurized air for a "hover" mattress. Air may be diverted from the outlet side of the waste air management system 84, into an air hose 116 that is attached to a "hover" mattress. Since the "hover" mattress requires higher air pressure and higher airflow than the low velocity low pressure airflow normally produced by the waste air management system, the fan 96 of the waste air management system 84 may advantageously have two or more speeds. When the "hover" mattress is in use, the fan 96 of the waste air management system 84 may be speeded up to a higher RPM, thus delivering higher air pressures and air volumes, accepting a brief period of more fan noise. In contrast, under normal conditions when the "hover" mattress is not inflated, the fan 96 may be operated at a slower speed to reduce the annoying fan noise.

In some examples, when the output of the waste air management system 84 is diverted into an air hose (e.g., 116) that is hooked to an inflatable "hover" mattress, the diversion valve may automatically close the normal exhaust ducting 102. Therefore, the air pressure in the diversion air hose 116 may be substantially increased, as required to inflate the inflatable "hover" mattress.

Figure 28:
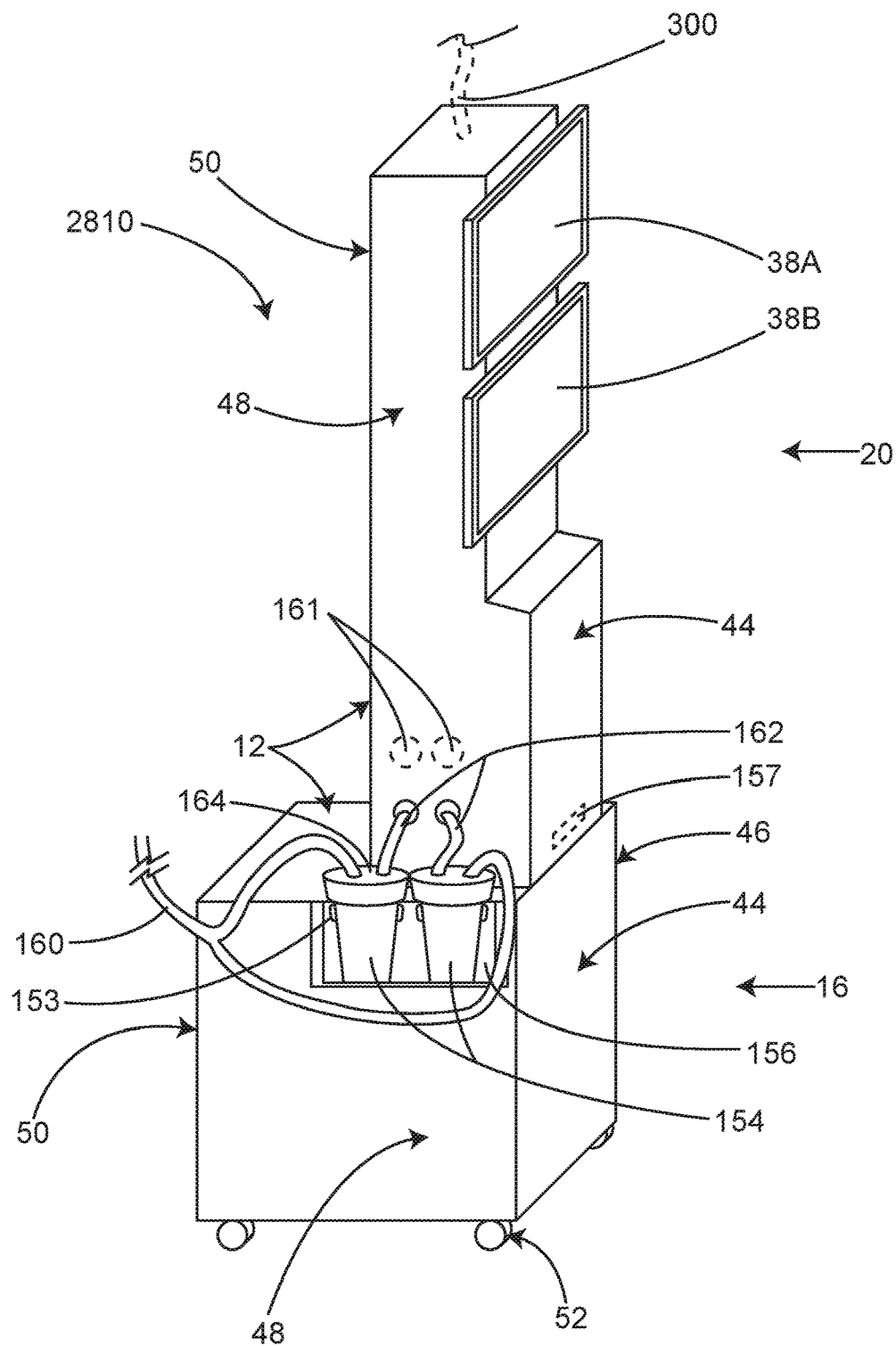
FIG. 28 shows a perspective view of an illustrative system including fluid suction canisters, in accordance with at least one example.

As shown in the illustrative module 2810 of FIG. 28, in some examples, one or more fluid suction canisters 154 for waste fluid and blood may be conveniently mounted on the module 2810. A vacuum hose 300 from the OR ceiling to, for example, the top of the tower of the module 2810 can eliminate the need for that hose to traverse the floor from a wall outlet. Mounting the fluid suction canisters 154 on the module 2810 also allows the suction hose 160 from the surgical field to reach the fluid suction canister 156 without touching the floor.

In some examples as shown in FIG. 28, the one or more fluid suction canisters 154 may be accommodated in bucket-like recesses 156 formed in or coupled to the module 2810, on the side facing away from the patient 48 or the rear side 50 of the module 2810. In the case of multiple canisters, the suction hose 160 from the surgical field may be split into two or more "tail" hoses that can each be hooked to the top of a collection canister 154 (e.g., fluid suction canister, waste fluid storage device). In some examples, two or more vacuum hoses 162 may emerge from the module 2810 cowling 12 to be attached to the top of the fluid suction canisters 154. In some examples, the two or more vacuum hoses 162 can include one or more flow valves 161. In some examples, each vacuum hose 162 can have a flow valve 161, to control which fluid suction canister 154 is receiving the vacuum at any given time. The one or more flow valves 161 can include any suitable flow managing device.

Figure 29:
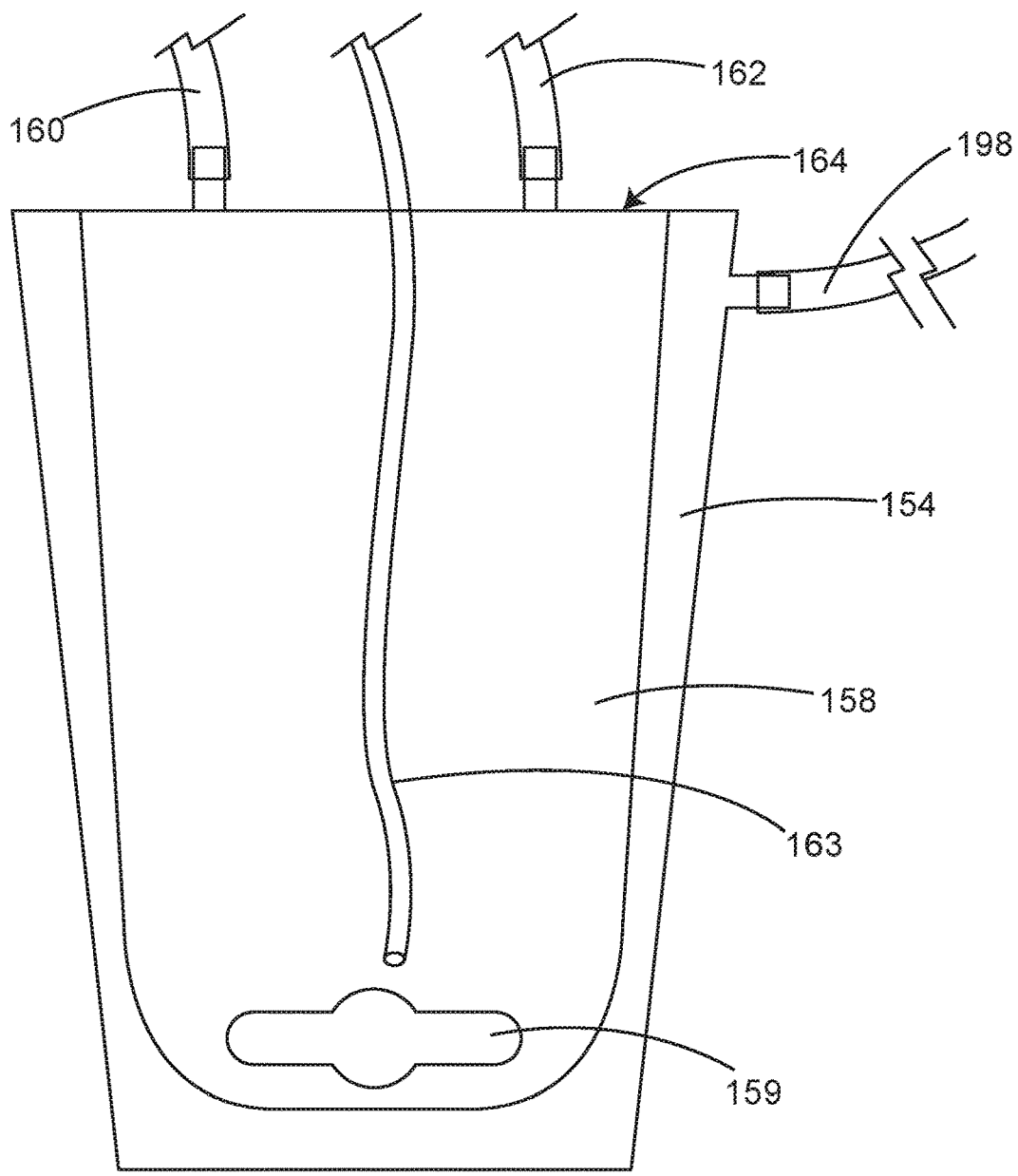
FIG. 29 shows a side view of an illustrative fluid suction bag that may be used with the systems described herein, in accordance with at least one example.

In some examples as shown in FIG. 29, the one or more fluid suction canisters 154 may include a disposable fluid suction bag 158 that serves as an inner liner for fluid suction canister 154, or can replace fluid suction canister 154. The disposable fluid suction bag 158 prevents the more robust and expensive fluid suction canister 154 from being contaminated by blood and bodily fluids. In this case, the vacuum hose 162 from the module 2810 and the suction hose 160 from the surgical field both enter the top of the disposable fluid suction bag 158. In some examples, the top of the disposable fluid suction bag 158 can include a molded plastic cover 164 with a diameter that is larger than the upper diameter of the fluid suction bag 158. The outer rim of the molded plastic cover 164 is designed to create an airtight seal with the upper edge of the fluid suction canister 154. When the molded plastic cover 164 is sealed to the upper edge of the fluid suction canister 154, a vacuum 198 can be introduced into the space between the fluid suction bag 158 and the fluid suction canister 154. The negative pressure vacuum 198 in the space between the fluid suction bag 158 and the fluid suction canister 154 may be more negative than the negative pressure vacuum inside the fluid suction bag 158, in order to maintain the fluid suction bag 158 in a fully expanded condition.

In some examples, the negative pressure vacuum 198 in the space between the fluid suction bag 158 and the fluid suction canister 154 can be induced by one or more vacuum pumps in the module 2810. Advantageously, these vacuum pumps can be capable of creating a more negative air pressure than the hospital vacuum system that is applied to the inside of the fluid suction bag 158.

In some examples, the fluid suction bag 158 can be made of plastic film. In some examples, the fluid suction bag 158 can be made of blow-molded plastic. Other plastic bag construction techniques are anticipated. In some examples, the fluid suction bag 158 is made of inexpensive polyethylene or polypropylene plastic materials.

In some examples, one or more fluid level sensors 153, such as, but not limited to, optical or infrared sensors, may be conveniently mounted in the wall of the bucket-like recesses 156 in the module 10, adjacent the fluid suction canister(s) 154. Optical and infrared sensors rely on the relative increased absorption of transmitted light by blood and fluid compared to air in order to determine a fluid level. In some examples, the fluid level monitors may automatically activate or deactivate the vacuum valves to a given canister, thereby automatically shifting the blood and fluid flow to a new canister as the previous one is filled. In some examples, the surgical nurse can be wirelessly notified on their portable monitor, that one or more canisters are full of blood and fluid and may need to be replaced before the surgical procedure is finished.

Blood and fluid sucked from the surgical sight frequently contains many air bubbles and foam that falsely expand the blood and fluid volume and may cause the canister to overflow, if volume were to be measured by weight for example. In some examples, optical or infrared fluid level sensors 153 may be advantageous compared to other fluid level sensors because they respond to an absolute volume of fluid (including air bubbles and foam) in the fluid suction bag 158 or the fluid suction canister 154. In some examples, optical or infrared fluid level sensors 153 ideally serve as a shutoff sensor, preventing the overflow of blood and fluids into the hospital vacuum system.

In some examples, optical or infrared fluid level sensors 153 may not be ideal for determining an accurate blood and fluid volume in the fluid suction bag 158 or the fluid suction canister 154. An accurate blood and fluid volume needs to subtract the volume added by air bubbles and foam. In some examples, weight is the most accurate determination of the blood and fluid volume in the fluid suction bag 158 or the fluid suction canister 154, because it excludes the confounding influence of air bubbles. By subtracting the dry weight of the fluid suction bag 158 and/or the fluid suction canister 154 from the measured weight of the canister containing blood and fluid, the volume of blood and fluid can easily and accurately be determined, irrespective of the volume of air bubbles and foam in the blood and fluid.

In some examples, an electronic scale 155 is positioned to weigh the fluid suction canister 154. Measuring the weight of the blood and fluid is far more accurate than the traditional method of visually measuring or "guesstimating" the volume of blood and fluid in a fluid suction bag 158 or the fluid suction canister 154. Since blood and fluid has virtually the same specific gravity as water, each 1 gram of blood and fluid weight equates to 1 ml of blood and fluid volume. The volume of the air bubbles and foam are automatically excluded.

In some examples, the fluid suction bag 158 and/or the fluid suction canister 154 can be attached to an electronic scale 155 for measuring the weight of the fluid suction bag 158 and/or the fluid suction canister 154 plus the blood and fluid in the bag or canister. In some examples, the electronic output of the electronic scale 155 that can be attached to the fluid suction canister 154 is directly reported on a patient monitor display 38A, 38B. In some examples, the electronic output of the electronic scale 155 that is attached to the fluid suction canister 154 is digitized and reported (e.g., generated and a signal sent) to a processor (such as processing circuitry 157) that is programmed to record the beginning weight (e.g., establish a zero point) of the fluid suction bag 158 and/or the fluid suction canister 154 and together (operably coupled) with a controller 165a of a control module 165b, automatically subtract that beginning weight from subsequent recorded fluid suction canister 154 weights, to determine the blood and fluid loss during surgery. In some examples, the total blood and fluid loss and in some cases blood and fluid loss per hour determined (e.g., calculated) by the processor, are then reported (e.g., displayed) on a patient monitor display 38A, 38B. In some examples, the total blood and fluid loss and in some cases blood and fluid loss per hour determined by the processor, may be automatically recorded in the electronic anesthetic record (e.g., a memory, machine readable medium). Other time values besides fluid loss per hour can be used, such as fluid loss per minute, fluid loss per second, etc.

In some examples, it may be desirable to determine the blood loss during surgery rather than total blood and fluid loss, since some or even most of the "fluid" is irrigation fluid introduced by the surgeon. The blood loss can be determined by comparing information about a concentration of a blood characteristic in the waste fluid. Blood characteristics that can be used include, but are not limited to, hematocrit concentration and hemoglobin concentration. For example, blood loss can be calculated if the hematocrit (Hct) or hemoglobin concentration (Hgb) of the patient, the hematocrit (Hct) or hemoglobin concentration (Hgb) of the fluid in the suction canister 154 and the volume of the blood and fluid in the suction canister 154 (excluding air bubbles and foam) are known. The formula is: Blood loss=$Hct_{canister}/Hct_{patient} \times$ fluid $vol_{canister}$. Accurate measurement of the fluid volume of the canister by weight has been discussed. The Hct of the patient can be directly measured by infrared spectroscopy or by recent lab results. The Hct of the canister can be measured or approximated by a variety of techniques including but not limited to: infrared spectroscopy, centrifugation, visible light photo absorption and microfluidic cell counting. In some examples, the total blood and in some cases blood loss per hour determined by the processor, may be automatically recorded in the electronic anesthetic record. In some examples, the processor may include an algorithm for more accurately determining the need for a blood transfusion. For example, the processor can determine if a measured blood loss value has traversed a blood loss threshold.

In some examples, it may be desirable to agitate and mix the contents of the fluid suction bag 158 or the fluid suction canister 154 in order to assure a more accurate determination of the Hct of the blood and fluid in the canister. In some examples, it may be desirable include a magnetic stirrer in the fluid suction bag 158 or the fluid suction canister 154. A small bar magnet 159 with N and S poles is placed in the bottom of the fluid suction bag 158 or the fluid suction canister 154. A corresponding bar magnet is mounted on a spinning shaft and positioned to spin horizontally just below the bucket-like recesses 156 in the module 10. The opposite poles of each magnet are attracted to each other causing the magnet 159 in the canister to spin in unison with the magnet below the bucket-like recesses 156, mixing the blood and fluid in the canister. In some embodiments the bar magnet 159 in the canister may be coated in plastic. In some embodiments the plastic coating may be molded to include a substantially sphere-shaped bump located near the midpoint of the magnet 159. The bump may provide an axis of rotation for the magnet 159 to more easily spin in the blood and fluid.

In some examples, it may be desirable to agitate and mix the contents of the fluid suction bag 158 or the fluid suction canister 154 in order to assure a more accurate determination of the Hct of the blood and fluid in the canister. In some examples, it may be desirable include a bubbler in the fluid suction bag 158 or the fluid suction canister 154. In some embodiments, the proximal end of a small tube 163 may be hooked to an air source within the module 10 and terminate with its open distal end near the bottom of the fluid suction bag 158 or the fluid suction canister 154. Small air bubbles pumped into the blood and fluid in the canister agitate and mix the contents as they rise to the surface. The bubbles also assure that the blood in the canister is fully oxygenated, making the quantification with infrared spectroscopy or visible light photo absorption easier and more accurate, in some cases only requiring a single wavelength of light. In some embodiments the small tube 163 may also serve as a sampling tube for withdrawing a small amount of the contents of the fluid suction canister 154 or fluid suction bag 158, for analysis of the hematocrit.

In some examples, a suction hose from the anesthesia suction device may be attached to fluid suction bag 158 or the fluid suction canister 154, in order to eliminate the need for additional suction canisters. This combination is possible because the fluid suction bags 158 or the fluid suction canisters 154 are mounted on the module 2810, adjacent the patient.

In some examples, module 3010 can include a disinfecting (e.g., sanitizing) system. For example, Ultraviolet light (UV), especially UV light in the "C" portion of the spectrum can kill nearly all types of microorganisms. In some examples, UV-C includes lights emitting wavelengths in the 200 nm to 280 nm range. Some germicidal lights may go as high as wavelengths of 300 nm. In recent years UV-C has steadily gained acceptance as an effective technique for disinfection in the OR. The challenges with UV-C disinfection include: adequate UV power or intensity ("field strength"), adequate duration of exposure, expense, adequate "sight lines" to assure that the upper surfaces of the equipment in the OR (especially the surfaces contacting the patient, the staff and the supplies) are radiated and adequate protection of the relatively delicate UV-C bulbs when not in use.

Figure 30:
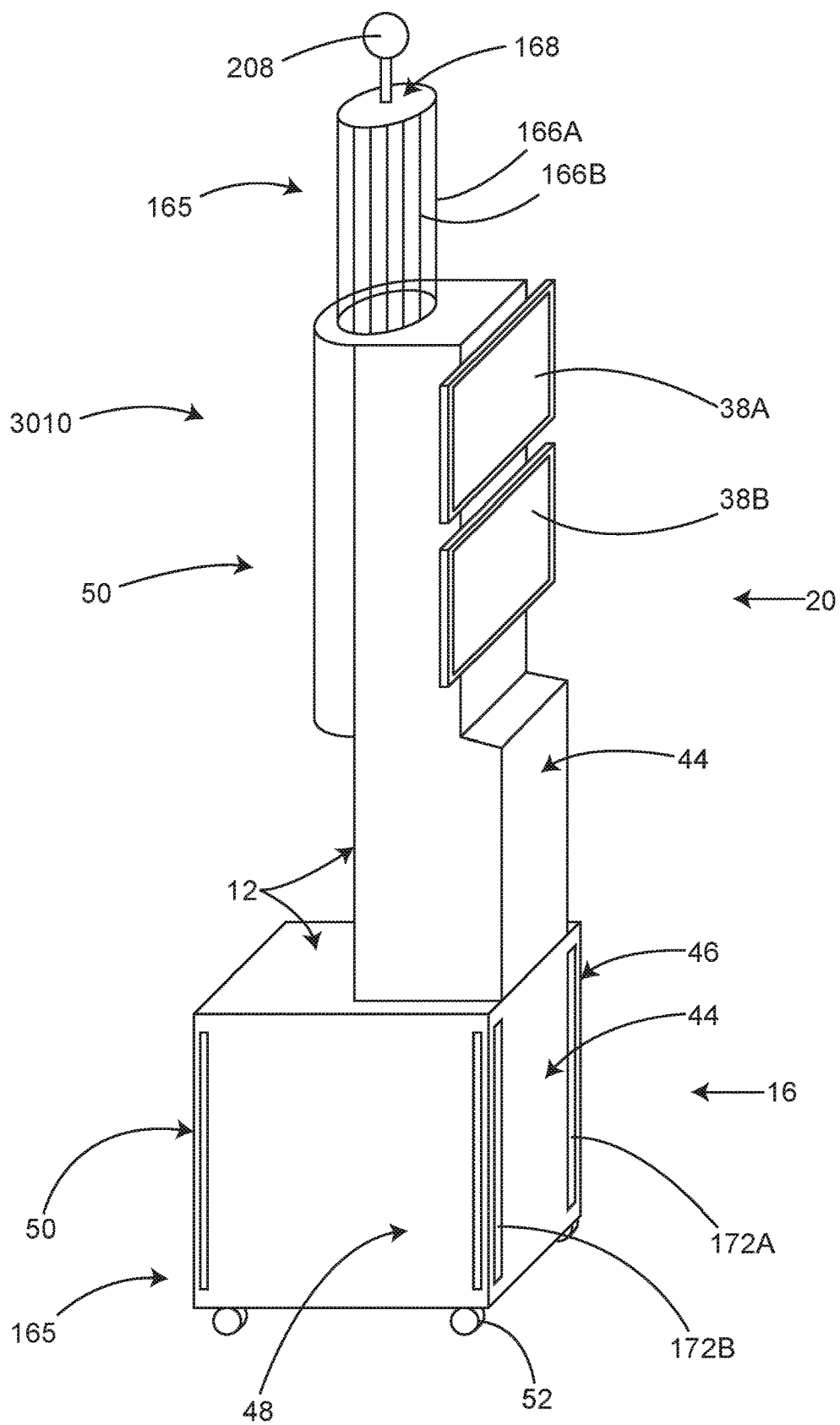
FIG. 30 shows perspective view of an illustrative sanitizing system including UV lights, in accordance with at least one example.
Figure 31:
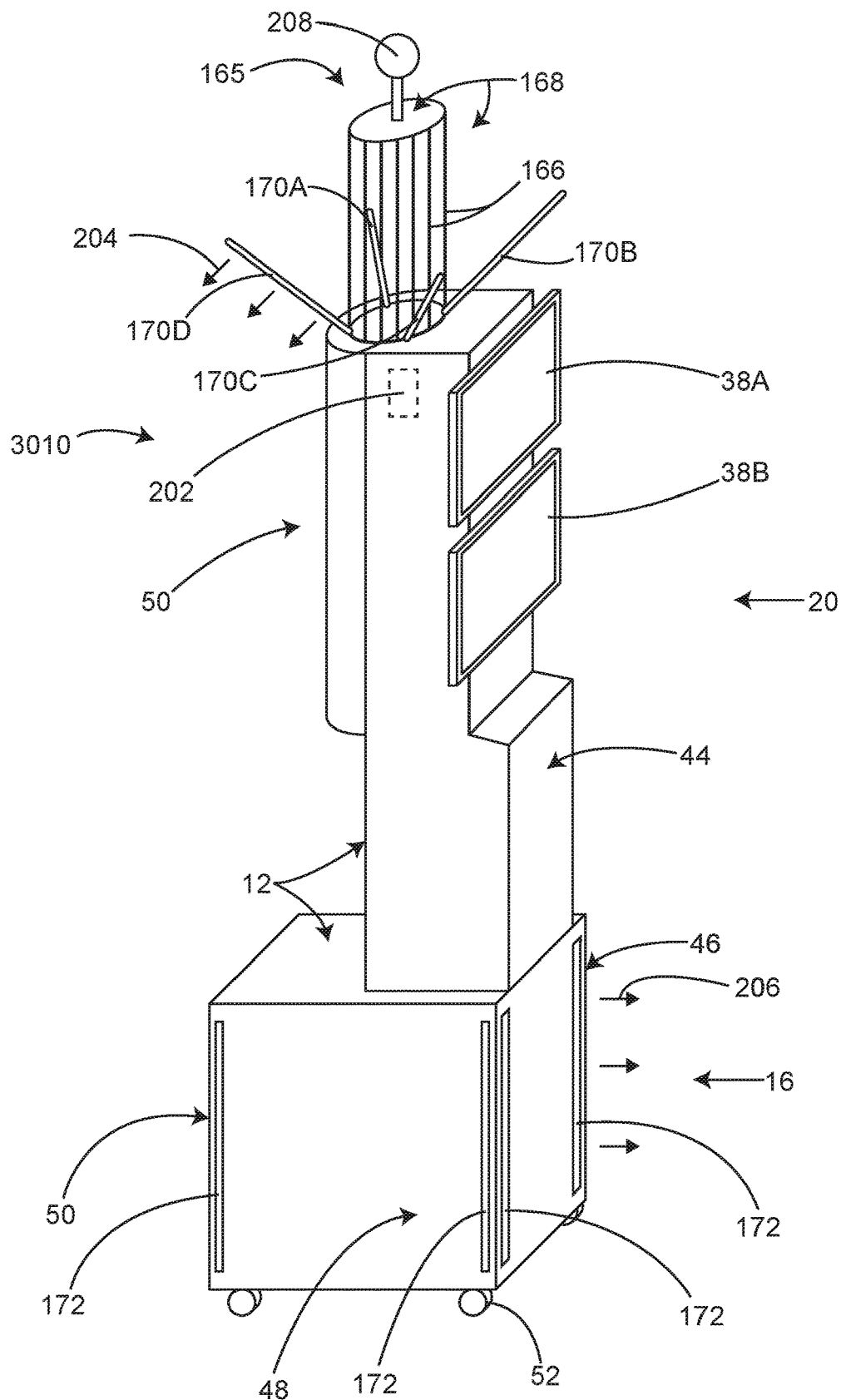
FIG. 31 shows a perspective view of the illustrative sanitizing system of FIG. 30 depicting features of the UV lights, in accordance with at least one example.

In some examples, and as shown in FIGS. 30 and 31, the module 3010 may be used as a storage and mounting platform for a disinfecting system 165, such as a sanitizing system including UV-C lights 166. Other suitable disinfecting systems may also be mounted to module 3010, including but not limited to, a spray disinfecting system or an ozone disinfecting system. In some examples, a cartridge 168 for mounting multiple UV-C lights 166 (which may look like fluorescent light tubes) may be safely housed in the tower-like upper section 20 of module 10.

In some examples as shown in FIGS. 30 and 31, the UV-C cartridge 168 may be elevated from its storage location within the upper section 20 of module 3010, emerging from the top of module 3010. (However, in some examples the cartridge 168 may remain on top of the module 3010 and not emerge or be retracted into the module 3010).

In some examples, the UV-C cartridge 168 may advantageously be located 5-9 feet in the air when it is located on the top of module 10. From this relatively high location in the OR, the UV-C lights 166 can advantageously shine outward and/or downward onto the upper surfaces of the equipment in the room; the surfaces contacting the patient, the staff and the supplies.

In some examples, the UV-C cartridge 168 may be elevated above the module 3010 by an air cylinder actuator 202 or other electro-mechanical mechanism for UV-C exposure and then safely stored within the upper section 20 between exposures. In other words, when in use, the sanitizing system 165 at least a portion of the system 165 can be extended out of the module 3010, and when not in use, at least a portion of the sanitizing system 165 can be retracted into the module 3010 and stored in the module 10.

In some examples as shown in FIG. 31, the UV-C cartridge 168 may include UV-C lights that extend outward 170 creating "sight lines" 204 that can radiate and disinfect module 3010. The UV-C lights that extend outward 170 may be housed in module 3010 as part of the UV-C cartridge 168 and then automatically deploy outward when the UV-C cartridge 168 is elevated. The UV-C lights shining on the module 3010 advantageously disinfect the module 3010 automatically.

In some examples, as shown in FIGS. 30 and 31, the UV-C lights 172 may be mounted on module 3010 near the floor. UV-C lights near the floor 172, advantageously have "sight lines" 206 to the undersurfaces of equipment and the floor of the OR. The combination of the UV-C lights 166 shining downward and the UV-C lights 172 near the floor shining upward, outward and/or downward, creates the maximum probability of having a clear "sight line" 204, 206 to an organism in any location.

In some examples, the UV-C disinfection system may be controlled by a timer. At a designated time when the OR is not in use, 3 AM for example, the UV-C cartridge 168 may be automatically elevated above the module 3010 by the air cylinder actuator or other electro-mechanical mechanism 202, for UV-C exposure. Then after a prescribed exposure time, the actuator 202 may automatically retract the UV-C cartridge 168 back into the upper section 20 for safe storage. Since each OR would presumably have its own module 3010, each room can be automatically and economically disinfected with UV-C light, one or more times each day. The disinfection system can include one or more motion sensors 208 to detect motion. For example, if a person is in the room or in a location where they could be exposed to the UV light, based on the detection of motion, the disinfection system can be altered, or the output reduced. In some examples, detection of motion can include the processor (e.g., 157) determining that the disinfection system should be interrupted and sending an instruction to the actuator 202 to retract the disinfection system or to the controller to turn off the disinfection system.

In some examples, UV-C lights 166 may be mounted on rear side 50 of the upper section 20 of module 3010. In this location, warming blankets that are hung from the top rear side 50 of the module 3010 between surgical cases may be exposed to UV-C light and disinfected on the side of the blanket contacting the patient. The UV-C lights 166 would be blocked from shining around the room by the blankets hanging in front of the lights, therefore even though personnel may be in the room during case turnover, they will not be exposed to UV-C light. The side of the blankets facing the patient can be disinfected between cases without the need for wiping them off.

In some examples, the various features and inventions described herein for safely and efficiently relocating and housing unrelated equipment in the OR, may be advantageously adapted to house equipment elsewhere in the operating room or elsewhere in the hospital or surgery center. For example, equipment or digital displays used by the surgeon may be housed in a module very similar to module 10 but be preferentially located near the side of the surgical table on the surgical side of the anesthesia screen 30, rather than near the head of the table. It is anticipated that the various features and inventions described herein for safely and efficiently relocating and housing equipment in the OR, may be used to create modules with different form factors, or modules for different purposes, or modules for use in different locations, or modules for use by different surgical staff, without deviating from the intended scope of this invention.

In some examples, the module 10 of the instant invention may also include the components of an anesthetic gas machine (e.g., 40). The components of an anesthetic gas machine can include but are not limited to: $O_2$, $N_2O$ and air supply lines and tanks; piping, valves and flow meters for $O_2$, $N_2O$ and air; anesthetic gas vaporizers; a circle system breathing circuit with a $CO_2$ absorption canister and ventilation bag; a mechanical ventilator; pressure and gas concentration monitors. Including the anesthetic gas machine 40 components and functions in the module 10, advantageously eliminates another piece of equipment from cluttering the operating room and requiring cleaning.

Figure 33:
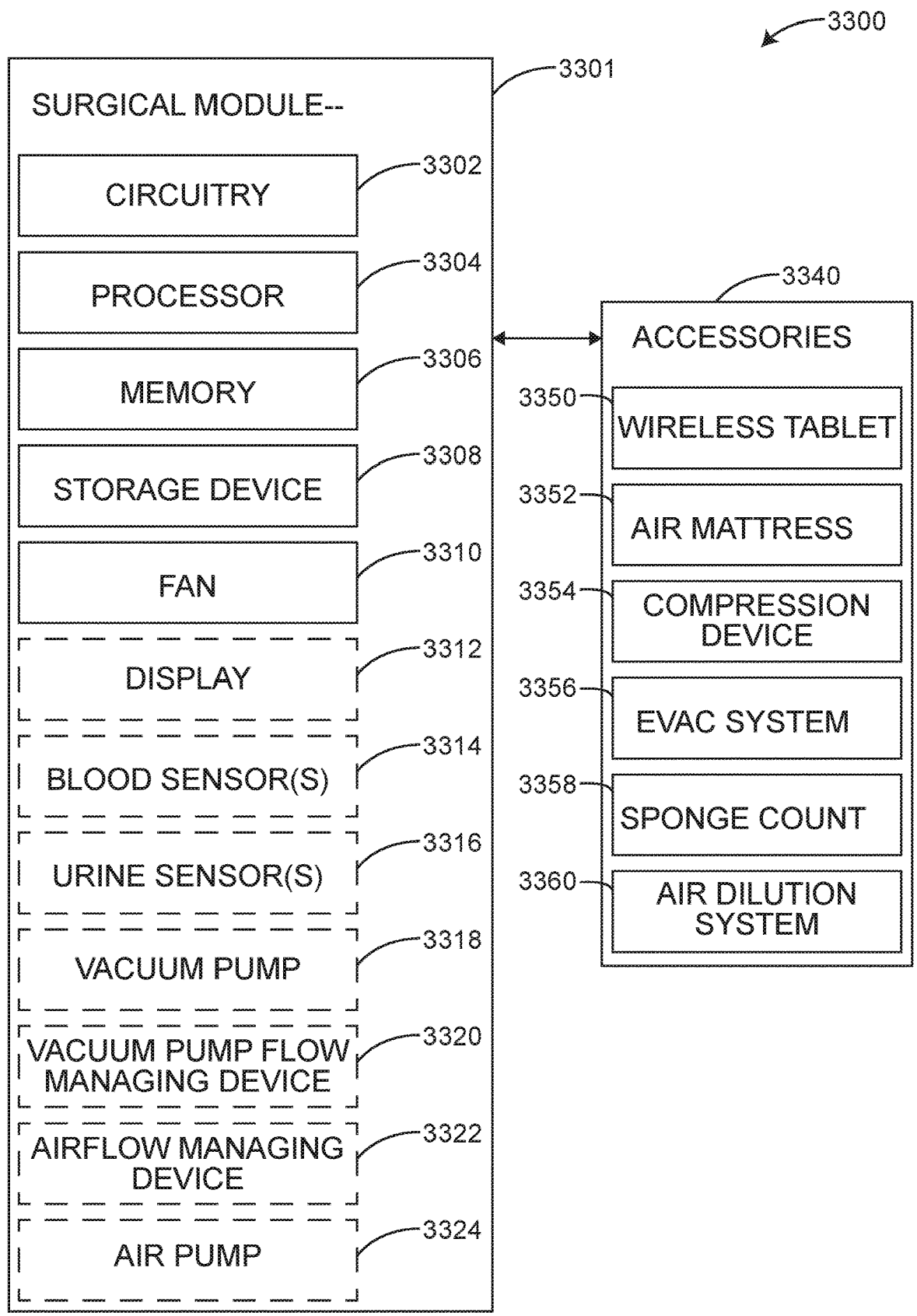
FIG. 33 illustrates a system, in accordance with at least one example.

FIG. 33 illustrates an electronic and/or electromechanical system 3300 of a surgical module (e.g. 10) in accordance with some examples. The system 3300 can include any of the features described in FIGS. 1-32B to perform techniques 3400-4000 described in relation to FIGS. 34-40, for example, by using the processor 157. The system 3300 can include circuitry 3302. In some examples, the circuitry 3302 can include but is not limited to, electronic circuits, a control module processing circuitry and/or a processor, 3304 (e.g., 157, FIG. 1). The circuitry/processor 3302/3304 may be in communication with a memory 3306 and/or a storage device 3308. A single processor can coordinate and control multiple, or even all the aspects of the system 3300 (module 10), or multiple processors can control all the aspects of the system 3300 (module 10). In some examples the storage device 3308 can include at least a portion of the patient's anesthetic record saved thereon. The system 3300 can also include a fan 3310 and a display 3312 (e.g., 38A, 38B, 38C). The system 3300 can also include any of the circuitry and electronic and/or electromechanical components described herein, including but not limited to, blood measuring sensor(s) 3314 (e.g., weight sensor or scale, light sensor, optical sensor, ultrasonic sensor etc.); a urine sensor(s) 3316, a vacuum pump 3318, a vacuum pump flow managing device 3320, an airflow managing device (e.g., a diversion valve for diverting airflow) 3322. The system 3300 may also include or interface with accessories or other features 3340 such as any of: a wireless tablet 3350, a surgical mattress 3352, a surgical compression device 3354, a dead zone evacuation system 3356, a sponge counting and detection system 3358 a positive pressure air dilution system 3360, as well as any of the other systems described herein.

The circuitry 3302, which in some examples can include processor 3304 of the surgical module 10 can receive information from the various sensors described herein, make various determinations based on the information from the sensors, output the information or determinations from the information for output on the display or wireless tablet, output instructions to provide an alert or an alarm, apply vacuums, power various components such as a fan, actuate actuators, flow managing devices, diversion valves, etc. as described herein. For the sake of brevity, select systems and combinations are described in further detail above and in the example sets provided in the Notes and Various Examples section below. Other embodiments are possible and within the scope of this disclosure.

Figure 34:
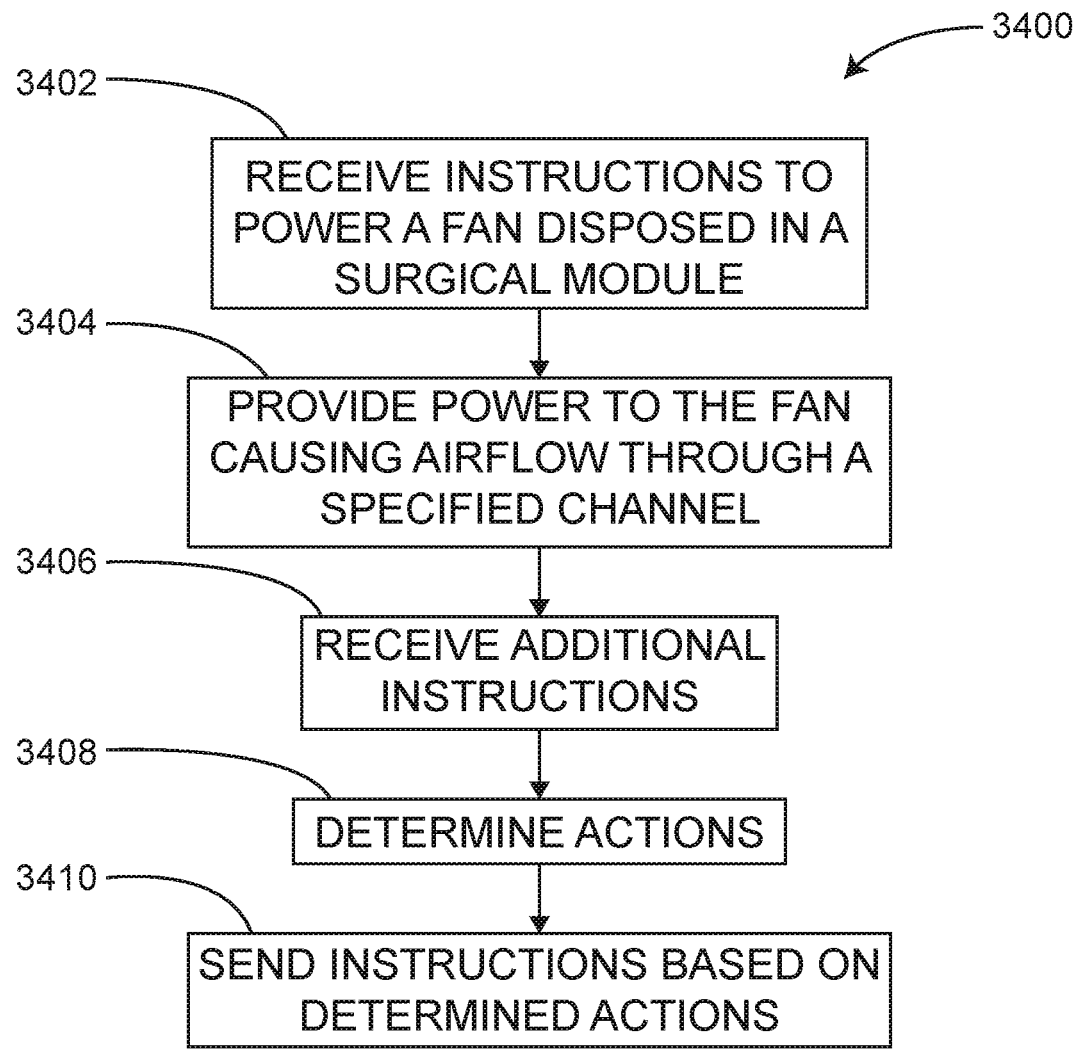
FIG. 34 illustrates a flow chart showing a technique for operating a module, in accordance with at least one example.

FIG. 34 illustrates a flow chart showing a technique 3400 for vacuuming air in an operating room using system 3300 (e.g., including any module, such as module 10, described herein) in accordance with some examples. The technique 3400 can include operation 3402 to receive instructions to power a fan disposed in a surgical module. Operation 3404 can include providing power to the fan to cause air to flow through a specified channel of the module. The specified channel can include a plenum and a vent tube as described herein. Operation 3406 can include receiving additional instructions, operation 3408 determining actions and operation 3410 sending instructions based on the determined actions. Technique 3400 can include additional steps as well as the more detailed steps outlined in Example Set 1 under the Various Notes and Embodiments section.

Figure 35:
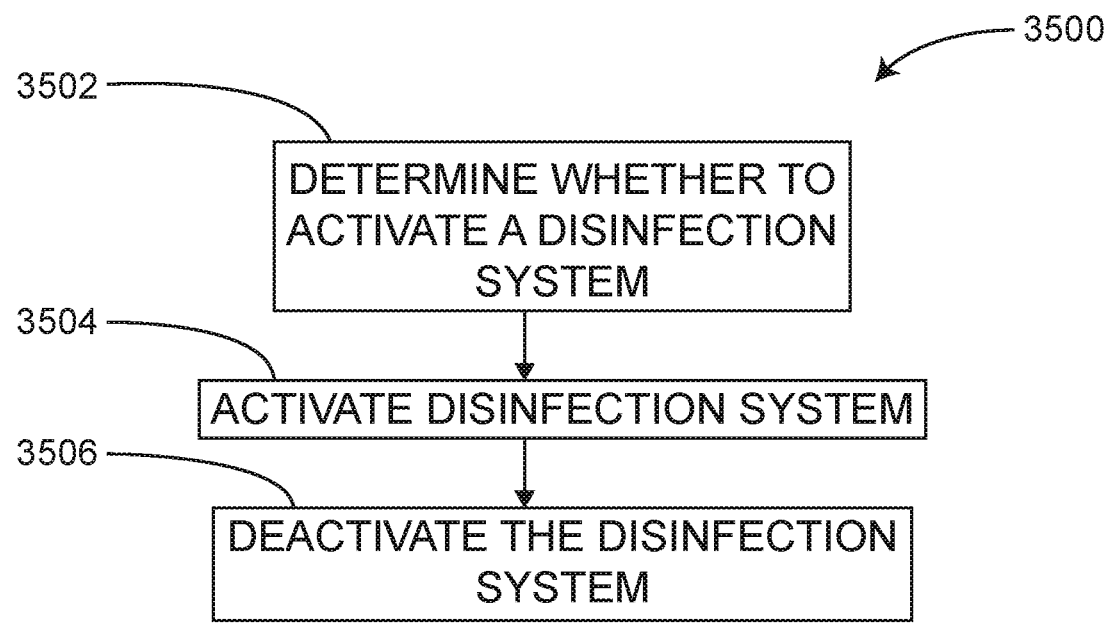
FIG. 35 illustrates another flow chart showing a technique for operating a module, in accordance with at least one example.

FIG. 35 illustrates a flow chart showing a technique 3500 for reducing germs in an operating room using system 3300 (e.g., including any module, such as module 10) in accordance with some examples. The technique 3500 can include operation 3502 including determining whether to activate a disinfection system. Operation 3504 can include activating the disinfection system. Operation 3506 can include deactivating the disinfections system (such as by receiving an instruction to deactivate the system or after a period of time passes). Technique 3500 can include additional steps as well as the more detailed steps outlined in Example Set 2 under the Various Notes and Embodiments section.

Figure 36:
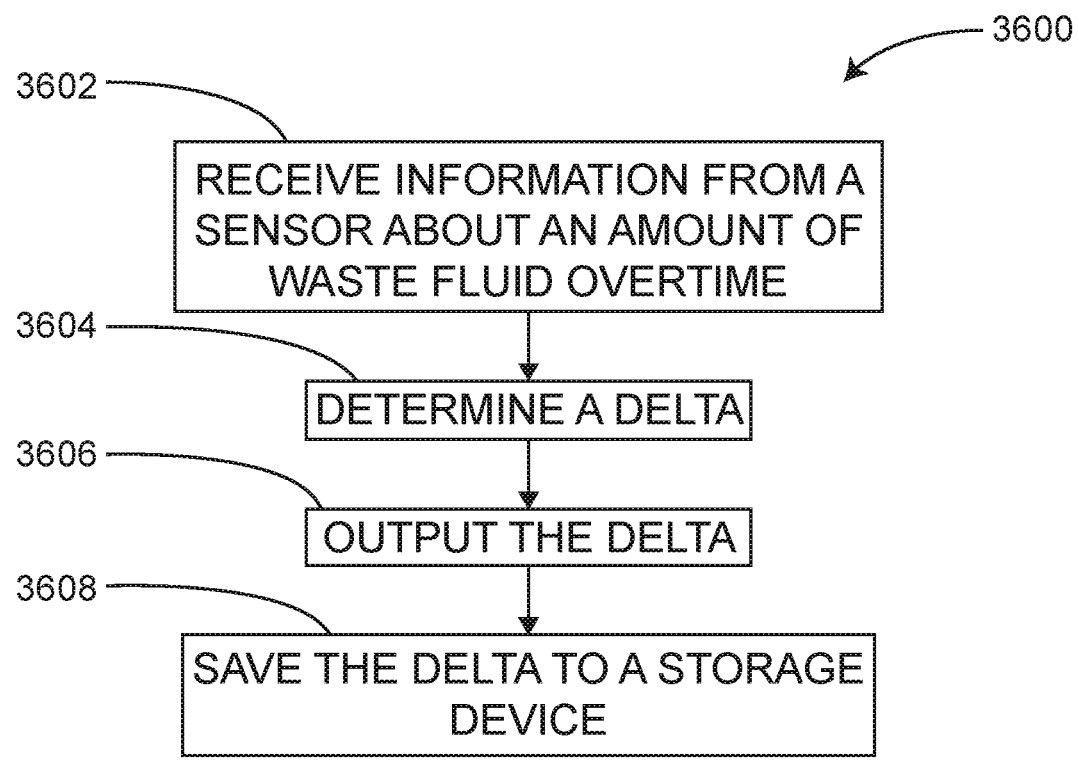
FIG. 36 illustrates another flow chart showing a technique for operating a module, in accordance with at least one example.

FIG. 36 illustrates a flow chart showing a technique 3600 for monitoring waste fluid during a surgery using system 3300 (e.g., including any module, such as module 10) in accordance with some examples. The technique 3600 can include operation 3602 including receiving information from a sensor about an amount of waste fluid collected over time. Operation 3604 can include determining a delta. Operation 3606 can include outputting the delta, such as for display by an electronic device mounted on the system 3300 or on a wireless tablet device. Operation 3608 can include saving the delta to a storage device. In some examples, the storage device can include at least a portion of the patient's anesthetic record thereon. Technique 3600 can include additional steps as well as the more detailed steps outlined in Example Set 3 under the Various Notes and Embodiments section.

Figure 37:
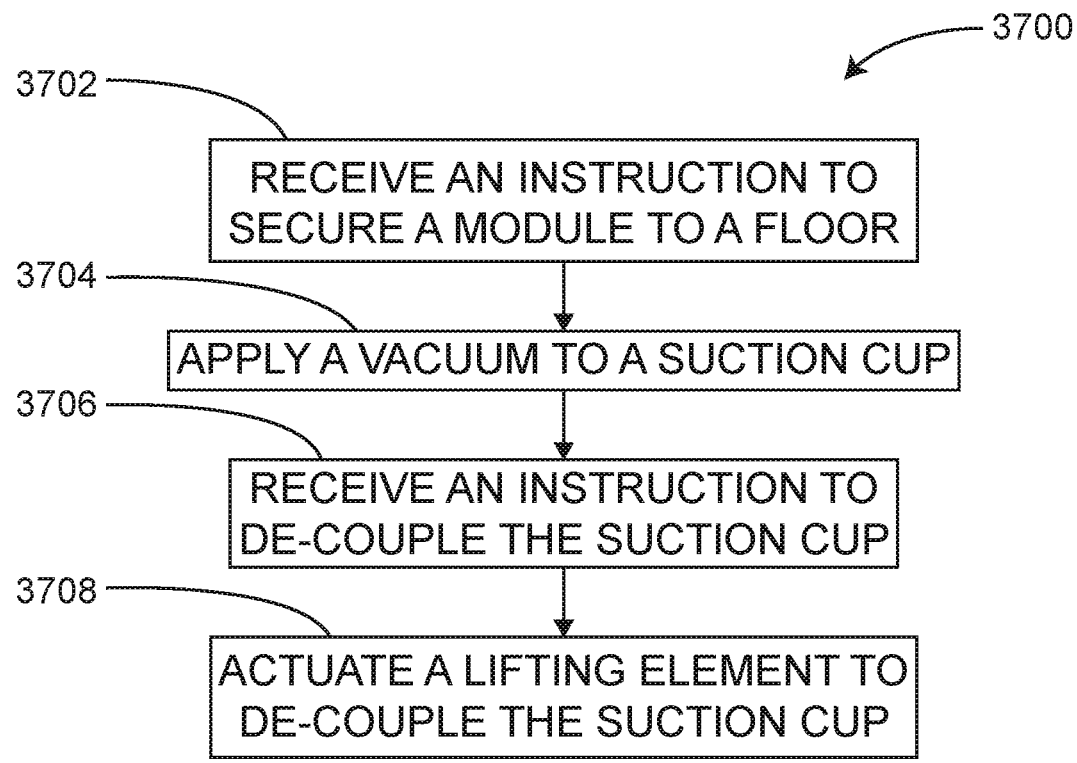
FIG. 37 illustrates another flow chart showing a technique for operating a module, in accordance with at least one example.

FIG. 37 illustrates a flow chart showing a technique 3700 for applying vacuums using system 3300 (e.g., including any module, such as module 10), in accordance with some examples. The technique 3700 can include operation 3702 receiving an instruction to secure a module to a floor. Operation 3704 can include applying a vacuum to a suction cup. Operation 3706 can include receiving an instruction to de-couple the suction cup, and based on the instruction, in operation 3708 releasing the vacuum (e.g., by venting to atmosphere) and actuating a lifting element to de-couple the suction cup. Technique 3700 can also include methods of applying the vacuum to waste fluid systems described herein. Technique 3700 can include additional steps as well as the more detailed steps outlined in Example Set 4 under the Various Notes and Embodiments section.

Figure 38:
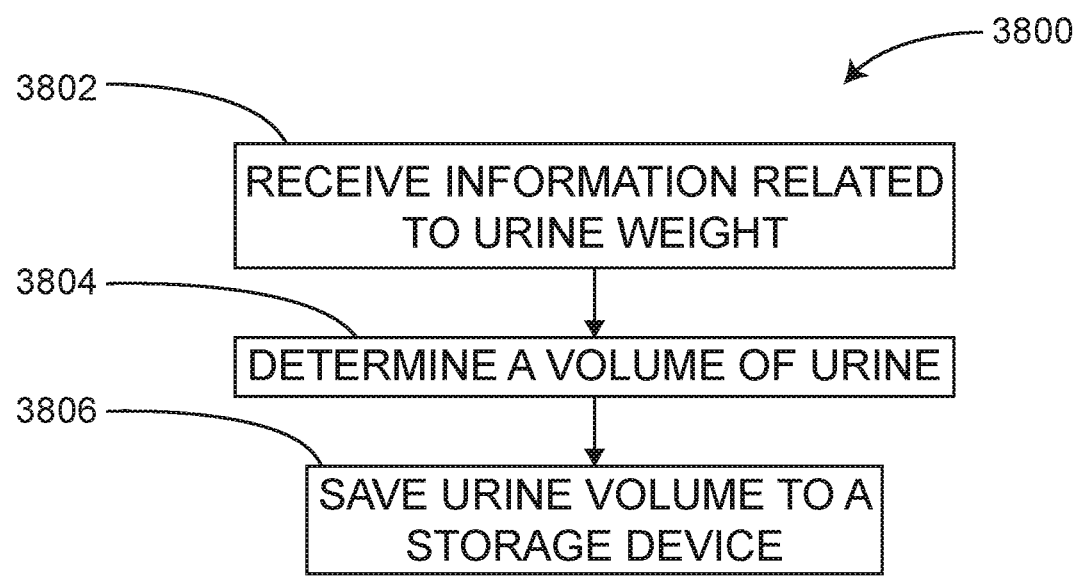
FIG. 38 illustrates another flow chart showing a technique for operating a module, in accordance with at least one example.

FIG. 38 illustrates a flow chart showing a technique 3800 for measuring urine output from a catheterized patient using system 3300 (e.g., including any module, such as module 10), in accordance with some examples. The technique 3800 can include operation 3802 receiving information related to urine weight output. Operation 3804 can include determining a volume of urine from the urine weight. Operation 3806 can include saving the urine volume to a storage device. In some examples the storage device can include at least a portion of a patient's anesthetic record stored thereon. Technique 3800 can include additional steps as well as the more detailed steps outlined in Example Set 5 under the Various Notes and Embodiments section.

Figure 39:
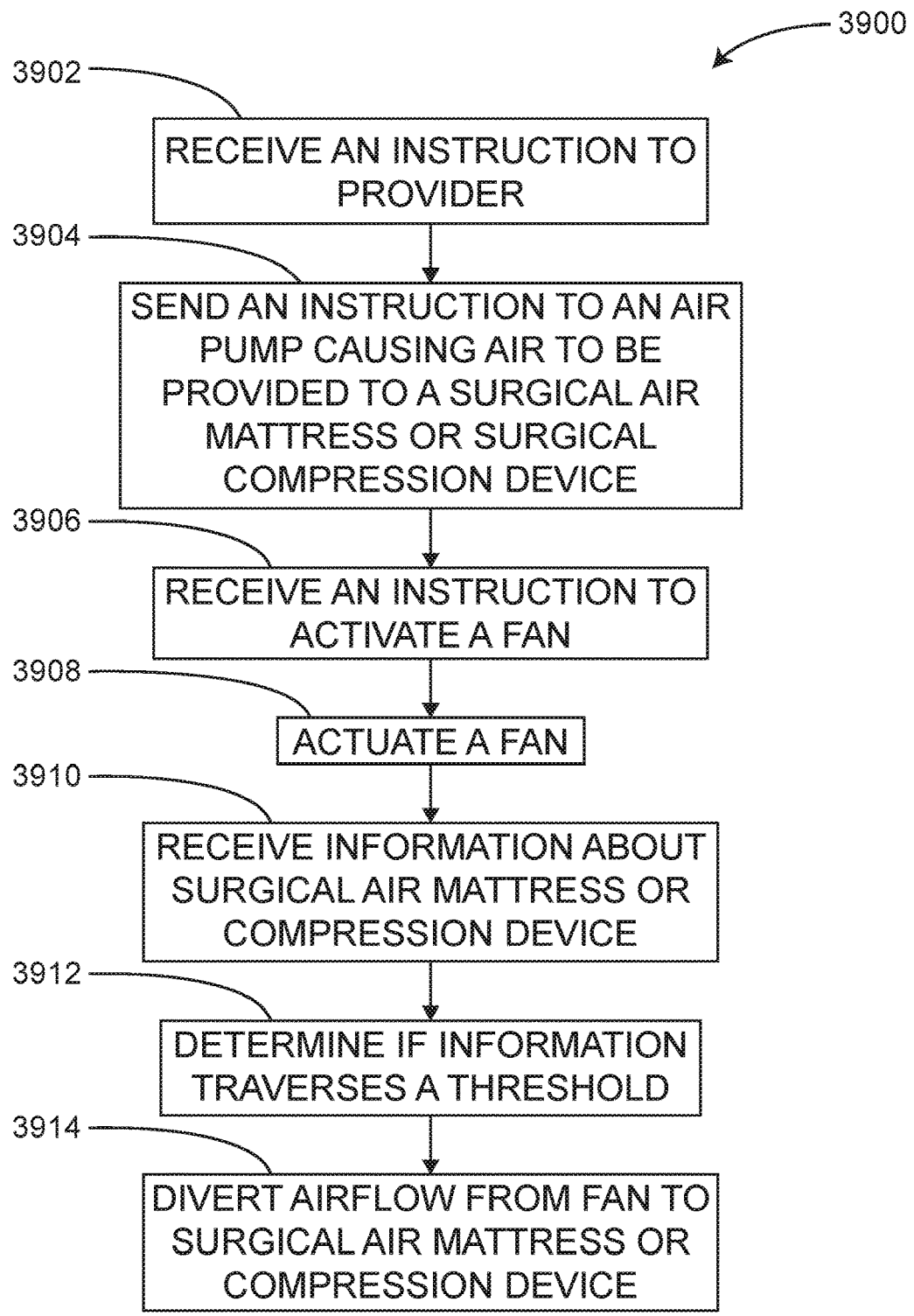
FIG. 39 illustrates another flow chart showing a technique for operating a module, in accordance with at least one example.

FIG. 39 illustrates a flow chart showing a technique 3900 for operating a module (e.g., any module herein, such as module 10) using system 3300, in accordance with some examples. The technique 3900 can include operation 3902 receiving an instruction to provide air. Operation 3904 sending an instruction to an air pump causing air to be provided to a surgical air mattress or a surgical compression device. Operation 3906 can include receiving an instruction to activate a fan. Operation 3908 can include activating the fan. Operation 3910 can include receiving information about the surgical air mattress or the surgical compression device. Operation 3912 can include determining if the information traverses a threshold. Operation 3914 can include diverting airflow from the fan to the surgical air mattress of the surgical compression device. Technique 3900 can include additional steps as well as the more detailed steps outlined in Example Set 6 under the Various Notes and Embodiments section.

Figure 40:
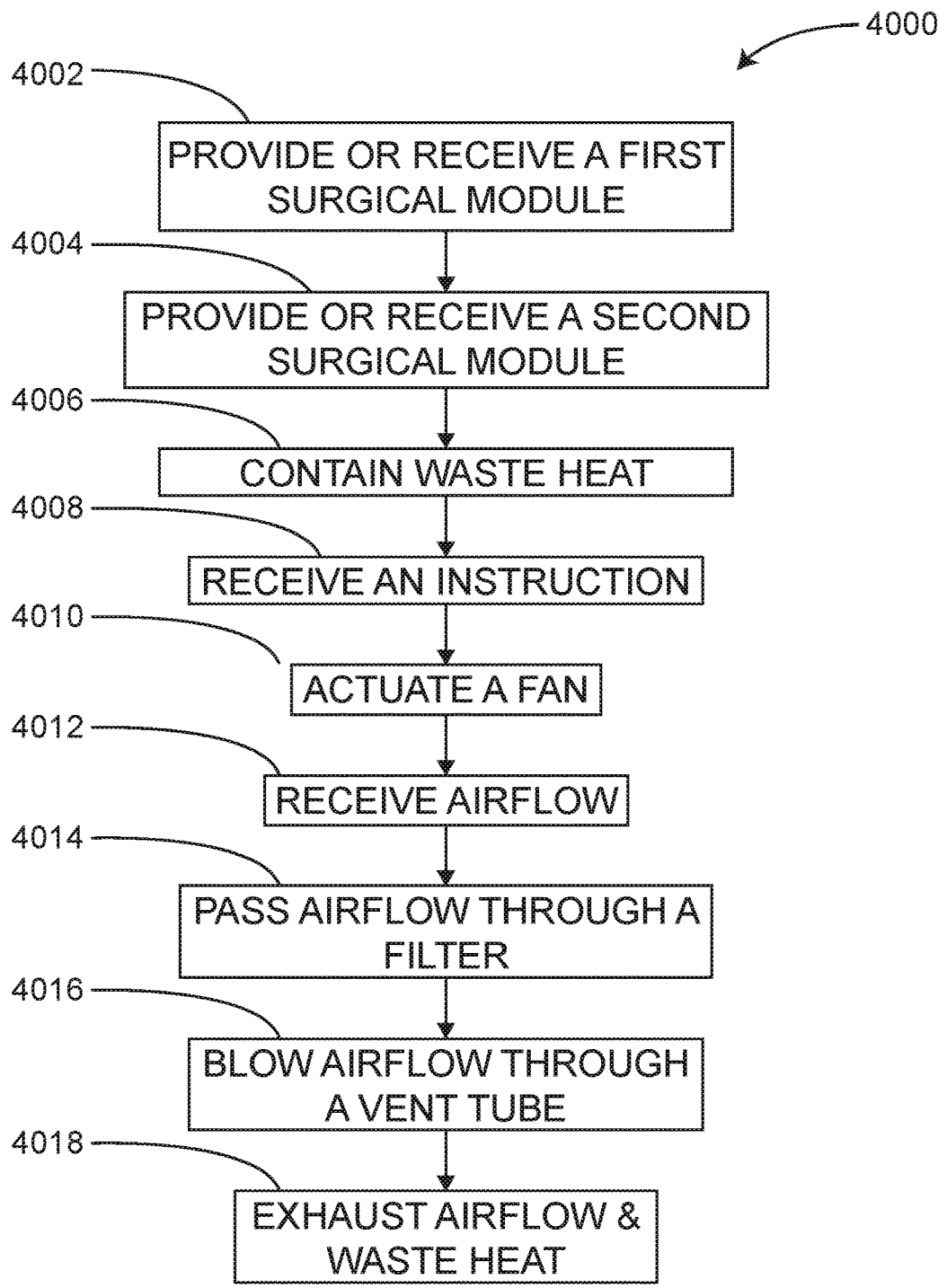
FIG. 40 illustrates another flow chart showing a technique for operating a module, in accordance with at least one example.

FIG. 40 illustrates a flow chart showing a technique 4000 for filtering air in a surgical field using system 3300 (e.g., including any module, such as module 10), in accordance with some examples. The technique 400 can include operation 4002 of providing or receiving a first electronic or electromechanical surgical equipment module. Operation 4004 of providing or receiving a second electronic or electromechanical surgical equipment module. Operation 4006 can include containing the waste heat generated by the modules inside of the housing. Operation 4008 can include receiving an instruction. Operation 4010 can include actuating a fan based on the received instruction. Upon operation of the fan, operation 4012 can include receiving airflow into the housing. Operation 4014 can include passing the airflow through a filter. Operation 4016 can include blowing airflow through a vent tube, and operation 4018 can include exhausting at least a portion of the airflow and the waste heat out of the housing. Technique 4000 can include additional steps as well as the more detailed steps outlined in Example Set 7 under the Various Notes and Embodiments section.

Figure 41:
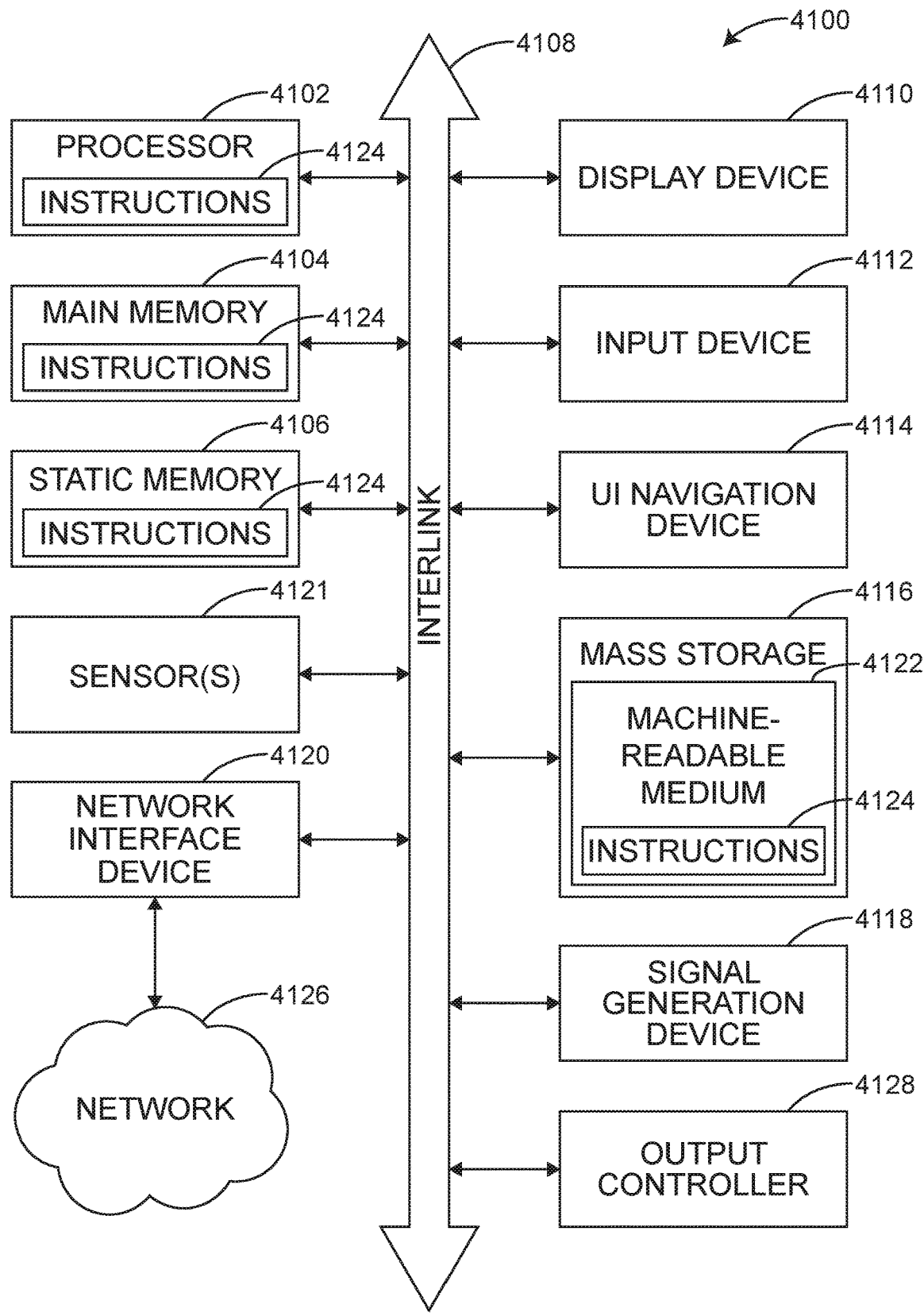
FIG. 41 illustrates generally an example of a block diagram of a machine (e.g., of module 10) upon which any one or more of the techniques (e.g., methodologies) discussed herein may perform in accordance with some embodiments.

FIG. 41 illustrates generally an example of a block diagram of a machine (e.g., of module 10) upon which any one or more of the techniques (e.g., methodologies) discussed herein may perform in accordance with some embodiments. In alternative embodiments, the machine 4100 may operate as a standalone device or may be connected (e.g., networked) to other machines. In a networked deployment, the machine 4100 may operate in the capacity of a server machine, a client machine, or both in server-client network environments. The machine 4100 may be a personal computer (PC), a tablet PC, a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate on, logic or a number of components, modules, or like mechanisms. Such mechanisms are tangible entities (e.g., hardware) capable of performing specified operations when operating. In an example, the hardware may be specifically configured to carry out a specific operation (e.g., hardwired). In an example, the hardware may include configurable execution units (e.g., transistors, circuits, etc.) and a computer readable medium containing instructions, where the instructions configure the execution units to carry out a specific operation when in operation. The configuring may occur under the direction of the execution units or a loading mechanism. Accordingly, the execution units are communicatively coupled to the computer readable medium when the device is operating. For example, under operation, the execution units may be configured by a first set of instructions to implement a first set of features at one point in time and reconfigured by a second set of instructions to implement a second set of features.

Machine (e.g., computer system) 4100 may include a hardware processor 4102 (e.g., a central processing unit (CPU), a graphics processing unit (GPU), a hardware processor core, or any combination thereof), a main memory 4104 and a static memory 4106, some or all of which may communicate with each other via an interlink (e.g., bus) 4108. The machine 4100 may further include a display unit 4110, an alphanumeric input device 4112 (e.g., a keyboard), and a user interface (UI) navigation device 4114 (e.g., a mouse). In an example, the display unit 4110, alphanumeric input device 4112 and UI navigation device 4114 may be a touch screen display. The display unit 4110 may include goggles, glasses, or other AR or VR display components. For example, the display unit may be worn on a head of a user and may provide a heads-up-display to the user. The alphanumeric input device 4112 may include a virtual keyboard (e.g., a keyboard displayed virtually in a VR or AR setting.

The machine 4100 may additionally include a storage device (e.g., drive unit) 4116, a signal generation device 4118 (e.g., a speaker), a network interface device 4120, and one or more sensors 4121, such as a global positioning system (GPS) sensor, compass, accelerometer, or other sensor. The machine 4100 may include an output controller 4128, such as a serial (e.g., universal serial bus (USB), parallel, or other wired or wireless (e.g., infrared (IR), near field communication (NFC), etc.) connection to communicate or control one or more peripheral devices.

The storage device 4116 may include a machine readable medium 4122 that is non-transitory on which is stored one or more sets of data structures or instructions 4124 (e.g., software) embodying or utilized by any one or more of the techniques or functions described herein. The instructions 4124 may also reside, completely or at least partially, within the main memory 4104, within static memory 4106, or within the hardware processor 4102 during execution thereof by the machine 4100. In an example, one or any combination of the hardware processor 4102, the main memory 4104, the static memory 4106, or the storage device 4116 may constitute machine readable media.

While the machine readable medium 4122 is illustrated as a single medium, the term "machine readable medium" may include a single medium or multiple media (e.g., a centralized or distributed database, or associated caches and servers) configured to store the one or more instructions 4124.

The term "machine readable medium" may include any medium that is capable of storing, encoding, or carrying instructions for execution by the machine 4100 and that cause the machine 4100 to perform any one or more of the techniques of the present disclosure, or that is capable of storing, encoding or carrying data structures used by or associated with such instructions. Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 4124 may further be transmitted or received over a communications network 4126 using a transmission medium via the network interface device 4120 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 4102.11 family of standards known as Wi-Fi®, as the personal area network family of standards known as Bluetooth® that are promulgated by the Bluetooth Special Interest Group, peer-to-peer (P2P) networks, among others. In an example, the network interface device 4120 may include one or more physical jacks (e.g., Ethernet, coaxial, or phone jacks) or one or more antennas to connect to the communications network 4126. In an example, the network interface device 4120 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 4100, and includes digital or analog communications signals or other intangible medium to facilitate communication of such software.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The modules described herein with respect to FIGS. 1-42, and including the machine 4100, can include features to help with medical aspects including monitoring medication and anesthesia delivery, and other functions, as well as documenting medication and anesthesia delivery, and other functions. In general, doctors and nurses are not interested in replacing themselves and their jobs with automated drug delivery or automated anesthesia systems. However, there is great interest in automated record keeping. Virtually all anesthesia providers would prefer the "old" paper record and a pen to the "new" computer records. Filling out the electronic anesthetic record (EAR) using a computer keyboard, mouse and various menus is widely viewed as a slow, cumbersome and distracting process. The challenge with automated record keeping is automating the data input that documents the numerous activities, anesthesia related events, fluid, gas and medication administration, ventilator settings, pressure off-loading effectiveness, as well as outputs such as blood loss and urine output, that constitute an anesthetic experience.

The second challenge in implementing an automated electronic anesthetic record (EAR) 201 or electronic medical record (EMR) 201 is to force as little change in the caregiver's routine as possible onto the clinicians using this system. Medical personnel tend to be creatures of habit and tradition and they generally do not like change. For example, IV medications are traditionally administered from a syringe and the dose is determined by the caregiver observing the plunger moving relative to a scale printed on the syringe. Maintaining this general technique of drug administration may have the highest probability of acceptance by healthcare users who are typically slow to embrace changes in their routine.

Figure 42:
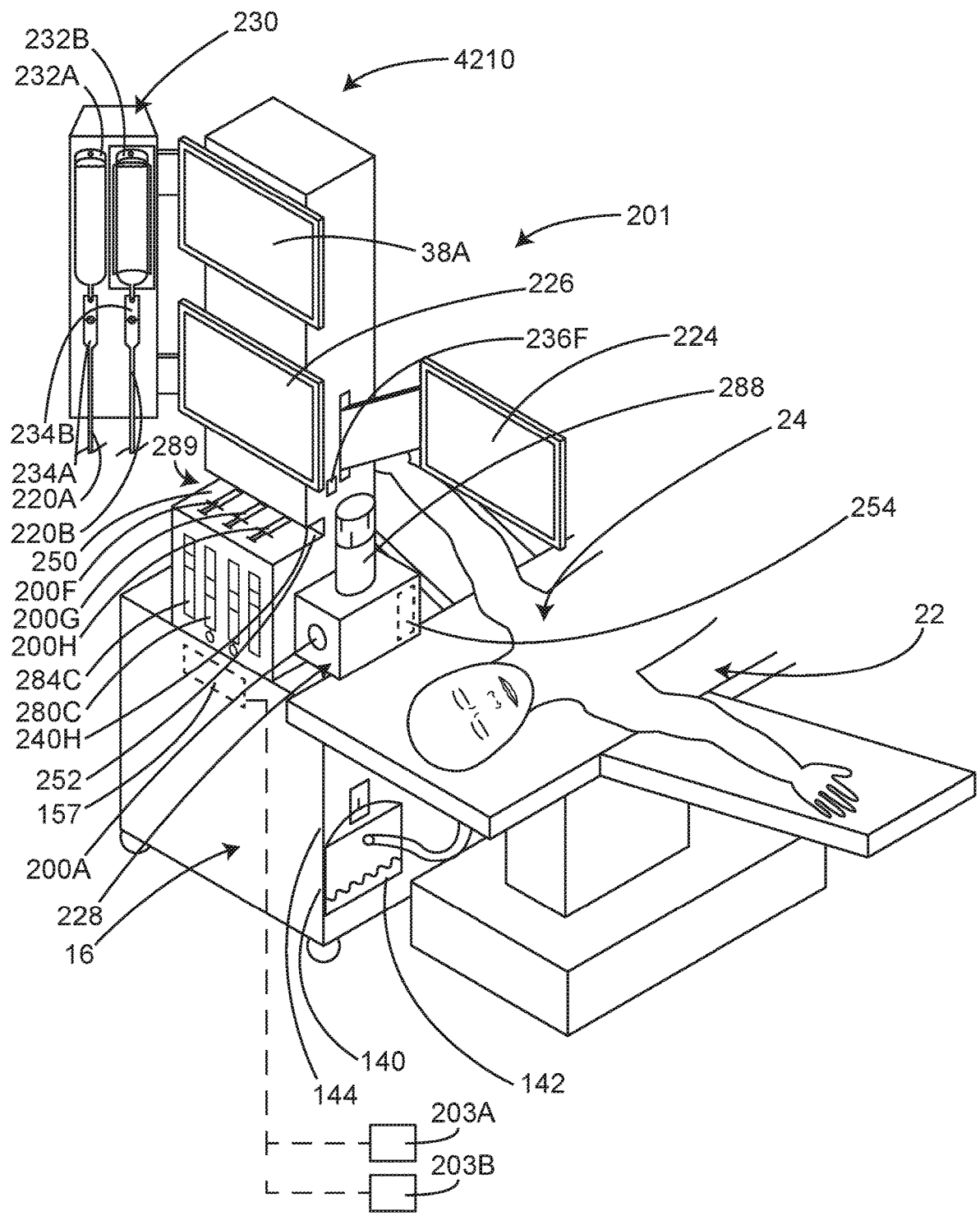
FIG. 42 illustrates an isometric view of an example system for generating an automated electronic anesthetic record located proximate to a patient, in accordance with at least one example.

FIG. 42 illustrates an isometric view of a relocation module 4210. Relocation module 4210 can include any of the features shown and described in FIGS. 1-41, including module 10 of FIG. 1. Relocation module 4210 can include an example system for generating an automated electronic anesthetic record (EAR) (e.g., system 228), wherein the system 228 can be located proximate to a patient. The module 4210 can be a module for housing unrelated electronic and electromechanical surgical equipment (as described, for example, with respect to module 10 of FIG. 1). However, the module 4210 does not need to include all of the features described herein, and does not need to include all the features of module 10, although it may. For example, the module 4210, and any other example modules described herein, need not necessarily be configured to house unrelated electronic and electromechanical surgical equipment in all examples, and other modules can include the system for generating an automated EAR 201. Like numerals can represent like components, therefore not all of the components are described in further detail.

The module 4210 can include automated EAR system 201 that can include one or more systems (e.g., 228, 230) configured to measure (e.g., monitor) and record one or more of functions involved in a surgical anesthetic environment, and can include life support functions. The one or more systems 228, 230 can measure and record data automatically. However, in some examples, a user may initiate the system to measure and/or record data. These various measurements may be electronically recorded and displayed on the electronic anesthetic record display 226. Inputs to the automated EAR system 201 may be managed by the anesthetic record input component 224. The anesthetic record input component 224 can include a touch-screen display that organizes all of the inputs to the EAR 203 into easily accessed and utilized information. In some examples, and as shown in FIG. 42, the medication identification and measurement system 228 of this disclosure may be located proximate the patient 24. The control displays for the medication identification and measurement system 228 may include a dedicated display proximate the medication identification and measurement system 228 or may be shared space on the anesthetic record input component 224. In these locations, the information and controls of the medication identification and measurement system 228 can be viewed by the anesthesiologist or other user, in a single field of vision with the patient and surgical field.

As shown in FIG. 42, the automated EAR 203 of this disclosure may be attached to and stored within the relocation module 4210. The relocation module 4210 can conveniently provide direct access to the patient's 24 head and therefore provides convenient mounting support location for the system. In some examples, the components and systems of the automated EAR system 201 of this disclosure can be supported by other mounting supports, including but not limited to an IV pole, a boom-mounted rack system, a wheeled rack system and a surgical table mounting bracket. One or more computers including processing circuitry 157, of the automated EAR system 201 of this disclosure may be conveniently and safely housed inside the relocation module 4210. In some examples, it is also anticipated that some or all of the components of automated EAR system 201 of this disclosure could be used in other healthcare settings such as the intensive care unit, the emergency room or on the ward.

In some examples, the touch-screen anesthetic record input component 224 can convert to a qwerty-type keyboard to allow uncommon anesthetic and surgical events or deviations from pre-recorded scripts, to be manually documented. This allows the standard computer keyboard that is used for data entry in most electronic anesthetic records, to be eliminated. Standard keyboards are known to be contaminated with pathogenic organisms and are nearly impossible to clean and decontaminate due to their irregular surfaces. In contrast, the smooth glass or plastic face of a touch-screen monitor is easy to clean with no crevasses to hide organisms.

In some examples, the automated EAR system 201 of this disclosure can include a system for automatically measuring and recording the administration of IV medications. In some examples, the system for automatically measuring and recording the administration of IV medications includes a medication identification and measurement system 228. As shown in FIG. 42, the medication identification and measurement system 228 may be advantageously positioned proximate the patient 24, such as near the patient's head so that medications can be conveniently administered while tending to and observing the patient.

In some examples, the medication identification and measurement system 228 may include one or more sensors, such as one or more of: a barcode reader (e.g., 236A, FIG. 44), a radio-frequency identification (RFID) interrogator (e.g., 238A, FIG. 44), or any other suitable sensor for accurately and reliably identifying a medication for IV administration. As defined herein, a barcode reader can include any other type of identifying reader, such as, but not limited to, a QR code reader. Likewise, the RFID interrogator can be any type of interrogator and is not limited to those interrogators based on radio frequency.

In some examples, instead of, or in addition to one or more of an RFID interrogator and a barcode reader, the system can receive an input to determine the identity. For example, the system can include one or more of: a sensor configured to identify the one or more IV medications or fluids, or an input configured to receive the identity of the one or more IV medications or fluids, such as via the anesthetic record input component 224.

In some examples, the barcode reader may be a "computer vision" or "machine vision" camera 236 with the capability of reading barcodes. The term "machine vision" is often associated with industrial applications of a computer's ability to see, while the term "computer vision" is often used to describe any type of technology in which a computer is tasked with digitizing an image, processing the data it contains and taking some kind of action. In this disclosure we will use the terms "machine vision" and "computer vision" interchangeably. Traditionally, machine vision includes technology and methods used to provide imaging-based automatic inspection and analysis, process control, and robot guidance. Machine vision is sometimes used in manufacturing environments. Machine vision refers to many technologies, software and hardware products including processing circuitry, integrated systems and methods.

The inventors have discovered that machine vision can be useful beyond its traditional uses. The inventors discovered that machine vision can be advantageous in implementing an automated EAR 203 because it offers reliable measurements, gauging, object recognition, pattern recognition and liquid fill level measurements. Machine vision does not get tired or distracted. Machine vision excels at quantitative measurement of a structured scene because of its speed, accuracy and repeatability. However, it does require the scene to be structured to perform the desired function.

Machine vision can be very accurate for measuring size of an object at a known distance or the distance of an object of known size. However, it cannot do both. Therefore, in some examples it is important to know the exact location of a syringe (e.g., 200C, FIG. 45) for example and thus know the distance from the camera (e.g., 236A, FIG. 45) to the syringe (e.g., 200C, FIG. 45) in order for the machine vision to calculate the distance of the movement of the plunger within the syringe. This is what we mean by the "scene being structured."

Machine vision may be advantageous for the automated EAR system 201 (EAR) of this disclosure because it "sees" and measures, but does not touch or interfere with the anesthesia provider doing their normal job of injecting medications or administering IV fluids. Further, the same visual image that is used by the machine vision software can be displayed on a screen 226 to give the operator (whose fingers are pushing the plunger of the syringe) a close-up view of the syringe. The machine vision is looking at the same view of the syringe as the operator.

The machine vision camera, or digital camera, can include machine vision software, or the machine vision camera can be in electrical communication with (e.g., operably coupled to) one or more hardware processors, such as processing circuitry 152 and one or more machine-readable mediums, that when implemented on the processing circuitry 157, can perform the functions described herein. The processing circuitry 157 can be stored in the module 4210, remote from the module 4210 (e.g. in a wired or wireless manner). As shown in FIG. 33, the processing circuitry 157 can be or include a processor 3304 that interacts with accessories 3340 of the illustrative module 4210. For example, systems 228 and 230 can be included as accessories 3340 in communication with other components of the surgical module 3301 as shown and described in FIG. 33.

In some examples, the RFID interrogator 238 may be either High Frequency (HF) or Near Field (NF) RFID in order to advantageously limit the read-range to a distance of less than 12 inches. In some examples, the RFID read-range may advantageously be limited, such as to less than 8 inches so that only a specific medication injection is identified at any time. In a possibly more preferred example, the RFID read-range may be limited to less than 4 inches to further prevent mis-readings. NF-RFID has a short read-range by definition and the read-range of HF-RFID can be easily limited by restricting the size of the antenna on the tag. In contrast, longer read-range RFID such as Ultra-high Frequency (UHF-RFID) may confusingly interrogate every RFID tag in the operating room and thus be unable to identify which medication is being delivered to the medication identification and measurement system 228.

Figure 43:
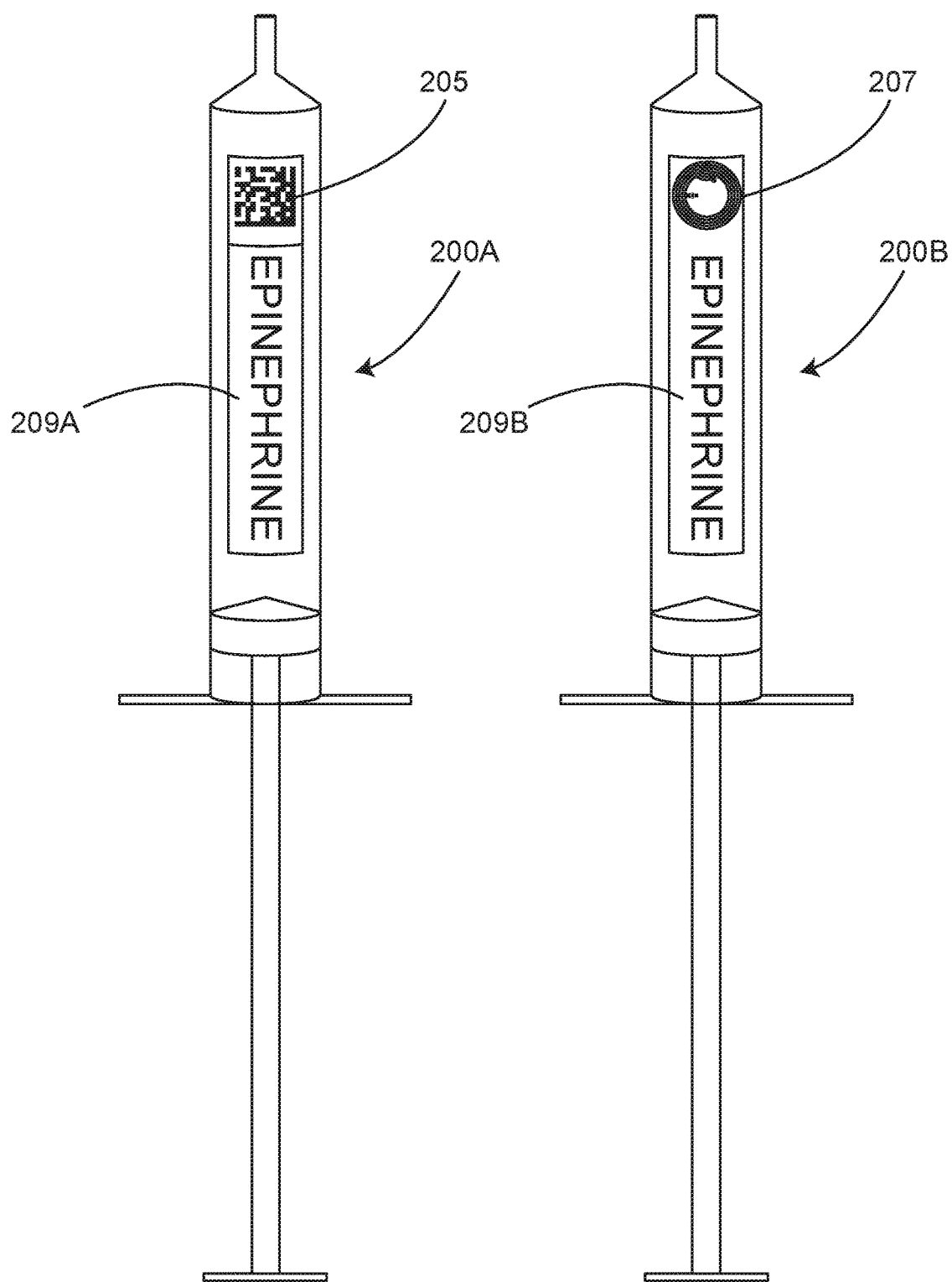
FIG. 43 illustrates a plan view of an example of preloaded syringes 200A and 200B that can be used with the system of FIG. 42, in accordance with at least one example.

FIG. 43 illustrates a plan view of an example of preloaded syringes 200A and 200B that can be used with the system of FIG. 42

The one or more preloaded syringes 200A and 200B may be labeled with a unique barcode label 205 or an RFID tag 207 that may identify one or more of the drug, the concentration, the lot number, the expiration date, the manufacturer and other important information. In some examples, a unique barcode label 205 may be a "2-D" barcode label in order to include more information on a smaller area than traditional barcode labels. In some examples, the barcode label 205 or RFID tag 207 includes the drug identifying label 209A and 209B for convenient use by the caregiver.

In some examples, the syringes 200A and 200B can be filled at the point of use and may be labeled with drug labels 209A and 209B and either barcode labels 205 or RFID tags 207 that are removably attached to the drug bottle or vial at the factory or pharmacy. The drug labels 209A and 209B and either barcode labels 205 or RFID tags 207 may be easily removed from the drug bottle or vial and adhesively attached to the syringe 200A or 200B at the time that the syringe 200A or 200B is loaded with the drug by the caregiver. Instead of, or in addition to the barcode labels 205 or RFID tags 207, any other suitable "tag/reader" system known in the arts, may be used.

Figure 44:
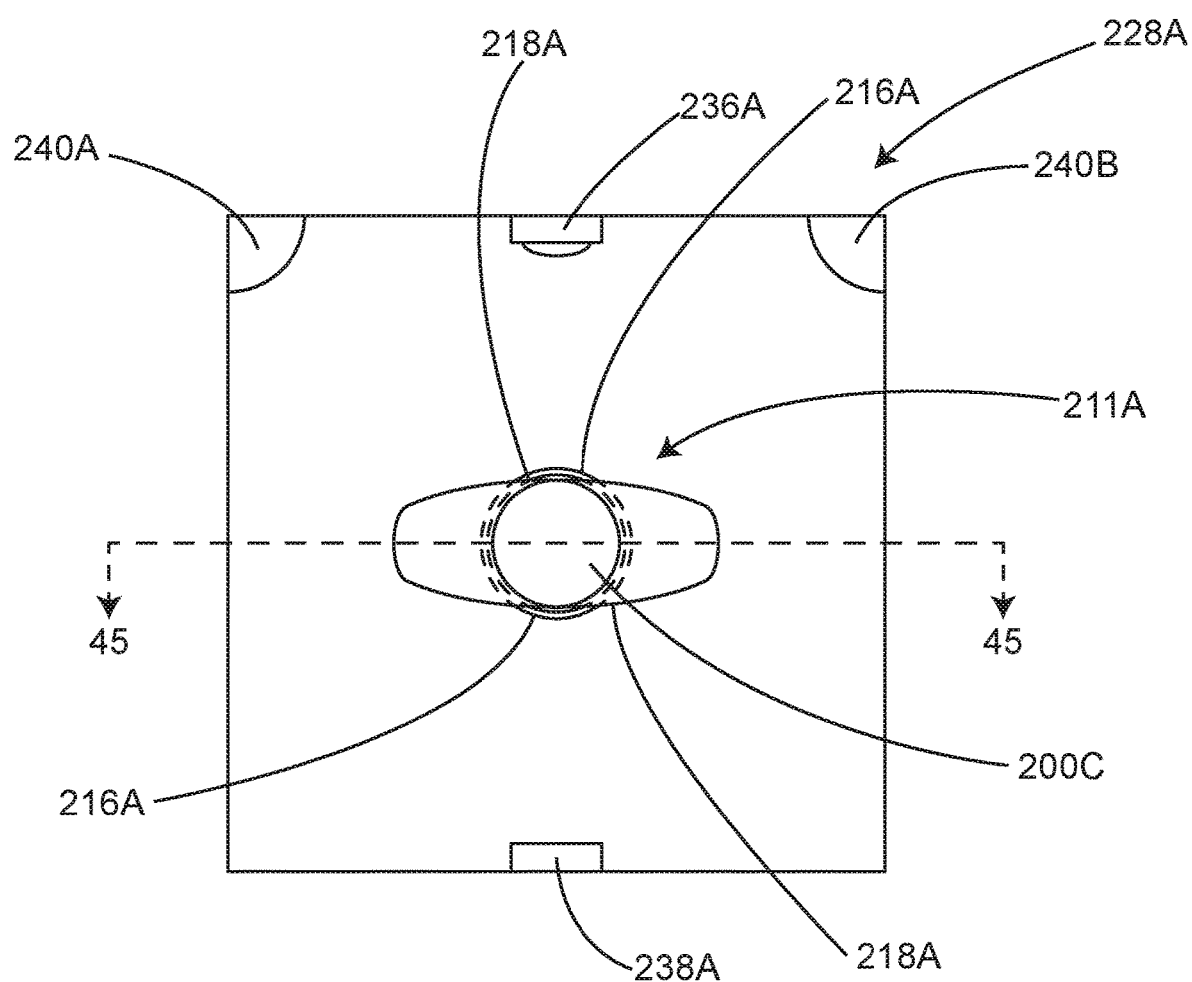
FIG. 44 illustrates a side view of an example medication identification and measurement system and a syringe that can be used with the system of FIG. 42, to monitor drug delivery, in accordance with at least one example.
Figure 45:
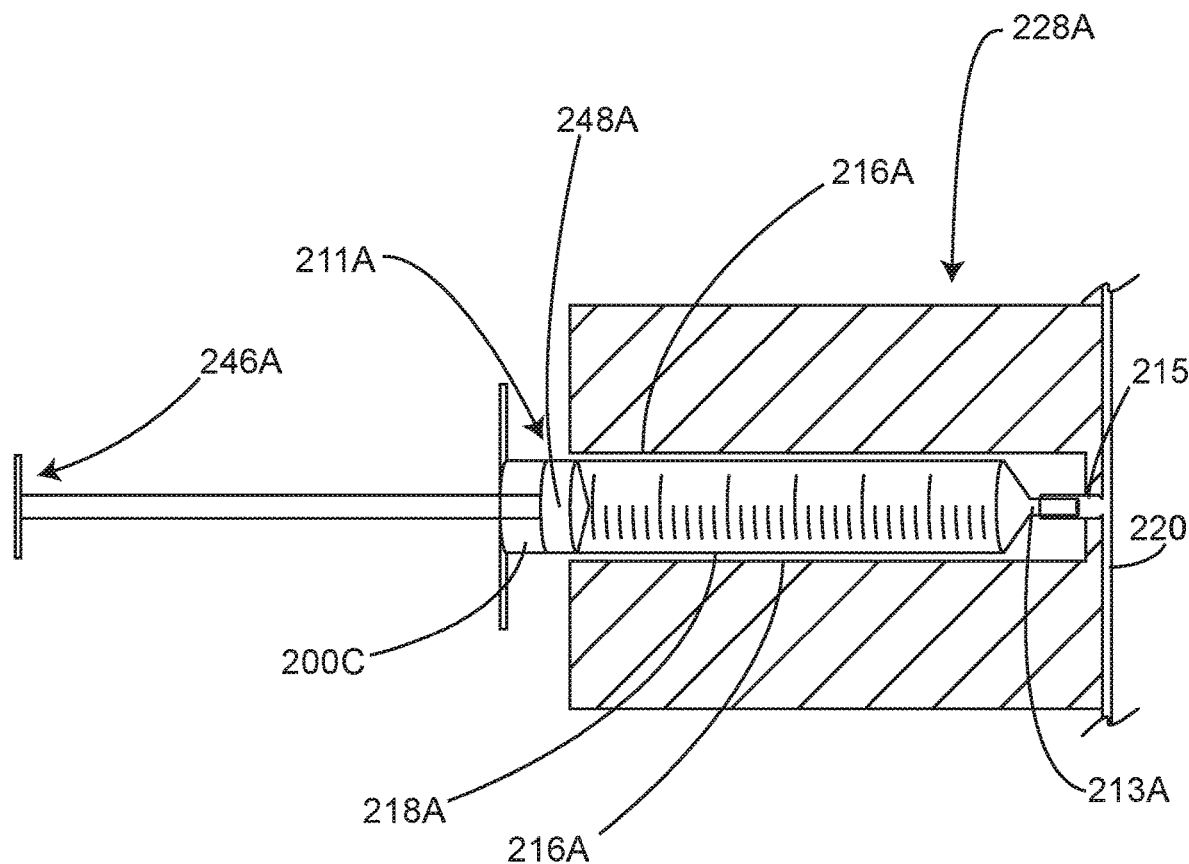
FIG. 45 illustrates a cross-sectional view of the medication identification and measurement system and a syringe (not shown in cross-section) of FIG. 44, taken along line 45-45, in accordance with at least one example.

FIG. 44 illustrates a side view of an example medication identification and measurement system and a syringe that can be used with the system of FIG. 42, to monitor drug delivery. FIG. 45 illustrates a cross-sectional view of the medication identification and measurement system and a syringe (not shown in cross-section) of FIG. 44, taken along line 45-45.

As shown in FIGS. 44 and 45, the medication identification and measurement system 228A of this disclosure may include one or more injection portals 211A. The injection portal 211A may be a receptacle for accommodating a syringe 200C in a fixed and known location and can be configured to orient the Luer taper connector 213A to mate with an injection port 215. The injection port 215 can be secured within the injection portal 211A and can be in fluid communication with IV tubing 220. In some examples, the injection portal 211A may be a clear tube 216A that is sized to accommodate the syringe barrel 218A of a specific size syringe 200C. In this example, multiple injection portals 211A would be required to accommodate syringes 200C of different sizes.

Figure 46:
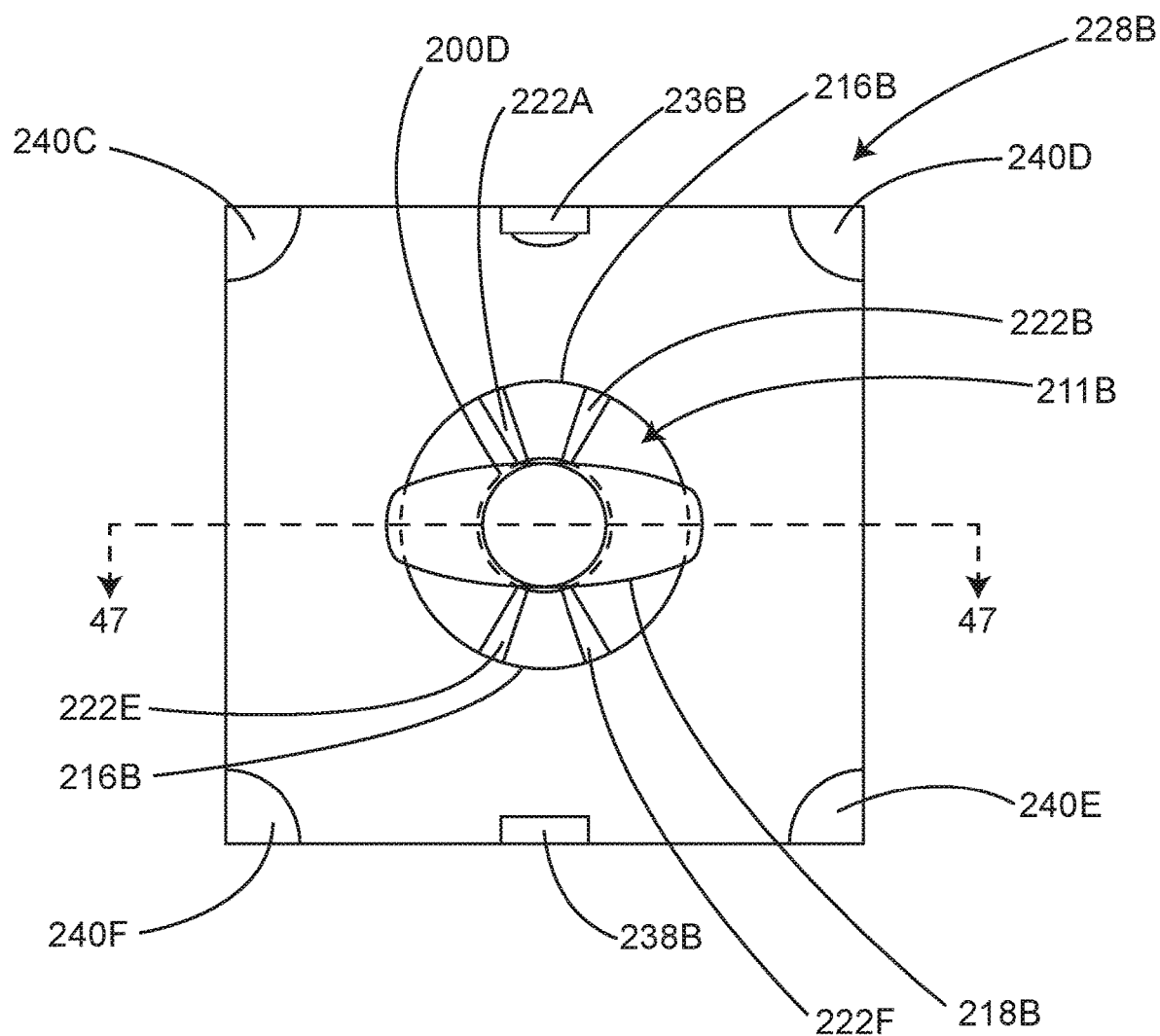
FIG. 46 illustrates a side view of a second example medication identification and measurement system and a syringe that can be used with the system of FIG. 42, in accordance with at least one example.
Figure 47:
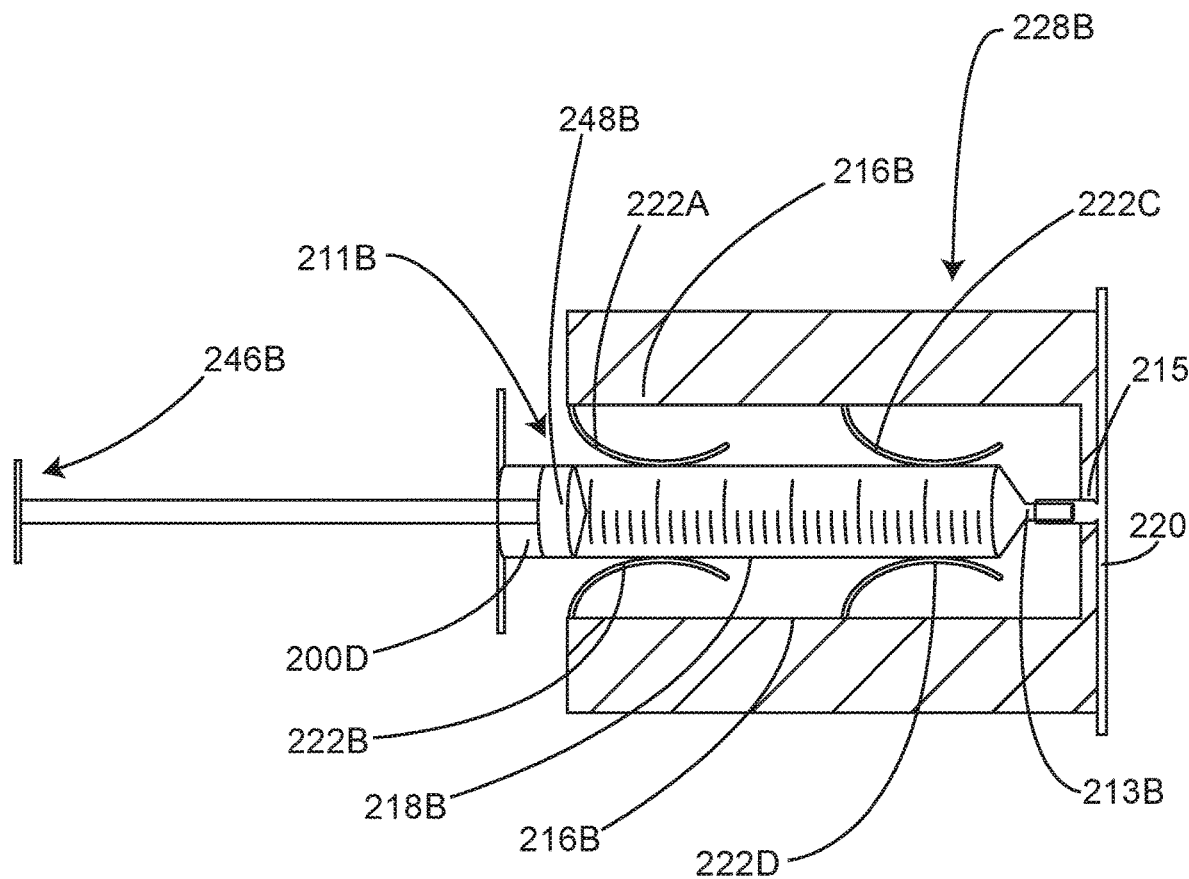
FIG. 47 illustrates a cross-sectional view of the second example of a medication identification and measurement system and the syringe (not shown in cross-section) of FIG. 46, taken along line 47-47, in accordance with at least one example.

FIG. 46 illustrates a side view of a second example medication identification and measurement system and a syringe that can be used with the system of FIG. 42. FIG. 47 illustrates a cross-sectional view of the second example of a medication identification and measurement system and the syringe (not shown in cross-section) of FIG. 46.

As shown in FIGS. 46 and 47, the injection portal 211B of the medication identification and measurement system 228B may be large enough to accommodate syringes 200D of multiple sizes within the space defined by a real or imaginary injection portal tube 216B. In this embodiment, accurately orienting the Luer taper connector 213B to mate with an injection port 215 may be accomplished by one or more orienting members such as one or more spring positioning members 222A-F that engage with the syringe barrel 218B to center it in the injection portal 211B. In some examples, there may be two or more rows of spring positioning members 222A-F. For example, spring positioning members 222A, B, E, F may be located near the entrance to the injection portal 211B and spring positioning members 222C, D may be located near the injection port 215 to assure accurate positioning for mating with the Luer taper connector 213B. Spring positioning members 222 may include not only spring wires or metal or plastic spring pieces but any flexible material or combination of materials or shapes that can be deformed by the syringe barrel 218B entering the injection portal 211B and retain a memory (e.g., elastically deformable, substantially elastically deformable, resiliently deformable, resilient member) so as to urge the syringe barrel 218B into a centered position within the space defined by a real or imaginary injection portal tube 216B.

One possible objective of the spring positioning members 222A-F is to "automatically" center and align the Luer taper connector 213B of the syringe 200B with the injection port 215, so that the operator can simply and conveniently push the syringe 200D into the injection portal 211B and no further manual alignment may be needed. The spring positioning members 222A-F can also obviate the need for the operator to touch either the Luer taper connector 213B of the syringe 200B or the injection port 215, thus beneficially preventing accidental infectious contamination by the operators' fingers and gloves.

Figure 48:
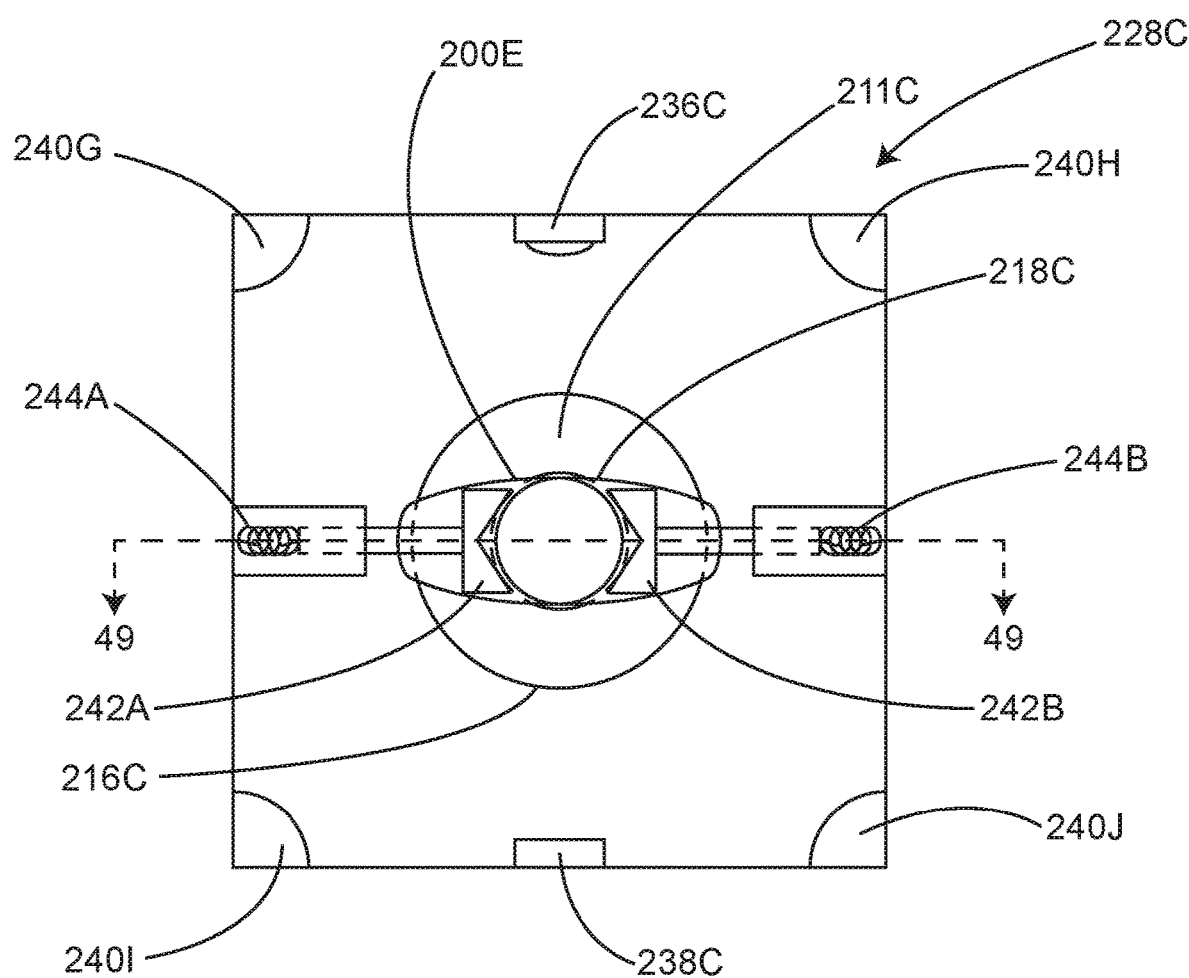
FIG. 48 illustrates a side view of a third example of a medication identification and measurement system and a syringe that can be used with the system of FIG. 42, in accordance with at least one example.
Figure 49:
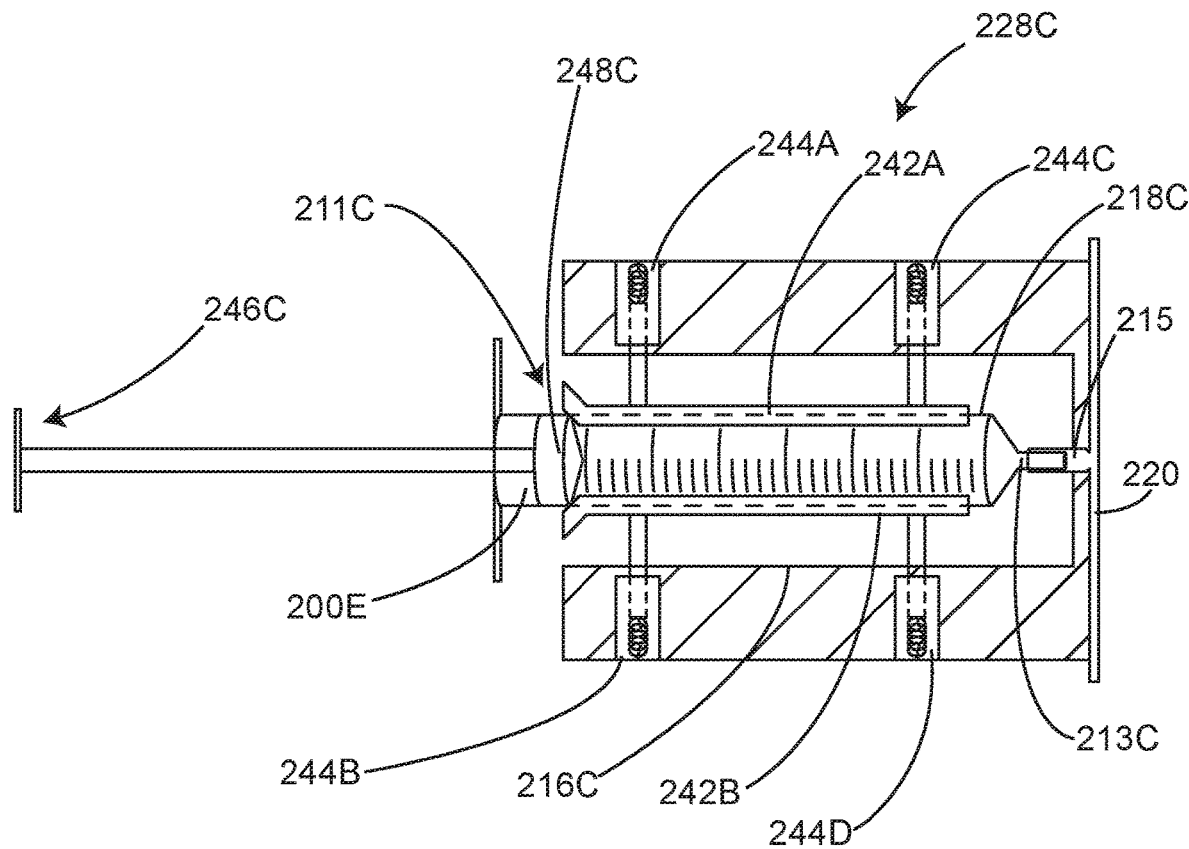
FIG. 49 illustrates a cross-sectional view of the third example of a medication identification and measurement system and the syringe (not shown in cross-section) of FIG. 48, taken along line 49-49, in accordance with at least one example.

FIG. 48 illustrates a side view of a third example of a medication identification and measurement system and a syringe that can be used with the system of FIG. 42. FIG. 49 illustrates a cross-sectional view of the third example of a medication identification and measurement system and the syringe 200E (not shown in cross-section) of FIG. 48, taken along line 49-49.

As shown in FIGS. 48 and 49, syringe barrel 218C may be centered and held in place by one or more orienting members, such as compression positioning members 242A, B. The compression positioning members 242A, B may be urged apart by inserting the syringe barrel 218C there between. Springs 244A-D can compress and create a pressure pushing the compression positioning members 242A,B against syringe barrel 218C. The compression positioning members 242A, B shown in the FIGS. 48 and 49 are merely illustrative and many other sizes, shapes, numbers and locations of compression positioning members 242 are anticipated.

Compression positioning members 242A, B may be simple spring 244A-D activated devices (e.g., resilient members) as shown in FIGS. 48 and 49 or may be any mechanism that can expand (e.g., resiliently expand) to accommodate syringe barrels of various sizes and urge the syringe barrel 218C into a centered position within the space defined by a real or imaginary injection portal tube 216C. This example shows spring 244A, D activated compression positioning members 242A, B but many other mechanical activation mechanisms are anticipated. The compression positioning members 242A, B can be elastically deformable, substantially elastically deformable, resiliently deformable, include one or more resilient members.

Other examples of positioning members designed to hold an inserted syringe 200 in the center of the injection portal 211 and thus orienting the Luer taper 213 for mating with the injection port 215 are anticipated. Positioning the inserted syringe 200 in the center of the injection portal 211 allows the machine vision to work from a known distance and thus calculations of syringe plunger movement can be very accurate.

In some examples, instead of the positioning members holding a syringe centrally, the positioning members can be designed to hold an inserted syringe 200 at a known, but off center position in the injection portal 211, such as if the injection port 215 is positioned off center in the injection portal 211. Any arrangement of the positioning members that aligns the inserted syringe 200 at a known position may be provided.

In some examples, and as shown in FIGS. 45, 47 and 49 the medication identification and measurement system 228A-C of this disclosure may include one or more "machine vision" cameras 236A-C that input digital images into a processor having processing circuitry 157, as shown and described in FIG. 1 157 (FIG. 1), or 3304 (FIG. 33), that is programmed to analyze machine vision images. In some examples, one of the images that the machine vision cameras 236A-C may "see" is a barcode label 205 on the syringe 200C-E, that has been inserted into the injection portal 211A-C, for identifying the medication in the syringe. As previously noted, the barcode label 205 can identify the brand name and/or generic name of the medication in the syringe. In some examples, the barcode label 205 also may identify one or more of the concentration of the medication, the lot number, the expiration date and other information that may be useful for inventory management.

As shown in FIGS. 44, 46 and 48, the medication identification and measurement system 228A-C of this disclosure can include one or more radio frequency identification (RFID) interrogation antennas 238A-C that input RFID information into a processor, such as processing circuitry 157 (FIG. 1) or 3304 (FIG. 33) that is programmed to analyze RFID data. In some examples, the RFID interrogation antennas 238A-C can interrogate a RFID tag 207 attached to the syringe 200C-E, that has been inserted into the injection portal 211A-C, for identifying the medication in the syringe. In some examples, short range RFID such as near field (NF) or high frequency (HF) may be advantageous because they will only detect the syringe that is adjacent to or inside the medication identification and measurement system 228A-C, and not detect the various other medication syringes that may be sitting on the worktable.

As shown in FIGS. 44, 46, 48 the medication identification and measurement system 228A-C of this disclosure may include a RFID interrogator 238A-C. In some examples, the RFID interrogator 238A-C that can include antennas that may be located inside the medication identification and measurement system 228A-C. In some examples, the RFID interrogator 238A-C antennas may be located external to but proximate the medication identification and measurement system 228A-C. As the syringe (e.g., 200C, 200D, 200E) is brought into proximity of the medication identification and measurement system 228A-C, the RFID interrogator 238A-C interrogates the RFID tag 207 on the syringe 200, thereby accurately and reliably identifying a medication for IV administration. In some examples, the RFID tag 207 may include one or more of: the generic and brand name of the drug, the concentration, the lot number, the expiration date, the manufacturer and other important information that may be recorded. In some examples, the generic and brand name of the drug and the concentration of the drug can be displayed in the injection section of the display screen of the anesthetic record input component 224.

Machine vision is very accurate for measuring the size of an object at a known distance or the distance of an object of known size. However, it cannot do both. Therefore, in some examples it is important to know the exact location of a syringe and thus know the distance from the camera to the syringe in order to accurately calculate the distance of the movement of the plunger within the syringe.

Syringes are available in multiple sizes such as 3 cc, 6 cc and 12 cc, each of which is a different diameter. The machine vision processor must know both the internal diameter of the barrel of the syringe and the distance that the syringe plunger moves down the barrel, in order to calculate the volume of medication injected. The machine vision of this disclosure can measure the diameter of the syringe because it is held in at known distance and in a centered location relative to the machine vision cameras 236A-C. Alternately, the automated EAR system 201 of this disclosure may be programmed to know that the particular hospital uses only Monoject® syringes for example and the internal diameter of each Monoject® syringe size may be pre-programmed into the computer. In this case, the machine vision only needs to differentiate 3 cc, 6 cc and 12 cc syringe sizes from each other. The first step for the machine vision processor is to determine the internal diameter of the barrel of the syringe.

In some examples, the machine vision system, including the machine vision camera and a processor 157 (e.g., processing circuitry) in electrical communication with the machine vision camera can visually detect and determine other geometry information about the syringe besides the outside diameter, such as determining the inside diameter, or the inner or outer length of the syringe. The automated EAR system 201 can use the geometry information to determine the size or type of the syringe, or can use the geometry information to calculate a volume of the syringe.

In some examples, as the syringe 200 is advanced into the injection portal 211A-C, the image of the syringe 200 entering the injection portal 211A-C is displayed in real time in the injection section of the display screen of the anesthetic record input component 224. Therefore, the caregiver can watch the syringe advance and engage with the injection port 215A-C. In some examples, the injection portal tube 216A or the spring positioning members 222A-E or the compression positioning members 242A,B, urge the syringe 200 into position to mate with the injection port 215A-C but the actual connection can also be observed as it is happening by the caregiver on the display screen of the anesthetic record input component 224. Even though the caregiver is not physically holding the injection port 215A-C as they typically would and are they can watch the engagement of the Luer connector 213 with the injection port 215A-C on a display screen, the view is essentially identical to the thousands of injections that they have made during their career. In some examples, the actual image of the syringe can be displayed on the display screen 226, while in other examples the data obtained by the camera can be converted to a representation of the syringe displayed on the display screen 226.

In some examples, once the syringe 200 is securely connected to the injection port 215A-C, the caregiver pushes on the plunger 246A-C of the syringe 200C-E, injecting the medication into the injection port 215A-C and IV tubing 220A-C. The caregiver can visualize the plunger seal 248A-C move down the syringe barrel 218A-C and can determine the volume of medication injected by the graduated markings on the syringe C-E. Thus, the engagement of the Luer connector 213 with the injection port 215A-C and the injected volume are observed by the caregiver on the display screen 226 of the anesthetic record input component 224 and the traditional method and routine of injection is minimally altered by the EAR system 201 of this disclosure.

In some examples, the processing circuitry 157 or a computer may also simultaneously generate a running total of the volume and dosage of the injected medication and display these numbers on the display screen 226 of the anesthetic record input component 224. In some examples, the processing circuitry 157 or a computer may also simultaneously generate its own graduated scale and superimpose the scale on the image of the syringe 200C-E or next to the image of the syringe 200C-E, for added visual clarity of the injected volume and dose.

In some examples, the machine vision determination of the injected volume may be calculated by multiplying the internal cross-sectional area of the syringe ($\pi r^2$) by the distance that the syringe plunger moves. The radius of the syringe may be determined in one or more ways. For example, the machine vision function may determine that the syringe approximates a 3 cc or 12 cc syringe and the computer is programmed to know that the hospital uses a specific brand of syringes and the internal diameter (radius) of each of these syringe sizes is precisely known. Another example may require the machine vision to measure the outer diameter of the syringe and then subtract an approximated wall thickness from the measured diameter to determine the internal diameter.

In some examples, the machine vision determination of the distance that the syringe plunger moves may be by "observing" the movement of the black rubber plunger seal against the visible scale printed on the syringe. In this example, the machine vision is programmed to recognize the markings on the syringe.

In some examples, the machine vision determination of the distance that the syringe plunger moves may be by observing the movement of the black rubber plunger seal relative to a scale calculated by the machine vision computer. The geometrical calculation of the scale that determines the distance that the syringe plunger moves may be easiest along the widest part of the syringe that corresponds with the center of the syringe, which is a known distance from the machine vision camera. Alternatively, the computer-constructed scale may be applied to the side of the syringe facing the camera, if the radius of the syringe is subtracted from the known distance to the center of the syringe in order to calculate the distance from the machine vision camera to the near side of the syringe.

In some examples, the movement of the black rubber plunger seal of the syringe is clearly identifiable by the machine vision camera and a scale to determine the distance moved by the plunger can either be "visualized" or constructed by the machine vision computer. Multiplying the distance that the plunger seal moves by the known or measured internal diameter of the syringe and thus cross-sectional area of the plunger seal, allows the processing circuitry 157 or an anesthetic record input computer 203B (FIG. 42) in electrical communication with the processing circuitry 157 to calculate an accurate injected volume. The anesthetic record input computer 203B may then display the measured injection volume and dosage on the display screen 226 of the anesthetic record input component 224. Without interfering with or changing the anesthesiologists' normal or traditional medication injection routines, an unobtrusive machine vision camera and computer can "observe" the medication injections and automatically record them in the electronic anesthetic record.

In some examples, the injected volume of medication may be determined by other methods. For example, non-visual optical sensing is well known in the arts. A light source shines on one or more light sensitive elements such as photodiodes for example, and the position of the plunger of the syringe can be roughly determined by the obstruction of the light beam by the plunger. Other fluid measurement methods include adding magnetic material to the syringe plunger and detecting movement of the plunger with a magnetic proximity sensor. Alternatively, fluid flow may be measured with fluid flow meters in the IV fluid stream. These examples are not meant to be an exhaustive list but rather to illustrate that there are alternative technologies to machine vision, for noncontact measurement of fluid flow from a syringe that are anticipated in this disclosure.

Securing the injection port 215 within the injection portal 211 prevents the caregiver from touching the injection port 215. Normally caregivers wear gloves to protect themselves from infectious contaminates from the patient and operating room and their gloves are nearly always contaminated. Anything they touch will be contaminated. They typically pick up and hold the IV injection port 215A-C with one hand while inserting the Luer taper connector 213 of the syringe 200 into the injection port 215A-C. In the process, the injection port is frequently contaminated with pathogenic organisms from their gloves that can enter the patient's blood stream with the next injection, causing serious infections. It is therefore advantageous from the infection prevention point of view, if the Luer connection and injection can be accomplished while never touching the injection port 215A-C.

In some examples as shown in FIGS. 44, 46 and 48 the medication identification and measurement system 228A-C of this disclosure may include one or more ultraviolet lights 240A-J that shine on the injection port 215A-C. The one or more ultraviolet lights (UV) are inside the medication identification and measurement system 228A-C, keeping the injection portal 211A-C and the injection port 215A-C disinfected. In some examples, the ultraviolet lights 240A-J may preferably be in the UV-C part of the spectrum. UV-C light has been shown to have superior germicidal powers over other parts of the UV spectrum. The UV lights 240A-J may shine continuously or intermittently. By making the injection port 215A-C untouchable because it is inside the medication identification and measurement system 228A-C and radiating the injection port 215A-C with UV-C light, the injection port 215A-C should be effectively disinfected between each injection and eliminate injection port contamination as a source of bloodstream infection.

In some examples as shown in FIG. 42, a worktable 250 may be located proximate the head of the patient. In some examples, the worktable 250 may be incorporated into relocation module 4210. In some examples, the worktable 250 may be used for holding the various medication syringes 200F-H being used for the surgical anesthetic. In some examples, the Luer tapers 213 of the various medication syringes 200F-H are simply capped in the traditional way while sitting on the worktable between injections.

In some examples as shown in FIG. 42, the various medication syringes 200F-H are not capped between injections in order to prevent accidental contamination of the Luer tapers 213 by the contaminated fingers or gloves of the healthcare provider, during the capping process. In this example, the uncapped Luer tapers 213 of syringes 200F-H may be placed under a protective overhang 252 that is 1-2.5 in. above and along the rear of the worktable 250. In some examples, ultraviolet lights 240H may be attached on the underside of the protective overhang 252, shining down on the exposed Luer tapers 213 of syringes 200F-H. In some examples, the ultraviolet lights 240H are preferably in the UV-C part of the spectrum. Any of the UV lights 240A-J may shine continuously or intermittently.

In some examples, the uncapped Luer tapers 213 of syringes 200F-H are kept sterile by eliminating capping and thus not inadvertently touching Luer tapers 213 of syringes 200F-H, and by storing the uncapped Luer tapers 213 of syringes 200F-H under a protective overhang 252, and by radiating the uncapped Luer tapers 213 with UV-C light.

Figure 50:
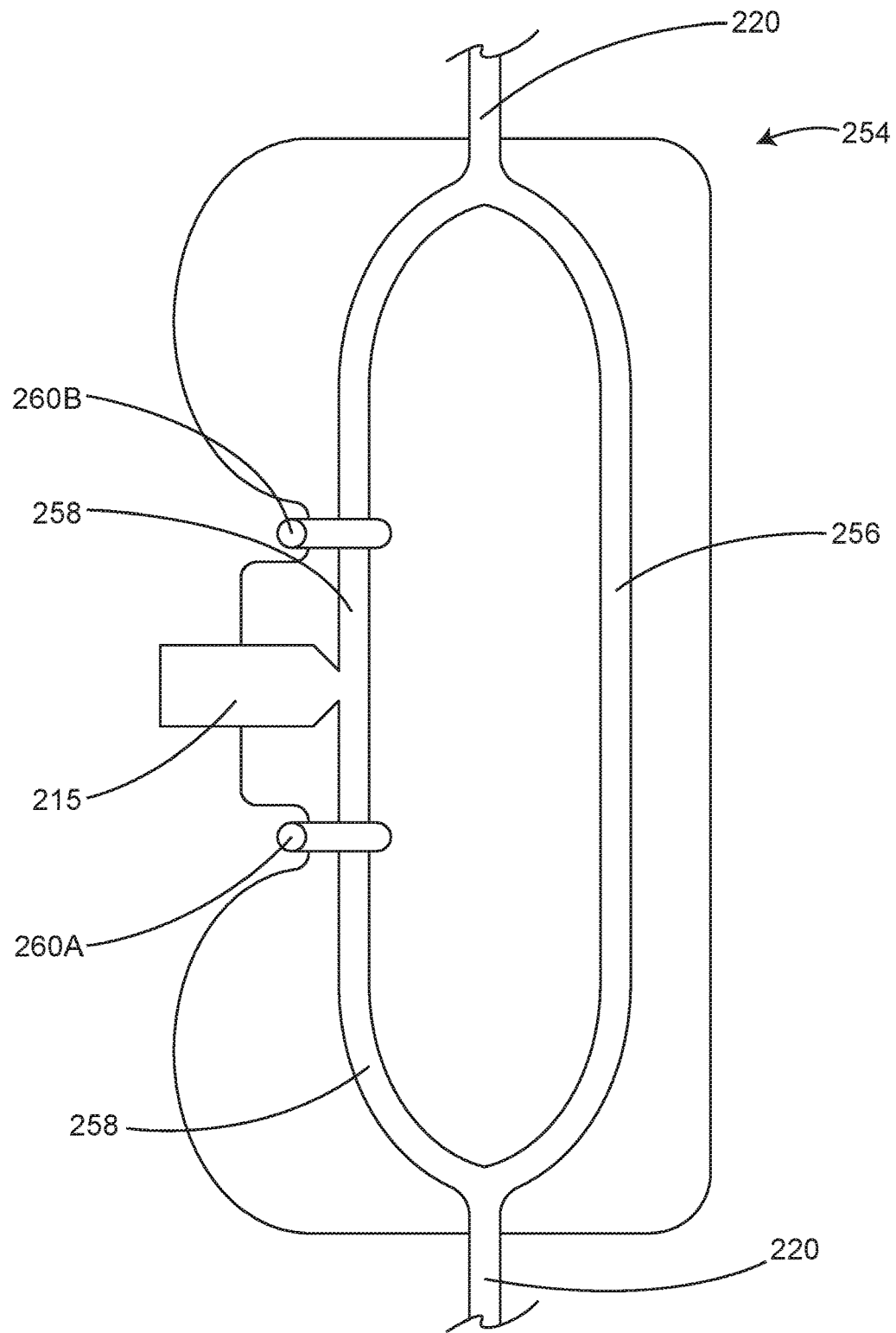
FIG. 50 illustrates an example injection port cassette that can be used with the system of FIG. 42, as detailed in 45, 47 and 49, in accordance with at least one example.

FIG. 50 illustrates an example injection port cassette that can be used with the system of FIG. 42, as detailed in 45, 47 and 49. As shown in FIG. 50, the injection port 215D may be mounted on an injection port cassette 254 in order to make the attachment to the medication identification and measurement system 228A-C easier and more secure. The injection port cassette 254 may be a piece of molded plastic onto which the injection port 215D and IV tubing 220 may be attached. The injection port cassette 254 may be shaped and sized to fit into a slot in the medication identification and measurement system 228A-C. When the injection port cassette 254 is fit into a slot in the medication identification and measurement system 228A-C, the injection port 215D can be positioned substantially in the center of the injection portal 211 for mating with the Luer tapers 213. The injection port cassette 254 can also be configured to be removed intact from the medication identification and measurement system 228A-C so that the patient can be transferred and the IV tubing 220 can be moved with the patient and continue to operate normally.

In some examples, and as shown in FIG. 50, the injection port cassette 254 can include an IV bypass channel 256 in the IV tubing 220. The IV bypass channel 256 can allow the IV fluids to flow unencumbered by the medication injection apparatus. The injection port cassette 254 can include a medication channel 258 in the IV tubing 220 and, the medication channel 258 may include one or more stop-flow clamps 260A, B. The stop-flow clamps 260A, B may be activated by anesthetic record input component 224 and anesthetic record computer if a medication error is noted. The stop-flow clamps 260A, B may be powered by electromechanical solenoids that squeeze the IV tubing flat obstructing the flow. Other electromechanical flow obstructers are anticipated.

In some situations, such as when administering a drug to a patient allergic to that drug, or administering potent cardiovascular drugs to a patient with normal vital signs, or administering a drug with a likely mistaken identity, the automated anesthetic record computer of this disclosure may automatically activate the stop-flow clamps 260A, B to compress the medication channel 258 tubing upstream and/or downstream from the injection port 215D. Compressing the IV tubing both upstream and downstream from the injection port 215D prevents the injection of any medication into the IV tubing. An alert to the adverse condition of the injection may be displayed on the anesthetic record input component 224, where the stop-flow condition can be overridden by the operator touching a manual override switch on the anesthetic record input component 224, if the injection was not erroneous. While the stop-flow can occur in the medication channel 258, the IV fluid flow can continue normally in the parallel bypass channel 256.

The stop-flow clamps 260A, B can allow the microprocessor (e.g., processor, hardware processing circuitry) of the anesthetic record input component 224 to not only warn the operator of a pending medication error, but physically prevent the injection. Equally important is that the stop-flow clamps 260A, B can be quickly released by the operator touching a manual override switch in the event that the apparent error was in fact a planned event.

Figure 51:
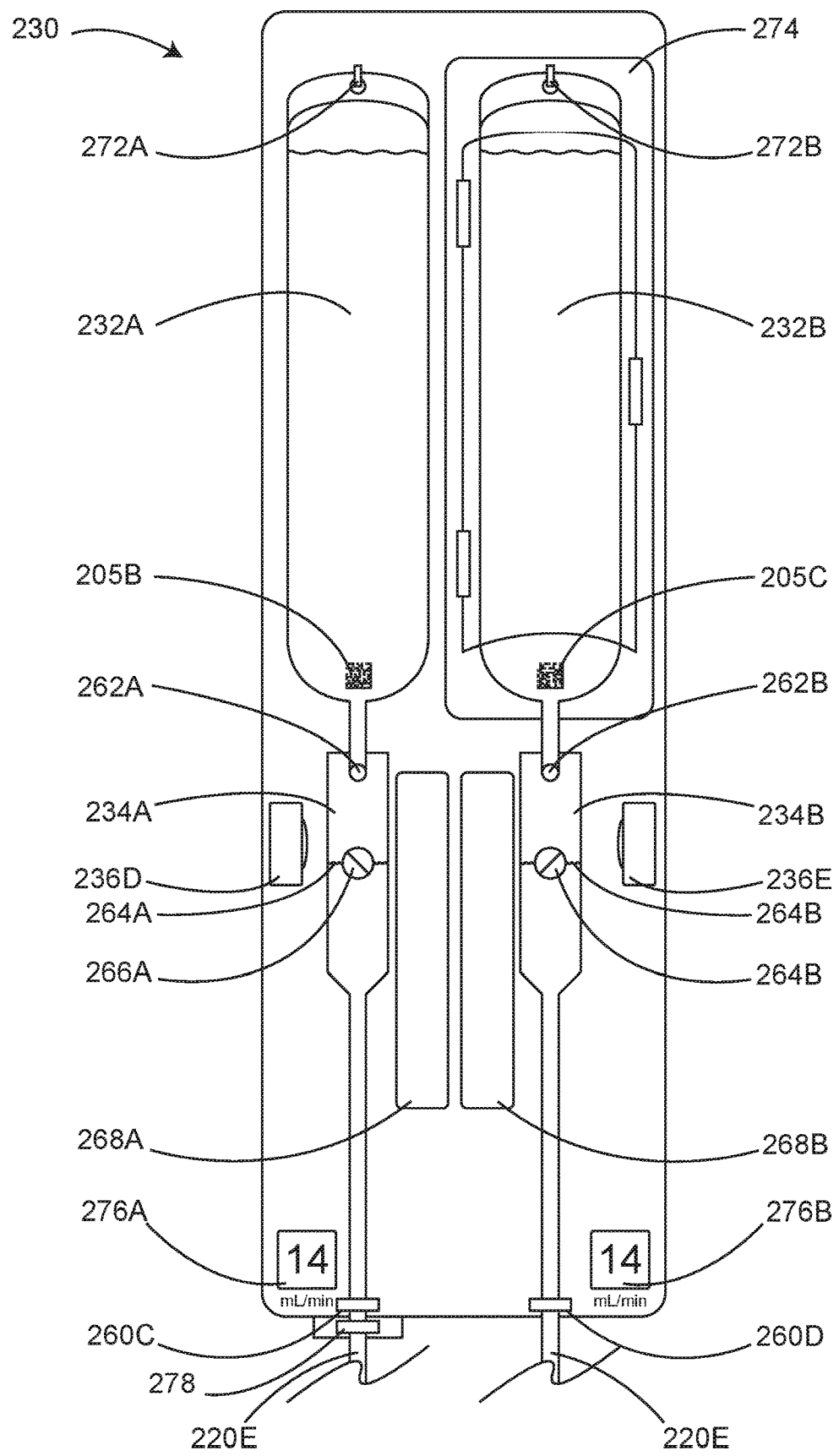
FIG. 51 illustrates a side view of an example IV fluid identification and measurement system 230 that can be used with the systems of FIG. 42-49, and injection port cassette of FIG. 50, in accordance with at least one example.

FIG. 51 illustrates a side view of an example IV fluid identification and measurement system 230 that can be used with the systems of FIG. 42-49, and injection port cassette of FIG. 50. In some examples, the automated EAR of this disclosure includes a system for automatically measuring and recording the administration of IV fluids. As shown in FIGS. 42 and 51, the automated EAR 201 can include an IV fluid identification and measurement system 230. In some examples, the IV fluid identification and measurement system 230 can be mounted onto module 4210. Alternately, the IV fluid identification and measurement system 230 may be mounted to an IV pole or racking system independent from the module 4210. The system for automatically measuring and recording the administration of IV fluids is not limited to use in anesthesia or in the operating room, but has applicability for use throughout the hospital and other health care settings, including but not limited to the ICU, ER, wards, rehabilitation centers and long term care settings.

In some examples, the IV fluid identification and measurement system 230 may be configured to accommodate one or more IV bags of IV fluid 232A, B. Each bag of IV fluid can include a drip chamber 234A, B and IV tubing 220D, E. IV flow rates may be controlled with the traditional manually operated roller clamp that variably pinches the IV tubing 220D, E to control or even stop the flow of IV fluids. In some examples, IV flow rates may be controlled with the automatically operated electromechanical flow rate clamps 278 that variably pinch the IV tubing 220D to control or even stop the flow of IV fluids. The automatically operated electromechanical flow rate clamps 278 may be controlled by the electronic anesthetic record computer in module 4210 or by a microprocessor (e.g., processor, hardware processing circuitry) located within the IV fluid identification and measurement system 230.

In some examples, the system for automatically measuring and recording the administration of IV medications and fluids 228, 230 includes one or more of a barcode reader and an RFID interrogator (such as 236D, E) for accurately and automatically identifying a fluid for IV administration. Because of the close proximity to the adjacent bags, barcode identification may be preferable in order to prevent an RFID interrogator from reading the RFID tag on a neighboring bag. In some examples, as shown in FIG. 51, one or more barcode labels 205B, C may be applied to the IV bags 232A, B in a location where they can be read by a barcode reader or machine vision camera 236D, E, or another machine vision camera located in a suitable position. In some examples, a dedicated barcode reader or a machine vision camera may be positioned adjacent the barcode label 205B, C location, specifically for reading the barcode label 205B, C.

In some examples, the drip chamber 234A, B of the IV set can be positioned adjacent the one or more machine vision cameras 236D, E. In some examples, a standard background 268A, B may be positioned on the opposite side of the drip chamber 234A, B from the machine vision cameras 236D, E. The standard background 268A, B may be a plain background or may be an advantageous color, pattern, color design or illumination that highlights each of the falling drops, for easier identification by the machine vision software. The machine vision software can include one or more machine-readable mediums that when implemented on hardware processing circuitry of the system or in electrical communication with the system, can perform the functions described herein.

In some examples, the machine vision software is programmed to cause the processing circuitry 157 to look for a fluid meniscus 264A, B in the drip chamber 234A, B. In this case "seeing" a fluid meniscus 264A, B indicates that there is fluid in the drip chamber 234A, B and therefore the IV bag 232A, B is not empty, and air is not inadvertently entering the IV tubing.

In some examples, if the machine vision software fails to "see" a fluid meniscus 264A, B meaning that the drip chamber 234A, B is empty and thus the IV bag 232A, B is empty, stop-flow clamps 260C, D may be automatically activated to compress the IV tubing 220D, E in order to prevent air from entering the IV tubing 220D, E. In some examples, the empty IV bag condition detected by the machine vision software can be displayed as an alert to the caregiver on the anesthetic record input component 224.

The combination of the machine vision camera 236D, 236E in electrical communication with processing circuitry (e.g., 157, FIGS. 1 and 42, processor 3304, FIG. 33) can count the number of drops of fluid per unit of time in a drip chamber 234A, B to calculate or to estimate the flow rate of an IV. The size of the drip chamber inlet orifice determines the volume of liquid in each drop. The inlet orifices of standard drip chambers are sized to create drops sizes that result in 10, 12, 15, 20, 45 and 60 drops per ml. Given a particular drop volume (size), 10 drops per ml for example, the system can count the number of drops falling in a known period of time and use that data to calculate or to estimate the flow rate. If these estimates were attempted by a human, they may be less accurate at higher flow rates (higher drop counts) because the drops are so fast, it can be difficult to count the drops. Eventually, at even higher flow rates the individual drops become a solid stream of fluid and the flow rate cannot be visually estimated.

In some examples, the machine vision system is configured to look for falling drops of fluid 262A, B within the drip chamber 234A, B. When drops have been identified, the machine vision system (e.g., machine vision camera 236D or 236E operably coupled to processing circuitry 157) may first measure the diameter of the drop to determine which of the standard drop sizes or volumes it is counting. Most hospitals standardize on several infusion set sizes, 10, 20 and 60 drops per cc for example. Therefore, when these limited choices of infusion set brands and sizes have been programmed into the computer, the machine vision system only needs to differentiate between these choices, which is much easier than accurately measuring the diameter of the drops. Unlike the human eye, the machine vision can accurately count the falling drops even at high flow rates to calculate an IV fluid flow rate.

In some examples, the machine vision system, including the machine vision cameras 236D, E and the machine vision software implemented by hardware processing circuitry 157 does not "see" falling drops. In this situation, either the fluid is flowing in a steady stream that is not identifiable by the machine vision software or the fluid has stopped flowing. In some examples, these two opposite conditions can be differentiated by inserting a floating object 266A, B into the drip chambers 234A, B. In some examples, the floating object 266A, B may be a ball-shaped float 266A, B and in some examples the float may be patterned or multi-colored to more easily identify movement or spinning of the float. In some examples, if the machine vision system cannot identify falling drops, it then looks to the floating object 266A, B for additional information. If the floating object 266A, B is not moving or spinning, the fluid flow has stopped. If the float 266A, B is moving or spinning and drops cannot be identified, the fluid is flowing in a steady stream and the flow rate cannot be measured by machine vision.

In some examples, the IV fluid identification and measurement system 230 may be configured to accommodate one or more bags of IV fluid 232A, B and each of these IV bags may be hanging from an electronic IV scale 272A, B. The electronic IV scale 272A can measure the combined weight of the IV bag and fluid 232A, the drip chamber 234A and the IV tubing 220D. The electronic IV scale 272B can measure the weight or combined weight of one or more of the IV bag and fluid 232B, the drip chamber 234B, the IV tubing 220E and the pressure infuser 274. In both of these examples, the electronic IV scale 272A, B can accurately measure the change in combined weight that occurs due to the drainage of the IV fluid from the IV bag. The change in weight per unit time can be converted to flow rates by processing circuitry 157 in electrical communication with the electronic IV scale 272A, 272B, for example, by the anesthetic record computer 203B and displayed on the anesthetic record input component 224.

In some examples, the calculated flow rates for each IV bag 232A, B may also be displayed on one or more digital flow-rate displays 276A, B mounted on the IV fluid identification and measurement system 230. The digital flow-rate displays 276A, B may be small LED or LCD display screens that conveniently tell the operator the flow rate while they are manually adjusting the flow rate near the IV bags 232A, B and drip chambers. 234A, B. The digital flow-rate displays 276A, B are particularly convenient when the IV fluid identification and measurement system 230 is a free standing entity mounted on an IV pole for example while being used on the ward or ICU.

In some examples, when the falling drops 262A, B cannot be detected and yet the floats 266A, B are moving or spinning, the fluid is determined to be flowing in a steady stream and the flow rate cannot be measured by machine vision. In this case the anesthetic record computer may automatically query the change in weight per unit time as measured by the electronic IV scale 272A, B to determine the IV flow rate. At high flow rates, the change in weight per unit time as measured by the electronic IV scale 272A, B will most likely be more accurate than counting drops, in determining the IV flow rate.

The IV flow rate as determined by the change in weight per unit time can also be compared to the IV flow rates determined by counting drops to verify the accuracy of each method. Without interfering with or changing the anesthesiologists' normal or traditional IV routines, an unobtrusive machine vision camera and computer can "observe" the IV flow rates and automatically record them in the electronic anesthetic record.

Figure 52:
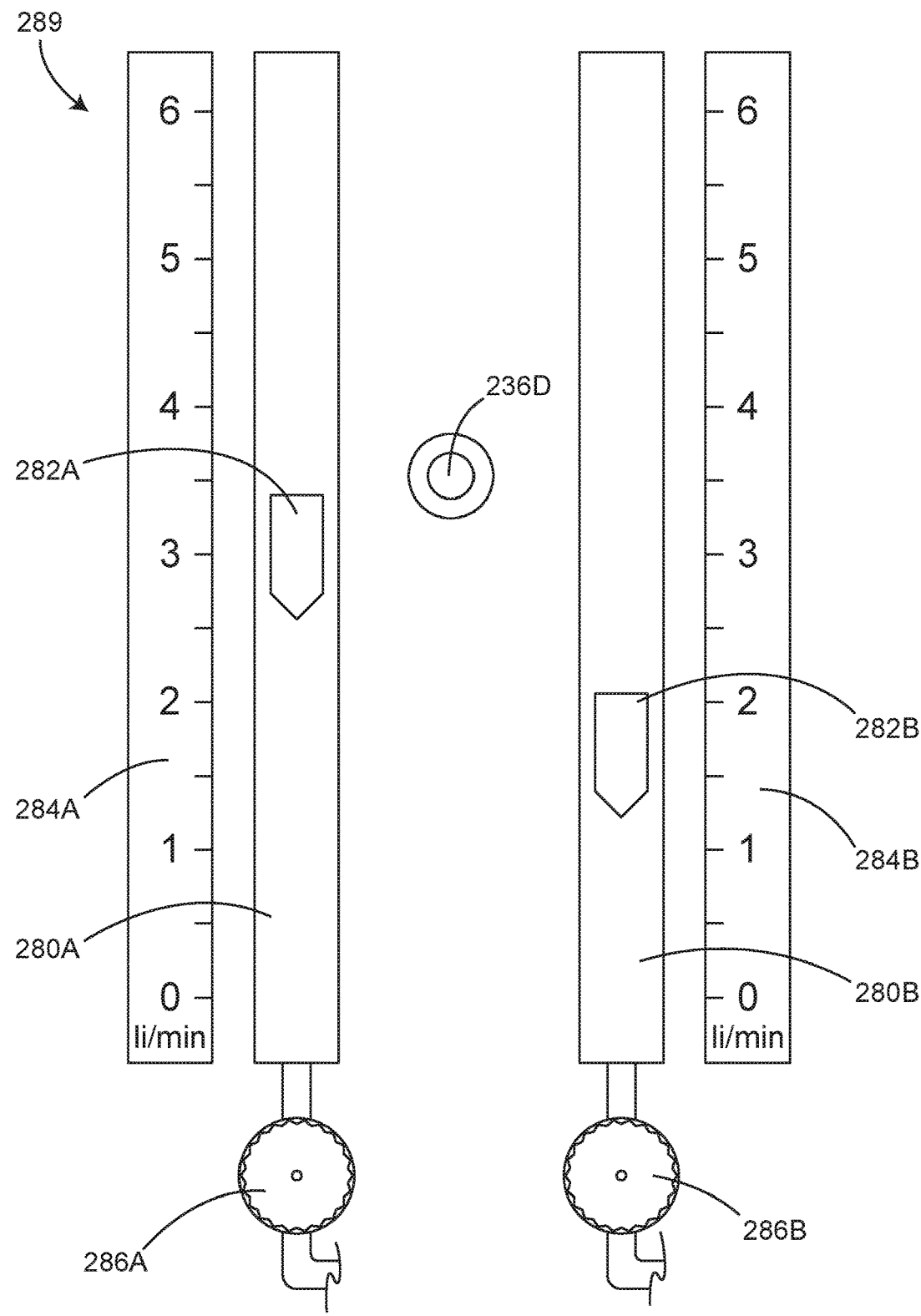
FIG. 52 illustrates side view of an example of a gas flow meter system that can be used with the system of FIG. 42, in accordance with at least one example.

FIG. 52 illustrates side view of an example of a gas flow meter system 289 that can be used with the system of FIG.

Figure 53:
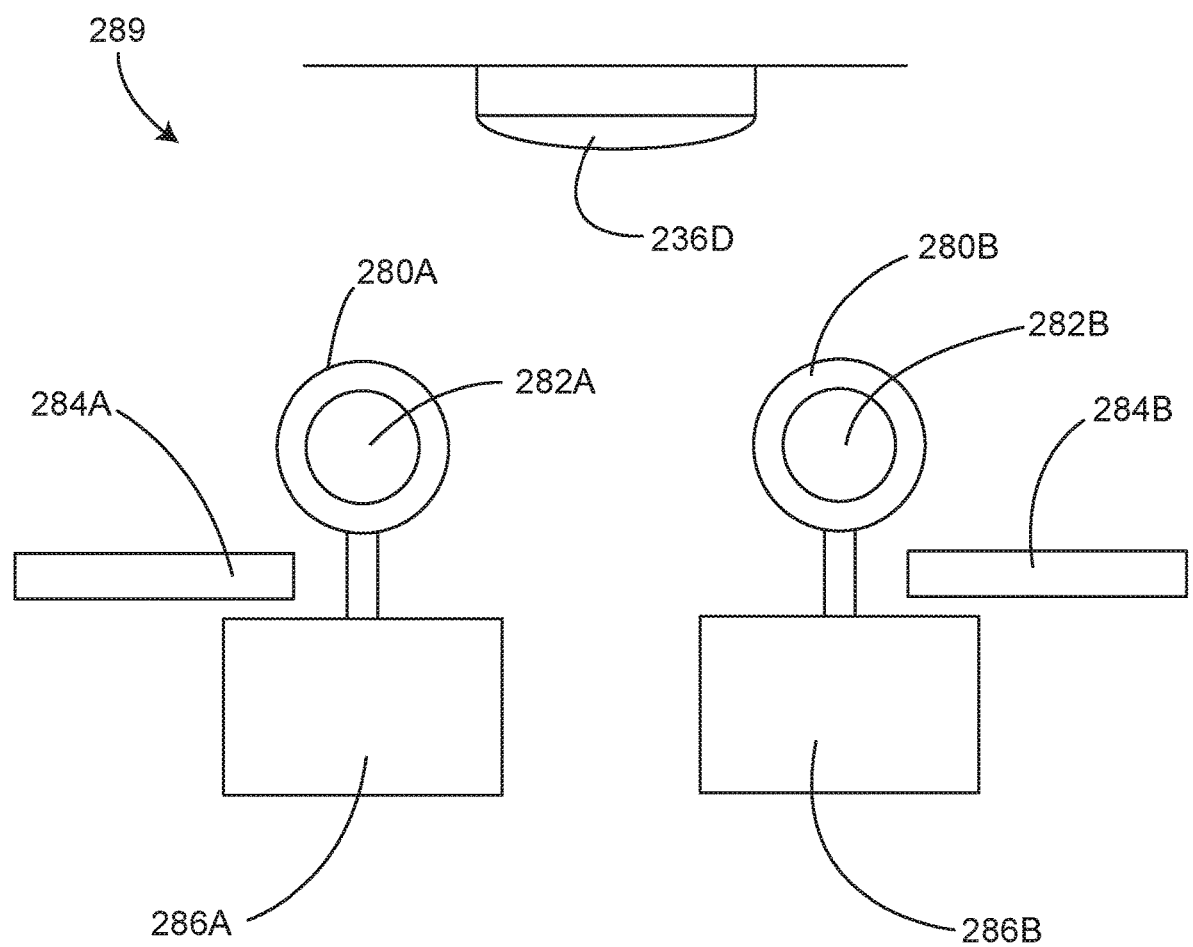
FIG. 53 illustrates a top view of the example gas flow meter system of FIG. 52.
Figure 54:
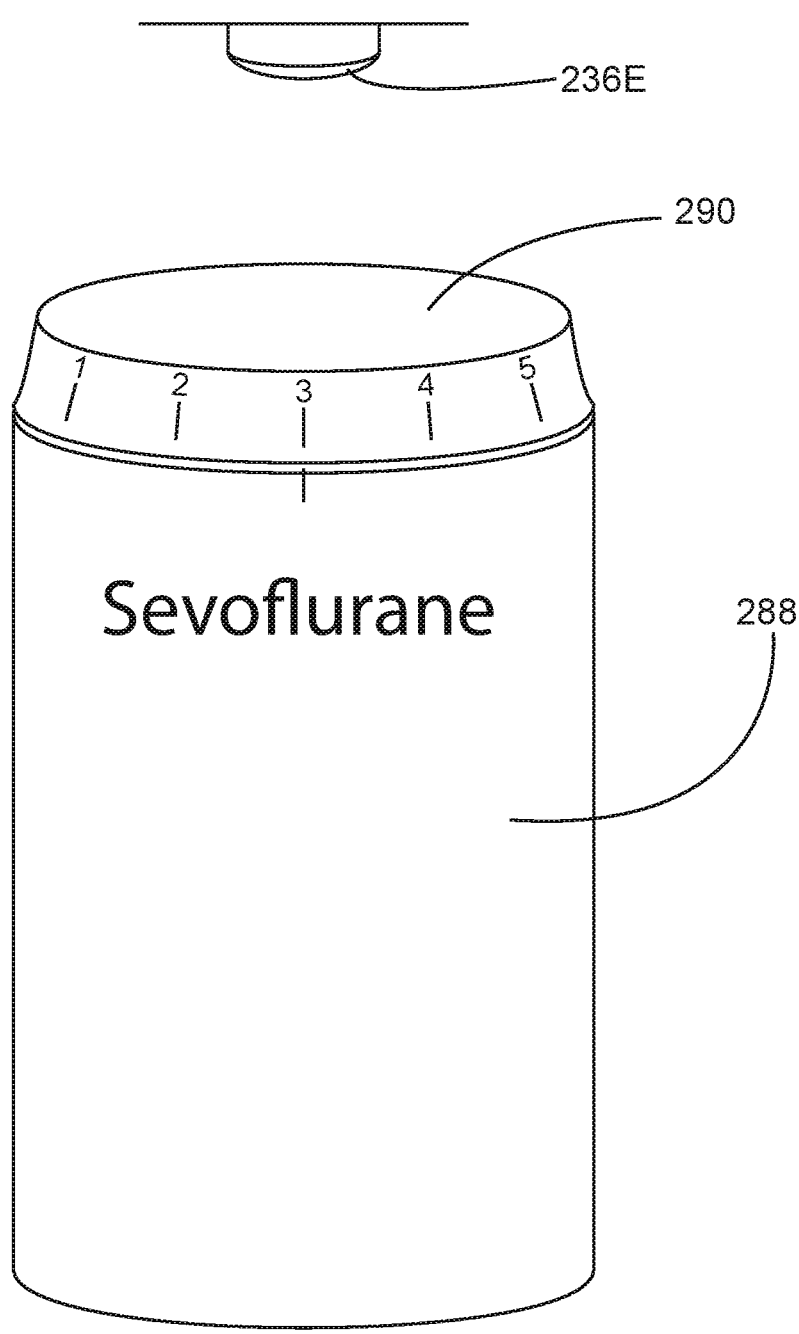
FIG. 54 illustrates a side view of an example anesthetic gas vaporizer monitoring system that can be used with the system of FIG. 42, in accordance with at least one example.

42. FIG. 53 illustrates a top view of the example gas flow meter system 289 of FIG. 52. FIG. 54 illustrates a side view of an example anesthetic gas vaporizer monitoring system including a vaporizer 288 that can be used with the system of FIG. 42.

Some ventilation gas flow meters on anesthesia machines are made by floating a small metal float in a gas stream flowing through a glass tube. The inside of the glass tube is tapered from narrow at the bottom to wider at the top, thus requiring higher flow rates to raise the float higher in the glass tube. As shown in FIGS. 52, 53, the gas flow meter tubes 280A, B have floats 282A, B suspended by the gas flow within the tubes 280A, B. The gas flow in each gas flow meter tube 280A, B is controlled by the flow control valves 286A, B. The height of the floating effect correlates with the flow rate of the gas within the tube and can be measured by comparing the height of the floats 282A, B to the gas flow rate scales 284A, B located adjacent the flow meter tubes 280A, B. In these examples, float 282A indicates approximately 3.5 li/min of gas flow and float 282B indicates approximately 2 li/min of gas flow.

In some examples, the automated EAR system 201 of this disclosure can use machine vision to unobtrusively "observe" the flow rate of the ventilation gas flow meters (e.g., 289; FIG. 42, 52, 53). In some examples, the machine vision camera 236D is located far enough from the gas flow meter tubes 280A, B to have a "view" of the entire tube. The camera 236D and computer can differentiate the float 282A, B from the background and accurately locate float 282A, B within the gas flow meter tubes 280A, B. The machine vision computer is programmed with a scale that corresponds to the gas flow rate scales 284A, B. Comparing float 282A, B locations with the scale programmed into the computer, accurately determines the gas flow rate within the gas flow meter tubes 280A, B. Without changing or interfering with the anesthesiologists' normal or traditional gas control routines, an unobtrusive machine vision camera and computer can "observe" the gas flow rates and generate data that is automatically recorded in the electronic anesthetic record, or used to calculate other data that is recorded (e.g., stored) in the electronic anesthetic record 203A.

In some examples, the automated EAR system 201 of this disclosure uses machine vision to unobtrusively "observe" the concentration of the anesthetic gas from the anesthetic gas vaporizer. As shown in FIG. 54, the anesthetic gas vaporizer 288 can include a canister with a rotating vaporizer control knob 290 used to adjust the concentration of the anesthetic gas flowing from the vaporizer 288. For example, the control knob 290 can be located on the top of the vaporizer 288, but other configurations such as locating the control knob 290 on the side of the vaporizer 288 are possible. In some examples, a machine vision camera 236E is positioned on the anesthesia machine or on the module 4210 so that it can "see" either the numerical scale printed on the control knob 290 or a scale programmed into the computer that corresponds to the numerical scale printed on the control knob 290. The machine vision camera and computer can accurately determine the concentration of delivered anesthetic gases. Without changing or interfering with the anesthesiologists' normal or traditional anesthetic gas control routines, an unobtrusive machine vision camera and computer can "observe" the anesthetic gas flow concentrations and automatically record them in the electronic anesthetic record.

In some examples, the automated EAR system 201 of this disclosure accepts data from the electronic scales and hematocrit determinations of the fluid suction canisters or bags disclosed herein. The calculated blood loss is automatically recorded in the EAR 203A and displayed on the anesthetic record input component 224 and the electronic anesthetic record display 226.

In some examples, the automated EAR system 201 of this disclosure is in electrical communication with and is configured to accept (e.g., receive) data from the electronic urine bag scales disclosed herein. The calculated urine output can be automatically recorded in the EAR 203A and displayed on the anesthetic record input component 224 and the electronic anesthetic record display 226.

In some examples, the automated EAR system 201 of this disclosure is in electrical communication with and is configured to receive data from an IV extravasation monitor that is either hard wired or wirelessly connected to the patients' IV site. An IV extravasation monitor can be designed to detect inadvertent leakage from the IV site into the surrounding tissue, which generally means that the IV is "blown" and some infused drugs could cause significant tissue damage. One example of an IV extravasation monitor previously disclosed by this inventor includes the placement of one or more thermometers (thermocouples or thermistors) adjacent the IV catheter entrance site into the vein and adjacent the tip of the IV catheter. A thermometer is programmed to continuously measure the temperature difference ($\Delta T$) between these two sites. If the $\Delta T$ changes over time, it can be assumed that leakage of cool or warm IV fluids is occurring at either the catheter entrance site into the vein or that the tip of the catheter has eroded through the vein wall. The cool IV fluids will cool the tissue and the adjacent thermometer will detect a cooling of the tissue at that site. When an increasing temperature differential is detected, an alarm will be activated and the automated EAR 203A of this disclosure will be notified.

In some examples, the automated EAR system 201 of this disclosure is in electrical communication with and is configured to receive data from a patient support mattress. In some examples, the patient support mattress is an air mattress. One example of a patient support air mattress is disclosed in U.S. Pat. Nos. 9,962,122 and 10,433,792, incorporated into this disclosure in their entirety. The air mattress may include an air pressure sensor to detect the air pressure within the air chambers of the system. The first requisite is that the patient support mattress is not "hammocking," in other words that the upper surface is not stretched tight enough to prevent the body part from sinking into the air mattress. The second requisite is that a body part is not "bottoming out" on the hard surface below the patient support mattress. The third requisite is that the air chambers are partially inflated in order to allow the patient to sink into the mattress. If these three requisites are satisfied, the pressure per square area of skin cannot be greater than the pressure per square area within the air chamber, which is the definition of the measured air pressure within the air chamber. This skin pressure safety monitor is both simple and inexpensive and more accurate compared to other electronic pressure detection systems for avoiding pressure injuries.

In some examples, when the patient is sunk into the patient support air mattress disclosed in U.S. Pat. Nos. 9,962,122 and 10,433,792, the air pressure within the air chambers may be measured and recorded. If the measured air pressure per square area is less than the capillary perfusion pressure of the skin, it can be assumed that there are no areas of the patient's skin where blood flow has been occluded by pressure from the support mattress. In other words, if the requisite criteria listed above are satisfied, the air pressure in the air chambers of the mattress serves as a reliable monitor of the maximum pressure applied to any dependent skin surface. This air pressure can be automatically recorded in the EAR 203A and displayed on the anesthetic record input component 224 and the electronic anesthetic record display 226, providing assurance to the caregiver and documentation that the patient's skin has been adequately protected from pressure injury.

In some examples, the automated EAR of this disclosure is in electrical communication with and is configured to receive data from a system for automatically counting and detecting surgical sponges. A system for automatically counting and detecting surgical sponges has been previously disclosed in US Patent Application 2015/0216610 and U.S. Pat. No. 10,461,397 which are incorporated into this disclosure in their entirety. These disclosures by this inventor describe a system of incorporating RFID tags into surgical sponges. Each of the RFID tags and thus each of the sponges is interrogated as the sponges enter the sterile surgical field and each is individually recorded. Later, each of the sponges is interrogated as the sponges leave the sterile surgical field and each is individually recorded. This electronic RFID sponge counting is presumably more accurate and reliable than the manual sponge count by the nurse. If a discrepancy is noted in the sponge count, RFID antennae may be used to detect the location of the missing sponge, even if it is still in the patient.

In some examples, the data from the RFID sponge counting is automatically entered into the EAR 203A or electronic surgical record. An accurate sponge count can assure the care providers that a "retained surgical item" has not occurred. The itemized sponge count also aids in inventory management and billing.

In some examples, the automated EAR system 201 of this disclosure is in electrical communication with and is configured to receive data from a Sequential Compression Device (SCD) that may be housed within module 1410. An SCD is an inflatable leg wrap that sequentially applies pressure to the legs of a patient during surgery in order to prevent deep vein thrombosis (DVT). The use of the SCD and the applied air pressures may be automatically entered into the EAR 203A or electronic surgical record. Documentation that SCD was used during surgery also aids in inventory management and billing.

In some examples, the automated EAR system 201 of this disclosure is in electrical communication with and is configured to receive data from an Electrosurgical Unit (ESU) that may be housed within module 1410. The ESU use history and settings may be automatically entered into the EAR 203A or electronic surgical record. Documentation that SCD was used during surgery also aids in inventory management and billing.

In some examples, the automated EAR system 201 of this disclosure is in electrical communication with and is configured to receive data from a peritoneal insufflator that may be housed within module 1410. Peritoneal insufflators are used to insufflate the patient's peritoneum during laparoscopic and robotic surgery. The insufflator use history and pressure settings may be automatically entered into the EAR 203A or electronic surgical record. Documentation that insufflator was used during surgery also aids in inventory management and billing.

When the aforementioned data has been automatically recorded into the EAR 203A, documentation steps by the healthcare providers is drastically simplified. In some examples, the only remaining items in need of documentation are the special events such as intubation, extubation, surgical incision, going on bypass, going off bypass and surgical mishaps.

In some examples, the automated EAR system 201 of this disclosure captures anesthetic event data by capitalizing on the fact that anesthesiologists, surgeons and nurses compulsively tend to meticulously follow their personal routines. For each "event" they will inevitably follow their routine and use the same description each time to record the event. For example, a particular anesthesiologist may routinely intubate all adult male patients with a Miller 3 laryngoscope and an 8.0 endotracheal tube unless there is an abnormality. The provider's routine written record of the event may state, "Miller 3, 8.0 ET taped 23 cm at teeth, atraumatic, BBS" and that provider will write the same description every time. The provider has done a thousand of these intubations and believes their way is best and therefore there is no need for experimentation or unique descriptive procedure notes. This observation of routine applies to surgeons as well—both in the details of each surgical procedure and the dictated surgical note describing the surgical procedure. Therefore, the automatic EAR 203A, or EAR computer 203B can be programmed to "automatically" document most procedures and special events if it knows who the provider is and a few facts about the patient.

For example, if the EAR system 201 knows who is providing the anesthesia, knows their preferences, knows how they prefer to describe anesthesia events such as intubation and knows that the patient is an adult male, it can "automatically" enter anesthesia providers' standard description of the intubation event into the record and will be correct more than 95% of the time. Therefore, the anesthesia provider simply indicates on the anesthetic record input component 224 that intubation occurred by touching the intubation icon and the event will be automatically recorded and the time noted. In the unusual event of a patient abnormality or a deviation from their normal routine, the anesthesia provider can manually enter the variant information, to provide an accurate record. In some examples, the relative rarity of data being manually entered into the EAR 203A allows for the elimination of the computer keyboard and mouse, to be replaced by an easy-to-clean touch screen display.

The automated EAR system 201 of this disclosure captures anesthetic event data but it must be noted that the same technologies described herein for capturing anesthetic event data can be used throughout the hospital or outpatient health care system to capture and record medication administration, IV fluid administration, vital signs and patient monitor inputs, provider events and other data. Non-operating room heath care locations are intended to be included within the scope of this disclosure. While this disclosure focuses on the totality of functions offered by module 10, 1410, each of the individual functions can be offered independently of module 10, 1410.

The use of the term Electronic Anesthetic Record as defined herein can include an electronic surgical record, or an electronic medical record, and is not limited to anesthetic or surgical applications. Aspects of the modules described herein can also be employed in recovery, hospital room and long-term care settings.

In an example, the module 4210 of FIGS. 42-54, like module 10 of FIG. 1, can include a housing having a lower section 14 and a tower-like upper section 18, wherein the lower section 14 is configured to house unrelated waste heat-producing electronic and electromechanical surgical equipment, and wherein the tower-like upper section is located on top of the lower section. The module 4210 can also include a cowling that substantially confines waste heat generated by the unrelated waste heat-producing electronic and electromechanical surgical equipment. In addition, the module 4210 can include a system for monitoring the administration of one or more IV medications and fluids 228, 230. The system 228, 230 can include: a barcode reader or an RFID 238 interrogator configured to identify the one or more IV medications or fluids; a machine vision digital camera 236 to capture an image of one or more of a syringe 200 or a drip chamber 234; processing circuitry 157 (3304, FIG. 33) operably coupled to the barcode reader 236 or the RFID interrogator 238 to receive the identity of the one or more IV medications or fluids, the processing circuitry 157 operably coupled to the machine vision digital camera to receive the captured image and determine a volume of medication administered from the syringe or fluid administered from an IV bag based on the image; and a display 226 operably coupled to the processing circuitry 157, the display 226 configured to receive instructions from the processing circuitry 157 to output the identity and determined volume of medication administered from the syringe or fluid administered from an IV bag.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects. The terms approximately, about or substantially are defined herein as being within 10% of the stated value or arrangement.

The above description is intended to be illustrative, and not restrictive. For example, the above-described examples (or one or more aspects thereof) may be used in combination with each other. Other examples can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

NOTES AND VARIOUS EXAMPLES

Each of these non-limiting examples may stand on its own, or may be combined in various permutations or combinations with one or more of the other examples. The examples are supported by the preceding written description as well as the drawings of this disclosure.

Example Set 1

Example 1 is a method of vacuuming air in an operating room, the method comprising: receiving, using circuitry, one or more instructions to provide power to a fan disposed in a surgical module, wherein the housing is configured to store unrelated electronic and electromechanical surgical equipment within the housing; and providing power to the fan, using the circuitry, wherein providing power to the fan causes air from a surgical field to be collected into a plenum through an inlet vent, and causes heat generated by the electronic surgical equipment to be collected into the plenum, wherein providing power to the fan causes the collected air and heat to create an airflow that passes through a specified channel in the housing, and wherein the controlled airflow causes the equipment stored in the module to be cooled and the airflow to be cleaned before being exhausted out of the housing through an outlet vent.

In Example 2, the subject matter of Example 1 includes, wherein receiving the one or more instructions, using the circuitry, includes receiving an instruction to actuate a noise canceling device, wherein the noise canceling device is configured to cancel at least a portion of a noise generated by the fan.

In Example 3, the subject matter of Examples 1-2 includes, wherein the plenum substantially separates the air collected through the inlet vent from being in contact with the electronic and electromechanical equipment.

In Example 4, the subject matter of Examples 1-3 includes, wherein the circuitry includes processing circuitry, the method further comprising: receiving an instruction, using the processor, to divert at least a portion of the airflow to an air mattress; and sending an instruction, using the processor, to a flow management device to divert at least portion of the airflow to the air mattress; and diverting, using the flow management device, at least a portion of the airflow to the air mattress.

In Example 5, the subject matter of Examples 1-4 includes, wherein the circuitry includes a processor, the method further comprising: sensing, using a sensor, information related to an air mattress; receiving, using the processor, the information from the sensor; determining, using the processor and the information received from the sensor, to divert at least a portion of the airflow to the air mattress; and sending an instruction; using the processor, to a flow management device to divert at least a portion of the airflow to the air mattress.

In Example 6, the subject matter of Example 5 includes, wherein determining, using the processor, to divert at least a portion of the airflow to the air mattress includes determining that the information sensed by the sensor has traversed a threshold.

In Example 7, the subject matter of Examples 1-6 includes, wherein the circuitry includes a processor, the method further comprising: receiving an instruction, using the processor, to divert at least a portion of the airflow to a compression device; and sending an instruction, using the processor, to a flow management device to divert at least portion of the airflow to the compression device; and diverting, using the flow management device, at least a portion of the airflow to compression device.

In Example 8, the subject matter of Examples 1-7 includes, wherein the circuitry includes a processor, the method further comprising: sensing, using a sensor, information related to a compression device; receiving, using the processor, the information from the sensor; determining, using the processor and the information received from the sensor, to divert at least a portion of the airflow to the compression device; and sending an instruction; using the processor, to a flow management device to divert at least a portion of the airflow to the compression device.

In Example 9, the subject matter of Example 8 includes, wherein determining, using the processor, to divert at least a portion of the airflow to the air mattress includes determining that the information sensed by the sensor has traversed a threshold.

In Example 10, the subject matter of Examples 1-9 includes, sensing, using a sensor, a pressure in the specified channel, receiving, using the processor, the pressure; determining, using the processor, that the pressure has traversed a threshold, and if the pressure has traversed the threshold, adjusting, using the processor, an output of the fan.

In Example 11, the subject matter of Examples 1-10 includes, wherein the housing comprises a heat-resistant cowling.

Example 12 is at least one non-transitory machine-readable medium including instructions for vacuuming air in an operating room, which when executed by processing circuitry, cause the processing circuitry to perform operations comprising: receiving one or more instructions to provide power to a fan disposed in a surgical module, wherein the housing is configured to store unrelated electronic and electromechanical surgical equipment within the housing; providing power to the fan, wherein providing power to the fan causes air from a surgical field to be collected into a plenum through an inlet vent, and causes heat generated by the electronic surgical equipment to be collected into the plenum, wherein providing power to the fan causes the collected air and heat to create an airflow that passes through a specified channel in the housing, and wherein the controlled airflow causes the equipment stored in the module to be cooled and the airflow to be cleaned before being exhausted out of the housing through an outlet vent.

In Example 13, the subject matter of Example 12 includes, wherein the processing circuitry is further configured to perform operations to: receive the one or more instructions including an instruction to actuate a noise canceling device, wherein the noise canceling device is configured to cancel at least a portion of a noise generated by the fan.

In Example 14, the subject matter of Examples 12-13 includes, wherein the plenum substantially separates the air collected through the inlet vent from being in contact with the electronic and electromechanical equipment.

In Example 15, the subject matter of Examples 12-14 includes, wherein the processing circuitry is further configured to perform operations to: receive an instruction to divert at least a portion of the airflow to an air mattress; and send an instruction to a flow management device to divert at least portion of the airflow to the air mattress; and divert at least a portion of the airflow to the air mattress.

In Example 16, the subject matter of Examples 12-15 includes, wherein the processing circuitry is further configured to perform operations to: sense, using a sensor, information related to an air mattress; receive, using the processor, the information from the sensor; determine, using the processor and the information received from the sensor, to divert at least a portion of the airflow to the air mattress; and send an instruction; using the processor, to a flow management device to divert at least a portion of the airflow to the air mattress.

In Example 17, the subject matter of Example 16 includes, wherein determining to divert at least a portion of the airflow to the air mattress includes determining that the information sensed by the sensor has traversed a threshold.

In Example 18, the subject matter of Examples 12-17 includes, wherein the processing circuitry is further configured to perform operations to: receive an instruction to divert at least a portion of the airflow to a compression device; and send an instruction to a flow management device to divert at least portion of the airflow to the compression device; and divert, using the flow management device, at least a portion of the airflow to compression device.

In Example 19, the subject matter of Examples 12-18 includes, wherein the processing circuitry is further configured to perform operations to: sense, using a sensor, information related to a compression device; receive the information from the sensor; determine from the received information, to divert at least a portion of the airflow to the compression device; and send an instruction to a flow management device to divert at least a portion of the airflow to the compression device.

In Example 20, the subject matter of Example 19 includes, wherein determining to divert at least a portion of the airflow to the air mattress includes determining that the information sensed by the sensor has traversed a threshold.

In Example 21, the subject matter of Examples 12-20 includes, wherein the processing circuitry is further configured to perform operations to: sense using a sensor, pressure information related to a pressure in the specified channel, receive the pressure information; determine that the pressure has traversed a threshold, and if the pressure has traversed the threshold, adjust an output of the fan.

In Example 22, the subject matter of Examples 12-21 includes, wherein the housing comprises a heat-resistant cowling.

Example 23 is at least one machine-readable medium including instructions that, when executed by processing circuitry, cause the processing circuitry to perform operations to implement of any of Examples 1-22.

Example 24 is an apparatus comprising means to implement of any of Examples 1-22.

Example 25 is a system to implement of any of Examples 1-22.

Example 16 is a method to implement of any of Examples 1-12.

Example Set 2

Example 1 is a method of reducing germs in an operating room, the method comprising: determining, using a processor, to activate a disinfection system based on a disinfection time stored on a memory; and sending instructions, based on the disinfection time, to turn on the disinfection system, wherein the disinfection system is located at a top end portion of a housing having electronic and electro-mechanical medical equipment disposed therein.

In Example 2, the subject matter of Example 1 includes, wherein the disinfection system includes UV-C lights configured to shine outward and or downward from the top end portion of the housing, and wherein turning on the disinfection system includes turning on the UV-C lights.

In Example 3, the subject matter of Examples 1-2 includes, sending instructions based on the disinfection time, using the processor, to actuate an electro-mechanical mechanism configured to deploy the disinfection system, wherein when the electro-mechanical mechanism is actuated, the disinfection system is caused to move in a direction outward from the housing.

In Example 4, the subject matter of Example 3 includes, sending instructions based on an end disinfection time, using the processor, to actuate the electro-mechanical mechanism to retract the disinfection system, wherein when the electro-mechanical mechanism is retracted, the disinfection system is caused to move in a direction towards the housing.

In Example 5, the subject matter of Examples 1-4 includes, receiving from motion sensor, using the processor, information about motion in the medical setting around the housing and preventing actuation, or turning off the disinfection system if motion is sensed within a specified range.

In Example 6, the subject matter of Examples 1-5 includes, wherein sending instructions, based on the disinfection time, to turn on the disinfection system, includes turning on a second disinfection system located closer to a bottom end portion of the housing, wherein the bottom end portion is opposite the top end portion.

Example 7 is at least one non-transitory machine-readable medium including instructions for reducing germs in an operating room, which when executed by processing circuitry, cause the processing circuitry to perform operations comprising: activate a disinfection system, based on a disinfection time stored on a memory; and turn on the disinfection system, wherein the disinfection system is located at a top end portion of a housing having electronic and electro-mechanical medical equipment disposed therein.

In Example 8, the subject matter of Example 7 includes, wherein the disinfection system includes UV-C lights configured to shine outward and or downward from the top end portion of the housing, and wherein turning on the disinfection includes turning on the UV-C lights.

In Example 9, the subject matter of Examples 7-8 includes, sending instructions to actuate an electro-mechanical mechanism configured to deploy the disinfection system, based on the disinfection time, wherein when the electro-mechanical mechanism is actuated, the disinfection system is caused to move in a direction outward from the housing.

In Example 10, the subject matter of Example 9 includes, sending instructions to actuate the electro-mechanical mechanism to retract the disinfection system, based on an end disinfection time, wherein when the electro-mechanical mechanism is retracted, the disinfection system is caused to move in a direction towards the housing.

In Example 11, the subject matter of Examples 7-10 includes, receiving from a motion sensor, information about motion in the medical setting around the housing, and preventing actuation, or turning off the disinfection system if motion is sensed within a specified range.

In Example 12, the subject matter of Examples 7-11 includes, wherein sending instructions, based on the disinfection time, to turn on the disinfection system, includes turning on a second disinfection system located closer to a bottom end portion of the housing, wherein the bottom end portion is opposite the top end portion.

Example 13 is at least one machine-readable medium including instructions that, when executed by processing circuitry, cause the processing circuitry to perform operations to implement of any of Examples 1-12.

Example 14 is an apparatus comprising means to implement of any of Examples 1-12.

Example 15 is a system to implement of any of Examples 1-12.

Example 16 is a method to implement of any of Examples 1-12.

Example Set 3

Example 1 is a method of monitoring waste fluid during a surgery, the method comprising: receiving from a sensor, using a processor, information about an amount of a waste fluid collected in a waste fluid storage device, wherein the information includes, a first fluid amount measured at a first time and a second fluid amount measured at a second time; determining, using the processor, a delta between the first fluid amount and the second fluid amount, using the information; outputting the delta, using the processor, to display the delta on an electronic device, wherein the electronic device is coupled to a housing configured to store unrelated waste-heat producing electronic and electromechanical surgical equipment; and saving, using the processor, to a storage device having at least a portion of a patient's anesthetic record stored thereon, at least a portion of the information.

In Example 2, the subject matter of Example 1 includes, wherein the amount of waste fluid is a weight of the waste fluid.

In Example 3, the subject matter of Examples 1-2 includes, receiving from a second sensor, using the processor, information about a volume of blood in the waste fluid storage device; receiving from a third sensor, using the processor, information about a concentration of a blood characteristic in the waste fluid; receiving, from a memory, using the processor, information about a concentration of a blood characteristic in the patient prior to the surgery; determining an amount of blood in the waste fluid, using the processor, wherein determining the amount of blood in the waste fluid is determined by dividing the information about a concentration of a blood characteristic in the waste fluid by the information about a concentration of a blood characteristic in a patient prior to the surgery to establish a concentration ratio, and multiplying the concentration ratio by the information about a volume of blood in the waste fluid storage device; and outputting the amount of blood in the waste fluid, using the processor, to display the amount of blood in the waste fluid on the electronic device.

In Example 4, the subject matter of Example 3 includes, wherein the information about the volume of blood in the waste fluid storage device includes a correction to ignore a volume of foam in the waste fluid storage device.

In Example 5, the subject matter of Examples 3-4 includes, saving, to the storage device having at least a portion of a patient's anesthetic record stored thereon, the amount of blood in the waste fluid.

In Example 6, the subject matter of Examples 1-5 includes, wherein outputting the delta includes wirelessly sending the information to a tablet device in a surgical field.

In Example 7, the subject matter of Examples 1-6 includes, outputting, using the processor, an alert to a tablet device in a surgical field, the alert related to the amount of fluid or a measured level of fluid in the fluid storage device.

In Example 8, the subject matter of Examples 1-7 includes, wherein outputting the delta includes sending the information to a display mounted on a housing having a first surgical module and a second surgical module stored therein, wherein the first and second surgical modules include electrical and electro-mechanical surgical equipment, and wherein the first and second surgical modules support separate surgical functions.

In Example 9, the subject matter of Examples 1-8 includes, wherein saving at least a portion of the information includes determining an amount of blood in the waste fluid, and automatically saving information about the amount of blood in the waste fluid to the storage device having at least a portion of the patient's anesthetic record stored thereon.

In Example 10, the subject matter of Examples 1-9 includes, wherein the information includes a first fluid amount and a second fluid amount, and wherein determining the delta includes determining a rate of change between the first fluid amount measured at the first time and the second fluid amount measured at the second time, and outputting the rate of change, using the processor, to display the delta on the electronic device.

In Example 11, the subject matter of Examples 1-10 includes, activating, with the processor, a stirrer located proximate the fluid storage device to agitate and mix the waste fluid in the fluid storage device, wherein the stirrer is coupled to a housing including a substantially heat-confining cowling, the housing having a first surgical module and a second surgical module stored therein, wherein the first and second surgical modules include electrical and electro-mechanical surgical equipment, and wherein the first and second surgical modules support different surgical functions.

In Example 12, the subject matter of Examples 1-11 includes, activating, with the processor, a vacuum pump to induce a negative air pressure on an inside of a fluid suction bag disposed in the fluid storage device.

In Example 13, the subject matter of Examples 1-12 includes, determining, with the processor, that a level of fluid in the fluid storage device has traversed a threshold; and activating, with the processor, a vacuum valve to a to shift a flow of waste fluid from the fluid storage device to a second fluid storage device.

Example 14 is at least one non-transitory machine-readable medium including instructions for monitoring waste fluid during a surgery, which when executed by processing circuitry, cause the processing circuitry to perform operations comprising: receiving information about an amount of a waste fluid collected in a waste fluid storage device, from a sensor, wherein the information includes, a first fluid amount measured at a first time and a second fluid amount measured at a second time; determining, a delta between the first fluid amount and the second fluid amount, using the information; outputting the delta, to display the delta on an electronic device, wherein the electronic device is coupled to a housing configured to store unrelated waste-heat producing electronic and electromechanical surgical equipment; and saving at least a portion of the information, to a storage device having at least a portion of a patient's anesthetic record stored thereon.

In Example 15, the subject matter of Example 14 includes, wherein the amount of waste fluid is a weight of the waste fluid.

In Example 16, the subject matter of Examples 14-15 includes, the operations further comprising: receiving information about a volume of blood in the waste fluid storage device, from a second sensor; receiving information about a concentration of a blood characteristic in the waste fluid, from a third sensor; receiving information about a concentration of a blood characteristic in the patient prior to the surgery from a memory, using the processor; determining an amount of blood in the waste fluid, wherein determining the amount of blood in the waste fluid is determined by dividing the information about a concentration of a blood characteristic in the waste fluid by the information about a concentration of a blood characteristic in a patient prior to the surgery to establish a concentration ratio, and multiplying the concentration ratio by the information about a volume of blood in the waste fluid storage device; and outputting the amount of blood in the waste fluid, using the processor, to display the amount of blood in the waste fluid on the electronic device.

In Example 17, the subject matter of Example 16 includes, wherein the information about the volume of blood in the waste fluid storage device includes a correction to ignore a volume of foam in the waste fluid storage device.

In Example 18, the subject matter of Examples 16-17 includes, the operations further comprising: saving, to the storage device having at least a portion of a patient's anesthetic record stored thereon, the amount of blood in the waste fluid.

In Example 19, the subject matter of Examples 14-18 includes, wherein outputting the delta includes wirelessly sending the information to a tablet device in a surgical field.

In Example 20, the subject matter of Examples 14-19 includes, the operations further comprising: outputting, using the processor, an alert to a tablet device in a surgical field, the alert related to the amount of fluid or a measured level of fluid in the fluid storage device.

In Example 21, the subject matter of Examples 14-20 includes, wherein outputting the delta includes sending the information to a display mounted on a housing having a first surgical module and a second surgical module stored therein, wherein the first and second surgical modules include electrical and electro-mechanical surgical equipment, and wherein the first and second surgical modules support separate surgical functions.

In Example 22, the subject matter of Examples 14-21 includes, wherein saving at least a portion of the information includes determining an amount of blood in the waste fluid, and automatically saving information about the amount of blood in the waste fluid to the storage device having at least a portion of the patient's anesthetic record stored thereon.

In Example 23, the subject matter of Examples 14-22 includes, wherein the information includes a first fluid amount and a second fluid amount, and wherein determining the delta includes determining a rate of change between the first fluid amount measured at the first time and the second fluid amount measured at the second time, and outputting the rate of change, using the processor, to display the delta on the electronic device.

In Example 24, the subject matter of Examples 14-23 includes, the operations further comprising: sending instructions to activate a stirrer located proximate the fluid storage device to agitate and mix the waste fluid in the fluid storage device, wherein the stirrer is coupled to a housing including a substantially heat-confining cowling, the housing having a first surgical module and a second surgical module stored therein, wherein the first and second surgical modules include electrical and electro-mechanical surgical equipment, and wherein the first and second surgical modules support different surgical functions.

In Example 25, the subject matter of Examples 14-24 includes, the operations further comprising: sending instructions to activate a vacuum pump to induce a negative air pressure on an inside of a fluid suction bag disposed in the fluid storage device.

In Example 26, the subject matter of Examples 14-25 includes, the operations further comprising: determining, with the processor, that a level of fluid in the fluid storage device has traversed a threshold; and activating, with the processor, a vacuum valve to a to shift a flow of waste fluid from the fluid storage device to a second fluid storage device.

Example 27 is at least one machine-readable medium including instructions that, when executed by processing circuitry, cause the processing circuitry to perform operations to implement of any of Examples 1-26.

Example 28 is an apparatus comprising means to implement of any of Examples 1-26.

Example 29 is a system to implement of any of Examples 1-26.

Example 30 is a method to implement of any of Examples 1-26.

Example Set 4

Example 1 is a method comprising: receiving an instruction, using circuitry, to secure a surgical module to a floor; applying a vacuum to a suction cup, using the circuitry, wherein the vacuum is provided by a vacuum pump operably coupled to the suction cup, and wherein the suction cup is located under the surgical module, and wherein applying the vacuum to the suction cup causes the suction cup to create a suction coupling with the floor.

In Example 2, the subject matter of Example 1 includes, wherein the vacuum is a continuous vacuum.

In Example 3, the subject matter of Examples 1-2 includes, wherein the vacuum pump is disposed within a housing of the surgical module.

In Example 4, the subject matter of Examples 1-3 includes, wherein the vacuum pump is a hospital vacuum source.

In Example 5, the subject matter of Examples 1-4 includes, receiving, using the circuitry, an instruction to decouple the surgical module from the floor; and actuating, using the circuitry, a lifting element to release the vacuum applied to the suction cup to decouple the surgical module from the floor.

In Example 6, the subject matter of Examples 1-5 includes, receiving, using the circuitry, an instruction to apply a vacuum to a waste fluid storage device; and applying, using the circuitry, a vacuum to the waste fluid storage device, wherein the vacuum is provided by the vacuum pump.

Example 7 is at least one non-transitory machine-readable medium including instructions for securing a surgical module to a floor, which when executed by circuitry, cause the circuitry to perform operations comprising: receiving an instruction to secure a surgical module to a floor; applying a vacuum to a suction cup, wherein the vacuum is provided by a vacuum pump operably coupled to the suction cup, and wherein the suction cup is located under the surgical module, and wherein applying the vacuum to the suction cup causes the suction cup to create a suction coupling with the floor.

In Example 8, the subject matter of Examples 6-7 includes, wherein the vacuum is a continuous vacuum.

In Example 9, the subject matter of Examples 6-8 includes, wherein the vacuum pump is disposed within a housing of the surgical module.

In Example 10, the subject matter of Examples 6-9 includes, wherein the vacuum pump is a hospital vacuum source.

In Example 11, the subject matter of Examples 6-10 includes, wherein the circuitry further performs operations to: receive an instruction to decouple the surgical module from the floor; and actuate a lifting element to release the vacuum applied to the suction cup to decouple the surgical module from the floor.

In Example 12, the subject matter of Examples 6-11 includes, wherein the circuitry further performs operations to receive an instruction to apply a vacuum to a waste fluid storage device; and apply a vacuum to the waste fluid storage device, wherein the vacuum is provided by the vacuum pump.

Example 13 is at least one machine-readable medium including instructions that, when executed by processing circuitry, cause the processing circuitry to perform operations to implement of any of Examples 1-12.

Example 14 is an apparatus comprising means to implement of any of Examples 1-12.

Example 15 is a system to implement of any of Examples 1-12.

Example 16 is a method to implement of any of Examples 1-12.

Example Set 5

Example 1 is a method for measuring urine output from a catheterized patient, the method comprising: receiving from a sensor, using circuitry, information corresponding to at least a weight of urine collected in a urine bag at a first time and a second weight of urine collected in the urine bag at a second time, wherein the sensor is operably coupled to a urine bag hanger configured to receive the urine bag, and wherein the urine bag hanger is coupled to a housing; determining, using the circuitry and the information, a volume of urine that corresponds to the weight of urine collected between the first time and the second time; saving, using the circuitry, to a storage device having at least a portion of a patient's anesthetic record stored thereon, a volume of urine output collected in the urine bag between the first time and the second time.

In Example 2, the subject matter of Example 1 includes, wherein the sensor is an electronic scale sensor.

In Example 3, the subject matter of Examples 1-2 includes, wherein the circuitry includes a processor.

In Example 4, the subject matter of Examples 1-3 includes, determining, using the circuitry and the information, a delta or rate of urine collected between the first time and the second time, and outputting the delta or rate, using the circuitry, to display the delta or rate of urine collected on an electronic device, wherein the electronic device is coupled to a housing configured to store unrelated waste-heat producing electronic and electromechanical surgical equipment.

In Example 5, the subject matter of Examples 1-4 includes, sensing, with the sensor, when the urine bag is initially placed on the urine bag hanger; and zeroing the first weight, using the circuitry, when the sensor senses that the urine bag is initially placed on the urine bag hanger to establish a start point for measuring the collection of urine.

Example 6 is at least one non-transitory machine-readable medium including instructions for performing operations to measure urine output from a catheterized patient, the method comprising: receiving information corresponding to at least a weight of urine collected in a urine bag at a first time and a second weight of urine collected in the urine bag at a second time using a sensor, wherein the sensor is operably coupled to a urine bag hanger configured to receive the urine bag, and wherein the urine bag hanger is coupled to a housing; determining, using the information, a volume of urine that corresponds to the weight of urine collected between the first time and the second time; saving to a storage device having at least a portion of a patient's anesthetic record stored thereon, a volume of urine output collected in the urine bag between the first time and the second time.

In Example 7, the subject matter of Example 6 includes, wherein the sensor is an electronic scale sensor.

In Example 8, the subject matter of Examples 6-7 includes, wherein the circuitry includes a processor.

In Example 9, the subject matter of Examples 6-8 includes, the operations further comprising: determining, using the information, a delta or rate of urine collected between the first time and the second time, and outputting the delta or rate to display the delta or rate of urine collected on an electronic device, wherein the electronic device is coupled to a housing configured to store unrelated waste-heat producing electronic and electromechanical surgical equipment.

In Example 10, the subject matter of Examples 6-9 includes, the operations further comprising: sensing, with the sensor, when the urine bag is initially placed on the urine bag hanger; and zeroing the first weight when the sensor senses that the urine bag is initially placed on the urine bag hanger to establish a start point for measuring the collection of urine.

Example 11 is at least one machine-readable medium including instructions that, when executed by processing circuitry, cause the processing circuitry to perform operations to implement of any of Examples 1-10.

Example 12 is an apparatus comprising means to implement of any of Examples 1-10.

Example 13 is a system to implement of any of Examples 1-10.

Example 14 is a method to implement of any of Examples 1-10.

Example Set 6

Example 1 is a method comprising: receiving an instruction, using processing circuitry, to provide air to at least one of a surgical air mattress or a surgical body compression device; sending an instruction, using the processing circuitry, to an air pump, causing air to be provided to at least one of the surgical air mattress or the surgical body compression device, wherein the air pump is disposed within a housing, and wherein the housing is configured to house a first surgical module and a second surgical module comprising unrelated waste heat-producing electronic and electromechanical surgical equipment.

In Example 2, the subject matter of Example 1 includes, receiving an instruction, using the processing circuitry, to activate a fan disposed within the housing; actuating the fan, using the processing circuitry, wherein actuating the fan causes an airflow to be received into an inlet vent of the housing, the airflow to be passed through an air cleaning device, and the airflow along with waste heat produced by the electronic and electromechanical surgical equipment to be exhausted through an outlet vent.

In Example 3, the subject matter of Example 2 includes, receiving information from a sensor, using the processing circuitry, the information indicating a sensed condition of the surgical air mattress or the surgical body compression device; and determining, using the processing circuitry, if the sensed condition has traversed a threshold, and if the sensed condition has traversed the threshold, actuating, using the processing circuitry, a flow managing device to divert at least a portion of the airflow to the surgical air mattress or the surgical body compression device to supplement the air provided by the air pump, based on the information received from the sensor.

In Example 4, the subject matter of Examples 2-3 includes, receiving an instruction, using the processing circuitry, to activate a noise cancellation device configured to cancel at least a portion of a noise generated by the fan or the air pump.

Example 5 is at least one non-transitory machine-readable medium including instructions for supplying air to a surgical air mattress or a surgical body compression device, which when executed by processing circuitry, cause the processing circuitry to perform operations comprising: receive an instruction to provide air to at least one of a surgical air mattress or a surgical body compression device; send an instruction, using the processing circuitry, to an air pump, to provide air to at least one of the surgical air mattress or the surgical body compression device, wherein the air pump is disposed within a housing, and wherein the housing is configured to house a first surgical module and a second surgical module comprising unrelated waste heat-producing electronic and electromechanical surgical equipment.

In Example 6, the subject matter of Example 5 includes, wherein the instructions further cause the processing circuitry to: receive an instruction to activate a fan disposed within the housing; activate the fan based on the instruction to activate the fan, wherein activating the fan causes an airflow to be received into an inlet vent of the housing, the airflow to be passed through an air cleaning device, and the airflow along with waste heat produced by the electronic and electromechanical surgical equipment to be exhausted through an outlet vent.

In Example 7, the subject matter of Example 6 includes, wherein the instructions further cause the processing circuitry to: receive information from a sensor indicating a second sensed condition of the surgical air mattress or the surgical body compression device; and determine if the second sensed condition has traversed a threshold, and if the second sensed condition has traversed the threshold, actuating a flow managing device to divert at least a portion of the airflow to the surgical air mattress or the surgical body compression device to supplement the air provided by the air pump, based on the information received from the sensor.

In Example 8, the subject matter of Examples 6-7 includes, wherein the instructions further cause the processing circuitry to: receive an instruction to activate a noise cancellation device configured to cancel at least a portion of a noise generated by the fan or the air pump.

Example 9 is at least one machine-readable medium including instructions that, when executed by processing circuitry, cause the processing circuitry to perform operations to implement of any of Examples 1-8.

Example 10 is an apparatus comprising means to implement of any of Examples 1-8.

Example 11 is a system to implement of any of Examples 1-8.

Example 12 is a method to implement of any of Examples 1-8.

Example Set 7

Example 1 is a method for filtering air in a surgical field, the method comprising: providing or receiving, into a housing having a heat-resistant cowling, a first surgical module; providing or receiving, into the housing, a second surgical module, wherein the first surgical module and the second surgical module are unrelated waste heat-producing electronic and electromechanical surgical equipment; containing, substantially within the housing, the waste heat generated by the first surgical module and the second surgical module; receiving an instruction, using circuitry, to activate a fan disposed within the housing; actuating the fan, using the circuitry, to create an airflow; receiving the airflow through an inlet vent and into a plenum, wherein the plenum includes, a plenum wall separating the first surgical module and the second surgical module from the plenum; passing the airflow through a filter, to remove infectious particles generated during a surgery; blowing at least a portion of the airflow through a vent tube; and exhausting, through an outlet vent, at least a portion of the airflow and at least a portion of the waste heat.

In Example 2, the subject matter of Example 1 includes, wherein providing or receiving the first surgical module includes providing or receiving anesthesia monitoring equipment, and wherein providing or receiving the second surgical module includes providing or receiving electrosurgical grounding equipment, and wherein the first surgical module and the second surgical module are cooled by the airflow.

In Example 3, the subject matter of Examples 1-2 includes, wherein receiving the airflow includes collecting air from a specified location proximate a head of a patient during a surgery.

In Example 4, the subject matter of Examples 1-3 includes, positioning a vacuum hose proximate a head of a patient during a surgery, wherein the vacuum hose is operably couplable to the inlet vent, and wherein receiving the air includes receiving the air through the vacuum hose.

In Example 5, the subject matter of Examples 1-4 includes, positioning a vacuum hose between a patient and a surgeon, wherein the vacuum hose is operably couplable to the inlet vent, and wherein receiving the airflow includes receiving the airflow through the vacuum hose.

In Example 6, the subject matter of Examples 1-5 includes, positioning a vacuum hose proximate a patient and a surgeon, wherein the vacuum hose is operably couplable to the inlet vent, and wherein receiving the airflow includes receiving the airflow through the vacuum hose.

In Example 7, the subject matter of Examples 1-6 includes, operably coupling a vacuum hose to the inlet vent, and positioning the vacuum hose proximate a lateral side body of a patient to evacuate the air from a ventilation dead zone, and wherein receiving the airflow includes receiving the airflow through the vacuum hose.

In Example 8, the subject matter of Examples 1-7 includes, wherein exhausting the airflow includes exhausting the airflow through the outlet vent positioned at least four feet above a floor that the housing is positioned on.

In Example 9, the subject matter of Examples 1-8 includes, wherein receiving the airflow includes collecting air from a specified location between a height of a surgical table and a floor of the surgical field during a surgery, and exhausting the airflow includes exhausting the airflow at least four feet above a floor that the housing is positioned on.

In Example 10, the subject matter of Examples 1-9 includes, inches of a surgical table in a surgical field during a surgery.

In Example 11, the subject matter of Examples 1-10 includes, positioning, under an arm-board of a surgical table and adjacent an anesthesia screen, a lower bulbous portion of the housing.

In Example 12, the subject matter of Examples 1-11 includes, positioning, under an arm-board of a surgical table and adjacent an anesthesia screen, a lower bulbous portion of the housing; and positioning, adjacent an anesthesia screen, an upper tower-like portion of the housing, the upper tower-like portion including one or more displays.

In Example 13, the subject matter of Examples 1-12 includes, positioning, under an arm-board of a surgical table and adjacent an anesthesia screen, a lower bulbous portion of the housing; and positioning, adjacent an anesthesia screen, an upper tower-like portion of the housing; and receiving the first and second surgical modules into a lower bulbous portion of the housing.

Example 14 is at least one non-transitory machine-readable medium including instructions for filtering air within a surgical field, which when executed by circuitry, cause the circuitry to perform operations comprising: cause one or more power sources to provide power to a first surgical module stored in an insulated housing, the first surgical module being associated with a first surgical function, and the first surgical module producing a first waste heat; cause the one or more power sources to provide power to a second surgical module stored in the housing, the second surgical module associated with a second surgical function, and the second surgical module producing a second waste heat, wherein the first surgical module and second surgical module are directed to different surgical functions; and receive an instruction to activate a fan disposed in the housing; activate the fan, wherein actuating the fan causes air to be collected from a specified location and to deliver an airflow to the housing causing the airflow to pass through a filter to remove infectious particles associated with the surgical field, and to pass at least a portion of the airflow through a vent tube, and to exhaust at least a portion of the airflow and at least a portion of the first and second waste heat through an outlet vent.

In Example 15, the subject matter of Example 14 includes, wherein the circuitry further performs operations to: receive an instruction to activate a noise cancellation device configured to cancel at least a portion of a noise generated by the fan.

In Example 16, the subject matter of Examples 14-15 includes, wherein causing the one or more power sources to power the first surgical module includes powering an anesthesia monitor.

In Example 17, the subject matter of Examples 14-16 includes, wherein to cause the one or more power sources to power the second surgical module includes powering an electrosurgical generator.

In Example 18, the subject matter of Examples 14-17 includes, wherein to cause the one or more power sources to power the first and second surgical modules includes powering an anesthesia monitor and powering an electrosurgical generator.

In Example 19, the subject matter of Examples 14-18 includes, wherein to activate the fan includes activating the fan positioned and configured to collect the air from a specified location proximate a head of a patient during a surgery.

In Example 20, the subject matter of Examples 14-19 includes, wherein to activate the fan includes activating the fan positioned and configured to evacuate the air from a ventilation dead zone proximate a lateral side body of a patient.

In Example 21, the subject matter of Examples 14-20 includes, wherein to activate the fan includes activating a fan positioned and configured to exhaust at least a portion of the airflow at least four feet above a floor that the housing is positioned on.

In Example 22, the subject matter of Examples 14-21 includes, wherein to activate the fan causes air to be collected from a location at or below the height of the surgical table in a surgical field during a surgery, and wherein to exhaust the air from the housing, includes exhausting the air at least five feet above the floor that the housing is positioned on.

In Example 23, the subject matter of Example 22 includes, wherein to activate the fan causes air to be collected at a location between an underside of a surgical table and a floor that the surgical table is positioned above.

In Example 24, the subject matter of Examples 14-23 includes, wherein the housing substantially confines the waste heat produced by the first and second surgical modules.

Example 25 is at least one machine-readable medium including instructions that, when executed by processing circuitry, cause the processing circuitry to perform operations to implement of any of Examples 1-24.

Example 26 is an apparatus comprising means to implement of any of Examples 1-24.

Example 27 is a system to implement of any of Examples 1-24.

Example 28 is a method to implement of any of Examples 1-24.

Example Set 8

In an example 1, a module for housing unrelated electronic and electromechanical equipment for use during surgery including an ultraviolet operating room disinfection system, the module comprising:
 a lower section for housing unrelated electronic and electromechanical equipment;
 a tower-like upper section located on top of the lower section;
 the top of the tower-like upper section terminates at least 5 feet above the floor;
 a water-resistant cowling enclosing at least a portion of the lower section and the tower-like upper section; and
 a cartridge containing one or more ultraviolet-C producing lights that is protectively housed within the tower-like upper section;
 the cartridge containing one or more ultraviolet-C producing lights that emerges upward from the top of the tower-like upper section to substantially seat itself on the top of the tower-like upper section when activated;
 wherein the elevated location on top of the tower-like upper section allows the ultraviolet-C light to disinfect the patient and staff-contacting upper surfaces of the equipment in the operating room.

1a. The module of any preceding example, wherein the one or more ultraviolet-C producing lights in the cartridge containing the one or more ultraviolet-C producing lights are arranged to project ultraviolet-C light in the full 360o surrounding the module.

1b. The module of any preceding example, wherein one or more of the ultraviolet-C producing lights in the cartridge containing the one or more ultraviolet-C producing lights are oriented to shine on the module and thus disinfect it by pivoting to an angle that extends the one or more lights outward from the sides of the tower-like upper section when activated.

1c. The module of any preceding example, wherein at least four of the ultraviolet-C producing lights are oriented to shine on the module and thus disinfect it by pivoting to a partially horizontal angle that extends the four or more lights outward from the tower-like upper section when activated allowing them to shine directly on all sides of the module.

1d. The module of any preceding example, wherein at least four ultraviolet-C producing lights are mounted in the four corners of the lower section near the floor and are oriented to shine on the floor and undersides of the equipment in the operating room.

1e. The module of any preceding example, wherein the lower section has a bulbous form configured to allow that the rear portion of the tower-like upper section to be positioned adjacent the anesthesia side of one of the arm-boards of the surgical table with the bulbous lower section fitting into the unused space under the arm board.

In an example 2, a module for housing unrelated electronic and electromechanical equipment for use during surgery including a waste blood and fluid suction system, the module comprising:
 a lower section for housing unrelated electronic and electromechanical equipment;
 a tower-like upper section located on top of the lower section;
 a water-resistant cowling enclosing at least a portion of the lower section and the tower-like upper section; and
 one or more bucket-like recesses in or on the cowling of the lower section for mounting one or more fluid suction canisters;
 the fluid suction canisters mounted on the one or more bucket-like recesses are operably connected to a vacuum source controlled from within the module;
 wherein the bucket-like recesses for mounting one or more fluid suction canisters also include one or more electronic scales for measuring the combined weight of each fluid suction canister and its blood and fluid contents.

2a. The module of any preceding example, wherein the one or more electronic scales for measuring the combined weight of each fluid suction canister and its blood and fluid contents allow an accurate calculation of the volume of the blood and fluid in the one or more canisters while omitting the false volume produced by air bubbles and foam.

2b. The module of any preceding example, wherein the bucket-like recesses for mounting one or more fluid suction canisters also include one or more optical or infrared fluid level sensors for sensing the combined volume of blood, fluid, air bubbles and foam in the canister.

2c. The module of any preceding example, wherein the optical or infrared fluid level sensors for sensing the combined volume of blood, fluid, air bubbles and foam in the one or more canisters are operably connected to the vacuum source controlled from within the module and can automatically stop the vacuum applied to any canister that that has been filled to its useful capacity.

2d. The module of any preceding example, wherein the bucket-like recesses for mounting one or more fluid suction canisters also include one or more optical or infrared sensors for determining the hematocrit of the blood and fluid in the canister.

2e. The module of any preceding example, wherein the output of the one or more optical or infrared sensors for determining the hematocrit of the blood and fluid in the canister plus the measurement of the volume of blood and fluid in the canister as determined by weight is inputted to a microprocessor in the module to calculate blood loss.

2f. The module of any preceding example, wherein the lower section has a bulbous form configured to allow that the rear portion of the tower-like upper section to be positioned adjacent the anesthesia side of one of the arm-boards of the surgical table with the bulbous lower section fitting into the unused space under the arm board.

In an example 3, a module for housing unrelated electronic and electromechanical equipment for use during surgery and providing a mounting location for equipment accessing the surgical field, the module comprising:
 a bulbous lower section for housing unrelated electronic and electromechanical equipment;
 at least a portion of the bulbous lower section fits into an unused space under the arm-board of a surgical table;
 a tower-like upper section located on top of the lower section;
 the tower-like upper section is taller than the height of the anesthesia screen;
 a water-resistant cowling enclosing at least a portion of the lower section and the tower-like upper section;
 wherein the tower-like upper section can be positioned adjacent the anesthesia side of an arm-board of a surgical table adjacent the anesthesia screen, and the rear side of the tower-like upper section that is facing the surgical field can be used for mounting various pieces of surgical equipment that need direct access to the surgical field from the head end.

3a. The module of any preceding example, wherein the upper portion of the tower-like upper section that is facing the surgical field can be used for mounting monitor screens such as patient vital sign monitor screens, surgical scope monitor screens, surgical check list monitor screens, safety check list monitor screens, communications and message monitor screens, clocks and timing device screens.

3b. The module of any preceding example, wherein the upper portion of the tower-like upper section that is facing the surgical field can be used for mounting surgical lights aiming at the surgical field.

3c. The module of any preceding example, wherein the upper portion of the tower-like upper section that is facing the surgical field can be used for mounting articulating arms that can "reach" across the upper edge of the anesthesia screen, into the sterile surgical field and hold surgical lights, surgical instruments, surgical scopes or surgical retractors.

3d. The module of any preceding example, wherein the upper portion of the tower-like upper section that is facing the surgical field can be used for mounting one or more video cameras for recording the surgical procedure.

3e. The module of any preceding example, wherein the upper portion of the tower-like upper section that is facing the surgical field can be used for mounting a sterile storage container for surgical supplies.

In an example 4, a module for housing unrelated electronic and electromechanical equipment for use during surgery including suction cups for anchoring the module to the floor, the module comprising:
 a lower section for housing unrelated electronic and electromechanical equipment;
 a tower-like upper section located on top of the lower section;
 a water-resistant cowling enclosing at least a portion of the lower section and the tower-like upper section; and
 one or more suction cups on the underside of the lower section that may be lowered to engage with the floor,
 wherein a suction anchor for stabilizing the module is created when the one or more suction cups are lowered to engage with the floor and a vacuum from a vacuum source controlled in the module is applied to the inside of the suction cups.

4a. The module of any preceding example, wherein the vacuum source is the hospital vacuum supplied to the module.

4b. The module of any preceding example, wherein the vacuum source is a vacuum pump housed within the module.

4c. The module of any preceding example, wherein the one or more suction cups are lowered by pneumatic cylinder actuators to engage with the floor.

4d. The module of any preceding example, wherein the one or more suction cups are lowered by electromechanical actuators to engage with the floor.

4e. The module of any preceding example, wherein the one or more suction cups are lowered by manual actuators to engage with the floor.

In an example 5, a surgical field ventilation optimization system powered by a waste air management system housed in a module, the surgical field ventilation optimization system comprising:
 one or more sterile hoses that are placed in the sterile surgical field with their distal ends located on top of the surgical drape substantially in the space between the surgical wound and the surgeon, where the ventilation flow boundary layer dead zone that naturally forms in front of the surgeon is located;
 the distal ends of the one or more hoses include one or more holes in the hoses that allow 5-50 CFM of airflow;
 the proximal ends of the one or more sterile hoses are attached to a vacuum source;
 wherein, a vacuum is applied to the proximal end of the one or more sterile hoses causing air to enter the distal ends of the hoses evacuating and effectively deflating the flow boundary layer dead zone that naturally forms in front of the surgeon.

5a. The surgical field ventilation optimization system of any preceding example, wherein the vacuum source is a waste air management system housed in a module.

5b. The surgical field ventilation optimization system of any preceding example, wherein the vacuum source is a waste air management system housed in a module for housing unrelated electronic and electromechanical equipment during surgery.

5c. The surgical field ventilation optimization system of any preceding example, wherein the distal ends of the one or more hoses are adhesively attached to the sterile drape.

5d. The surgical field ventilation optimization system of any preceding example, wherein the proximal ends of the one or more hoses may be combined in order to reduce the number of hoses being attached to the vacuum source.

5e. The surgical field ventilation optimization system of any preceding example, wherein evacuating and deflating the flow boundary layer dead zone that naturally forms in front of the surgeon results in the ventilation airflow remaining unimpeded which keeps the airborne contaminating particles airborne, thus preventing them from settling into the open wound.

Example Set 9

Example 1 is a module for housing unrelated electronic and electromechanical surgical equipment including a system to measure and record administration of one or more IV medications or fluids for IV administration, the module comprising: a housing having a lower section and a tower-like upper section, wherein the lower section is configured to house unrelated waste heat-producing electronic and electromechanical surgical equipment, and wherein the tower-like upper section is located on top of the lower section, wherein the upper section is configured to accommodate mounting of equipment controls, display screens and monitor screens at a convenient height for viewing and operating; a cowling that substantially confines waste heat generated by the unrelated waste heat-producing electronic and electromechanical surgical equipment; and a system for measuring and recording the administration of the one or more IV medications and fluids, the system comprising: a barcode reader or an RFID interrogator configured to identify at least one of the one or more IV medications or fluids; and a machine vision digital camera in electrical communication with processing circuitry configured to determine a volume of medication administered from a syringe or fluid administered from an IV bag through an IV drip chamber into an IV tubing based on an image generated by the machine vision digital camera.

In Example 2, the subject matter of Example 1 includes, the system to measure and record the administration of the one or more IV medications or fluids further comprising: an injection portal; and one or more orienting members, wherein the injection portal includes an injection port that is configured to be in fluid communication with the IV tubing and the one or more orienting members are configured to guide syringes of varying diameters to mate with the injection port within the injection portal.

In Example 3, the subject matter of Example 2 includes, wherein the system to measure and record the administration of the one or more IV medications or fluids further comprises: a display in electrical communication with the machine vision digital camera, wherein the machine vision digital camera is configured to capture an image of a syringe when the syringe is inserted inside the injection portal, and wherein the display is configured to output a visual image or representation of the syringe.

In Example 4, the subject matter of Examples 2-3 includes, wherein the machine vision digital camera is located to capture an image of an inside of the injection portal, and wherein the processing circuitry is configured to interpret the image of a syringe when the syringe is inserted into the injection portal to measure the volume of medication injected from the syringe by determining a size and an internal diameter of the syringe and measuring a distance a plunger of the syringe moves to calculate an injected volume.

In Example 5, the subject matter of Examples 1-4 includes, wherein the RFID interrogator is configured to identify at least one of the one or more IV medications or fluids for IV administration that has been labeled with an RFID tag.

In Example 6, the subject matter of Examples 1-5 includes, wherein the machine vision digital camera that is in electrical communication with the processing circuitry is configured to read a barcode to identify a medication or fluid for IV administration that has been labeled with a barcode.

In Example 7, the subject matter of Examples 1-6 includes, wherein the system to measure and record the administration of the one or more IV medications or fluids further comprises: a display in electrical communication with the machine vision digital camera, wherein the display is configured to output medication and fluid identification and injection information including one or more of: a brand name of a drug, a generic name of a drug, a concentration of a drug, a dosage of a drug, a dosage delivered, a fluid flow rate, a fluid volume delivered, a patient allergy, an alert for over-dosing, an alert for a drug allergy and an alert for drug interactions on the display.

In Example 8, the subject matter of Example 7 includes, wherein the system to measure and record the administration of the one or more IV medications or fluids further comprises or is in electrical communication with one or more of: an electronic anesthetic record (EAR) and an electronic medical record (EMR), and wherein the system automatically records at least some of the administration of the one or more IV medications in one or both of the (EAR) and the (EMR).

In Example 9, the subject matter of Examples 2-8 includes, wherein the system to measure and record the administration of the one or more IV medications or fluids further comprises: a mechanical clamp configured to clamp the IV tubing, the mechanical clamp positioned upstream or downstream from the injection port, wherein the mechanical clamp can be automatically actuated to mechanically compress the IV tubing to stop the administration of the one or more IV medications or fluids when an adverse condition is determined by the processing circuitry.

In Example 10, the subject matter of Examples 2-9 includes, wherein the injection portal includes one or more UV lights that shine on the injection port.

In Example 11, the subject matter of Examples 1-10 includes, wherein the machine vision digital camera is located adjacent to the IV drip chamber, and wherein the processing circuitry is configured to interpret the image of drops in the IV drip chamber and determine a volume of fluid flowing from the IV bag by determining a size of drops and a number of drops per unit time to calculate a fluid flow rate.

In Example 12, the subject matter of Examples 1-11 includes, wherein the system to measure and record the administration of the one or more IV medications or fluids further comprises: a hanger configured to support an IV bag; and an electronic scale in electrical communication with a processor, wherein the electronic scale is configured to measure a combined weight of the IV bag, the IV drip chamber, the IV tubing and the fluids in the IV bag, and wherein the processor is configured to determine a reduction in the measured combined weight over time to determine the weight of the IV fluids infused over time and convert the measured combined weight over time to a fluid flow rate and an infused fluid volume.

In Example 13, the subject matter of Examples 1-12 includes, wherein the system to measure and record the administration of the one or more IV medications or fluids further comprises: a hanger configured to receive the IV bag; an electronic scale in electrical communication with a processor, wherein the hanger is configured to support the IV bag; and a float located in the IV drip chamber, wherein the machine vision digital camera is located adjacent to the IV drip chamber, and wherein the processing circuitry is configured to determine a volume of fluid flowing from the IV bag by determining a size of drops and a number of the drops per unit time to calculate a fluid flow rate, wherein the electronic scale is configured to measure a combined weight of the IV bag, the IV drip chamber, the IV tubing and the fluid in the IV bag, and wherein the processing circuitry is configured to determine a reduction in the measured combined weight over time to determine a weight of the IV fluids infused over time and convert the measured combined weight over time to a fluid flow rate and infused fluid volume, wherein at higher flow rates, when the drops in the IV drip chamber coalesce into a fluid stream that is uninterpretable by the machine vision camera and processing circuitry, the fluid stream causes a float in the IV drip chamber to move indicating that fluid is flowing, and wherein when the system fails to identify individual drops and detects that the float is moving, the processing circuitry is configured to measure a fluid flow rate by determining a reduction of the combined weight of the IV bag, the IV drip chamber, the IV tubing and the fluid in the IV bag over time.

In Example 14, the subject matter of Examples 1-13 includes, wherein the system to measure and record the administration of the one or more IV medications or fluids further comprises: one or more electro-mechanical clamps in electrical communication with the processing circuitry, wherein the machine vision digital camera is located adjacent the IV drip chamber that is configured to be connected to the IV bag, wherein the processing circuitry is configured to interpret the image including a fluid meniscus level in the IV drip chamber, and wherein when the fluid meniscus is not present, the processing circuitry causes actuation of the one or more electro-mechanical clamps to compress the IV tubing to stop a portion of an IV infusion before air can enter the IV tubing.

Example 15 is a module for housing unrelated electronic and electromechanical surgical equipment including a system to measure and record administration of one or more IV medications or fluids for IV administration to a patient, the module comprising: a housing having a lower section and a tower-like upper section, wherein the lower section is configured to house unrelated waste heat-producing electronic and electromechanical surgical equipment, and wherein the tower-like upper section is located on top of the lower section, wherein the upper section is configured to accommodate mounting of equipment controls, display screens and monitor screens at a convenient height for viewing and operating; a cable and hose management system located on a patient side of the module, wherein the patient side of the module is configured to face a patient and provide the closest and most direct access to the patient when the module is positioned adjacent an anesthesia side of an arm-board of a surgical table; and a system to measure and record the administration of the one or more IV medications and fluids, the system comprising: a barcode reader or an RFID interrogator configured to identify at least one of the one or more IV medications or fluids; and a machine vision digital camera in electrical communication with processing circuitry configured to determine a volume of medication administered from a syringe or fluid administered from an IV bag through an IV drip chamber into an IV tubing based on an image generated by the machine vision digital camera.

In Example 16, the subject matter of Example 15 includes, wherein the system to measure and record the administration of the one or more IV medications or fluids further comprises: an injection portal; and one or more orienting members, wherein the injection portal includes an injection port that is configured to be in fluid communication with the IV tubing and the one or more orienting members are configured to guide syringes of varying diameters to mate with the injection port within the injection portal.

In Example 17, the subject matter of Example 16 includes, wherein the system to measure and record the administration of the one or more IV medications or fluids further comprises: a display in electrical communication with the machine vision digital camera, wherein the machine vision digital camera is configured to capture an image of the syringe when the syringe is inserted inside the injection portal, and wherein the display is configured to output a visual image or representation of the syringe.

In Example 18, the subject matter of Examples 16-17 includes, wherein the machine vision digital camera is located to capture an image of an inside of the injection portal, and wherein the processing circuitry is configured to interpret the image of the syringe when the syringe is inserted into the injection portal to measure the volume of medication injected from the syringe by determining a size and an internal diameter of the syringe and measuring a distance a plunger of the syringe moves to calculate an injected volume.

In Example 19, the subject matter of Examples 15-18 includes, wherein the RFID interrogator is configured to identify at least one of the one or more IV medications or fluids for IV administration that has been labeled with an RFID tag.

In Example 20, the subject matter of Examples 15-19 includes, wherein the machine vision digital camera is in electrical communication with the processing circuitry is configured to read a barcode to identify a medication or fluid for IV administration that has been labeled with a barcode.

In Example 21, the subject matter of Examples 15-20 includes, wherein the system to measure and record the administration of the one or more IV medications or fluids further comprises: a display in electrical communication with the machine vision digital camera, wherein the display is configured to output medication and fluid identification and injection information including one or more of: a brand name of a drug, a generic name of a drug, a concentration of a drug, a dosage of a drug, a dosage delivered, a fluid flow rate, a fluid volume delivered, a patient allergy, an alert for over-dosing, an alert for a drug allergy and an alert for drug interactions on the display.

In Example 22, the subject matter of Example 21 includes, wherein the system to measure and record the administration of the one or more IV medications or fluids further comprises or is in electrical communication with one or more of: an electronic anesthetic record (EAR) and an electronic medical record (EMR), and wherein the system automatically records at least some of the administration of the one or more IV medications in one or both of the (EAR) and the (EMR).

In Example 23, the subject matter of Examples 16-22 includes, wherein the injection portal includes one or more UV lights that shine on the injection port.

In Example 24, the subject matter of Examples 15-23 includes, wherein the machine vision digital camera is located adjacent to the IV drip chamber, and wherein the processing circuitry is configured to interpret the image of drops in the IV drip chamber and determine a volume of fluid flowing from the IV bag by determining a size of drops and a number of drops per unit time to calculate a fluid flow rate.

In Example 25, the subject matter of Examples 15-24 includes, wherein the system to measure and record the administration of the one or more IV medications or fluids further comprises: a hanger configured to support an IV bag; and an electronic scale in electrical communication with a processor, wherein the electronic scale is configured to measure a combined weight of the IV bag, the IV drip chamber, the IV tubing and the fluids in the IV bag, and wherein the processor is configured to determine a reduction in the measured combined weight over time to determine the weight of the IV fluids infused over time and convert the measured combined weight over time to a fluid flow rate and an infused fluid volume.

Example 26 is a module comprising: a housing having a lower section and a tower-like upper section, wherein the lower section is configured to house unrelated waste heat-producing electronic and electromechanical surgical equipment, and wherein the tower-like upper section is located on top of the lower section; a cowling that substantially confines waste heat generated by the unrelated waste heat-producing electronic and electromechanical surgical equipment; a system for monitoring the administration of one or more IV medications and fluids, the system comprising: a barcode reader or an RFID interrogator configured to identify the one or more IV medications or fluids; a machine vision digital camera to capture an image of one or more of a syringe or a drip chamber; processing circuitry operably coupled to the barcode reader or the RFID interrogator to receive the identity of the one or more IV medications or fluids, the processing circuitry operably coupled to the machine vision digital camera to receive the captured image and determine a volume of medication administered from the syringe or fluid administered from an IV bag based on the image; and a display operably coupled to the processing circuitry, the display configured to receive instructions from the processing circuitry to output the identity and determined volume of medication administered from the syringe or fluid administered from an IV bag.

Example 27 is at least one machine-readable medium including instructions that, when executed by processing circuitry, cause the processing circuitry to perform operations to implement of any of Examples 1-26.

Example 28 is an apparatus comprising means to implement of any of Examples 1-26.

Example 29 is a system to implement of any of Examples 1-26.

Example 30 is a method to implement of any of Examples 1-26.

What is claimed is:

1. A module for housing unrelated electronic and electromechanical surgical equipment including a system to measure and record administration of one or more IV medications or fluids for IV administration, the module comprising:
    a housing having a lower section and a tower-like upper section, wherein the lower section is configured to house unrelated waste heat-producing electronic and electromechanical surgical equipment, and wherein the tower-like upper section is located on top of the lower section, wherein the upper section is configured to accommodate mounting of equipment controls, display screens and monitor screens at a convenient height for viewing and operating;
    a cowling that substantially confines waste heat generated by the unrelated waste heat-producing electronic and electromechanical surgical equipment; and
    a system for measuring and recording the administration of the one or more IV medications and fluids, the system comprising:
    a barcode reader or an RFID interrogator configured to identify at least one of the one or more IV medications or fluids; and
    a machine vision digital camera in electrical communication with processing circuitry configured to determine a volume of medication administered from a syringe or fluid administered from an IV bag through an IV drip chamber into an IV tubing based on an image generated by the machine vision digital camera.

2. The module of claim 1, the system to measure and record the administration of the one or more IV medications or fluids further comprising:
    an injection portal; and
    one or more orienting members, wherein the injection portal includes an injection port that is configured to be in fluid communication with the IV tubing and the one or more orienting members are configured to guide syringes of varying diameters to mate with the injection port within the injection portal.

3. The module of claim 2, wherein the system to measure and record the administration of the one or more IV medications or fluids further comprises:
    a display in electrical communication with the machine vision digital camera, wherein the machine vision digital camera is configured to capture an image of a syringe when the syringe is inserted inside the injection portal, and wherein the display is configured to output a visual image or representation of the syringe.

4. The module of claim 2, wherein the machine vision digital camera is located to capture an image of an inside of the injection portal, and wherein the processing circuitry is configured to interpret the image of a syringe when the syringe is inserted into the injection portal to measure the volume of medication injected from the syringe by determining a size and an internal diameter of the syringe and measuring a distance a plunger of the syringe moves to calculate an injected volume.

5. The module of claim 1, wherein the RFID interrogator is configured to identify at least one of the one or more IV medications or fluids for IV administration that has been labeled with an RFID tag.

6. The module of claim 1, wherein the machine vision digital camera that is in electrical communication with the processing circuitry is configured to read a barcode to identify a medication or fluid for IV administration that has been labeled with a barcode.

7. The module of claim 1, wherein the system to measure and record the administration of the one or more IV medications or fluids further comprises:
    a display in electrical communication with the machine vision digital camera, wherein the display is configured to output medication and fluid identification and injection information including one or more of: a brand name of a drug, a generic name of a drug, a concentration of a drug, a dosage of a drug, a dosage delivered, a fluid flow rate, a fluid volume delivered, a patient allergy, an alert for over-dosing, an alert for a drug allergy and an alert for drug interactions on the display.

8. The module of claim 7, wherein the system to measure and record the administration of the one or more IV medications or fluids further comprises or is in electrical communication with one or more of: an electronic anesthetic record (EAR) and an electronic medical record (EMR), and wherein the system automatically records at least some of the administration of the one or more IV medications in one or both of the (EAR) and the (EMR).

9. The module of claim 2, wherein the system to measure and record the administration of the one or more IV medications or fluids further comprises:
a mechanical clamp configured to clamp the IV tubing, the mechanical clamp positioned upstream or downstream from the injection port, wherein the mechanical clamp can be automatically actuated to mechanically compress the IV tubing to stop the administration of the one or more IV medications or fluids when an adverse condition is determined by the processing circuitry.

10. The module of claim 2, wherein the injection portal includes one or more UV lights that shine on the injection port.

11. The module of claim 1, wherein the machine vision digital camera is located adjacent to the IV drip chamber, and wherein the processing circuitry is configured to interpret the image of drops in the IV drip chamber and determine a volume of fluid flowing from the IV bag by determining a size of drops and a number of drops per unit time to calculate a fluid flow rate.

12. The module of claim 1, wherein the system to measure and record the administration of the one or more IV medications or fluids further comprises:
a hanger configured to support an IV bag; and
an electronic scale in electrical communication with a processor, wherein the electronic scale is configured to measure a combined weight of the IV bag, the IV drip chamber, the IV tubing and the fluids in the IV bag, and wherein the processor is configured to determine a reduction in the measured combined weight over time to determine the weight of the IV fluids infused over time and convert the measured combined weight over time to a fluid flow rate and an infused fluid volume.

13. The module of claim 1, wherein the system to measure and record the administration of the one or more IV medications or fluids further comprises:
a hanger configured to receive the IV bag;
an electronic scale in electrical communication with a processor, wherein the hanger is configured to support the IV bag; and
a float located in the IV drip chamber,
wherein the machine vision digital camera is located adjacent to the IV drip chamber, and wherein the processing circuitry is configured to determine a volume of fluid flowing from the IV bag by determining a size of drops and a number of the drops per unit time to calculate a fluid flow rate,
wherein the electronic scale is configured to measure a combined weight of the IV bag, the IV drip chamber, the IV tubing and the fluid in the IV bag, and wherein the processing circuitry is configured to determine a reduction in the measured combined weight over time to determine a weight of the IV fluids infused over time and convert the measured combined weight over time to a fluid flow rate and infused fluid volume,
wherein at higher flow rates, when the drops in the IV drip chamber coalesce into a fluid stream that is un-interpretable by the machine vision camera and processing circuitry, the fluid stream causes a float in the IV drip chamber to move indicating that fluid is flowing, and wherein when the system fails to identify individual drops and detects that the float is moving, the processing circuitry is configured to measure a fluid flow rate by determining a reduction of the combined weight of the IV bag, the IV drip chamber, the IV tubing and the fluid in the IV bag over time.

14. The module of claim 1, wherein the system to measure and record the administration of the one or more IV medications or fluids further comprises:
one or more electro-mechanical clamps in electrical communication with the processing circuitry,
wherein the machine vision digital camera is located adjacent the IV drip chamber that is configured to be connected to the IV bag, wherein the processing circuitry is configured to interpret the image including a fluid meniscus level in the IV drip chamber, and
wherein when the fluid meniscus is not present, the processing circuitry causes actuation of the one or more electro-mechanical clamps to compress the IV tubing to stop a portion of an IV infusion before air can enter the IV tubing.

15. A module for housing unrelated electronic and electromechanical surgical equipment including a system to measure and record administration of one or more IV medications or fluids for IV administration to a patient, the module comprising:
a housing having a lower section and a tower-like upper section, wherein the lower section is configured to house unrelated waste heat-producing electronic and electromechanical surgical equipment, and wherein the tower-like upper section is located on top of the lower section, wherein the upper section is configured to accommodate mounting of equipment controls, display screens and monitor screens at a convenient height for viewing and operating;
a cable and hose management system located on a patient side of the module, wherein the patient side of the module is configured to face a patient and provide the closest and most direct access to the patient when the module is positioned adjacent an anesthesia side of an arm-board of a surgical table; and
a system to measure and record the administration of the one or more IV medications and fluids, the system comprising:
a barcode reader or an RFID interrogator configured to identify at least one of the one or more IV medications or fluids; and
a machine vision digital camera in electrical communication with processing circuitry configured to determine a volume of medication administered from a syringe or fluid administered from an IV bag through an IV drip chamber into an IV tubing based on an image generated by the machine vision digital camera.

16. The module of claim 15, wherein the system to measure and record the administration of the one or more IV medications or fluids further comprises:
an injection portal; and
one or more orienting members, wherein the injection portal includes an injection port that is configured to be in fluid communication with the IV tubing and the one or more orienting members are configured to guide syringes of varying diameters to mate with the injection port within the injection portal.

17. The module of claim 16, wherein the system to measure and record the administration of the one or more IV medications or fluids further comprises:
a display in electrical communication with the machine vision digital camera, wherein the machine vision digital camera is configured to capture an image of the syringe when the syringe is inserted inside the injection portal, and wherein the display is configured to output a visual image or representation of the syringe.

18. The module of claim 16, wherein the machine vision digital camera is located to capture an image of an inside of the injection portal, and wherein the processing circuitry is configured to interpret the image of the syringe when the syringe is inserted into the injection portal to measure the volume of medication injected from the syringe by determining a size and an internal diameter of the syringe and measuring a distance a plunger of the syringe moves to calculate an injected volume.

19. The module of claim 15, wherein the RFID interrogator is configured to identify at least one of the one or more IV medications or fluids for IV administration that has been labeled with an RFID tag.

20. The module of claim 15, wherein the machine vision digital camera is in electrical communication with the processing circuitry is configured to read a barcode to identify a medication or fluid for IV administration that has been labeled with a barcode.

21. The module of claim 15, wherein the system to measure and record the administration of the one or more IV medications or fluids further comprises:
  a display in electrical communication with the machine vision digital camera, wherein the display is configured to output medication and fluid identification and injection information including one or more of: a brand name of a drug, a generic name of a drug, a concentration of a drug, a dosage of a drug, a dosage delivered, a fluid flow rate, a fluid volume delivered, a patient allergy, an alert for over-dosing, an alert for a drug allergy and an alert for drug interactions on the display.

22. The module of claim 21, wherein the system to measure and record the administration of the one or more IV medications or fluids further comprises or is in electrical communication with one or more of: an electronic anesthetic record (EAR) and an electronic medical record (EMR), and wherein the system automatically records at least some of the administration of the one or more IV medications in one or both of the (EAR) and the (EMR).

23. The module of claim 16, wherein the injection portal includes one or more UV lights that shine on the injection port.

24. The module of claim 15, wherein the machine vision digital camera is located adjacent to the IV drip chamber, and wherein the processing circuitry is configured to interpret the image of drops in the IV drip chamber and determine a volume of fluid flowing from the IV bag by determining a size of drops and a number of drops per unit time to calculate a fluid flow rate.

25. The module of claim 15, wherein the system to measure and record the administration of the one or more IV medications or fluids further comprises:
  a hanger configured to support an IV bag; and
  an electronic scale in electrical communication with a processor, wherein the electronic scale is configured to measure a combined weight of the IV bag, the IV drip chamber, the IV tubing and the fluids in the IV bag, and wherein the processor is configured to determine a reduction in the measured combined weight over time to determine the weight of the IV fluids infused over time and convert the measured combined weight over time to a fluid flow rate and an infused fluid volume.

26. A module comprising:
  a housing having a lower section and a tower-like upper section, wherein the lower section is configured to house unrelated waste heat-producing electronic and electromechanical surgical equipment, and wherein the tower-like upper section is located on top of the lower section;
  a cowling that substantially confines waste heat generated by the unrelated waste heat-producing electronic and electromechanical surgical equipment;
  a system for monitoring the administration of one or more IV medications and fluids, the system comprising:
    at least one of a sensor configured to identify the one or more IV medications or fluids, or an input configured to receive the identity of the one or more IV medications or fluids;
    a machine vision digital camera to capture an image of one or more of a syringe or a drip chamber;
    processing circuitry operably coupled to the sensor to receive the identity of the one or more IV medications or fluids, the processing circuitry operably coupled to the machine vision digital camera to receive the captured image and determine a volume of medication administered from the syringe or fluid administered from an IV bag based on the image; and
    a display operably coupled to the processing circuitry, the display configured to receive instructions from the processing circuitry to output the identity and determined volume of medication administered from the syringe or fluid administered from an IV bag.

* * * * *

UNITED STATES PATENT AND TRADEMARK OFFICE
CERTIFICATE OF CORRECTION

PATENT NO. : 10,869,800 B2  
APPLICATION NO. : 16/879406  
DATED : December 22, 2020  
INVENTOR(S) : Augustine et al.

Page 1 of 1

It is certified that error appears in the above-identified patent and that said Letters Patent is hereby corrected as shown below:

On the Title Page

On page 2, in Column 2, Item (56) under "Other Publications", Line 7, delete "No," and insert --No. 16/601,924,-- therefor Signed and Sealed this  
Thirtieth Day of March, 2021

Drew Hirshfeld  
*Performing the Functions and Duties of the*  
*Under Secretary of Commerce for Intellectual Property and*  
*Director of the United States Patent and Trademark Office*